US012611457B2

(12) United States Patent
Codarri Deak et al.

(10) Patent No.: US 12,611,457 B2
(45) Date of Patent: **\*Apr. 28, 2026**

(54) BISPECIFIC ANTIBODIES SPECIFICALLY BINDING TO PD1 AND LAG3

(71) Applicant: Hoffmann-La Roche Inc., Little Falls, NJ (US)

(72) Inventors: Laura Codarri Deak, Schlieren (CH); Jens Fischer, Penzberg (DE); Sabine Imhof-Jung, Penzberg (DE); Christian Klein, Schlieren (CH); Stefan Seeber, Penzberg (DE); Patrick Alexander Aaron Weber, Schlieren (CH)

(73) Assignee: Hoffmnn-La Roche Inc., Little Falls, NJ (US)

( \* ) Notice: Subject to any disclaimer, the term of this patent is extended or adjusted under 35 U.S.C. 154(b) by 131 days.

This patent is subject to a terminal disclaimer.

(21) Appl. No.: 17/653,846

(22) Filed: Mar. 7, 2022

(65) Prior Publication Data

US 2022/0387586 A1      Dec. 8, 2022

Related U.S. Application Data

(63) Continuation of application No. 15/944,394, filed on Apr. 3, 2018, now Pat. No. 11,285,207.

(30) Foreign Application Priority Data

Apr. 5, 2017    (EP) ..................................... 17165125

(51) Int. Cl.
| | |
|---|---|
| A61K 39/395 | (2006.01) |
| A61K 35/17 | (2025.01) |
| A61K 39/00 | (2006.01) |
| A61K 45/06 | (2006.01) |
| A61P 31/12 | (2006.01) |
| A61P 35/00 | (2006.01) |
| C07K 16/28 | (2006.01) |
| C07K 16/30 | (2006.01) |

(52) U.S. Cl.
CPC .......... *A61K 39/3955* (2013.01); *A61K 35/17* (2013.01); *A61K 39/001102* (2018.08); *A61P 31/12* (2018.01); *A61P 35/00* (2018.01); *C07K 16/2803* (2013.01); *C07K 16/2809* (2013.01); *C07K 16/2818* (2013.01); *C07K 16/3007* (2013.01); *A61K 2039/505* (2013.01); *A61K 2039/507* (2013.01); *A61K 45/06* (2013.01); *A61K 2300/00* (2013.01); *C07K 2317/24* (2013.01); *C07K 2317/31* (2013.01); *C07K 2317/33* (2013.01); *C07K 2317/41* (2013.01); *C07K 2317/52* (2013.01); *C07K 2317/522* (2013.01); *C07K 2317/526* (2013.01); *C07K 2317/55* (2013.01); *C07K 2317/64* (2013.01); *C07K 2317/66* (2013.01); *C07K 2317/71* (2013.01); *C07K 2317/74* (2013.01); *C07K* *2317/75* (2013.01); *C07K 2317/76* (2013.01); *C07K 2317/77* (2013.01); *C07K 2317/92* (2013.01); *C07K 2317/94* (2013.01); *C07K 2319/00* (2013.01); *C07K 2319/30* (2013.01); *C07K 2319/74* (2013.01); *C07K 2319/75* (2013.01)

(58) Field of Classification Search
CPC ........ A61K 39/3955; A61K 39/001102; A61P 35/00; A61P 35/02; A61P 35/04; C07K 16/2809; C07K 2317/31
See application file for complete search history.

(56) References Cited

U.S. PATENT DOCUMENTS

| | | | |
|---|---|---|---|
| 5,750,373 | A | 5/1998 | Garrard et al. |
| 6,500,422 | B2 | 12/2002 | Biffoni et al. |
| 7,563,869 | B2 | 7/2009 | Honjo et al. |
| 7,595,048 | B2 | 9/2009 | Honjo et al. |
| 7,985,840 | B2 | 7/2011 | Fuh et al. |
| 8,552,156 | B2 | 10/2013 | Takayanagi et al. |
| 9,067,999 | B1 | 6/2015 | Honjo et al. |
| 9,084,776 | B2 | 7/2015 | Korman et al. |
| 9,163,087 | B2 | 10/2015 | Kuchroo et al. |
| 9,382,323 | B2 | 7/2016 | Brinkmann et al. |
| 9,834,607 | B2 | 12/2017 | Kuchroo et al. |
| 9,880,176 | B2 | 1/2018 | Jaga et al. |
| 9,945,869 | B2 | 4/2018 | Stubenrauch et al. |
| 10,287,352 | B2 | 5/2019 | Codarri-Deak et al. |
| 10,344,089 | B2 | 7/2019 | Thudium et al. |
| 10,392,445 | B2 | 8/2019 | Amann et al. |
| 10,562,903 | B2 | 2/2020 | Bartels et al. |
| 10,596,173 | B2 | 3/2020 | Lu et al. |
| 10,718,762 | B2 | 7/2020 | Seeber et al. |

(Continued)

FOREIGN PATENT DOCUMENTS

| | | |
|---|---|---|
| CA | 3082655 A1 | 2/2016 |
| CN | 101490085 | 7/2009 |

(Continued)

OTHER PUBLICATIONS

Agata, Y., et al., "Expression of the PD-1 antigen on the surface of stimulated mouse T and B lymphocytes" Int Immunol 8(5):765-772 (Feb. 6, 1996).

(Continued)

*Primary Examiner* — Karen A. Canella

(57) ABSTRACT

The invention relates to bispecific antibodies comprising a first antigen binding domain that specifically binds to PD1 and a second antigen binding domain that specifically binds to LAG3. The invention further relates to methods of producing these molecules and to methods of using the same.

32 Claims, 25 Drawing Sheets
Specification includes a Sequence Listing.

(56) References Cited

U.S. PATENT DOCUMENTS

| | | |
|---|---|---|
| 10,761,097 B2 | 9/2020 | Stubenrauch et al. |
| 10,781,262 B2 | 9/2020 | Klein et al. |
| 10,934,352 B2 | 3/2021 | Kuchroo et al. |
| 11,130,810 B2 | 9/2021 | Codarri-Deak et al. |
| 11,214,618 B2 | 1/2022 | Tuna et al. |
| 11,214,620 B2 | 1/2022 | Campbell et al. |
| 11,285,207 B2 | 3/2022 | Codarri Deak et al. |
| 11,413,331 B2 | 8/2022 | Deak et al. |
| 2006/0165685 A1 | 7/2006 | Kreysch et al. |
| 2007/0036783 A1 | 2/2007 | Humeau et al. |
| 2007/0071675 A1 | 3/2007 | Wu et al. |
| 2007/0122378 A1 | 5/2007 | Freeman et al. |
| 2009/0175867 A1 | 7/2009 | Thompson et al. |
| 2009/0217401 A1 | 8/2009 | Korman et al. |
| 2010/0190266 A1 | 7/2010 | Sakita et al. |
| 2010/0247521 A1 | 9/2010 | Jones et al. |
| 2011/0070238 A1 | 3/2011 | Triebel et al. |
| 2012/0189617 A1 | 7/2012 | Takayanagi et al. |
| 2012/0244112 A1 | 9/2012 | Ast et al. |
| 2013/0156774 A1 | 6/2013 | Kuchroo et al. |
| 2014/0242076 A1 | 8/2014 | Kadouche et al. |
| 2014/0242080 A1 | 8/2014 | Jaeger et al. |
| 2014/0242611 A1 | 8/2014 | Bazin et al. |
| 2014/0271684 A1 | 9/2014 | Li et al. |
| 2015/0024410 A1 | 1/2015 | Jaga et al. |
| 2015/0044690 A1 | 2/2015 | Nakada et al. |
| 2015/0090936 A1 | 4/2015 | Hu et al. |
| 2015/0203579 A1 | 7/2015 | Papadopoulos et al. |
| 2015/0204847 A1 | 7/2015 | Thomas et al. |
| 2015/0210769 A1 | 7/2015 | Freeman et al. |
| 2015/0216970 A1 | 8/2015 | Grogan et al. |
| 2015/0218274 A1 | 8/2015 | Sabatos-Peyton et al. |
| 2015/0259420 A1 | 9/2015 | Triebel et al. |
| 2015/0274827 A1 | 10/2015 | Pfizenmaier et al. |
| 2015/0315296 A1 | 11/2015 | Schaefer et al. |
| 2016/0222116 A1 | 8/2016 | Korman et al. |
| 2016/0257749 A1 | 9/2016 | Lifke et al. |
| 2016/0376367 A1 | 12/2016 | Yuan et al. |
| 2017/0114135 A1 | 4/2017 | Codarri-Deak et al. |
| 2017/0198037 A1 | 7/2017 | Bonvini et al. |
| 2017/0247454 A1 | 8/2017 | Benz et al. |
| 2018/0072804 A1 | 3/2018 | Lifke et al. |
| 2018/0326010 A1 | 11/2018 | Codarri Deak et al. |
| 2018/0326011 A1 | 11/2018 | Codarri Deak et al. |
| 2018/0326054 A1 | 11/2018 | Codarri Deak et al. |
| 2018/0328920 A1 | 11/2018 | Seeber et al. |
| 2019/0185566 A1 | 6/2019 | Koller et al. |
| 2019/0248877 A1 | 8/2019 | Amann et al. |
| 2019/0322748 A1 | 10/2019 | Codarri-Deak et al. |
| 2019/0382480 A1 | 12/2019 | Lifke et al. |
| 2019/0382489 A1 | 12/2019 | Benz et al. |
| 2019/0382507 A1 | 12/2019 | Amann et al. |
| 2020/0188526 A1 | 6/2020 | Klein et al. |
| 2020/0199234 A1 | 6/2020 | Georges et al. |
| 2020/0247904 A1 | 8/2020 | Amann et al. |
| 2020/0277372 A1 | 9/2020 | Codarri Deak et al. |
| 2020/0392237 A1 | 12/2020 | Bacac et al. |
| 2021/0009656 A1 | 1/2021 | Bruenker et al. |
| 2021/0024610 A1 | 1/2021 | Koller et al. |
| 2021/0087291 A1 | 3/2021 | Klein et al. |
| 2021/0163617 A1 | 6/2021 | Ferrara et al. |
| 2022/0072103 A1 | 3/2022 | Codarri Deak et al. |

FOREIGN PATENT DOCUMENTS

| | | |
|---|---|---|
| CN | 103608040 A | 2/2014 |
| CN | 103858010 | 6/2014 |
| CN | 104428315 B1 | 9/2017 |
| EA | 005404 B1 | 2/2005 |
| EA | 201690333 A1 | 6/2016 |
| EP | 3455254 A1 | 3/2019 |
| JP | 2005-526018 A1 | 9/2005 |
| JP | 2007-523602 A | 8/2007 |
| JP | 2012-503984 A | 2/2012 |
| JP | 2012-515766 | 7/2012 |
| JP | 2013-521769 A | 6/2013 |
| JP | 2014-506793 A | 3/2014 |
| JP | 2014-523401 A | 9/2014 |
| JP | 2017-505125 A | 2/2017 |
| RU | 2342950 C2 | 1/2009 |
| RU | 2406760 C2 | 12/2010 |
| RU | 2412947 C2 | 2/2011 |
| RU | 2494107 C2 | 9/2013 |
| SG | 2014012298 | 6/2014 |
| TW | 201019958 A1 | 6/2010 |
| TW | 201406784 A | 2/2014 |
| TW | 201540727 A | 11/2015 |
| WO | 96/27603 A1 | 9/1996 |
| WO | 00/24782 A2 | 5/2000 |
| WO | 01/77342 | 10/2001 |
| WO | 02/02773 A2 | 1/2002 |
| WO | 02/02773 A3 | 1/2002 |
| WO | 03/042402 A2 | 5/2003 |
| WO | 03/063792 A2 | 8/2003 |
| WO | 2004/004771 A1 | 1/2004 |
| WO | 2004/056875 A1 | 7/2004 |
| WO | 2004/069876 A2 | 8/2004 |
| WO | 2004/072286 A1 | 8/2004 |
| WO | 2004/078928 A2 | 9/2004 |
| WO | 2004/087196 A2 | 10/2004 |
| WO | 2005/020972 A2 | 3/2005 |
| WO | 2005/020972 A3 | 3/2005 |
| WO | 2005/087797 A1 | 9/2005 |
| WO | 2006/121168 A1 | 11/2006 |
| WO | 2006/133396 A2 | 12/2006 |
| WO | 2007/005874 A2 | 1/2007 |
| WO | 2007/062466 A1 | 6/2007 |
| WO | 2008/071447 A2 | 6/2008 |
| WO | 2008/083174 A2 | 7/2008 |
| WO | 2008/138920 A1 | 11/2008 |
| WO | 2008/156712 A1 | 12/2008 |
| WO | 2009/014708 A2 | 1/2009 |
| WO | 2009/024531 A1 | 2/2009 |
| WO | 2009/052623 A1 | 4/2009 |
| WO | 2009/101611 A1 | 8/2009 |
| WO | 2009/114335 A2 | 9/2009 |
| WO | 2010/10051 A1 | 1/2010 |
| WO | 2010/019570 A2 | 2/2010 |
| WO | 2010/027423 A2 | 3/2010 |
| WO | 2010/027828 A2 | 3/2010 |
| WO | 2010/029434 A1 | 3/2010 |
| WO | 2010/029435 A1 | 3/2010 |
| WO | 2010/036959 A2 | 4/2010 |
| WO | 2010/063011 A2 | 6/2010 |
| WO | 2010/084999 A1 | 7/2010 |
| WO | 2010/089411 A2 | 8/2010 |
| WO | 2010/112193 A1 | 10/2010 |
| WO | 2010/145792 A1 | 12/2010 |
| WO | 2011/066342 A2 | 6/2011 |
| WO | 2011/109789 A2 | 9/2011 |
| WO | 2011/110604 A1 | 9/2011 |
| WO | 2011/110621 A1 | 9/2011 |
| WO | 2011/155607 A1 | 12/2011 |
| WO | 2011/159877 A2 | 12/2011 |
| WO | 2012/020006 A2 | 2/2012 |
| WO | 2012/107417 A1 | 8/2012 |
| WO | 2012/130831 A1 | 10/2012 |
| WO | 2012/145493 A1 | 10/2012 |
| WO | 2013/004970 A1 | 1/2013 |
| WO | 2013/006490 A2 | 1/2013 |
| WO | 2013/014668 A1 | 1/2013 |
| WO | 2013/113663 A1 | 8/2013 |
| WO | 2013/164694 A1 | 11/2013 |
| WO | 2014/008218 A1 | 1/2014 |
| WO | 2014/009465 A1 | 1/2014 |
| WO | 2014/023679 A1 | 2/2014 |
| WO | 2014/055784 A1 | 4/2014 |
| WO | 2014/131711 A1 | 9/2014 |
| WO | 2014/140180 A1 | 9/2014 |
| WO | 2014/179664 A2 | 11/2014 |
| WO | 2015/018528 A1 | 2/2015 |
| WO | 2015/048312 A1 | 4/2015 |
| WO | 2015/052230 A1 | 4/2015 |
| WO | 2015/085847 A1 | 6/2015 |

(56) References Cited

FOREIGN PATENT DOCUMENTS

| | | | |
|---|---|---|---|
| WO | 2015/095423 | A2 | 6/2015 |
| WO | 2015/095423 | A3 | 6/2015 |
| WO | 2015/107026 | A1 | 7/2015 |
| WO | 2015/112800 | A1 | 7/2015 |
| WO | 2015/112900 | A1 | 7/2015 |
| WO | 2015/116539 | A1 | 8/2015 |
| WO | 2015/138920 | A1 | 9/2015 |
| WO | 2015/150447 | A1 | 10/2015 |
| WO | 2015/164665 | A1 | 10/2015 |
| WO | 2015/200119 | A1 | 12/2015 |
| WO | 2016/028672 | A1 | 2/2016 |
| WO | 2016/065038 | A1 | 4/2016 |
| WO | 2016/068801 | A1 | 5/2016 |
| WO | 2016/071448 | A1 | 5/2016 |
| WO | 2016/075278 | A1 | 5/2016 |
| WO | 2016/079050 | A1 | 5/2016 |
| WO | 2016/092419 | A1 | 6/2016 |
| WO | 2016/106159 | A1 | 6/2016 |
| WO | 2016/126858 | A2 | 8/2016 |
| WO | 2016/200782 | A1 | 12/2016 |
| WO | 2016/210129 | A1 | 12/2016 |
| WO | 2017/015560 | A2 | 1/2017 |
| WO | 2017/037203 | A1 | 3/2017 |
| WO | 2017/055399 | A1 | 4/2017 |
| WO | 2017/055404 | A1 | 4/2017 |
| WO | 2017/055443 | A1 | 4/2017 |
| WO | 2017/060144 | A1 | 4/2017 |
| WO | 2017/096026 | A1 | 6/2017 |
| WO | 2017/150447 | A1 | 9/2017 |
| WO | 2017/172517 | A1 | 10/2017 |
| WO | 2017/194442 | A1 | 11/2017 |
| WO | 2017/194641 | A1 | 11/2017 |
| WO | 2017/220555 | A1 | 12/2017 |
| WO | 2017/220569 | A1 | 12/2017 |
| WO | 2018/056821 | A1 | 3/2018 |
| WO | 2018/184964 | A1 | 10/2018 |
| WO | 2018/184965 | A1 | 10/2018 |
| WO | 2018/185043 | A1 | 10/2018 |
| WO | 2018/185046 | A1 | 10/2018 |
| WO | 2018/185232 | A1 | 10/2018 |
| WO | 2018/189220 | A1 | 10/2018 |
| WO | 2018185135 | A1 | 10/2018 |
| WO | 2019/086497 | A2 | 5/2019 |
| WO | 2019/175071 | A1 | 9/2019 |
| WO | 2019/197600 | A1 | 10/2019 |
| WO | 2020/127618 | A1 | 6/2020 |
| WO | 2021/209402 | A2 | 10/2021 |
| WO | 2021/260064 | A1 | 12/2021 |
| WO | 2022/148732 | | 7/2022 |

OTHER PUBLICATIONS

Aggarwal, B., "Signalling pathways of the TNF superfamily: a double-edged sword" Nat Rev Immunol 3(9):745-756 (Sep. 1, 2003).

Almagro, J., et al., "Humanization of antibodies" Front Biosci 13:1619-1633 (Jan 1, 2008).

Anderson, A.C., et al., "Promotion of Tissue Inflammation by the Immune Receptor Tim-3 Expressed on Innate Immune Cells" Science 318(5853):1141-1143 (Nov. 16, 2007).

Araki, K., et al., "Programmed Cell Death 1-Directed Immunotherapy for Enhancing T-Cell Function" Cold Spring Harb Symp Quant Biol 78:239-247 ( 2013).

Ascierto, P. et al., "Clinical Experiences With Anti-CD137 and Anti-PD1 Therapeutic Antibodies" Semin Oncol 27(5):508-516 (Oct. 1, 2010).

Ascierto, P., et al., "2015: The Year of Anti-PD-1/PD-L1s Against Melanoma and Beyond" Ebiomedicine 2(2):92-93 (Feb. 1, 2015).

Banner, D., et al., "Crystal Structure of the Soluble Human 55 kd TNF Receptor-Human TNFβ Complex: Implications for TNF Receptor Activation" Cell 73(3):431-445 (May 7, 1993).

Barber, D. et al., "Restoring function in exhausted CD8 T cells during chronic viral infection" Nature 439(7077):682-687 (Feb. 9, 2006).

Barthelemy, P., et al., "Comprehensive Analysis of the Factors Contributing to the Stability and Solubility of Autonomous Human VH Domains" J Biol Chem 283(6):3639-3654 (Feb. 8, 2008).

Baumann, R., et al., "Functional expression of CD134 by neutrophils" Eur J Immunol 34(8):2268-2275 (Aug. 1, 2004).

Beechem, J., Methods in Enzymology "Chapter 2: Global Analysis of Biochemical and Biophysical Data" Brand, L, and Johnson, M., eds, San Diego, CA -USA:Academic Press, vol. 210:37-54 ( 1992).

Beiboer, S.H., et al., "Guided selection of a pan carcinoma specific antibody reveals similar binding characteristics yet structural divergence between the original murine antibody and its human equivalent" J Mol Biol 296(3):833-849 (Feb. 25, 2000).

Bennett, F., et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses" J Immunol 170(2):711-718 (Jan. 15, 2003).

Bernett, M., et al., "Multiple Bispecific Checkpoint Combinations Promote T cell activation" Poster (Investor Relations presentation) Xencor Inc., Monrovia, California—US, p. 1 (2016) https://investors.xencor.com/static-files/f388d30a-3d0d-4a69-9a43-876a3b38f79f.

Blackburn, S., et al., "Coregulation of CD8+ T cell exhaustion by multiple inhibitory receptors during chronic viral infection" Nat Immunol 10(1):29-37 (Jan. 1, 2009).

Blank and MacKensen et al., "Contribution of the PD-L1/PD-1 pathway to T-cell exhaustion: an update on implications for chronic infections and tumor evasion" Cancer Immunol Immun 56(5):739-745 (May 1, 2007).

Bodmer, J. et al., "The molecular architecture of the TNF superfamily" Trends Biochem Sci 27(1):19-26 (Jan. 1, 2002).

Brahmer, J., et al., "Phase I Study of Single-Agent Anti-Programmed Death-1 (MDX-1106) in Refractory Solid Tumors: Safety, Clinical Activity, Pharmacodynamics, and Immunologic Correlates" J Clin Oncol 28(19):3167-3175 (Jul. 1, 2010).

Brand, F. X., et al., "Prospect for Anti-HER2 Receptor Therapy in Breast Cancer" Anticancer Res 26(1B):463-470 (Jan. 31, 2006).

Broll, K., et al., "CD137 Expression in Tumor Vessel Walls High Correlation With Malignant Tumors" Am J Clin Pathol 115(4):543-549 (Apr. 1, 2001).

Buechele, C., et al., "4-1BB ligand modulates direct and Rituximab-induced NK-cell reactivity in chronic lymphocytic leukemia" Eur J Immunol 42(3):737-748 (Mar. 1, 2012).

Cemerski et al., "T cell activation and anti-tumor efficacy of anti-LAG-3 antibodies is independent of LAG-3—MHCII blocking capacity" Journal for Immuno Therapy of Cancer 3(Suppl 2):183 ( Nov. 2015).

Chames, P., et al., "Therapeutic antibodies: successes, limitations and hopes for the future" Br J Pharmacol 157(2):220-233 (May 1, 2009).

Chen, S., et al., "Combination of 4-1BB Agonist and PD-1 Antagonist Promotes Antitumor Effector/Memory CD8 T Cells in a Poorly Immunogenic Tumor Model" Cancer Immunol Res 3(2):149-160 (Feb. 1, 2015).

Chen, X. et al., "Fusion Protein Linkers: Property, Design and Functionality" Adv Drug Deliv Rev 65(10):1357-1369 (Oct. 15, 2013).

Chen, X., et al., "A novel human IL-2 mutein with minimal systemic toxicity exerts greater antitumor efficacy than wild-type IL-2" Cell Death Dis 9(10 Suppl 989):1-12 (Oct. 1, 2018).

Choi, B., et al., "4-1BB Functions as a Survival Factor in Dendritic Cells" J Immunol 182(7):4107-4115 (Apr. 1, 2009).

Choi, Y., et al., "Predicting antibody complementarity determining region structures without classification" Mol Biosyst 7(12):3327-3334 (Dec. 1, 2011).

Colman P.M., "Effects of amino acid sequence changes on antibody-antigen interactions" Res Immunol 145:33-36 ( 1994).

Croft, M et al., "The significance of OX40 and OX40L to T-cell biology and immune disease" Immunol Rev 229(1):173-191 (May 1, 2009).

Cuadros, C., et al., "Vaccination with dendritic cells pulsed with apoptotic tumors in combination with anti-OX40 and anti-4-1BB

(56) References Cited

OTHER PUBLICATIONS monoclonal antibodies induces T cell-mediated protective immunity in Her-2/neu transgenic mice." Int J Cancer 116(6):934-943 (Oct. 10, 2005).

Curran, M., et al., "Combination CTLA-4 blockade and 4-1BB activation enhances tumor rejection by increasing T-cell infiltration, proliferation, and cytokine production" Plos One 6(4):e19499, 1-11 (Apr. 29, 2011).

Dashivets, T., et al., "Oxidation in the complementarity-determining regions differentially influences the properties of therapeutic antibodies" MABS 8(8):1525-1535 (Nov. 1, 2016).

De Genst, E., et al., "Antibody repertoire development in camelids" Dev Comp Immunol 30(1-2):187-198 ( 2006).

Dempke, W.C.M., et al., "Second- and third-generation drugs for immuno-oncology treatment—The more the better?" Eur J Cancer 74:55-72 (Mar. 1, 2017).

Dermer, G., et al., "Another anniversary for the war on cancer" Nat Biotechnol 12:320 (Mar. 1, 1994).

Diehl, L., et al., "In Vivo Triggering Through 4-1BB Enables Th-Independent Priming of CTL in the Presence of an Intact CD28 Costimulatory Pathway" J Immunol 168(8):3755-3762 (Apr. 15, 2002).

Dong et al., "Expressions of inhibitory receptors PD-1 and LAG-3 on CD4 + T cells in the patients with chronic hepatitis B virus infection and their significance" Chin. J. Clin. Lab. Sci. (Abstract in English), 34(2):100-102 (Feb. 5, 2016).

Dong, X., et al., "Time-resolved FRET reveals the structural mechanism of SERCA-PLB regulation" Biochem Biophys Res Commun 449(2):196-201 (Jun. 27, 2014).

Dubrot, J., et al., "Treatment with anti-CD137 mAbs causes intense accumulations of liver T cells without selective antitumor immunotherapeutic effects in this organ" Cancer Immunol Immun 59(8):1223-1233 (Aug. 1, 2010).

Everett et al., "Abstract PR06: a LAG-3/PD-L1 bispecific antibody inhibits tumour growth in two syngeneic colon carcinoma models" Cancer Immunology Research 5(3 Suppl PR06):1-4 (Mar. 2017).

Frankel, A.E., et al., "Characterization of diphtheria fusion proteins targeted to the human interleukin-3 receptor" Protein Eng 13(8):575-581 (Aug. 1, 2000).

Freshney, R.I., et al. Culture of Animal Cells: A Manual of Basic Technique New York: Alan R. Liss, Inc.,:1-7 ( 1983).

Futagawa, T., et al., "Expression and function of 4-1 BB and 4-1BB ligand on murine dendritic cells" Int Immunol 14(3):275-286 (Mar. 1, 2002).

Gakamsky, D., et al., "Use of fluorescence lifetime technology to provide efficient protection from false hits in screening applications" Anal Biochem 409(1):89-97 (Feb. 1, 2011).

Gehring, A., et al., "Profile of Tumor Antigen-Specific CD8 T Cells in Patients With Hepatitis B Virus-Related Hepatocellular Carcinoma" Gastroenterology 137(2):682-690 (Aug. 1, 2009).

George, J. et al., "Differential Effects of Anti-β2-Glycoprotein I Antibodies on Endothelial Cells and on the Manifestations of Experimental Antiphospholipid Syndrome" Circulation 97(9):900-906 (Mar. 10, 1998).

Golden-Mason, L., et al., "Negative Immune Regulator Tim-3 is Overexpressed on T Cells in Hepatitis C Virus Infection and Its Blockade Rescues Dysfunctional CD4 and CD8 T Cells" J Virol 83(18):9122-9130 (Sep. 1, 2009).

Golden-Mason, L., et al., "Upregulation of PD-1 Expression on Circulating and Intrahepatic Hepatitis C Virus-Specific CD8 T Cells Associated with Reversible Immune Dysfunction" J Virol 81(17):9249-9258 (Sep. 1, 2007).

Gribbon, P., et al., "Fluorescence readouts in HTS: No. gain without pain?" Drug Discov Today 8(22):1035-1043 (Nov. 15, 2003).

Griffiths, A., et al., "Human anti-self antibodies with high specificity from phage display libraries" EMBO J 12(2):725-734 (Feb. 1, 1993).

Guo, Z., et al., "Combined TIM-3 blockade and CD137 activation affords the long-term protection in a murine model of ovarian cancer." J Transl Med 11(215):1-11 (Sep. 17, 2013).

Gura, T., "Systems for Identifying New Drugs Are Often Faulty" Science 278(5340):1041-1042 (Nov. 7, 1997).

Hafler, D., et al., "TIMs: central regulators of immune responses" J Exp Med 205(12):2699-2701 (Nov. 24, 2008).

Heinisch, I., et al., "CD137 activation abrogates granulocytemacrophage colony-stimulating factor-mediated anti-apoptosis in neutrophils" Eur J Immunol 30(12):3441-3446 (Dec. 1, 2000).

Hornig, N., et al., "Combination of a Bispecific Antibody and Costimulatory Antibody-Ligand Fusion Proteins for Targeted Cancer Immunotherapy" J Immunother 35(5):418-429 (Jun. 1, 2012).

Hornig, N., et al., "Evaluating combinations of costimulatory antibody-ligand fusion proteins for targeted cancer immunotherapy" Cancer Immunol Immunother 62(8):1369-1380 (May 17, 2013).

Hu, C.Y., et al., "Interleukin-2 reverses CD8+ T cell exhaustion in clinical malignant pleural effusion of lung cancer" Clin Exp Immunol 186(1):106-114 (Oct. 1, 2016).

Huard, B., et al., "Characterization of the major histocompatibility complex class II binding site on LAG-3 protein" PNAS USA 94(11):5744-5749 (May 27, 1997).

International Preliminary Report on Patentability—PCT/EP2015/075820:pp. 1-8 (May 18, 2017).

International Preliminary Report on Patentability—PCT/EP2016/073186 (Report Issuance Date: Apr. 3, 2018, Chapter I),:pp. 1-6 (Apr. 12, 2018).

International Preliminary Report on Patentability—PCT/EP2016/073248 (Report Issuance Date: Apr. 3, 2018, Chapter I),:pp. 1-13 (Apr. 12, 2018).

International Preliminary Report on Patentability—PCT/EP2017/061241 (Report Issuance Date: Nov. 13, 2018, Chapter I),:pp. 1-8 (Nov. 13, 2018).

International Preliminary Report on Patentability—PCT/EP2018/058034 (Report Issuance Date: Oct. 8, 2019, Chapter I),:pp. 1-10 (Oct. 17, 2019).

International Preliminary Report on Patentability—PCT/EP2018/058037 (Report Issuance Date: Oct. 8, 2019, Chapter I),:pp. 1-10 (Oct. 17, 2019).

International Preliminary Report on Patentability—PCT/EP2018/058382 (Report Issuance Date: Oct. 8, 2019, Chapter I),:pp. 1-12 (Oct. 8, 2019).

International Preliminary Report on Patentability—PCT/EP2018/058385 (Report Issuance Date: Oct. 8, 2019, Chapter I),:pp. 1-11 (Oct. 8, 2019).

International Search Report—PCT/EP2016/073186 (w/Written Opinion),:pp. 1-10 (Dec. 9, 2016).

International Search Report—PCT/EP2015/075820:pp. 1-8 (Feb. 4, 2016).

International Search Report—PCT/EP2016/073248:pp. 1-11 (Feb. 15, 2017).

International Search Report—PCT/EP2017/061241 (w/Written Opinion),:pp. 1-18 (Aug. 3, 2017).

International Search Report—PCT/EP2018/058034 (w/Written Opinion),:pp. 1-18 (Jun. 6, 2018).

International Search Report—PCT/EP2018/058037:pp. 1-10 (Jun. 6, 2018).

International Search Report—PCT/EP2018/058382:pp. 1-10 (Jul. 17, 2018).

International Search Report—PCT/EP2018/058385 (w/Written Opinion),:pp. 1-24 (Jun. 6, 2018).

Isenberg, I., et al., "The Analysis of Fluorescence Decay by a Method of Moments" Biophys J 9(11):1337-1350 (Nov. 1, 1969).

Jain, R., "Barriers to drug delivery in solid tumors" SCI AM:58-65 (Jul. 1994).

Jameson, D.M. et al., "Investigations of protein-protein interactions using time-resolved fluorescence and phasors" Methods 59(3):278-286 (Mar. 1, 2013).

Jin, H., et al., "Cooperation of Tim-3 and PD-1 in CD8 T-cell exhaustion during chronic viral infection" PNAS 107(33):14733-14738 (Aug. 17, 2010).

Jones, R., et al., "Tim-3 expression defines a novel population of dysfunctional T cells with highly elevated frequencies in progressive HIV-1 infection" J Exp Med 205(12):2763-2779 (Nov. 24, 2008).

(56)        References Cited

OTHER PUBLICATIONS

Ju, S., et al., "Eradication of established renal cell carcinoma by a combination of 5-fluorouracil and anti-4-1BB monoclonal antibody in mice." Int J Cancer 122(12):2784-2790 (Jun. 15, 2008).
Jutz, S., et al., "A cellular platform for the evaluation of immune checkpoint molecules" Oncotarget 8(39):64892-64906 (May 4, 2017).
Kienzle, G., et al., "CD137 (ILA/4-1BB), expressed by primary human monocytes, induces monocyte activation and apoptosis of B lymphocytes" Int Immunol 12(1):73-82 (Jan. 1, 2000).
Kikushige, Y., et al., "TIM-3 as a Novel Therapeutic Target for Eradicating Acute Myelogenous Leukemia Stem Cells" Int J Hematol 98(6):627-633 (Dec. 1, 2013).
Kim, D., et al., "4-1BB Engagement Costimulates NKT Cell Activation and Exacerbates NKT Cell Ligand—Induced Airway Hyperresponsiveness and Inflammation" J Immunol 180(4):2062-2068 (Feb. 1, 2008).
Kim, Y. H., et al., "Mechanisms involved in synergistic anticancer effects of anti-4-1BB and cyclophosphamide therapy." Mol Cancer Ther 8(2):469-478 (Feb. 1, 2009).
Klebanoff, C., et al., "IL-15 enhances the in vivo antitumor activity of tumor-reactive CD8+ T Cells" PNAS USA 101(7):1969-1974 (Feb. 17, 2004).
Klimka, A. et al., "Human anti-CD30 recombinant antibodies by guided phage antibody selection using cell panning" Brit J Cancer 83(2):252-260 (Jun. 15, 2000).
Klooster et al., "Abstract B088: Generation of immuno-modulatory receptor binding bispecific antibodies to modulate tumor immunity" Cancer Immunology Research 4( Suppl 11):B088:1-4 (Nov. 2016).
Klooster, R., et al., "Generation of immuno-modulatory receptor binding bispecific antibodies to modulate tumor immunity (B088)" Poster ICIC, New York, NY-US, p. 1 ( Sep. 26, 2016) https://merus.nl/app/uploads/2019/02/Poster-ICIC-New-York-26Sep16.pdf.
Knutson, J.R., et al., "Simultaneous analysis of multiple fluorescence decay curves: A global approach" Chem Phys Lett 102(6):501-507 (Dec. 9, 1983).
Koguchi, K., et al., "Dysregulated T cell expression of TIM3 in multiple sclerosis" J Exp Med 203(6):1413-1418 (Jun. 12, 2006).
Kraman, M. et al., "A LAG-3/PD-L1 bispecific antibody inhibits tumour growth in two syngeneic colon carcinoma models" Cancer Res 77(13):1 (Jul. 1, 2017).
Kwon, B., et al., "cDNA sequences of two inducible T-cell genes" PNAS USA 86(6):1963-1967 (Mar. 1, 1989).
LaMotte-Mohs et al., "Abstract 3217: MGD013, a bispecific PD-1 × LAG-3 Dual-Affinity Re-Targeting (DART®) protein with T-cell immunomodulatory activity for cancer treatment" Cancer Research 76( Suppl 14):3217 (Jul. 2016).
Lebakken, C.S., et al., "A fluorescence lifetime based binding assay to characterize kinase inhibitors" J Biomol Screen 12(6):828-841 (Sep. 1, 2007).
Lee, H., et al., "Combinatorial therapy for liver metastatic colon cancer: dendritic cell vaccine and low-dose agonistic anti-4-1BB antibody costimulatory signal" J Surg Res 169(1):e43-50 (Jul. 1, 2011).
Levitsky, V., et al., "The clonal composition of a peptide-specific oligoclonal CTL repertoire selected in response to persistent EBV infection is stable over time." J Immunol 161(2):594-601 (Jun. 30, 1998).
Li and Ravetch, "Inhibitory Fcy Receptor Engagement Drives Adjuvant and Anti-Tumor Activities of Agonistic CD40 Antibodies" Science 333(6045):1030-1034 (Aug. 19, 2011).
Lin, W., et al., "Fc-dependent expression of CD137 on human NK cells: insights into agonistic effects of anti-CD137 monoclonal antibodies" Blood 112(3):699-707 (Aug. 1, 2008).
Lippincott-Schwartz, J. et al., "Antibodies as Cell Biological Tools" Current Protocols in Cell Biology:16.0.1-16.0.2 ( 2002).
Lou et al., "Effect of anti-LAG-3 antibodies on the protective effect and immune function in septic mice" The Third National Conference on Narcotic Pharmacology, Shanghai, China, pp. 273-274 ( Jul. 6, 2012).

Maeda, Y., et al., "Engineering of functional chimeric protein G-Vargula luciferase" Anal Biochem 249(2): 147-152 (Jul. 1, 1997).
Majeti, R., et al., "Dysregulated gene expression networks in human acute myelogenous leukemia stem cells" PNAS 106(9):3396-3401 (Mar. 3, 2009).
Malia, T., et al., "Epitope mapping and structural basis for the recognition of phosphorylated tau by the anti-tau antibody AT8" Proteins 84(4):427-434 (Apr. 1, 2016).
Mallender, W.D., et al., "Inter-Active-Site Distance and Solution Dynamics of a Bivalent-Bispecific Single-Chain Antibody Molecule" Biochemistry 33(33):10100-10108 (Aug. 1, 1994).
Maltman, B., et al., "9-Aminoacridine peptide derivatives as versatile reporter systems for use in fluorescence lifetime assays" Chem Commun [CAMB] 46(37):6929-6931 (Oct. 7, 2010).
Mariuzza, R. et al., "The structural basis of antigen-antibody recognition" Annu Rev Biophys Chem 16:139-159 (Jun. 1, 1987).
Markwick, L., et al., "Blockade of PD1 and TIM3 Restores Innate and Adaptive Immunity in Patients With Acute Alcoholic Hepatitis" Gastroenterology 148(3):590-602 (Mar. 1, 2015).
McMahan, R., et al., "Dual TIM-3/PD-1 Expression on Non-Effector CD4+ T Cells and HCV-Specific CD8+ T Cells is Associated with Development of Persistence in Acute HCV Infection" Hepatology (Abstract #1368), 50( Suppl 4) ( 2009).
Melero, I. et al., "Monoclonal Antibodies Against the 4-1BB T-cell Activation Molecule Eradicate Established Tumors" Nat Med 3(6):682-685 (Jun. 1, 1997).
Melero, I. et al., "NK1.1 Cells Express 4-1BB (CDw137) Costimulatory Molecule and Are Required for Tumor Immunity Elicited by Anti-4-1BB Monoclonal Antibodies" Cell Immunol 190(2 Suppl CI981396):167-172 (Dec. 15, 1998).
Merchant, A., et al., "An efficient route to human bispecific IgG" Nat Biotechnol 16(7):677-681 (Jul. 1, 1998).
Moger, J., et al., "The Application of Fluorescence Lifetime Readouts in High-Throughput Screening" J Biomol Screen 11(7):765-772 (Oct. 1, 2006).
Monney, L., et al., "Th1-specific cell surface protein Tim-3 regulates macrophage activation and severity of an autoimmune disease" Nature 415(6871):536-541 (Jan. 31, 2002).
Morales-Kastresana, A., et al., "Combined immunostimulatory monoclonal antibodies extend survival in an aggressive transgenic heptocellular carcinoma mouse model" Clin Cancer Res 19(22):6151-6162 (Nov. 1, 2013).
Morales-Kastresana, A., et al., "Essential complicity of perforin-granzyme and FAS-L mechanisms to achieve tumor rejection following treatment with anti-CD137 mAb" J Immunother Cancer 1(3):1-6 (May 29, 2013).
Mueller, D. et al., "A Novel Antibody-4-1BBL Fusion Protein for Targeted Costimulation in Cancer Immunotherapy" J Immunother 31(8):714-722 (Oct. 1, 2008).
Muretta, J., et al., "High-performance time-resolved fluorescence by direct waveform recording." Rev Sci Instrum 81(10 Suppl 103101):1-8 (Oct. 1, 2010).
Murillo, O., et al., "In vivo depletion of DC impairs the anti-tumor effect of agonistic anti-CD137 mAb" Eur J Immunol 39(9):2424-2436 (Sep. 1, 2009).
Nakamoto, N., et al., "Synergistic Reversal of Intrahepatic HCV-Specific CD8 T Cell Exhaustion by Combined PD-1/CTLA-4 Blockade" Plos Pathog 5(2):e1000313, 1-13 (Feb. 1, 2009).
Narazaki, H., et al., "CD137 agonist antibody prevents cancer recurrence: contribution of CD137 on both hematopoietic and nonhematopoietic cells" Blood 115(10):1941-1948 (Mar. 11, 2010).
Ngiow, S., et al., "Review: Prospects for TIM3-Targeted Antitumor Immunotherapy" Cancer Res 71(21):6567-6571 (Nov. 1, 2011).
Nishimoto, H., et al., "Costimulation of mast cells by 4-1BB, a member of the tumor necrosis factor receptor superfamily, with the high-affinity IgE receptor" Blood 106(13):4241-4248 (Dec. 15, 2005).
Ohaegbulam, K., et al., "Human cancer immunotherapy with antibodies to the PD-1 and PD-L1 pathway" Trends Mol Med 21(1):24-33 (Jan. 1, 2015).
Okazaki, T., et al., "New regulatory co-receptors: inducible costimulator and PD-1" Curr Opin Immunol 14(6):779-782 (Dec. 1, 2002).

(56) References Cited

OTHER PUBLICATIONS

Olofsson, P., et al., "CD137 is Expressed in Human Atherosclerosis and Promotes Development of Plaque Inflammation in Hypercholesterolemic Mice" Circulation 117(10):1292-1301 (Mar. 11, 2008).

Padlan, E. et al., "Anatomy of the Antibody Molecule" Mol Immunol 31(3):169-217 (Feb. 1, 1994).

Palazon, A., et al., "Agonist Anti-CD137 mAb Act on Tumor Endothelial Cells to Enhance Recruitment of Activated T Lymphocytes" Cancer Res 71(3):801-811 (Feb. 1, 2011).

Pan, Q., et al., "Blocking neuropilin-1 function has an additive effect with anti-VEGF to inhibit tumor growth" Cancer Cell 11(1):53-67 (Jan. 1, 2007).

Paterson, M.J., et al., "A fluorescence lifetime-based assay for serine and threonine kinases that is suitable for high-throughput screening" Anal Biochem 402(1):54-64 (Jul. 1, 2010).

Philips, G., et al., "Therapeutic uses of anti-PD-1 and anti-PD-L1 antibodies" Int Immunol 27(1):39-46 (Oct. 16, 2014).

Roitt, I.,, "Different antigen antibody binding is ensured by hypervariable sequences of antigen-recognizing centers" Immunologiya:110-111 (2000).

Rudikoff, S., et al., "Single amino acid substitution altering antigen-binding specificity" PNAS USA 79(6):1979-1983 (Mar. 1, 1982).

Sakuishi, K., et al., "Targeting Tim-3 and PD-1 pathways to reverse T cell exhaustion and restore anti-tumor immunity" J Exp Med 207(10):2187-2194 (Sep. 27, 2010).

Sakuishi, K., et al., "TIM3+FOXP3+ regulatory T cells are tissue-specific promoters of T-cell dysfunction in cancer" Oncoimmunology 2(4):e23849, 1-9 (Apr. 1, 2013).

Schwarz, H., et al., "ILA, the Human 4-1BB Homologue, is Inducible in Lymphoid and Other Cell Lineages" Blood 85(4):1043-1052 (Feb. 15, 1995).

Shao, Z., et al., "Mini-Review: CD137 ligand, a member of the tumor necrosis factor family, regulates immune responses via reverse signal transduction" J Leukocyte Biol 89(1):21-29 (Jan. 1, 2011).

Shen, L., et al., "Construction and Expression of Anti-B7-1 /B7-2-BsAb for Feature Analysis of its binding with antigen" Chinese J Immunol (w/Eng. Abstract), 31:927-931 (Jul. 14, 2015).

Sheridan, C., et al., "Cautious optimism surrounds early clinical data for PD-1 blocker" Nat Biotechnol 30(8):729-730 (Aug. 1, 2012).

Shi, W., et al., "Augmented antitumor effects of radiation therapy by 4-1BB antibody (BMS-469492) treatment." Anticancer Res 26(5A):3445-3453 (Sep. 2006).

Shindo, Y., et al., "Combination Immunotherapy with 4-1BB activation and PD-1 blockade enhances antitumor efficacy in a mouse model of subcutaneous tumor" Anticancer Res 35(1):129-136 (Jan. 1, 2015).

Sierro, S., et al., "The CD4-like molecule LAG-3, biology and therapeutic applications" Expert Opin Ther Tar 15(1):91-101 (Jan. 1, 2011).

Simeone, E et al., "Immunomodulating antibodies in the treatment of metastatic melanoma: The experience with anti-CTLA-4, anti-CD137, and anti-PD1" J Immunotoxcity 9(3):241-247 (Jul. 1, 2012).

Singer, M. et al., "Structure of Proteins" Genes & Genomes (Geny i genomy Moscow: Mir, 1991), 1:67-69 ( 1991).

Skosyrev, V.S., et al., "The Dependence of Stability of the Green Fluorescent Protein-Obelin Hybrids on the Nature of Their Constituent Modules and the Structure of the Amino Acid Linker" Bioorg Khim (Russ. J Bioorg Chem) 27(5):323-329 (Sep. 30, 2001).

Snell, L., et al., "T-cell intrinsic effects of GITR and 4-1BB during viral infection and cancer immunotherapy" Immunol Rev 244(1):197-217 (Nov. 1, 2011).

Song, J. et al., "Activation of NF-kB1 by OX40 Contributes to Antigen-Driven T Cell Expansion and Survival" J Immunol 180(11):7240-7248 (Jun. 1, 2008).

Stagg, J., et al., "Anti-ErbB-2 mAb therapy requires type I and II interferons and synergizes with anti-PD-1 or anti-CD137 mAb therapy" PNAS USA 108(17):7142-7147 (Apr. 26, 2011).

Strome, S., et al., "A Mechanistic Perspective of Monoclonal Antibodies in Cancer Therapy Beyond Target-Related Effects" Oncologist 12(9):1084-1095 (Sep. 1, 2007).

Takamura, S., et al., "Premature Terminal Exhaustion of Friend Virus-Specific Effector CD8 + T Cells by Rapid Induction of Multiple Inhibitory Receptors" J Immunol 184(9):4696-4707 (May 1, 2010).

Tan, S., et al., "An unexpected N-terminal loop in PD-1 dominates binding by nivolumab" Nat Commun 8(14369):1-10 (Feb. 6, 2017).

Teng, M., et al., "CD1d-Based Combination Therapy Eradicates Established Tumors in Mice" J Immunol 183(3):1911-1920 (Aug. 1, 2009).

Thorne, N., et al., "Apparent activity in high-throughput screening: origins of compound-dependent assay interference" Curr Opin Chem Biol 14(3):315-324 (Jun. 1, 2010).

Tokuriki, N. et al., "Stability effects of mutations and protein evolvability" Curr Opin Struct Biol 19(5):596-604 (Oct. 1, 2009).

Topalian, S., et al., "Survival, Durable Tumor Remission, and Long-Term Safety in Patients With Advanced Melanoma Receiving Nivolumab" J Clin Oncol 32(10):1020-1030 (Apr. 1, 2014).

Tribel, F., et al., "A soluble lymphocyte activation gene-3 (sLAG-3) protein as a prognostic factor in human breast cancer expressing estrogen or progesterone receptors" Cancer Lett 235(1):147-153 (Apr. 8, 2006).

Vajdos, F.F., et al., "Comprehensive functional maps of the antigen-binding site of an anti-ErbB2 antibody obtained with shotgun scanning mutagenesis" J Mol Biol 320(2):415-428 (Jul. 5, 2002).

Vig, B., et al., "Amino acids as promoieties in prodrug design and development" Adv Drug Deliv Rev 65(10):1370-1385 (Oct. 15, 2013).

Von Kempis, J., et al., "Differentiation-dependent and stimulus-specific expression of ILA, the human 4-1BB-homologue, in cells of mesenchymal origin" Steoarthr Cartilage 5(6):394-406 (Nov. 1, 1997).

Wang, S-C, et al., "PD-1 and Tim-3 pathways are associated with regulatory CD8+ T-cell function in decidua and maintenance of normal pregnancy" Cell Death Dis 6(5):e1738, 1-10 (May 1, 2015).

Ward, E., et al., "Binding activities of a repertoire of single immunoglobulin variable domains secreted from *Escherichia coli*" Nature 341(6242):544-546 (Oct. 12, 1989).

Watts, T., "TNF/TNFR family members in costimulation of T cell responses" Annu Rev Immunol 23:23-68 (Sep. 2005).

Wei, H. et al., "Dual targeting of CD137 co-stimulatory and PD-1 co-inhibitory molecules for ovarian cancer immunotherapy" Oncoimmunology 3(4):e28248, 1-3 (Mar. 28, 2014).

Wei, H., et al., "Combinatorial PD-1 blockade and CD137 activation has therapeutic efficacy in murine cancer models and synergizes with cisplatin" Plos One 8(12):e84927, 1-11 (Dec. 19, 2013).

Weinberg, A., et al., "Engagement of the OX-40 Receptor In Vivo Enhances Antitumor Immunity" J Immunol 164(4):2160-2169 (Feb. 15, 2000).

West, E.E., et al., "PD-L1 blockade synergizes with IL-2 therapy in reinvigorating exhausted T cells" J Clin Invest 123(6):2604-2615 (Jun. 3, 2013).

Wilcox, R., et al., "Cutting Edge: Expression of Functional CD137 Receptor by Dendritic Cells" J Immunol 168(9):4262-4267 (May 1, 2002).

Wilcox, R., et al., "Ligation of CD137 receptor prevents and reverses established anergy of CD8+ cytolytic T lymphocytes in vivo" Blood 103(1):177-184 (Jan. 1, 2004).

Woo, S., et al., "Immune inhibitory molecules LAG-3 and PD-1 synergistically regulate T cell function to promote tumoral immune escape" Cancer Res 72(4):917-927 (Feb. 15, 2012).

Wozney, J., Methods in Enzymology: Guide to Protein Purification "55: Using Purified Protein to Clone its Gene" Deutscher, Murray, ed., San Diego, CA—US: Academic Press, Inc.—Harcourt Brace Jovanivich, Publishers, vol. 182:738-751 ( 1990).

Xu, Z., et al., "Membrane-type TIM3 Promotes Anti-tumor Immunity in Tumor Bearing Mice" Chinese J Med Mol Biol (with English Abstract.), 4(3):200-203 (Jan. 31, 2007).

Zhang, N et al., "Targeted and untargeted CD137L fusion proteins for the immunotherapy of experimental solid tumors." Clin Cancer Res 13(9):2758-2767 (May 1, 2007).

(56)     References Cited

OTHER PUBLICATIONS

Zhang, X., et al., "CD137 Promotes Proliferation and Survival of Human B Cells" J Immunol 184(2):787-795 (Jan. 15, 2010).

Zhou, Q., et al., "Coexpression of Tim-3 and PD-1 identifies a CD8+ T-cell exhaustion phenotype in mice with disseminated acute myelogenous leukemia" Blood 117(17):4501-4510 (Apr. 28, 2011).

Zitvogel, L. et al., "Targeting PD-1/PD-L1 interactions for cancer immunotherapy" Oncoimmunology 1(8):1223-1225 (Nov. 1, 2012).

Zitvogel, L., et al., "Cancer despite immunosurveillance: immunoselection and immunosubversion" Nat Rev Immunol 6(10):715-727 (Oct. 1, 2006).

Doody et al., "Abstract B091: A LAG-3/PD-L1 bispecific antibody inhibits tumor growth in two syngeneic colon carcinoma models" American Association for Cancer Research; Cancer Immunology Research( Suppl 11):1 (Oct. 31, 2016) https://doi.org/10.1158/2326-6066.IMM2016-B091.

Everett et al., "Generation of Fcabs targeting human and murine LAG-3 as building blocks for novel bispecific antibody therapeutics" Methods (EPUB: Sep. 9, 2018), 154: pp. 60-69 (2019).

Klooster et al., Poster Generation of immuno-modulatory receptor binding bispecific antibodies to modulate tumor immunity (B088); XP055442867, pp. 1-9 (Sep. 23, 2016).

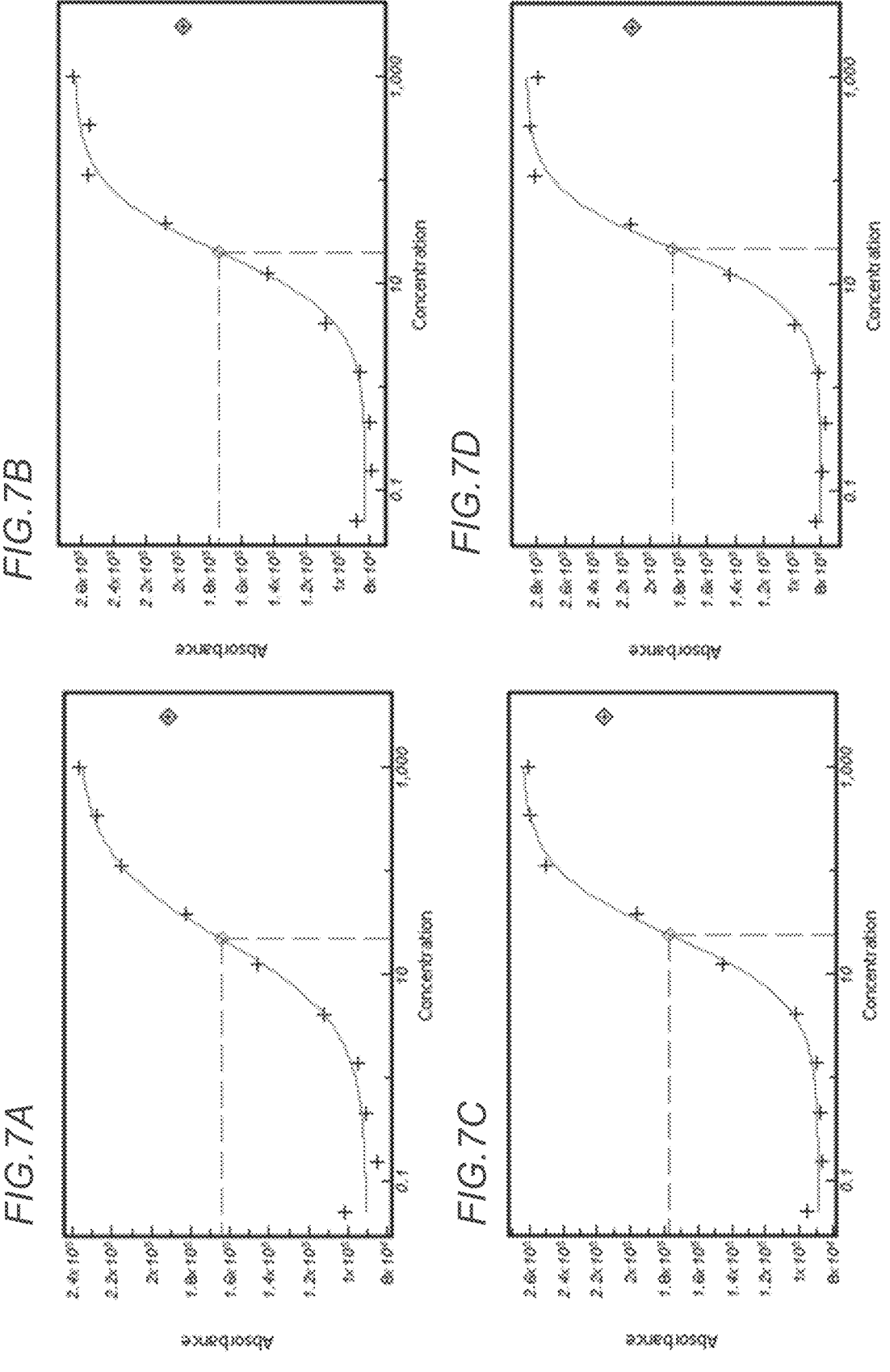

BISPECIFIC ANTIBODIES SPECIFICALLY BINDING TO PD1 AND LAG3

CROSS REFERENCE TO RELATED APPLICATIONS

This application is a continuation of U.S. application Ser. No. 15/944,394, filed Apr. 3, 2018, allowed, which is a non-provisional application claiming priority to European Application No. 17165125.0, filed Apr. 5, 2017, the contents of which are hereby incorporated herein by reference in their entirety.

SEQUENCE LISTING

The instant application contains a Sequence Listing submitted electronically in ASCII format and is hereby incorporated herein by reference in its entirety. Said ASCII copy, created on Mar. 27, 2022, is named P34215-US-1_Sequence_listing.txt, has 169 sequences and is 255,194 bytes in size.

FIELD OF THE INVENTION

The invention relates to bispecific antibodies comprising a first antigen binding domain that specifically binds to PD1 and a second antigen binding domain that specifically binds to LAG3, in particular to bispecific antibodies further comprising a Fc domain that comprises one or more amino acid substitution that reduces binding to an Fc receptor, in particular towards Fcγ receptor. The invention further relates to methods of producing these molecules and to methods of using the same.

BACKGROUND

The importance of the immune system in the protection against cancer is based on its capacity to detect and destroy abnormal cells. However, some tumor cells are able to escape the immune system by engendering a state of immunosuppression (Zitvogel et al., Nature Reviews Immunology 6 (2006), 715-727). T cells have an important role in antiviral and anti-tumour immune responses. Appropriate activation of antigen-specific T cells leads to their clonal expansion and their acquisition of effector function, and, in the case of cytotoxic T lymphocytes (CTLs) it enables them to specifically lyse target cells. T cells have been the major focus of efforts to therapeutically manipulate endogenous antitumour immunity owing to their capacity for the selective recognition of peptides derived from proteins in all cellular compartments; their capacity to directly recognize and kill antigen-expressing cells (by CD8$^+$ effector T cells; also known as cytotoxic T lymphocytes (CTLs)) and their ability to orchestrate diverse immune responses (by CD4$^+$ helper T cells), which integrates adaptive and innate effector mechanisms. T cell dysfunction occurs as a result of prolonged antigen exposure: the T cell loses the ability to proliferate in the presence of the antigen and progressively fails to produce cytokines and to lyse target cells1. The dysfunctional T cells have been termed exhausted T cells and fail to proliferate and exert effector functions such as cytotoxicity and cytokine secretion in response to antigen stimulation. Further studies identified that exhausted T cells are characterized by sustained expression of the inhibitory molecule PD-1 (programmed cell death protein 1) and that blockade of PD-1 and PD-L1 (PD-1 ligand) interactions can reverse T cell exhaustion and restore antigen-specific T cell responses in LCMV-infected mice (Barber et al., Nature 439 (2006), 682-687). However, targeting the PD-1-PD-L1 pathway alone does not always result in reversal of T cell exhaustion (Gehring et al., Gastroenterology 137 (2009), 682-690), indicating that other molecules are likely involved in T cell exhaustion (Sakuishi, J. Experimental Med. 207 (2010), 2187-2194).

Lymphocyte activation gene-3 (LAG3 or CD223) was initially discovered in an experiment designed to selectively isolate molecules expressed in an IL-2-dependent NK cell line (Triebel F et al., Cancer Lett. 235 (2006), 147-153). LAG3 is a unique transmembrane protein with structural homology to CD4 with four extracellular immunoglobulin superfamily-like domains (D1-D4). The membrane-distal IgG domain contains a short amino acid sequence, the so-called extra loop that is not found in other IgG superfamily proteins. The intracellular domain contains a unique amino acid sequence (KIEELE, SEQ ID NO:75) that is required for LAG3 to exert a negative effect on T cell function. LAG3 can be cleaved at the connecting peptide (CP) by metalloproteases to generate a soluble form, which is detectable in serum. Like CD4, the LAG3 protein binds to MHC class II molecules, however with a higher affinity and at a distinct site from CD4 (Huard et al. Proc. Natl. Acad. Sci. USA 94 (1997), 5744-5749). LAG3 is expressed by T cells, B cells, NK cells and plasmacytoid dendritic cells (pDCs) and is upregulated following T cell activation. It modulates T cell function as well as T cell homeostasis. Subsets of conventional T cells that are anergic or display impaired functions express LAG3. LAG3$^+$ T cells are enriched at tumor sites and during chronic viral infections (Sierro et al Expert Opin. Ther. Targets 15 (2011), 91-101). It has been shown that LAG3 plays a role in CD8 T cell exhaustion (Blackburn et al. Nature Immunol. 10 (2009), 29-37). Thus, there is a need for antibodies that antagonize the activity of LAG3 and can be used to generate and restore immune response to tumors.

Monoclonal antibodies to LAG3 have been described, for example, in WO 2004/078928 wherein a composition comprising antibodies specifically binding to CD223 and an anti-cancer vaccine is claimed. WO 2010/019570 discloses human antibodies that bind LAG3, for example the antibodies 25F7 and 26H10. US 2011/070238 relates to a cytotoxic anti-LAG3 antibody useful in the treatment or prevention of organ transplant rejection and autoimmune disease. WO 2014/008218 describes LAG3 antibodies with optimized functional properties (i.e. reduced deamidation sites) compared to antibody 25F7. Furthermore, LAG3 antibodies are disclosed in WO 2015/138920 (for example BAP050), WO 2014/140180, WO 2015/116539, WO 2016/028672, WO 2016/126858, WO 2016/200782 and WO 2017/015560.

Programmed cell death protein 1 (PD-1 or CD279) is an inhibitory member of the CD28 family of receptors, that also includes CD28, CTLA-4, ICOS and BTLA. PD-1 is a cell surface receptor and is expressed on activated B cells, T cells, and myeloid cells (Okazaki et al (2002) Curr. Opin. Immunol. 14: 391779-82; Bennett et al. (2003) J Immunol 170:711-8). The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Activated T cells transiently express PD1, but sustained hyperexpression of PD1 and its ligand PDL1 promote immune exhaustion, leading to persistence of viral infections, tumor evasion, increased infections and mortality. PD1 expression is induced by antigen recognition via the T-cell receptor and its expression is maintained primarily through continuous T-cell receptor signaling. After prolonged antigen exposure, the PD1 locus fails to be remethylated, which promotes continuous hyperexpression. Blocking the PD1 pathway can restore the exhausted T-cell functionality in cancer and chronic viral infections (Sheridan, Nature Biotechnology 30 (2012), 729-730). Monoclonal antibodies to PD-1 have been described, for example, in WO 2003/042402, WO 2004/004771, WO 2004/056875, WO 2004/072286, WO 2004/087196, WO 2006/121168, WO 2006/133396, WO 2007/005874, WO 2008/083174, WO 2008/156712, WO 2009/024531, WO 2009/014708, WO 2009/101611, WO 2009/114335, WO 2009/154335, WO 2010/027828, WO 2010/027423, WO 2010/029434, WO 2010/029435, WO 2010/036959, WO 2010/063011, WO 2010/089411, WO 2011/066342, WO 2011/110604, WO 2011/110621, WO 2012/145493, WO 2013/014668, WO 2014/179664, and WO 2015/112900.

Bispecific Fc diabodies having immunoreactivity with PD1 and LAG3 for use in the treatment of cancer or a disease associated with a pathogen such as a bacterium, a fungus or a virus are described in WO 2015/200119. However, there is a need of providing new bispecific antibodies that not only simultaneously bind to PD1 and LAG3 and thus selectively target cells expressing both PD1 and LAG3, but that also avoid blocking of LAG3 on other cells given the broad expression pattern of LAG3. The bispecific antibodies of the present invention do not only effectively block PD1 and LAG3 on T cells overexpressing both PD1 and LAG3, they are very selective for these cells and thereby side effects by administering highly active LAG3 antibodies may be avoided.

SUMMARY OF THE INVENTION

The present invention relates to bispecific antibodies comprising at least one antigen binding domain that specifically binds to programmed cell death protein 1 (PD1) and at least one second antigen binding domain that specifically binds to Lymphocyte activation gene-3 (LAG3). These bispecific antibodies are advantageous as they provide better selectivity and, potentially, efficacy than anti-PD1 and anti-LAG3 combination strategies. They are further characterized in that show a reduced sink effect (as shown by reduced internalization by T cells), they preferentially bind to conventional T cells as to Tregs and are able to rescue T cell effector functions from Treg suppression, they show increased tumor-specific T cell effector functions and increased tumor eradication in vivo.

In one aspect, the invention provides a bispecific antibody comprising a first antigen binding domain that specifically binds to programmed cell death protein 1 (PD1) and a second antigen binding domain that specifically binds to Lymphocyte activation gene-3 (LAG3), wherein said first antigen binding domain specifically binding to PD1 comprises a VH domain comprising
(i) HVR-H1 comprising the amino acid sequence of SEQ ID NO:1,
(ii) HVR-H2 comprising the amino acid sequence of SEQ ID NO:2, and
(iii) HVR-H3 comprising an amino acid sequence of SEQ ID NO:3; and
a VL domain comprising
(i) HVR-L1 comprising the amino acid sequence of SEQ ID NO:4;

(ii) HVR-L2 comprising the amino acid sequence of SEQ ID NO:5, and
(iii) HVR-L3 comprising the amino acid sequence of SEQ ID NO:6.

In particular, provided is a bispecific antibody comprising a first antigen binding domain that specifically binds to programmed cell death protein 1 (PD1) and a second antigen binding domain that specifically binds to Lymphocyte activation gene-3 (LAG3), wherein the bispecific antibody comprises a Fc domain that is an IgG, particularly an IgG1 Fc domain or an IgG4 Fc domain and wherein the Fc domain comprises one or more amino acid substitution that reduces binding to an Fc receptor, in particular towards Fcγ receptor.

In one aspect, provided is a bispecific antibody comprising a first antigen binding domain that specifically binds to PD1 and a second antigen binding domain that specifically binds to LAG3, wherein the second antigen binding domain that specifically binds to LAG3 comprises (a) a VH domain comprising
(i) HVR-H1 comprising the amino acid sequence of SEQ ID NO:14,
(ii) HVR-H2 comprising the amino acid sequence of SEQ ID NO:15, and
(iii) HVR-H3 comprising an amino acid sequence of SEQ ID NO:16; and
a VL domain comprising
(i) HVR-L1 comprising the amino acid sequence of SEQ ID NO:17,
(ii) HVR-L2 comprising the amino acid sequence of SEQ ID NO:18, and
(iii) HVR-L3 comprising the amino acid sequence of SEQ ID NO:19; or
(b) a VH domain comprising
(i) HVR-H1 comprising the amino acid sequence of SEQ ID NO:22,
(ii) HVR-H2 comprising the amino acid sequence of SEQ ID NO:23, and
(iii) HVR-H3 comprising an amino acid sequence of SEQ ID NO:24; and
a VL domain comprising
(i) HVR-L1 comprising the amino acid sequence of SEQ ID NO:25,
(ii) HVR-L2 comprising the amino acid sequence of SEQ ID NO:26, and
(iii) HVR-L3 comprising the amino acid sequence of SEQ ID NO:27; or
(c) a VH domain comprising
(i) HVR-H1 comprising the amino acid sequence of SEQ ID NO:30,
(ii) HVR-H2 comprising the amino acid sequence of SEQ ID NO:31, and
(iii) HVR-H3 comprising an amino acid sequence of SEQ ID NO:32; and
a VL domain comprising
(i) HVR-L1 comprising the amino acid sequence of SEQ ID NO:33,
(ii) HVR-L2 comprising the amino acid sequence of SEQ ID NO:34, and
(iii) HVR-L3 comprising the amino acid sequence of SEQ ID NO:35; or
(d) a VH domain comprising
(i) HVR-H1 comprising the amino acid sequence of SEQ ID NO:38,
(ii) HVR-H2 comprising the amino acid sequence of SEQ ID NO:39, and
(iii) HVR-H3 comprising an amino acid sequence of SEQ ID NO:40; and a VL domain comprising (i) HVR-L1 comprising the amino acid sequence of SEQ ID NO:41, (ii) HVR-L2 comprising the amino acid sequence of SEQ ID NO:42, and (iii) HVR-L3 comprising the amino acid sequence of SEQ ID NO:43; or (e) a VH domain comprising (i) HVR-H1 comprising the amino acid sequence of SEQ ID NO:46, (ii) HVR-H2 comprising the amino acid sequence of SEQ ID NO:47, and (iii) HVR-H3 comprising an amino acid sequence of SEQ ID NO:48; and a VL domain comprising (i) HVR-L1 comprising the amino acid sequence of SEQ ID NO:49, (ii) HVR-L2 comprising the amino acid sequence of SEQ ID NO:50, and (iii) HVR-L3 comprising the amino acid sequence of SEQ ID NO:51.

In another aspect, provided is a bispecific antibody comprising a first antigen binding domain that specifically binds to PD1 and a second antigen binding domain that specifically binds to LAG3, wherein the first antigen-binding domain specifically binding to PD1 comprises (a) a VH domain comprising the amino acid sequence of SEQ ID NO: 7 and a VL domain comprising the amino acid sequence of SEQ ID NO: 8, or (b) a VH domain comprising the amino acid sequence of SEQ ID NO: 9 and a VL domain comprising the amino acid sequence of SEQ ID NO: 10, or (c) a VH domain comprising the amino acid sequence of SEQ ID NO: 9 and a VL domain comprising the amino acid sequence of SEQ ID NO: 11, or (d) a VH domain comprising the amino acid sequence of SEQ ID NO: 9 and a VL domain comprising the amino acid sequence of SEQ ID NO: 12, or (e) a VH domain comprising the amino acid sequence of SEQ ID NO: 9 and a VL domain comprising the amino acid sequence of SEQ ID NO: 13.

In a particular aspect, provided is a bispecific antibody comprising a first antigen binding domain that specifically binds to PD1 and a second antigen binding domain that specifically binds to LAG3, wherein the first antigen-binding domain specifically binding to PD1 comprises a VH domain comprising the amino acid sequence of SEQ ID NO: 9 and a VL domain comprising the amino acid sequence of SEQ ID NO: 10.

In a further aspect, provided is a bispecific antibody comprising a first antigen binding domain that specifically binds to PD1 and a second antigen binding domain that specifically binds to LAG3 as described herein before, wherein the second antigen-binding domain specifically binding to LAG3 comprises (a) a VH domain comprising the amino acid sequence of SEQ ID NO: 20 and a VL domain comprising the amino acid sequence of SEQ ID NO: 21, or (b) a VH domain comprising the amino acid sequence of SEQ ID NO: 28 and a VL domain comprising the amino acid sequence of SEQ ID NO: 29, or (c) a VH domain comprising the amino acid sequence of SEQ ID NO: 36 and a VL domain comprising the amino acid sequence of SEQ ID NO: 37, or (d) a VH domain comprising the amino acid sequence of SEQ ID NO: 44 and a VL domain comprising the amino acid sequence of SEQ ID NO: 45, or (e) a VH domain comprising the amino acid sequence of SEQ ID NO: 52 and a VL domain comprising the amino acid sequence of SEQ ID NO: 53.

In an additional aspect, provided is a bispecific antibody comprising a first antigen binding domain that specifically binds to PD1 and a second antigen binding domain that specifically binds to LAG3 as described herein before, wherein the second antigen-binding domain specifically binding to LAG3 comprises (a) a VH domain comprising the amino acid sequence of SEQ ID NO: 54 and a VL domain comprising the amino acid sequence of SEQ ID NO: 55, or (b) a VH domain comprising the amino acid sequence of SEQ ID NO: 62 and a VL domain comprising the amino acid sequence of SEQ ID NO: 63, or (c) a VH domain comprising the amino acid sequence of SEQ ID NO: 64 and a VL domain comprising the amino acid sequence of SEQ ID NO: 65, or (d) a VH domain comprising the amino acid sequence of SEQ ID NO: 66 and a VL domain comprising the amino acid sequence of SEQ ID NO: 67.

Furthermore, provided is a bispecific antibody comprising a first antigen binding domain that specifically binds to PD1 and a second antigen binding domain that specifically binds to LAG3 as described herein before, wherein the first antigen binding domain specifically binding to PD1 comprises a VH domain comprising the amino acid sequence of SEQ ID NO: 9 and a VL domain comprising the amino acid sequence of SEQ ID NO: 10, and the second antigen binding domain specifically binding to LAG3 comprises a VH domain comprising the amino acid sequence of SEQ ID NO: 20 and a VL domain comprising the amino acid sequence of SEQ ID NO: 21 or a VH domain comprising the amino acid sequence of SEQ ID NO: 52 and a VL domain comprising the amino acid sequence of SEQ ID NO: 53.

In a further aspect, provided is a bispecific antibody comprising a first antigen binding domain that specifically binds to PD1 and a second antigen binding domain that specifically binds to LAG3 as described herein before, wherein the first antigen binding domain specifically binding to PD1 comprises a VH domain comprising the amino acid sequence of SEQ ID NO: 9 and a VL domain comprising the amino acid sequence of SEQ ID NO: 10, and the second antigen binding domain specifically binding to LAG3 comprises a VH domain comprising the amino acid sequence of SEQ ID NO: 20 and a VL domain comprising the amino acid sequence of SEQ ID NO: 21.

In another aspect, provided is a bispecific antibody comprising a first antigen binding domain that specifically binds to PD1 and a second antigen binding domain that specifically binds to LAG3 as described herein before, wherein the first antigen binding domain specifically binding to PD1 comprises a VH domain comprising the amino acid sequence of SEQ ID NO: 9 and a VL domain comprising the amino acid sequence of SEQ ID NO: 10, and the second antigen binding domain specifically binding to LAG3 comprises a VH domain comprising the amino acid sequence of SEQ ID NO: 56 and a VL domain comprising the amino acid sequence of SEQ ID NO: 57.

In a further aspect, provided is a bispecific antibody comprising a first antigen binding domain that specifically binds to PD1 and a second antigen binding domain that specifically binds to LAG3 as described herein before, wherein the bispecific antibody is a humanized or chimeric antibody. In particular, the bispecific antibody is a humanized antibody.

In a particular aspect, provided is a bispecific antibody comprising a first antigen binding domain that specifically binds to PD1 and a second antigen binding domain that specifically binds to LAG3 as described herein before, wherein the bispecific antibody comprises an Fc domain of human IgG1 subclass with the amino acid mutations L234A, L235A and P329G (numbering according to Kabat EU index).

Furthermore, provided is a bispecific antibody comprising a first antigen binding domain that specifically binds to PD1 and a second antigen binding domain that specifically binds to LAG3 as described herein before, wherein the bispecific antibody comprises an Fc domain comprising a modification promoting the association of the first and second subunit of the Fc domain. In one aspect, provided is a bispecific antibody, wherein the first subunit of the Fc domain comprises knobs and the second subunit of the Fc domain comprises holes according to the knobs into holes method. In particular, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In a further aspect, provided is a bispecific antibody comprising a first antigen binding domain that specifically binds to PD1 and a second antigen binding domain that specifically binds to LAG3, wherein the bispecific antibody comprises an Fc domain, a first Fab fragment comprising the antigen binding domain that specifically binds to PD1 and a second Fab fragment comprising the antigen binding domain that specifically binds to LAG3.

In one aspect, provided is a bispecific antibody comprising a first antigen binding domain that specifically binds to PD1 and a second antigen binding domain that specifically binds to LAG3, wherein in one of the Fab fragments the variable domains VL and VH are replaced by each other so that the VH domain is part of the light chain and the VL domain is part of the heavy chain. Particularly, provided is bispecific antibody, wherein in the first Fab fragment comprising the antigen binding domain that specifically binds to PD1 the variable domains VL and VH are replaced by each other.

In another aspect, provided is a bispecific antibody comprising a first antigen binding domain that specifically binds to PD1 and a second antigen binding domain that specifically binds to LAG3, wherein the bispecific antibody comprises a Fab fragment wherein in the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index). Particularly, provided is bispecific antibody, wherein in the second Fab fragment comprising the antigen binding domain that specifically binds to LAG3 the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

In a particular aspect, provided is a bispecific antibody comprising a first antigen binding domain that specifically binds to PD1 and a second antigen binding domain that specifically binds to LAG3, comprising (a) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 97, and a second light chain comprising an amino acid sequence with at least 95% sequence identity to the sequence of SEQ ID NO:99, or (b) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 100, and a second light chain comprising an amino acid sequence with at least 95% sequence identity to the sequence of SEQ ID NO:101, or (c) a first heavy chain comprising an amino acid sequence with at least 95% sequence identity to the sequence of SEQ ID NO: 102, a first light chain comprising an amino acid sequence with at least 95% sequence identity to the sequence of SEQ ID NO: 104, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105, or (d) a first heavy chain comprising an amino acid sequence with at least 95% sequence identity to the sequence of SEQ ID NO: 106, a first light chain comprising an amino acid sequence with at least 95% sequence identity to the sequence of SEQ ID NO: 107, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105.

More particularly, provided is a bispecific antibody comprising a first antigen binding domain that specifically binds to PD1 and a second antigen binding domain that specifically binds to LAG3, comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 100, and a second light chain comprising an amino acid sequence with at least 95% sequence identity to the sequence of SEQ ID NO:101.

In another aspect, provided is a bispecific antibody comprising a first antigen binding domain that specifically binds to PD1 and a second antigen binding domain that specifically binds to LAG3 as described herein before, wherein the bispecific antibody comprises a Fab fragment comprising the antigen binding domain that specifically binds to LAG3 which is fused to the C-terminus of the Fc domain.

In particular, provided is a bispecific antibody comprising a first antigen binding domain that specifically binds to PD1 and a second antigen binding domain that specifically binds to LAG3, comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 144, and a second light chain comprising an amino acid sequence with at least 95% sequence identity to the sequence of SEQ ID NO:101.

In a further aspect, provided is a bispecific antibody comprising a first antigen binding domain that specifically binds to PD1 and a second antigen binding domain that specifically binds to LAG3 as described herein before, wherein the bispecific antibody comprises a third Fab fragment comprising an antigen binding domain that specifically binds to LAG3. In one aspect, provided is a bispecific antibody, wherein the two Fab fragments comprising each an antigen binding domain that specifically binds to LAG3 are identical.

In another aspect, provided is a bispecific antibody comprising a first antigen binding domain that specifically binds to PD1 and a second antigen binding domain that specifically binds to LAG3 as described herein before, wherein the Fab fragment comprising the antigen binding domain that specifically binds to PD1 is fused via a peptide linker to the C-terminus of one of the heavy chains.

In a particular aspect, provided is a bispecific antibody comprising a first antigen binding domain that specifically binds to PD1 and a second antigen binding domain that specifically binds to LAG3, comprising (a) a first heavy chain comprising an amino acid sequence with at least 95% sequence identity to the sequence of SEQ ID NO: 118, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 119, and two second light chains comprising an amino acid sequence with at least 95% sequence identity to the sequence of SEQ ID NO:101, or (b) a first heavy chain comprising an amino acid sequence with at least 95% sequence identity to the sequence of SEQ ID NO: 120, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 121, and two second light chains comprising an amino acid sequence with at least 95% sequence identity to the sequence of SEQ ID NO:99, or (c) a first heavy chain comprising an amino acid sequence with at least 95% sequence identity to the sequence of SEQ ID NO: 122, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 103, and two second light chains comprising an amino acid sequence with at least 95% sequence identity to the sequence of SEQ ID NO:105.

In another aspect, provided is a bispecific antibody comprising a first antigen binding domain that specifically binds to PD1 and a second antigen binding domain that specifically binds to LAG3 as described herein before, wherein one of the Fab fragments comprising the antigen binding domain that specifically binds to LAG3 is fused via a peptide linker to the C-terminus of one of the heavy chains.

In a particular aspect, provided is a bispecific antibody comprising a first antigen binding domain that specifically binds to PD1 and a second antigen binding domain that specifically binds to LAG3, comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 145, and two second light chains comprising an amino acid sequence with at least 95% sequence identity to the sequence of SEQ ID NO:101.

In a further aspect, provided is a bispecific antibody comprising a first antigen binding domain that specifically binds to PD1 and a second antigen binding domain that specifically binds to LAG3 as described herein before, wherein the bispecific antibody comprises a fourth Fab fragment comprising an antigen binding domain that specifically binds to PD1. In one aspect, provided is a bispecific antibody, wherein the two Fab fragments comprising each an antigen binding domain that specifically binds to PD1 are identical.

In another aspect, provided is a bispecific antibody comprising a first antigen binding domain that specifically binds to PD1 and a second antigen binding domain that specifically binds to LAG3 as described herein before, wherein the two Fab fragments comprising each an antigen binding domain that specifically binds to PD1 are each fused via a peptide linker to the C-terminus to one of the heavy chains, respectively.

In a particular aspect, provided is a bispecific antibody comprising a first antigen binding domain that specifically binds to PD1 and a second antigen binding domain that specifically binds to LAG3, comprising (a) two heavy chains comprising each an amino acid sequence with at least 95% sequence identity to the sequence of SEQ ID NO: 114, two first light chains comprising each an amino acid sequence with at least 95% sequence identity to the sequence of SEQ ID NO: 115, and two second light chains comprising each an amino acid sequence with at least 95% sequence identity to the sequence of SEQ ID NO: 101, or (b) two heavy chains comprising each an amino acid sequence with at least 95% sequence identity to the sequence of SEQ ID NO: 116, two first light chains comprising each an amino acid sequence with at least 95% sequence identity to the sequence of SEQ ID NO: 115, and two second light chains comprising each an amino acid sequence with at least 95% sequence identity to the sequence of SEQ ID NO:99, or (c) two heavy chains comprising each an amino acid sequence with at least 95% sequence identity to the sequence of SEQ ID NO: 117, two first light chains comprising each an amino acid sequence with at least 95% sequence identity to the sequence of SEQ ID NO: 115, and two second light chains comprising an amino acid sequence with at least 95% sequence identity to the sequence of SEQ ID NO:105.

In yet another aspect, provided is a bispecific antibody comprising a first antigen binding domain that specifically binds to PD1 and a second antigen binding domain that specifically binds to LAG3, wherein the bispecific antibody comprises an Fc domain, two Fab fragments comprising each an antigen binding domain that specifically binds to LAG3 and a single chain Fab (scFab) comprising the antigen binding domain that specifically binds to PD1. In particular, the scFab comprising an antigen binding domain that specifically binds to PD1 is fused via a peptide linker to the C-terminus to one of the heavy chains.

In a particular aspect, provided is a bispecific antibody comprising a first antigen binding domain that specifically binds to PD1 and a second antigen binding domain that specifically binds to LAG3, comprising (a) a first heavy chain comprising an amino acid sequence with at least 95% sequence identity to the sequence of SEQ ID NO: 123, a second heavy chain comprising an amino acid sequence with at least 95% sequence identity to the sequence of SEQ ID NO: 119, and two light chains comprising each an amino acid sequence with at least 95% sequence identity to the sequence of SEQ ID NO: 101, or (b) a first heavy chain comprising an amino acid sequence with at least 95% sequence identity to the sequence of SEQ ID NO: 124, a second heavy chain comprising an amino acid sequence with at least 95% sequence identity to the sequence of SEQ ID NO: 121, and two light chains comprising each an amino acid sequence with at least 95% sequence identity to the sequence of SEQ ID NO:99, or (c) a first heavy chain comprising an amino acid sequence with at least 95% sequence identity to the sequence of SEQ ID NO: 125, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105.

In yet another aspect, provided is a bispecific antibody comprising a first antigen binding domain that specifically binds to PD1 and a second antigen binding domain that specifically binds to LAG3, wherein the bispecific antibody comprises an Fc domain, two Fab fragments comprising each an antigen binding domain that specifically binds to LAG3 and a VH and VL domain comprising the antigen binding domain that specifically binds to PD1. In one aspect, the VH domain of the antigen binding domain that specifically binds to PD1 is fused via a peptide linker to the C-terminus of one of the heavy chains and the VL domain of the antigen binding domain that specifically binds to PD1 is fused via a peptide linker to the C-terminus of the other one of the heavy chains. In a particular aspect, provided is a bispecific antibody, comprising a first heavy chain comprising an amino acid sequence with at least 95% sequence identity to the sequence of SEQ ID NO: 126, a second heavy chain comprising an amino acid sequence with at least 95% sequence identity to the sequence of SEQ ID NO: 127, and two light chains comprising each an amino acid sequence with at least 95% sequence identity to the sequence of SEQ ID NO: 109.

According to another aspect of the invention, there is provided a polynucleotide encoding the bispecific antibody as described herein before. The invention further provides a vector, particularly an expression vector, comprising a polynucleotide of the invention and a prokaryotic or eukaryotic host cell comprising the polynucleotide or the vector of the invention. In some embodiments the host cell is a eukaryotic cell, particularly a mammalian cell.

In another aspect, provided is a method for producing bispecific antibody comprising a first antigen binding domain that specifically binds to PD1 and a second antigen binding domain that specifically binds to LAG3 as described herein, comprising the steps of a) transforming a host cell with vectors comprising polynucleotides encoding said bispecific antibody, b) culturing the host cell according under conditions suitable for the expression of the bispecific antibody and c) recovering the bispecific antibody from the culture. The invention also encompasses a bispecific antibody produced by the method of the invention.

The invention further provides a pharmaceutical composition comprising a bispecific antibody comprising a first antigen binding domain that specifically binds to PD1 and a second antigen binding domain that specifically binds to LAG3 as described herein, and at least one pharmaceutically acceptable excipient.

Also encompassed by the invention is the bispecific antibody comprising a first antigen binding domain that specifically binds to PD1 and a second antigen binding domain that specifically binds to LAG3 as described herein, or the pharmaceutical composition comprising the bispecific antibody, for use as a medicament.

In another aspect, the invention provides a bispecific antibody comprising a bispecific antibody comprising a first antigen binding domain that specifically binds to PD1 and a second antigen binding domain that specifically binds to LAG3 as described herein, or the pharmaceutical composition comprising the bispecific antibody, for use i) in the modulation of immune responses, such as restoring T cell activity, ii) in stimulating an immune response or function, iii) in the treatment of infections, iv) in the treatment of cancer, v) in delaying progression of cancer, vi) in prolonging the survival of a patient suffering from cancer.

In one aspect, provided is the bispecific antibody comprising a first antigen binding domain that specifically binds to PD1 and a second antigen binding domain that specifically binds to LAG3 as described herein, or the pharmaceutical composition comprising the bispecific antibody, for use in the treatment of a disease in an individual in need thereof. In a specific aspect, the invention provides a bispecific antibody comprising a first antigen binding domain that specifically binds to PD1 and a second antigen binding domain that specifically binds to LAG3, or the pharmaceutical composition comprising the bispecific antibody, for use in the treatment of cancer. In a further specific aspect, a bispecific antibody comprising a first antigen binding domain that specifically binds to PD1 and a second antigen binding domain that specifically binds to LAG3, or the pharmaceutical composition comprising the bispecific antibody, for use in the modulation of immune responses is provided. In another aspect, a bispecific antibody comprising a first antigen binding domain that specifically binds to PD1 and a second antigen binding domain that specifically binds to LAG3, or a pharmaceutical composition comprising the bispecific antibody for use in the treatment of a chronic viral infection is provided.

The invention also provides a bispecific antibody comprising a first antigen binding domain that specifically binds to PD1 and a second antigen binding domain that specifically binds to LAG3 as described herein, or a pharmaceutical composition comprising the bispecific antibody for use in the prevention or treatment of cancer, wherein the bispecific antibody is administered in combination with a chemotherapeutic agent, radiation and/or other agents for use in cancer immunotherapy. In a particular aspect, provided is bispecific antibody comprising a first antigen binding domain that specifically binds to PD1 and a second antigen binding domain that specifically binds to LAG3 as described herein, or a pharmaceutical composition comprising the bispecific antibody for use in the prevention or treatment of cancer, wherein the bispecific antibody is administered in combination with an anti-CEA/anti-CD3 bispecific antibody.

Also provided is the use of the bispecific antibody comprising a first antigen binding domain that specifically binds to PD1 and a second antigen binding domain that specifically binds to LAG3 as described herein for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising a bispecific antibody comprising a first antigen binding domain that specifically binds to PD1 and a second antigen binding domain that specifically binds to LAG3 as described herein in a pharmaceutically acceptable form. In a specific aspect, the disease is cancer. In another specific aspect, the disease is a chronic viral infection. In another aspect, a method of modulating of immune responses in an individual, comprising administering to said individual a therapeutically effective amount of a composition comprising the bispecific antibody comprising a first antigen binding domain that specifically binds to PD1 and a second antigen binding domain that specifically binds to LAG3 as described herein in a pharmaceutically acceptable form is provided. In any of the above aspects the individual is preferably a mammal, particularly a human.

The invention also provides a bispecific antibody comprising a first antigen binding domain that specifically binds to PD1 and a second antigen binding domain that specifically binds to LAG3 as described herein, or a pharmaceutical composition comprising the bispecific antibody for use in the prevention or treatment of cancer, wherein the bispecific antibody is administered in combination with a chemotherapeutic agent, radiation and/or other agents for use in cancer immunotherapy.

Furthermore, provided is a method of inhibiting the growth of tumor cells in an individual comprising administering to the individual an effective amount of a bispecific antibody comprising a first antigen binding domain that specifically binds to PD1 and a second antigen binding domain that specifically binds to LAG3 as described herein to inhibit the growth of the tumor cells. The individual is preferably a mammal, particularly a human.

BRIEF DESCRIPTION OF THE DRAWINGS

FIG. 1A shows the bispecific 1+1 format, wherein the PD1 binding domain comprises a crossFab (with VH/VL domain exchange) and the LAG3 binding domain comprises CH1 and CK domains with amino acid mutations to support correct pairing ("charged variants"). The Fc part comprises the knob into hole mutations (illustrated by the black arrow) and the amino acid mutations L234A, L235A and P329G almost completely abolishing Fcγ receptor binding of the human IgG1 Fc domain (illustrated by the white area). FIG. 1B shows a 2+1 format with two anti-LAG3 binding Fab domains comprising mutations in CH1/CK and a PD1 binding Fab domain fused at the C-terminus of one heavy chain. FIG. 1C shows a similar 2+1 format with two anti-LAG3 binding FAB domains comprising mutations in CHUCK, but a PD1 binding single chain scFab domain fused at the C-terminus of one heavy chain. In FIG. 1D is shown a 2+1 format with two anti-LAG3 binding Fab domains and a PD1 binding VH and VL fused each to one of the C-termini of the heavy chains. FIG. 1E shows a construct similar to said of FIG. 1D, however with an engineered disulfide bond between VH and VL and in FIG. 1F a variant with a Furin site is shown. FIG. 1G shows the bispecific 2+2 format with two anti-LAG3 binding Fab domains comprising mutations in CHUCK and two PD1 binding crossFab domains fused at the C-terminus of each heavy chain. In FIG. 1H a bispecific 1+1 format is shown (called "trans"), wherein the PD1 binding domain comprises a crossFab (with VH/VL domain exchange) and the LAG3 binding domain is fused with its VH domain at the C-terminus of the Fc hole chain. The Lag3 domain comprises CH1 and CK domains with amino acid mutations to support correct pairing ("charged variants"). FIG. 1I shows a 2+1 trans format, wherein the PD1 binding domain comprises a crossFab (with VH/VL domain exchange) and one LAG3 binding domain comprising CH1 and CK domains with amino acid mutations to support correct pairing ("charged variants") and a second LAG3 binding domain is fused with its VH domain at the C-terminus of the Fc hole chain.

In FIG. 2A the effect of aLAG3 antibodies as described herein on Granzyme B secretion and in FIG. 2B the effect of aLAG3 antibodies on IL-2 secretion is shown.

FIG. 4A shows the Granzyme B release in comparison with aPD1 (0376) alone and FIG. 4B shows the IFN-γ release in comparison with aPD1 (0376) alone.

FIG. 5A and FIG. 5B show a comparison of bispecific anti-PD1/anti-LAG3 antibodies and monospecific anti-LAG3 antibodies. Only the bispecific formats were able to induce chemoluminescence. A competition experiment is shown in FIG. 5C. If the same bispecific antibody was provided in the presence of either an aLAG3 antibody (0156, MDX25F7) or anti-PD1 antibody (0376), the signal was either almost inhibited (for PD1 competition) or at least significantly reduced (Lag3). A further competition experiment is shown in FIG. 5D. Competition of the bispecific anti-PD1/anti-LAG3 antibody with the same anti-PD1 antibody (0376) and also recombinant LAG3:Fc protein (0160) almost abolished the signal, whereas presence of the same aLAG3 binder (0156) only led to partial inhibition and two further anti-LAG3 antibodies 0414 and 0416 did not modulate the signal significantly.

6A shows the binding curve for construct 0799 (anti-PD1 (0376)/anti-LAG3(0416) in 1+1 format). The binding curve for construct 8311 (anti-PD1(0376)/anti-LAG3(0416) in 1+2 format) is shown in FIG. 6B. FIG. 6C shows the binding curve for construct 0927 (anti-PD1(0376)/anti-LAG3(0414) in 1+1 format). The binding curve for construct 8310 (anti-PD1(0376)/anti-LAG3(0414) in 1+2 format) is shown in FIG. 6D.

FIGS. 7A-7F: Comparison of the simultaneous binding of bispecific anti-PD1/anti-LAG3 antibodies in different formats (2+1 vs. 2+2) and with different aLAG3 binders. FIG. 7A shows the binding curve for construct 8310 (anti-PD1 (0376)/anti-LAG3(0414) in 1+2 format). The binding curve for construct 8970 (anti-PD1(0376)/anti-LAG3(0414) in 2+2 format) is shown in FIG. 7B. FIG. 7C shows the binding curve for construct 8311 (anti-PD1(0376)/anti-LAG3(0416) in 1+2 format). The binding curve for construct 8984 (anti-PD1(0376)/anti-LAG3(0416) in 2+2 format) is shown in FIG. 7D. The binding curves for constructs 0725 (anti-PD1(0376)/anti-LAG3(0414) in trans 1+1 format) and 0750 (anti-PD1(0376)/anti-LAG3(0414) in trans 1+2 format) are shown in FIG. 7E in comparison to the binding curve of construct 0927 (anti-PD1(0376)/anti-LAG3(0414) in 1+1 format). These 3 constructs were also compared in the commercially available PD1/LAG3 combo Reporter assay and the corresponding binding curves are shown in FIG. 7F.

FIG. 8A shows the representative histogram of the experiment, the percentage of internalization for the different formats is shown in FIG. 8B.

FIG. 9A shows the fluorescent images as detected by confocal microscopy after 15 minutes, 1 hour and 3 hours. The activated CD4 cells are shown as black balls. The fluorescent images for a TIM3 antibody are shown as an example for strong internalization. A quantitative analysis of the images is shown in FIG. 9B.

FIGS. 10A to 10C show data from one representative donor showing the binding to conventional T cells (black curve) and Tregs (grey area). The binding of an anti-LAG3 antibody 0414 (hu IgG1 PGLALA) is shown in FIG. 10A, FIG. 10B and FIG. 10C show the binding of anti-PD1 antibody 0376 and bispecific anti-PD1/anti-LAG3 antibody (0927), respectively. In FIG. 10D the Delta of the geometric fluorescent mean intensity of a given molecule bound on conventional T cells versus the one on Tregs within the same sample are shown. Results (Median) are from 3 independent experiments with 3 different donors.

FIG. 12 shows a comparison of the effect on Granzyme B and IFN-$\gamma$ release caused by anti-PD1(0376) alone, the combination of anti-PD1(0376) with aLAG3(0414) and the bispecific antibody 0927 (anti-PD1 (0376)/anti-LAG3(0414) in 1+1 format). Shown is the fold increase in granzyme B and IFN$\gamma$ production relative to peptide-pool stimulated CD4 T cells from 12 melanoma patient PBMCs.

DETAILED DESCRIPTION OF THE INVENTION

Definitions

Figure 1:
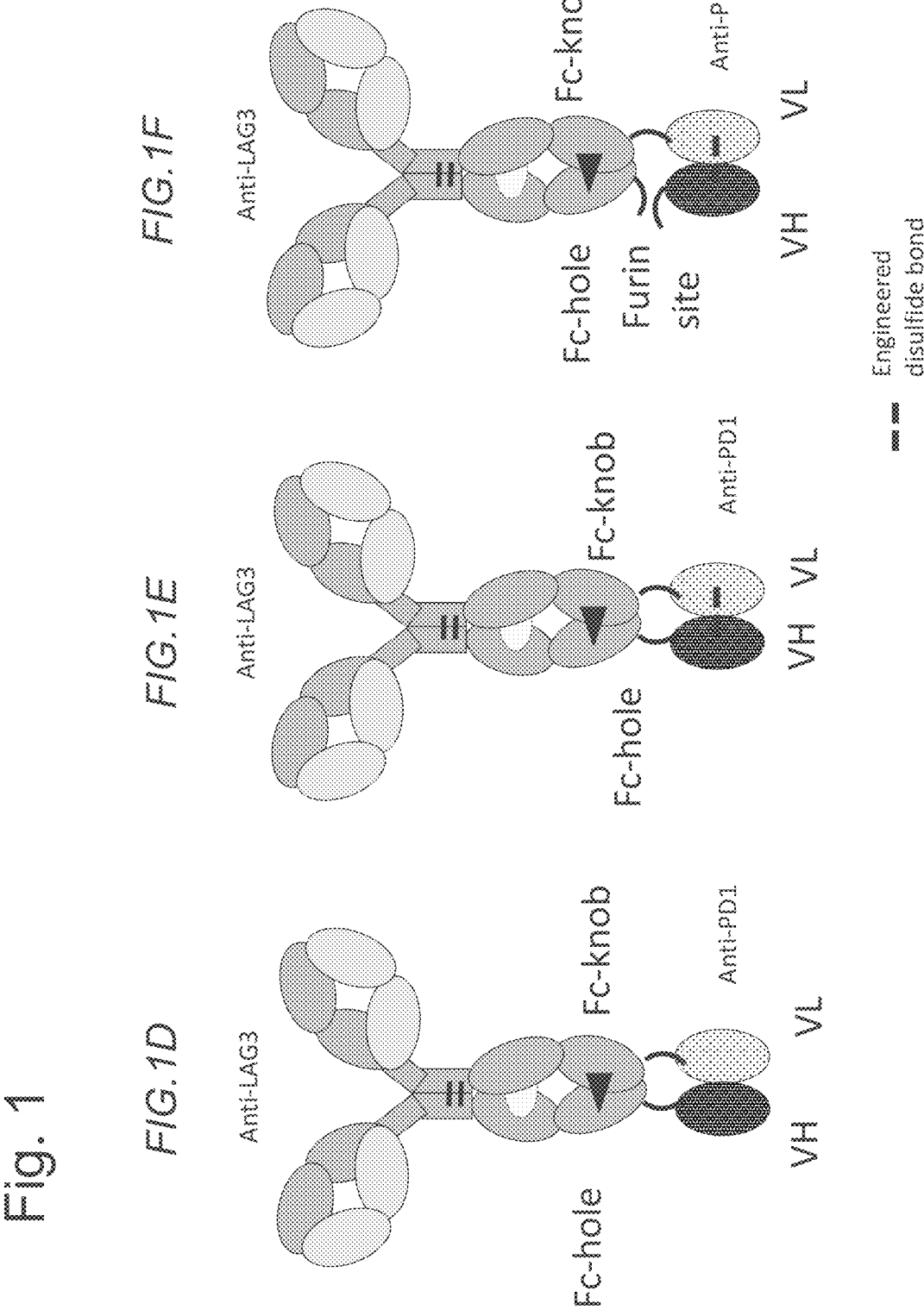
FIGS. 1A-1I: Schematic illustration of the different formats of the bispecific anti-PD1/anti-LAG3 antibodies described herein.
Figures 1, 1G:
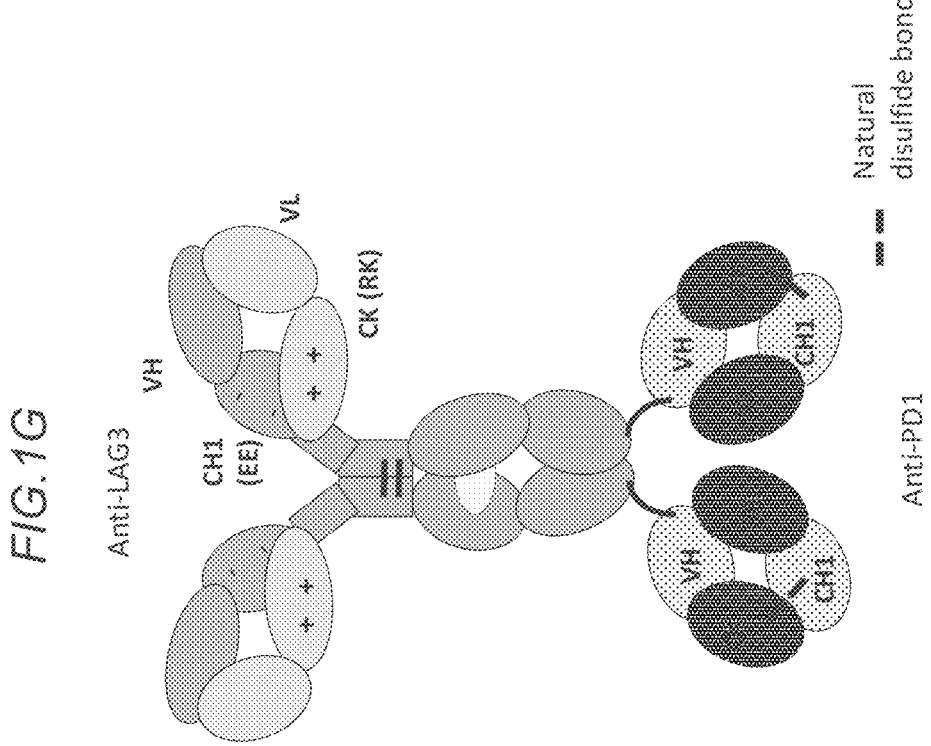

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antibody is able to specifically bind to at least two distinct antigenic determinants, for example two binding sites each formed by a pair of an antibody heavy chain variable domain (VH) and an antibody light chain variable domain (VL) binding to different antigens or to different epitopes on the same antigen. Such a bispecific antibody is an 1+1 format. Other bispecific antibody formats are 2+1 formats (comprising two binding sites for a first antigen or epitope and one binding site for a second antigen or epitope) or 2+2 formats (comprising two binding sites for a first antigen or epitope and two binding sites for a second antigen or epitope). Typically, a bispecific antibody comprises two antigen binding sites, each of which is specific for a different antigenic determinant.

The term "valent" as used within the current application denotes the presence of a specified number of binding domains in an antigen binding molecule. As such, the terms "bivalent", "tetravalent", and "hexavalent" denote the presence of two binding domain, four binding domains, and six binding domains, respectively, in an antigen binding molecule. The bispecific antibodies according to the invention are at least "bivalent" and may be "trivalent" or "multivalent" (e.g. "tetravalent" or "hexavalent"). In a particular aspect, the antibodies of the present invention have two or more binding sites and are bispecific. That is, the antibodies may be bispecific even in cases where there are more than two binding sites (i.e. that the antibody is trivalent or multivalent).

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies, triabodies, tetrabodies, cross-Fab fragments; linear antibodies; single-chain antibody molecules (e.g. scFv); multispecific antibodies formed from antibody fragments and single domain antibodies. For a review of certain antibody fragments, see Hudson et al., Nat Med 9, 129-134 (2003). For a review of scFv fragments, see e.g. Pluckthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869, 046. Diabodies are antibody fragments with two antigen binding domains that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies. Antibody fragments can be made by various techniques, including but not limited to proteolytic digestion of an intact antibody as well as production by recombinant host cells (e.g. E. coli or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group. Pepsin treatment yields an F(ab')$_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen binding domain which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein thera-peutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/ Maxibody), a serum transferrin (trans-body); a designed ankyrin repeat protein (DARPin), a variable domain of antibody light chain or heavy chain (single-domain anti-body, sdAb), a variable domain of antibody heavy chain (nanobody, aVH), $V_{NAR}$ fragments, a fibronectin (AdNec-tin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, micro-bodies such as the proteins from the knottin family, peptide aptamers and fibronectin (adnectin). CTLA-4 (Cytotoxic T Lymphocyte-associated Antigen 4) is a CD28-family recep-tor expressed on mainly CD4+ T-cells. Its extracellular domain has a variable domain-like Ig fold. Loops corre-sponding to CDRs of antibodies can be substituted with heterologous sequence to confer different binding proper-ties. CTLA-4 molecules engineered to have different bind-ing specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuf-fling of the natural variation exhibited by the family of A-domains. For further details see Nature Biotechnology 23(12), 1556-1561 (2005) and Expert Opinion on Investi-gational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increas-ing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

A single-domain antibody is an antibody fragment con-sisting of a single monomeric variable antibody domain. The first single domains were derived from the variable domain of the antibody heavy chain from camelids (nanobodies or VHH fragments). Furthermore, the term single-domain anti-body includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can beengineered to include upto 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

As used herein, the term "antigen binding domain" or "antigen-binding site" refers to the part of the antigen binding molecule that specifically binds to an antigenic determinant. More particularly, the term "antigen-binding domain" refers the part of an antibody that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH). In one aspect, the antigen binding domain is able to bind to its antigen and block or partly block its function. Antigen binding domains that specifically bind to PD1 or to LAG3 include antibodies and fragments thereof as further defined herein. In addition, antigen binding domains may include scaffold antigen binding proteins, e.g. binding domains which are based on designed repeat proteins or designed repeat domains (see e.g. WO 2002/020565).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-7}$ M or less, e.g. from $10^{-7}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

As used herein, the term "high affinity" of an antibody refers to an antibody having a Kd of $10^{-9}$ M or less and even more particularly $10^{-10}$ M or less for a target antigen. The term "low affinity" of an antibody refers to an antibody having a Kd of $10^{-8}$ or higher.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "a bispecific antibody comprising a first antigen binding domain that specifically binds to PD1 and a second antigen binding domain that specifically binds to LAG3" "a bispecific antibody that specifically binds PD1 and LAG3", "bispecific antigen binding molecule specific for PD1 and LAG3" or an "anti-PD1/anti-LAG3 antibody" are used interchangeably herein and refer to a bispecific antibody that is capable of binding PD1 and LAG3 with sufficient affinity such that the antibody is useful as a diagnostic and/or therapeutic agent in targeting PD1 and LAG3.

The term "PD1", also known as Programmed cell death protein 1, is a type I membrane protein of 288 amino acids that was first described in 1992 (Ishida et al., EMBO J., 11 (1992), 3887-3895). PD-1 is a member of the extended CD28/CTLA-4 family of T cell regulators and has two ligands, PD-L1 (B7-H1, CD274) and PD-L2 (B7-DC, CD273). The protein's structure includes an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals. This is consistent with binding of SHP-1 and SHP-2 phosphatases to the cytoplasmic tail of PD-1 upon ligand binding. While PD-1 is not expressed on naïve T cells, it is upregulated following T cell receptor (TCR)-mediated activation and is observed on both activated and exhausted T cells (Agata et al., Int. Immunology 8 (1996), 765-772). These exhausted T-cells have a dysfunctional phenotype and are unable to respond appropriately. Although PD-1 has a relatively wide expression pattern its most important role is likely as a coinhibitory receptor on T cells (Chinai et al, Trends in Pharmacological Sciences 36 (2015), 587-595). Current therapeutic approaches thus focus on blocking the interaction of PD-1 with its ligands to enhance T cell response. The terms "Programmed Death 1," "Programmed Cell Death 1," "Protein PD-1," "PD-1," PD1," "PDCD1," "hPD-1" and "hPD-I" can be used interchangeably, and include variants, isoforms, species homologs of human PD-1, and analogs having at least one common epitope with PD-1. The amino acid sequence of human PD1 is shown in at the UniProt website with accession no. Q15116 (SEQ ID NO:128).

The terms "anti-PD1 antibody" and "an antibody comprising an antigen binding domain that binds to PD1" refer to an antibody that is capable of binding PD1, especially a PD1 polypeptide expressed on a cell surface, with sufficient affinity such that the antibody is useful as a diagnostic and/or therapeutic agent in targeting PD1. In one aspect, the extent of binding of an anti-PD1 antibody to an unrelated, non-PD1 protein is less than about 10% of the binding of the antibody to PD1 as measured, e.g., by radioimmunoassay (RIA) or flow cytometry (FACS) or by a Surface Plasmon Resonance assay using a biosensor system such as a Biacore® system. In certain aspects, an antigen binding protein that binds to human PD1 has a $K_D$ value of the binding affinity for binding to human PD1 of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In one preferred embodiment the respective $K_D$ value of the binding affinities is determined in a Surface Plasmon Resonance assay using the Extracellular domain (ECD) of human PD1 (PD1-ECD) for the PD1 binding affinity. The term "anti-PD1 antibody" also encompasses bispecific antibodies that are capable of binding PD1 and a second antigen.

The terms "LAG3" or "Lag-3" or "Lymphocyte activation gene-3" or "CD223" as used herein refer to any native LAG3 from any vertebrate source, including mammals such as primates (e.g. humans) and rodents (e.g., mice and rats), unless otherwise indicated. The term encompasses "full-length," unprocessed LAG3 as well as any form of LAG3 resulting from processing in the cell. The term also encompasses naturally occurring variants of LAG3, e.g., splice variants or allelic variants. In one preferred embodiment the term "LAG3" refers to human LAG3. The amino acid sequence of an exemplary processed (without signal sequences) LAG3 is shown in SEQ ID NO:73. The amino acid sequence of an exemplary Extracellular Domain (ECD) LAG3 is shown in SEQ ID NO:74.

The terms "anti-LAG3 antibody" and "an antibody that binds to LAG3" refer to an antibody that is capable of binding LAG3 with sufficient affinity such that the antibody is useful as a diagnostic and/or therapeutic agent in targeting LAG3. In one aspect, the extent of binding of an anti-LAG3 antibody to an unrelated, non-LAG3 protein is less than about 10% of the binding of the antibody to LAG3 as measured, e.g., by a radioimmunoassay (RIA). In certain embodiments, an antibody that binds to LAG3 has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In certain aspects, an anti-LAG3 antibody binds to an epitope of LAG3 that is conserved among LAG3 from different species. In one preferred embodiment, an "anti-LAG3 antibody", "an antibody that specifically binds to human LAG3", and "an antibody that binds to human LAG3" refers to an antibody specifically binding to the human LAG3 antigen or its Extracellular Domain (ECD) with a binding affinity of a $K_D$-value of $1.0 \times 10^{-8}$ mol/1 or lower, in one embodiment of a $K_D$-value of $1.0 \times 10^{-9}$ mol/1 or lower, in one embodiment of a $K_D$-value of $1.0 \times 10^{-9}$ mol to $1.0 \times 10^{-13}$ mol/l. In this context the binding affinity is determined with a standard binding assay, such as surface plasmon resonance technique (BIAcore®, GE-Healthcare Uppsala, Sweden) e.g. using the LAG3 extracellular domain. The term "anti-LAG3 antibody" also encompasses bispecific antibodies that are capable of binding LAG3 and a second antigen.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. For example, the bispecific antibodies of the invention block the signaling through PD-1 and LAG3 so as to restore a functional response by T cells (e.g., proliferation, cytokine production, target cell killing) from a dysfunctional state to antigen stimulation.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, MD (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| CDR Definitions[1] | | | |
| CDR | Kabat | Chothia | AbM[2] |
| --- | --- | --- | --- |
| V$_H$ CDR1 | 31-35 | 26-32 | 26-35 |
| V$_H$ CDR2 | 50-65 | 52-58 | 50-58 |
| V$_H$ CDR3 | 95-102 | 95-102 | 95-102 |
| V$_L$ CDR1 | 24-34 | 26-32 | 24-34 |
| V$_L$ CDR2 | 50-56 | 50-52 | 50-56 |
| V$_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Fc domain" or "Fc region" herein is used to define a C-terminal region of an antibody heavy chain that contains at least a portion of the constant region. The term includes native sequence Fc regions and variant Fc regions. Particularly, a human IgG heavy chain Fc region extends from Cys226, or from Pro230, to the carboxyl-terminus of the heavy chain. However, the C-terminal lysine (Lys447) of the Fc region may or may not be present. The amino acid sequences of the heavy chains are always presented with the C-terminal lysine, however variants without the C-terminal lysine are included in the invention.

An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2, i.e. the peptides selected from the group consisting of GGGGS (SEQ ID NO:129) GGGGSGGGGS (SEQ ID NO:130), SGGGGSGGGG (SEQ ID NO:131) and GGGGSGGGGSGGGG (SEQ ID NO:132), but also include the sequences GSPGSSSSGS (SEQ ID NO:133), $(G4S)_3$ (SEQ ID NO:134), $(G4S)_4$ (SEQ ID NO:135), GSGSGSGS (SEQ ID NO:136), GSGSGNGS (SEQ ID NO:137), GGSGSGSG (SEQ ID NO:138), GGSGSG (SEQ ID NO:139), GGSG (SEQ ID NO:140), GGSGNGSG (SEQ ID NO:141), GGNGSGSG (SEQ ID NO:142) and GGNGSG (SEQ ID NO:143). Peptide linkers of particular interest are (G4S) (SEQ ID NO:129), $(G_4S)_2$ or GGGGSGGGGS (SEQ ID NO:130), $(G4S)_3$ (SEQ ID NO:134) and $(G_4S)_4$ (SEQ ID NO:135), more particularly $(G_4S)_2$ or GGGGSGGGGS (SEQ ID NO:130).

By "fused to" or "connected to" is meant that the components (e.g. an antigen binding domain and a FC domain) are linked by peptide bonds, either directly or via one or more peptide linkers.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain aspects, amino acid sequence variants of the bispecific antibodies of the invention provided herein are contemplated. For example, it may be desirable to improve the binding affinity and/or other biological properties of the bispecific antibodies. Amino acid sequence variants of the bispecific antibodies may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; He | Val |
| Arg (R) | Lys; Gin; Asn | Lys |
| Asn (N) | Gin; His; Asp, Lys; Arg | Gin |
| Asp (D) | Glu; Asn | Glu |
| Cys (C) | Ser; Ala | Ser |
| Gin (Q) | Asn; Glu | Asn |
| Glu (E) | Asp; Gin | Asp |
| Gly (G) | Ala | Ala |
| His (H) | Asn; Gin; Lys; Arg | Arg |
| Ile (I) | Leu; Val; Met; Ala; Phe; Norleucine | Leu |
| Leu (L) | Norleucine; lie; Val; Met; Ala; Phe | He |
| Lys (K) | Arg; Gin; Asn | Arg |
| Met (M) | Leu; Phe; He | Leu |
| Phe (F) | Trp; Leu; Val; He; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include bispecific antibodies with an N-terminal methionyl residue. Other insertional variants of the molecule include the fusion to the N- or C-terminus to a polypeptide which increases the serum half-life of the bispecific antibody.

In certain aspects, the bispecific antibodies provided herein are altered to increase or decrease the extent to which the antibody is glycosylated. Glycosylation variants of the molecules may be conveniently obtained by altering the amino acid sequence such that one or more glycosylation sites is created or removed, e.g. the carbohydrates attached to the Fc domain may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the bispecific antibodies of the invention may be made in order to create variants with certain improved properties. In one aspect, variants of bispecific antibodies are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the bispecific antibodies of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain aspects, it may be desirable to create cysteine engineered variants of the bispecific antibodies of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the bispecific antibodies provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc.

In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. In particular, the host cell is a prokaryotic or eukaryotic host cell. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

Bispecific Antibodies of the Invention

The invention provides novel bispecific antibodies comprising a first antigen binding domain that specifically binds to programmed cell death protein 1 (PD1) and a second antigen binding domain that specifically binds to Lymphocyte activation gene-3 (LAG3), with particularly advantageous properties such as producibility, stability, binding affinity, biological activity, specific targeting of certain T cells, targeting efficiency and reduced toxicity.

In certain aspects, a bispecific antibody comprising a first antigen binding domain that specifically binds to PD1 and a second antigen binding domain that specifically binds to LAG3 is provided that shows reduced internalization upon binding to the T cell surface. The internalization represents an important sink for the molecule which can be degraded within a few hours while the targeted receptors are rapidly re-expressed on the cell-surface ready to inhibit TCR-signalling. In further aspects, a bispecific antibody comprising a first antigen binding domain that specifically binds to PD1 and a second antigen binding domain that specifically binds to LAG3 is provided that preferentially binds to conventional T cells rather than to Tregs. This is advantageous because targeting LAG-3 on Tregs with blocking antibodies could be detrimental by increasing their suppressive function and eventually mask the positive blocking effect on other T cells. In a further aspect, a bispecific antibody comprising a first antigen binding domain that specifically binds to PD1 and a second antigen binding domain that specifically binds to LAG3 is provided that is able to rescue T cell effector functions from Treg suppression. In another aspect, a bispecific antibody comprising a first antigen binding domain that specifically binds to PD1 and a second antigen binding domain that specifically binds to LAG3 is provided that is able to induce Granzyme B secretion by CD4 T cells, when co-cultured with the tumor cell line ARH77 as shown in the assay provided herein. In a further aspect, a bispecific antibody comprising a first antigen binding domain that specifically binds to PD1 and a second antigen binding domain that specifically binds to LAG3 is provided that shows increased tumor-specific T cell effector functions and/or enhances the cytotoxic effect of T cells. In another aspect, a bispecific antibody comprising a first antigen binding domain that specifically binds to PD1 and a second antigen binding domain that specifically binds to LAG3 is provided that shows increased tumor eradication in vivo.

A. Exemplary Bispecific Antibodies that Bind to PD1 and LAG3

In one aspect, the invention provides a bispecific antibody comprising a first antigen binding domain that specifically binds to PD1 and a second antigen binding domain that specifically binds to LAG3, wherein said first antigen binding domain specifically binding to PD1 comprises a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence of SEQ ID NO:3; and a VL domain comprising (i) HVR-L1 comprising the amino acid sequence of SEQ ID NO:4;

(ii) HVR-L2 comprising the amino acid sequence of SEQ ID NO:5, and (iii) HVR-L3 comprising the amino acid sequence of SEQ ID NO:6.

In one aspect, the bispecific antibody comprises a Fc domain that is an IgG, particularly an IgG1 Fc domain or an IgG4 Fc domain and wherein the Fc domain has reduced or even abolished effector function. In particular, the Fc domain comprises one or more amino acid substitution that reduces binding to an Fc receptor, in particular towards Fcγ receptor.

In a further aspect, provided is a bispecific antibody comprising a first antigen binding domain that specifically binds to PD1 and a second antigen binding domain that specifically binds to LAG3, wherein the bispecific antibody comprises a Fc domain that is an IgG, particularly an IgG1 Fc domain or an IgG4 Fc domain and wherein the Fc domain comprises one or more amino acid substitution that reduces binding to an Fc receptor, in particular towards Fcγ receptor.

In another aspect, provided is a bispecific antibody comprising a first antigen binding domain that specifically binds to PD1 and a second antigen binding domain that specifically binds to LAG3, wherein the second antigen binding domain that specifically binds to LAG3 comprises (a) a VH domain comprising (i) HVR-H1 comprising the amino acid sequence of SEQ ID NO:14, (ii) HVR-H2 comprising the amino acid sequence of SEQ ID NO:15, and (iii) HVR-H3 comprising an amino acid sequence of SEQ ID NO:16; and a VL domain comprising (i) HVR-L1 comprising the amino acid sequence of SEQ ID NO:17, (ii) HVR-L2 comprising the amino acid sequence of SEQ ID NO:18, and (iii) HVR-L3 comprising the amino acid sequence of SEQ ID NO:19; or (b) a VH domain comprising (i) HVR-H1 comprising the amino acid sequence of SEQ ID NO:22, (ii) HVR-H2 comprising the amino acid sequence of SEQ ID NO:23, and (iii) HVR-H3 comprising an amino acid sequence of SEQ ID NO:24; and a VL domain comprising (i) HVR-L1 comprising the amino acid sequence of SEQ ID NO:25, (ii) HVR-L2 comprising the amino acid sequence of SEQ ID NO:26, and (iii) HVR-L3 comprising the amino acid sequence of SEQ ID NO:27; or (c) a VH domain comprising (i) HVR-H1 comprising the amino acid sequence of SEQ ID NO:30, (ii) HVR-H2 comprising the amino acid sequence of SEQ ID NO:31, and (iii) HVR-H3 comprising an amino acid sequence of SEQ ID NO:32; and a VL domain comprising (i) HVR-L1 comprising the amino acid sequence of SEQ ID NO:33, (ii) HVR-L2 comprising the amino acid sequence of SEQ ID NO:34, and (iii) HVR-L3 comprising the amino acid sequence of SEQ ID NO:35; or (d) a VH domain comprising (i) HVR-H1 comprising the amino acid sequence of SEQ ID NO:38, (ii) HVR-H2 comprising the amino acid sequence of SEQ ID NO:39, and (iii) HVR-H3 comprising an amino acid sequence of SEQ ID NO:40; and a VL domain comprising (i) HVR-L1 comprising the amino acid sequence of SEQ ID NO:41, (ii) HVR-L2 comprising the amino acid sequence of SEQ ID NO:42, and (iii) HVR-L3 comprising the amino acid sequence of SEQ ID NO:43; or (e) a VH domain comprising (i) HVR-H1 comprising the amino acid sequence of SEQ ID NO:46, (ii) HVR-H2 comprising the amino acid sequence of SEQ ID NO:47, and (iii) HVR-H3 comprising an amino acid sequence of SEQ ID NO:48; and a VL domain comprising (i) HVR-L1 comprising the amino acid sequence of SEQ ID NO:49, (ii) HVR-L2 comprising the amino acid sequence of SEQ ID NO:50, and (iii) HVR-L3 comprising the amino acid sequence of SEQ ID NO:51.

In a further aspect, provided is a bispecific antibody comprising a first antigen binding domain that specifically binds to PD1 and a second antigen binding domain that specifically binds to LAG3, wherein the first antigen binding domain specifically binding to PD1 comprises (a) a VH domain comprising the amino acid sequence of SEQ ID NO: 7 and a VL domain comprising the amino acid sequence of SEQ ID NO: 8, or (b) a VH domain comprising the amino acid sequence of SEQ ID NO: 9 and a VL domain comprising the amino acid sequence of SEQ ID NO: 10, or (c) a VH domain comprising the amino acid sequence of SEQ ID NO: 9 and a VL domain comprising the amino acid sequence of SEQ ID NO: 11, or (d) a VH domain comprising the amino acid sequence of SEQ ID NO: 9 and a VL domain comprising the amino acid sequence of SEQ ID NO: 12, or (e) a VH domain comprising the amino acid sequence of SEQ ID NO: 9 and a VL domain comprising the amino acid sequence of SEQ ID NO: 13.

In another aspect, provided is a bispecific antibody comprising a first antigen binding domain that specifically binds to PD1 and a second antigen binding domain that specifically binds to LAG3, wherein the first antigen binding domain that specifically binds to PD1 comprises (a) a VH domain comprising (i) HVR-H1 comprising the amino acid sequence of SEQ ID NO:80, (ii) HVR-H2 comprising the amino acid sequence of SEQ ID NO:81, and (iii) HVR-H3 comprising an amino acid sequence of SEQ ID NO:82; and a VL domain comprising (i) HVR-L1 comprising the amino acid sequence of SEQ ID NO:83, (ii) HVR-L2 comprising the amino acid sequence of SEQ ID NO:84, and (iii) HVR-L3 comprising the amino acid sequence of SEQ ID NO:85; or (b) a VH domain comprising (i) HVR-H1 comprising the amino acid sequence of SEQ ID NO:88, (ii) HVR-H2 comprising the amino acid sequence of SEQ ID NO:89, and (iii) HVR-H3 comprising an amino acid sequence of SEQ ID NO:90; and a VL domain comprising (i) HVR-L1 comprising the amino acid sequence of SEQ ID NO:91, (ii) HVR-L2 comprising the amino acid sequence of SEQ ID NO:92, and (iii) HVR-L3 comprising the amino acid sequence of SEQ ID NO:93.

In one aspect, provided is a bispecific antibody comprising a first antigen binding domain that specifically binds to PD1 and a second antigen binding domain that specifically binds to LAG3, wherein the first antigen binding domain specifically binding to PD1 comprises (a) a VH domain comprising the amino acid sequence of SEQ ID NO: 86 and a VL domain comprising the amino acid sequence of SEQ ID NO: 87, or (b) a VH domain comprising the amino acid sequence of SEQ ID NO: 94 and a VL domain comprising the amino acid sequence of SEQ ID NO: 95.

In another aspect, provided is a bispecific antibody comprising a first antigen binding domain that specifically binds to PD1 and a second antigen binding domain that specifically binds to LAG3, wherein the second antigen binding domain specifically binding to LAG3 comprises (a) a VH domain comprising the amino acid sequence of SEQ ID NO: 20 and a VL domain comprising the amino acid sequence of SEQ ID NO: 21, or (b) a VH domain comprising the amino acid sequence of SEQ ID NO: 28 and a VL domain comprising the amino acid sequence of SEQ ID NO: 29, or (c) a VH domain comprising the amino acid sequence of SEQ ID NO: 36 and a VL domain comprising the amino acid sequence of SEQ ID NO: 37, or (d) a VH domain comprising the amino acid sequence of SEQ ID NO: 44 and a VL domain comprising the amino acid sequence of SEQ ID NO: 45, or (e) a VH domain comprising the amino acid sequence of SEQ ID NO: 52 and a VL domain comprising the amino acid sequence of SEQ ID NO: 53.

In another aspect, provided is a bispecific antibody comprising a first antigen binding domain that specifically binds to PD1 and a second antigen binding domain that specifically binds to LAG3, wherein the second antigen binding domain that specifically binds to LAG3 comprises a VH domain comprising (i) HVR-H1 comprising the amino acid sequence of SEQ ID NO:56,
  (ii) HVR-H2 comprising the amino acid sequence of SEQ ID NO:57, and
  (iii) HVR-H3 comprising an amino acid sequence of SEQ ID NO:58; and a VL domain comprising (i) HVR-L1 comprising the amino acid sequence of SEQ ID NO:59,
  (ii) HVR-L2 comprising the amino acid sequence of SEQ ID NO:60, and
  (iii) HVR-L3 comprising the amino acid sequence of SEQ ID NO:61.

In a further aspect, provided is a bispecific antibody comprising a first antigen binding domain that specifically binds to PD1 and a second antigen binding domain that specifically binds to LAG3, wherein the second antigen binding domain specifically binding to LAG3 comprises (a) a VH domain comprising the amino acid sequence of SEQ ID NO: 54 and a VL domain comprising the amino acid sequence of SEQ ID NO: 55, or
  (b) a VH domain comprising the amino acid sequence of SEQ ID NO: 62 and a VL domain comprising the amino acid sequence of SEQ ID NO: 63, or
  (c) a VH domain comprising the amino acid sequence of SEQ ID NO: 64 and a VL domain comprising the amino acid sequence of SEQ ID NO: 65, or
  (d) a VH domain comprising the amino acid sequence of SEQ ID NO: 66 and a VL domain comprising the amino acid sequence of SEQ ID NO: 67.

In a particular aspect, provided is a bispecific antibody comprising a first antigen binding domain that specifically binds to PD1 and a second antigen binding domain that specifically binds to LAG3, wherein the first antigen binding domain specifically binding to PD1 comprises a VH domain comprising the amino acid sequence of SEQ ID NO: 9 and a VL domain comprising the amino acid sequence of SEQ ID NO: 10,
  and the second antigen binding domain specifically binding to LAG3 comprises a VH domain comprising the amino acid sequence of SEQ ID NO: 20 and a VL domain comprising the amino acid sequence of SEQ ID NO: 21 or a VH domain comprising the amino acid sequence of SEQ ID NO: 52 and a VL domain comprising the amino acid sequence of SEQ ID NO: 53.

In one aspect, the bispecific antibody of the invention comprises a first antigen binding domain specifically binding to PD1 comprising a VH domain comprising the amino acid sequence of SEQ ID NO: 9 and a VL domain comprising the amino acid sequence of SEQ ID NO: 10 and a second antigen binding domain specifically binding to LAG3 comprising a VH domain comprising the amino acid sequence of SEQ ID NO: 20 and a VL domain comprising the amino acid sequence of SEQ ID NO: 21.

In a further aspect, the bispecific antibody of the invention comprises a first antigen binding domain specifically binding to PD1 comprising a VH domain comprising the amino acid sequence of SEQ ID NO: 9 and a VL domain comprising the amino acid sequence of SEQ ID NO: 10 and a second antigen binding domain specifically binding to LAG3 comprising a VH domain comprising the amino acid sequence of SEQ ID NO: 52 and a VL domain comprising the amino acid sequence of SEQ ID NO: 53.

In another aspect, the bispecific antibody of the invention comprises a first antigen binding domain specifically binding to PD1 comprising a VH domain comprising the amino acid sequence of SEQ ID NO: 9 and a VL domain comprising the amino acid sequence of SEQ ID NO: 10 and a second antigen binding domain specifically binding to LAG3 comprising a VH domain comprising the amino acid sequence of SEQ ID NO: 62 and a VL domain comprising the amino acid sequence of SEQ ID NO: 63.

In yet another aspect, the bispecific antibody of the invention comprises a first antigen binding domain specifically binding to PD1 comprising a VH domain comprising the amino acid sequence of SEQ ID NO: 86 and a VL domain comprising the amino acid sequence of SEQ ID NO: 87 and a second antigen binding domain specifically binding to LAG3 comprising a VH domain comprising the amino acid sequence of SEQ ID NO: 62 and a VL domain comprising the amino acid sequence of SEQ ID NO: 63.

In yet another aspect, the bispecific antibody of the invention comprises a first antigen binding domain specifically binding to PD1 comprising a VH domain comprising the amino acid sequence of SEQ ID NO: 94 and a VL domain comprising the amino acid sequence of SEQ ID NO: 95 and a second antigen binding domain specifically binding to LAG3 comprising a VH domain comprising the amino acid sequence of SEQ ID NO: 62 and a VL domain comprising the amino acid sequence of SEQ ID NO: 63.

In a further aspect, the bispecific antibody comprising a first antigen binding domain that specifically binds to PD1 and a second antigen binding domain that specifically binds to LAG3 is a human, humanized or chimeric antibody. In particular, it is a humanized or chimeric antibody.

In one aspect, the bispecific antibody comprising a first antigen binding domain that specifically binds to PD1 and a second antigen binding domain that specifically binds to LAG3 is bivalent. This means that the bispecific antibody comprises one antigen binding domain that specifically binds to PD1 and one antigen binding domain that specifically binds to LAG3 (1+1 format).

In one aspect, provided is a bispecific antibody comprising a first antigen binding domain that specifically binds to PD1 and a second antigen binding domain that specifically binds to LAG3, wherein the bispecific antibody comprises an Fc domain, a first Fab fragment comprising the antigen binding domain that specifically binds to PD1 and a second Fab fragment comprising the antigen binding domain that specifically binds to LAG3. In a particular aspect, in one of the Fab fragments the variable domains VL and VH are replaced by each other so that the VH domain is part of the light chain and the VL domain is part of the heavy chain. In a particular aspect, in the first Fab fragment comprising the antigen binding domain that specifically binds to PD1 the variable domains VL and VH are replaced by each other.

In a particular aspect, provided is a bispecific antibody comprising a first antigen binding domain that specifically binds to PD1 and a second antigen binding domain that specifically binds to LAG3, wherein the bispecific antibody comprises (a) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 97, and a second light chain comprising an amino acid sequence with at least 95% sequence identity to the sequence of SEQ ID NO:99, or (b) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 100, and a second light chain comprising an amino acid sequence with at least 95% sequence identity to the sequence of SEQ ID NO:101, or (c) a first heavy chain comprising an amino acid sequence with at least 95% sequence identity to the sequence of SEQ ID NO: 102, a first light chain comprising an amino acid sequence with at least 95% sequence identity to the sequence of SEQ ID NO: 104, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105, or (d) a first heavy chain comprising an amino acid sequence with at least 95% sequence identity to the sequence of SEQ ID NO: 106, a first light chain comprising an amino acid sequence with at least 95% sequence identity to the sequence of SEQ ID NO: 107, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105.

More particularly, the bispecific antibody comprises (a) a first heavy chain comprising an amino acid sequence of SEQ ID NO: 96, a first light chain comprising an amino acid sequence of SEQ ID NO: 98, a second heavy chain comprising an amino acid sequence of SEQ ID NO: 97, and a second light chain comprising an amino acid sequence of SEQ ID NO:99, or (b) a first heavy chain comprising an amino acid sequence of SEQ ID NO: 96, a first light chain comprising an amino acid sequence of SEQ ID NO: 98, a second heavy chain comprising an amino acid sequence of SEQ ID NO: 100, and a second light chain comprising an amino acid sequence of SEQ ID NO:101, or (c) a first heavy chain comprising an amino acid sequence of SEQ ID NO: 102, a first light chain comprising an amino acid sequence of SEQ ID NO: 104, a second heavy chain comprising an amino acid sequence of SEQ ID NO: 103, and a second light chain comprising an amino acid sequence of SEQ ID NO:105, or (d) a first heavy chain comprising an amino acid sequence of SEQ ID NO: 106, a first light chain comprising an amino acid sequence of SEQ ID NO: 107, a second heavy chain comprising an amino acid sequence of SEQ ID NO: 103, and a second light chain comprising an amino acid sequence of SEQ ID NO:105.

More particularly, the bispecific antibody comprises a first heavy chain comprising an amino acid sequence of SEQ ID NO: 96, a first light chain comprising an amino acid sequence of SEQ ID NO: 98, a second heavy chain comprising an amino acid sequence of SEQ ID NO: 100, and a second light chain comprising an amino acid sequence of SEQ ID NO:101.

In a further aspect, provided is a bispecific antibody comprising a first antigen binding domain that specifically binds to PD1 and a second antigen binding domain that specifically binds to LAG3, wherein the bispecific antibody comprises an Fc domain, a first Fab fragment comprising the antigen binding domain that specifically binds to PD1 and a second Fab fragment comprising the antigen binding domain that specifically binds to LAG3 that is fused to the C-terminus of the Fc domain. Particularly, the Fab fragment comprising the antigen binding domain that specifically binds to LAG3 is fused to the C-terminus of the FC domain via its VH domain (trans 1+1 format).

In a particular aspect, the bispecific antibody comprises a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 144, and a second light chain comprising an amino acid sequence with at least 95% sequence identity to the sequence of SEQ ID NO:101. More particularly, the bispecific antibody comprises a first heavy chain comprising an amino acid sequence of SEQ ID NO: 96, a first light chain comprising an amino acid sequence of SEQ ID NO: 98, a second heavy chain comprising an amino acid sequence of SEQ ID NO: 144, and a second light chain comprising an amino acid sequence of SEQ ID NO:101.

In a further aspect, provided is a bispecific antibody comprising a first antigen binding domain that specifically binds to PD1 and a second antigen binding domain that specifically binds to LAG3, wherein the bispecific antibody comprises an Fc domain, a first Fab fragment comprising the antigen binding domain that specifically binds to PD1, a second Fab fragment comprising the antigen binding domain that specifically binds to LAG3 and a third Fab fragment comprising an antigen binding domain that specifically binds to LAG3. In a particular aspect, the the Fab fragment comprising the antigen binding domain that specifically binds to PD1 is fused via a peptide linker to the C-terminus of one of the heavy chains.

In this aspect, the bispecific antibody is trivalent with bivalent binding to LAG3 and monovalent binding to PD1. This means that the bispecific antibody comprises one antigen binding domain that specifically binds to PD1 and two antigen binding domains that specifically bind to LAG3 (2+1 format).

In a particular aspect, provided is a bispecific antibody comprising a first antigen binding domain that specifically binds to PD1 and a second antigen binding domain that specifically binds to LAG3, wherein the bispecific antibody comprises (a) a first heavy chain comprising an amino acid sequence with at least 95% sequence identity to the sequence of SEQ ID NO: 118, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 119, and two second light chains comprising an amino acid sequence with at least 95% sequence identity to the sequence of SEQ ID NO:101, or (b) a first heavy chain comprising an amino acid sequence with at least 95% sequence identity to the sequence of SEQ ID NO: 120, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 121, and two second light chains comprising an amino acid sequence with at least 95% sequence identity to the sequence of SEQ ID NO:99, or (c) a first heavy chain comprising an amino acid sequence with at least 95% sequence identity to the sequence of SEQ ID NO: 122, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 103, and two second light chains comprising an amino acid sequence with at least 95% sequence identity to the sequence of SEQ ID NO:105.

More particularly, the bispecific antibody comprises (a) a first heavy chain comprising an amino acid sequence of SEQ ID NO: 118, a first light chain comprising an amino acid sequence of SEQ ID NO: 115, a second heavy chain comprising an amino acid sequence of SEQ ID NO: 119, and two second light chains comprising an amino acid sequence of SEQ ID NO:101, or (b) a first heavy chain comprising an amino acid sequence of SEQ ID NO: 120, a first light chain comprising an amino acid sequence of SEQ ID NO: 115, a second heavy chain comprising an amino acid sequence of SEQ ID NO: 121, and two second light chains comprising an amino acid sequence of SEQ ID NO:99, or (c) a first heavy chain comprising an amino acid sequence of SEQ ID NO: 122, a first light chain comprising an amino acid sequence of SEQ ID NO: 115, a second heavy chain comprising an amino acid sequence of SEQ ID NO: 103, and two second light chains comprising an amino acid sequence of SEQ ID NO:105.

In a further aspect, provided is a bispecific antibody comprising a first antigen binding domain that specifically binds to PD1 and a second antigen binding domain that specifically binds to LAG3, wherein the bispecific antibody comprises an Fc domain, a first Fab fragment comprising the antigen binding domain that specifically binds to PD1, a second Fab fragment comprising the antigen binding domain that specifically binds to LAG3 and a third Fab fragment comprising an antigen binding domain that specifically binds to LAG3, wherein one of the Fab fragments comprising the antigen binding domain that specifically binds to LAG3 is fused via a peptide linker to the C-terminus of one of the heavy chains (trans 2+1 format).

In a particular aspect, provided is a bispecific antibody comprising a first antigen binding domain that specifically binds to PD1 and a second antigen binding domain that specifically binds to LAG3, wherein the bispecific antibody comprises a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 145, and two second light chains comprising an amino acid sequence with at least 95% sequence identity to the sequence of SEQ ID NO:101. More particularly, the bispecific antibody comprises a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 145, and two second light chains comprising an amino acid sequence with at least 95% sequence identity to the sequence of SEQ ID NO:101.

In a further aspect, provided is a bispecific antibody comprising a first antigen binding domain that specifically binds to PD1 and a second antigen binding domain that specifically binds to LAG3, wherein the bispecific antibody comprises an Fc domain, two Fab fragments comprising each an antigen binding domain that specifically binds to LAG3 and a single chain Fab (scFab) comprising the antigen binding domain that specifically binds to PD1. In particular, the scFab comprising an antigen binding domain that specifically binds to PD1 is fused via a peptide linker to the C-terminus to one of the heavy chains.

In a particular aspect, provided is a bispecific antibody comprising a first antigen binding domain that specifically binds to PD1 and a second antigen binding domain that specifically binds to LAG3, wherein the bispecific antibody comprises (a) a first heavy chain comprising an amino acid sequence with at least 95% sequence identity to the sequence of SEQ ID NO: 123, a second heavy chain comprising an amino acid sequence with at least 95% sequence identity to the sequence of SEQ ID NO: 119, and two light chains comprising each an amino acid sequence with at least 95% sequence identity to the sequence of SEQ ID NO: 101, or (b) a first heavy chain comprising an amino acid sequence with at least 95% sequence identity to the sequence of SEQ ID NO: 124, a second heavy chain comprising an amino acid sequence with at least 95% sequence identity to the sequence of SEQ ID NO: 121, and two light chains comprising each an amino acid sequence with at least 95% sequence identity to the sequence of SEQ ID NO:99, or (c) a first heavy chain comprising an amino acid sequence with at least 95% sequence identity to the sequence of SEQ ID NO: 125, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105.

More particularly, the bispecific antibody comprises (a) a first heavy chain comprising an amino acid sequence of SEQ ID NO: 123, a second heavy chain comprising an amino acid sequence of SEQ ID NO: 119, and two light chains comprising each an amino acid sequence of SEQ ID NO: 101, or (b) a first heavy chain comprising an amino acid sequence of SEQ ID NO: 124, a second heavy chain comprising an amino acid sequence of SEQ ID NO: 121, and two light chains comprising each an amino acid sequence of SEQ ID NO:99, or (c) a first heavy chain comprising an amino acid sequence of SEQ ID NO: 125, a second heavy chain comprising an amino acid sequence of SEQ ID NO: 103, and two light chains comprising each an amino acid sequence of SEQ ID NO:105.

In a further aspect, provided is a bispecific antibody comprising a first antigen binding domain that specifically binds to PD1 and a second antigen binding domain that specifically binds to LAG3, wherein the bispecific antibody comprises an Fc domain, two Fab fragments comprising each an antigen binding domain that specifically binds to LAG3 and a VH and VL domain comprising the antigen binding domain that specifically binds to PD1. In particular, the the VH domain of the antigen binding domain that specifically binds to PD1 is fused via a peptide linker to the C-terminus of one of the heavy chains and the VL domain of the antigen binding domain that specifically binds to PD1 is fused via a peptide linker to the C-terminus of the other one of the heavy chains.

In a particular aspect, provided is a bispecific antibody comprising a first antigen binding domain that specifically binds to PD1 and a second antigen binding domain that specifically binds to LAG3, wherein the bispecific antibody comprises a first heavy chain comprising an amino acid sequence with at least 95% sequence identity to the sequence of SEQ ID NO: 126, a second heavy chain comprising an amino acid sequence with at least 95% sequence identity to the sequence of SEQ ID NO: 127, and two light chains comprising each an amino acid sequence with at least 95% sequence identity to the sequence of SEQ ID NO: 109. More particularly, the bispecific antibody comprises a first heavy chain comprising an amino acid sequence of SEQ ID NO: 126, a second heavy chain comprising an amino acid sequence of SEQ ID NO: 127, and two light chains comprising each an amino acid sequence of SEQ ID NO: 109.

In a further aspect, provided is a bispecific antibody comprising a first antigen binding domain that specifically binds to PD1 and a second antigen binding domain that specifically binds to LAG3, wherein the bispecific antibody comprises an Fc domain, a first Fab fragment comprising the antigen binding domain that specifically binds to PD1, a second Fab fragment comprising the antigen binding domain that specifically binds to LAG3, a third Fab fragment comprising an antigen binding domain that specifically binds to LAG3, and a fourth Fab fragment comprising an antigen binding domain that specifically binds to PD1.

In this aspect, the bispecific antibody is tetravalent with bivalent binding to LAG3 and bivalent binding to PD1. This means that the bispecific antibody comprises two antigen binding domains that specifically bind to PD1 and two antigen binding domains that specifically bind to LAG3 (2+2 format).

In one aspect, the bispecific antibody of the invention comprises
(a) two light chains and two heavy chains of an antibody comprising two Fab fragments comprising the antigen binding domains that specifically bind to LAG3, and
(b) two additional Fab fragments comprising the antigen binding domains that specifically bind to PD1, wherein said additional Fab fragments are each connected via a peptide linker to the C-terminus of the heavy chains of (a).

In a particular aspect, the peptide linker is (G$_4$S)$_4$. In another aspect, the two additional Fab fragments comprising the antigen binding domains that specifically bind to PD1 are crossover Fab fragments wherein the variable domains VL and VH are replaced by each other and the VL-CH chains are each connected via a peptide linker to the C-terminus of the heavy chains of (a).

In one aspect, provided is a bispecific antibody comprising a first antigen binding domain that specifically binds to PD1 and a second antigen binding domain that specifically binds to LAG3, wherein the two Fab fragments comprising each an antigen binding domain that specifically binds to PD1 are each fused via a peptide linker to the C-terminus to one of the heavy chains, respectively.

In a particular aspect, provided is a bispecific antibody comprising a first antigen binding domain that specifically binds to PD1 and a second antigen binding domain that specifically binds to LAG3, wherein the bispecific antibody comprises
(a) two heavy chains comprising each an amino acid sequence with at least 95% sequence identity to the sequence of SEQ ID NO: 114, two first light chains comprising each an amino acid sequence with at least 95% sequence identity to the sequence of SEQ ID NO: 115, and two second light chains comprising each an amino acid sequence with at least 95% sequence identity to the sequence of SEQ ID NO: 101, or
(b) two heavy chains comprising each an amino acid sequence with at least 95% sequence identity to the sequence of SEQ ID NO: 116, two first light chains comprising each an amino acid sequence with at least 95% sequence identity to the sequence of SEQ ID NO: 115, and two second light chains comprising each an amino acid sequence with at least 95% sequence identity to the sequence of SEQ ID NO:99, or
(c) two heavy chains comprising each an amino acid sequence with at least 95% sequence identity to the sequence of SEQ ID NO: 117, two first light chains comprising each an amino acid sequence with at least 95% sequence identity to the sequence of SEQ ID NO: 115, and two second light chains comprising an amino acid sequence with at least 95% sequence identity to the sequence of SEQ ID NO:105.
More particularly, the bispecific antibody comprises
(a) two heavy chains comprising each an amino acid sequence of SEQ ID NO: 114, two first light chains comprising each an amino acid sequence of SEQ ID NO: 115, and two second light chains comprising each an amino acid sequence of SEQ ID NO: 101, or
(b) two heavy chains comprising each an amino acid sequence of SEQ ID NO: 116, two first light chains comprising each an amino acid sequence of SEQ ID NO: 115, and two second light chains comprising each an amino acid sequence of SEQ ID NO:99, or
(c) two heavy chains comprising each an amino acid sequence of SEQ ID NO: 117, two first light chains comprising each an amino acid sequence of SEQ ID NO: 115, and two second light chains comprising an amino acid sequence of SEQ ID NO:105.

Fc Domain Modifications Reducing Fc Receptor Binding and/or Effector Function

In certain aspects, provided is a bispecific antibody comprising a first antigen binding domain that specifically binds to PD1 and a second antigen binding domain that specifically binds to LAG3, wherein the bispecific antibody comprises a Fc domain comprising one or more amino acid modifications that reduce binding to an Fc receptor, in particular towards Fcγ receptor, and reduce or abolish effector function.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

The following section describes preferred aspects of the bispecific antigen binding molecules of the invention comprising Fc domain modifications reducing Fc receptor binding and/or effector function. In one aspect, the invention relates to a bispecific antibody comprising a first antigen binding domain that specifically binds to PD1 and a second antigen binding domain that specifically binds to LAG3, wherein the Fc domain comprises one or more amino acid substitution that reduces binding to an Fc receptor, in particular towards Fcγ receptor. In particular, the Fc domain is of human IgG1 subclass with the amino acid mutations L234A, L235A and P329G (numbering according to Kabat EU index).

The Fc domain confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc domain of the bispecific antibodies of the invention exhibits reduced binding affinity to an Fc receptor and/or reduced effector function, as compared to a native IgG Fc domain, in particular an IgG1 Fc domain or an IgG4 Fc domain. More particularly, the Fc domain is an IgG1 FC domain.

In one such aspect the Fc domain (or the bispecific antigen binding molecule of the invention comprising said Fc domain) exhibits less than 50%, preferably less than 20%, more preferably less than 10% and most preferably less than 5% of the binding affinity to an Fc receptor, as compared to a native IgG1 Fc domain (or the bispecific antigen binding molecule of the invention comprising a native IgG1 Fc domain), and/or less than 50%, preferably less than 20%, more preferably less than 10% and most preferably less than 5% of the effector function, as compared to a native IgG1 Fc domain (or the bispecific antigen binding molecule of the invention comprising a native IgG1 Fc domain). In one aspect, the Fc domain (or the bispecific antigen binding molecule of the invention comprising said Fc domain) does not substantially bind to an Fc receptor and/or induce effector function. In a particular aspect the Fc receptor is an Fcγ receptor. In one aspect, the Fc receptor is a human Fc receptor. In one aspect, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. In one aspect, the Fc receptor is an inhibitory Fc receptor. In a specific aspect, the Fc receptor is an inhibitory human Fcγ receptor, more specifically human FcγRIIB. In one aspect the effector function is one or more of CDC, ADCC, ADCP, and cytokine secretion. In a particular aspect, the effector function is ADCC. In one aspect, the Fc domain exhibits substantially similar binding affinity to neonatal Fc receptor (FcRn), as compared to a native IgG1 Fc domain. Substantially similar binding to FcRn is achieved when the Fc domain (or the the bispecific antigen binding molecule of the invention comprising said Fc domain) exhibits greater than about 70%, particularly greater than about 80%, more particularly greater than about 90% of the binding affinity of a native IgG1 Fc domain (or the bispecific antigen binding molecule of the invention comprising a native IgG1 Fc domain) to FcRn.

In a particular aspect, the Fc domain is engineered to have reduced binding affinity to an Fc receptor and/or reduced effector function, as compared to a non-engineered Fc domain. In a particular aspect, the Fc domain of the bispecific antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In another aspect, the amino acid mutation reduces the binding affinity of the Fc domain to an Fc receptor by at least 2-fold, at least 5-fold, or at least 10-fold. In one aspect, the bispecific antigen binding molecule of the invention comprising an engineered Fc domain exhibits less than 20%, particularly less than 10%, more particularly less than 5% of the binding affinity to an Fc receptor as compared to bispecific antibodies of the invention comprising a non-engineered Fc domain. In a particular aspect, the Fc receptor is an Fcγ receptor. In other aspects, the Fc receptor is a human Fc receptor. In one aspect, the Fc receptor is an inhibitory Fc receptor. In a specific aspect, the Fc receptor is an inhibitory human Fcγ receptor, more specifically human FcγRIIB. In some aspects the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the bispecific antigen binding molecule of the invention comprising said Fc domain) exhibits greater than about 70% of the binding affinity of a non-engineered form of the Fc domain (or the bispecific antigen binding molecule of the invention comprising said non-engineered form of the Fc domain) to FcRn. The Fc domain, or the bispecific antigen binding molecule of the invention comprising said Fc domain, may exhibit greater than about 80% and even greater than about 90% of such affinity. In certain embodiments the Fc domain of the bispecific antigen binding molecule of the invention is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Certain antibody variants with improved or diminished binding to FcRs are described. (e.g. U.S. Pat. No. 6,737,056; WO 2004/056312, and Shields, R. L. et al., J. Biol. Chem. 276 (2001) 6591-6604).

In one aspect of the invention, the Fc domain comprises an amino acid substitution at a position of E233, L234, L235, N297, P331 and P329. In some aspects, the Fc domain comprises the amino acid substitutions L234A and L235A ("LALA"). In one such embodiment, the Fc domain is an IgG1 Fc domain, particularly a human IgG1 Fc domain. In one aspect, the Fc domain comprises an amino acid substitution at position P329. In a more specific aspect, the amino acid substitution is P329A or P329G, particularly P329G. In one embodiment the Fc domain comprises an amino acid substitution at position P329 and a further amino acid substitution selected from the group consisting of E233P, L234A, L235A, L235E, N297A, N297D or P331S. In more particular embodiments the Fc domain comprises the amino acid mutations L234A, L235A and P329G ("P329G LALA"). The "P329G LALA" combination of amino acid substitutions almost completely abolishes Fcγ receptor binding of a human IgG1 Fc domain, as described in PCT Patent Application No. WO 2012/130831 A1. Said document also describes methods of preparing such mutant Fc domains and methods for determining its properties such as Fc receptor binding or effector functions. such antibody is an IgG1 with mutations L234A and L235A or with mutations L234A, L235A and P329G (numbering according to EU index of Kabat et al, Kabat et al., Sequences of Proteins of Immunological Interest, 5th Ed. Public Health Service, National Institutes of Health, Bethesda, MD, 1991).

In one aspect, the bispecific antibody of the invention comprises (all positions according to EU index of Kabat) (i) a homodimeric Fc-region of the human IgG1 subclass optionally with the mutations P329G, L234A and L235A, or (ii) a homodimeric Fc-region of the human IgG4 subclass optionally with the mutations P329G, S228P and L235E, or (iii) a homodimeric Fc-region of the human IgG1 subclass optionally with the mutations P329G, L234A, L235A, I253A, H310A, and H435A, or optionally with the mutations P329G, L234A, L235A, H310A, H433A, and Y436A, or (iv) a heterodimeric Fc-region wherein one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C, or (v) a heterodimeric Fc-region of the human IgG1 subclass wherein both Fc-region polypeptides comprise the mutations P329G, L234A and L235A and one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C.

In one aspect, the Fc domain is an IgG4 Fc domain. In a more specific embodiment, the Fc domain is an IgG4 Fc domain comprising an amino acid substitution at position S228 (Kabat numbering), particularly the amino acid substitution S228P. In a more specific embodiment, the Fc domain is an IgG4 Fc domain comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)). Thus, in one aspect, provided is a bispecific antibody, comprising (all positions according to EU index of Kabat) a heterodimeric Fc-region of the human IgG4 subclass wherein both Fc-region polypeptides comprise the mutations P329G, S228P and L235E and one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C.

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan, A. R. and Winter, G., Nature 322 (1988) 738-740; U.S. Pat. Nos. 5,648,260; 5,624,821; and WO 94/29351 concerning other examples of Fc region variants.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor. Effector function of an Fc domain, or bispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and Cyto-Tox 96© non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

The following section describes preferred aspects of the bispecific antibodies of the invention comprising Fc domain modifications reducing Fc receptor binding and/or effector function. In one aspect, the invention relates to the bispecific comprising a first antigen binding domain that specifically binds PD1 and a second antigen binding domain that specifically binds to LAG3, wherein the Fc domain comprises one or more amino acid substitution that reduces the binding affinity of the antibody to an Fc receptor, in particular towards Fcγ receptor. In another aspect, the invention relates to the bispecific antibody comprising a first antigen binding domain that specifically binds to PD1 and a second antigen binding domain that specifically binds to LAG3, wherein the Fc domain comprises one or more amino acid substitution that reduces effector function. In particular aspect, the Fc domain is of human IgG1 subclass with the amino acid mutations L234A, L235A and P329G (numbering according to Kabat EU index).

Fc Domain Modifications Promoting Heterodimerization

The bispecific antigen binding molecules of the invention comprise different antigen binding domains, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc domain of the bispecific antigen binding molecules of the invention a modification promoting the association of the desired polypeptides.

Accordingly, in particular aspects the invention relates to a bispecific antibody comprising a first antigen binding domain that specifically binds to PD1 and a second antigen binding domain that specifically binds to LAG3, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to a bispecific antibody comprising a first antigen binding domain that specifically binds to PD1 and a second antigen-binding site that specifically binds to LAG3, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues leads to the formation of a disulfide bridge between the two subunits of the Fc domain, further stabilizing the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

But also other knobs-in-holes technologies as described by EP 1 870 459, can be used alternatively or additionally. In one embodiment the multispecific antibody comprises the mutations R409D and K370E in the CH3 domain of the "knobs chain" and the mutations D399K and E357K in the CH3 domain of the "hole-chain" (numbering according to Kabat EU index).

In one aspect, the bispecific antibody comprises a T366W mutation in the CH3 domain of the "knobs chain" and the mutations T366S, L368A and Y407V in the CH3 domain of the "hole chain" and additionally the mutations R409D and K370E in the CH3 domain of the "knobs chain" and the mutations D399K and E357K in the CH3 domain of the "hole chain" (numbering according to the Kabat EU index).

In one aspect, the bispecific antibody comprises the mutations Y349C and T366W in one of the two CH3 domains and the mutations S354C, T366S, L368A and Y407V in the other of the two CH3 domains, or the multispecific antibody comprises the mutations Y349C and T366W in one of the two CH3 domains and the mutations S354C, T366S, L368A and Y407V in the other of the two CH3 domains and additionally the mutations R409D and K370E in the CH3 domain of the "knobs chain" and the mutations D399K and E357K in the CH3 domain of the "hole chain" (numbering according to the Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a bispecific antibody.

In one aspect, in the bispecific antibody the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, in this aspect in the tertiary structure of the multispecific antibody the CH3 domain of the first heavy chain and the CH3 domain of the second heavy chain form an interface that is located between the respective antibody CH3 domains, wherein the respective amino acid sequences of the CH3 domain of the first heavy chain and the amino acid sequence of the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The bispecific antibody according to this aspect is herein also referred to as "CH3(+/−)-engineered bispecific antibody" (wherein the abbreviation "+/−" stands for the oppositely charged amino acids that were introduced in the respective CH3 domains).

In one aspect, in the CH3(+/−)-engineered bispecific antibody the positively charged amino acid is selected from K, R and H, and the negatively charged amino acid is selected from E or D.

In one aspect, in the CH3(+/−)-engineered bispecific antibody the positively charged amino acid is selected from K and R, and the negatively charged amino acid is selected from E or D.

In one aspect, in the CH3(+/−)-engineered bispecific antibody the positively charged amino acid is K, and the negatively charged amino acid is E.

In one aspect, in the CH3(+/−)-engineered bispecific antibody in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one aspect, the approach described in WO 2013/157953 is used to support heterodimerization of the first heavy chain and the second heavy chain of the multispecific antibody. In one embodiment in the CH3 domain of one heavy chain the amino acid T at position 366 is substituted by K, and in the CH3 domain of the other heavy chain the amino acid L at position 351 is substituted by D (numbering according to Kabat EU index). In another embodiment in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another aspect, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one aspect, the approach described in WO 2012/058768 is used to support heterodimerization of the first heavy chain and the second heavy chain of the multispecific antibody. In one aspect, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:

substituting the amino acid T at position 411 by an amino acid selected from N, R, Q, K, D, E and W (numbering according to Kabat EU index), substituting the amino acid D at position 399 by an amino acid selected from R, W, Y, and K (numbering according to Kabat EU index), substituting the amino acid S at position 400 by an amino acid selected from E, D, R and K (numbering according to Kabat EU index), substituting the amino acid F at position 405 by an amino acid selected from I, M, T, S, V and W (numbering according to Kabat EU index;

substituting the amino acid N at position 390 by an amino acid selected from R, K and D (numbering according to Kabat EU index; and substituting the amino acid K at position 392 by an amino acid selected from V, M, R, L, F and E (numbering according to Kabat EU index).

In another aspect, the bispecific antibody is engineered according to WO 2012/058768), i.e. in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of the multispecific antibody, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In the last aforementioned embodiment, in the CH3 domain of the other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one aspect, the approach described in WO 2011/143545 is used to support heterodimerization of the first heavy chain and the second heavy chain of the multispecific antibody. In one aspect, amino acid modifications in the CH3 domains of both heavy chains are introduced at positions 368 and/or 409 (numbering according to Kabat EU index).

In one aspect, the approach described in WO 2011/090762 is used to support heterodimerization of the first heavy chain and the second heavy chain of the bispecific antibody. WO 2011/090762 relates to amino acid modifications according to the "knob-into-hole" (KiH) technology. In one embodiment in the CH3 domain of one heavy chain the amino acid T at position 366 is substituted by W, and in the CH3 domain of the other heavy chain the amino acid Y at position 407 is substituted by A (numbering according to Kabat EU index). In another embodiment in the CH3 domain of one heavy chain the amino acid T at position 366 is substituted by Y, and in the CH3 domain of the other heavy chain the amino acid Y at position 407 is substituted by T (numbering according to Kabat EU index).

In one aspect, the approach described in WO 2009/089004 is used to support heterodimerization of the first heavy chain and the second heavy chain of the bispecific antibody. In one embodiment in the CH3 domain of one heavy chain the amino acid K or N at position 392 is substituted by a negatively charged amino acid (in one embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one embodiment by E or D, in one preferred embodiment by D) (numbering according to Kabat EU index). In one even further aspect, in addition to or alternatively to the aforementioned substitutions, in the CH3 domain of the one heavy chain the amino acid K at position 439 and/or the amino acid K at position 370 is substituted independently from each other by a negatively charged amino acid (in one embodiment by E or D, in one preferred embodiment by D) (numbering according to Kabat EU index).

In one aspect, the approach described in WO 2007/147901 is used to support heterodimerization of the first heavy chain and the second heavy chain of the multispecific antibody. In one embodiment in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG.

In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index). In one embodiment of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a bispecific antibody comprising a first Fab fragment that specifically binds to PD1 and a second Fab fragment that specifically binds to LAG3, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252, WO2009/080253 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In a particular aspect, the invention relates to a bispecific antibody comprising a first Fab fragment that specifically binds to PD1 and a second Fab fragment that specifically binds to LAG3, wherein in one of the Fab fragments the variable domains VL and VH are replaced by each other so that the VH domain is part of the light chain and the VL domain is part of the heavy chain. In a particular aspect, the bispecific antibody is one, wherein in the first Fab fragment comprising the antigen binding domain that specifically binds to PD1 the variable domains VL and VH are replaced by each other.

In another aspect, and to further improve correct pairing, the bispecific antibody comprising a first Fab fragment that specifically binds to PD1 and a second Fab fragment that specifically binds to LAG3, can contain different charged amino acid substitutions (so-called "charged residues"). These modifications are introduced in the crossed or non-crossed CH1 and CL domains. Such modifications are described e.g. in WO2015/150447, WO2016/020309 and PCT/EP2016/073408.

In a particular aspect, the invention is concerned with a bispecific antibody comprising a first Fab fragment that specifically binds to PD1 and a second Fab fragment that specifically binds to LAG3, wherein in one of the Fab fragments in the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index). In a particular aspect, the bispecific antibody is one, wherein in the second Fab fragment comprising the antigen binding domain that specifically binds to TIM3 the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

In a particular aspect, the invention relates to a bispecific antibody comprising a first Fab fragment that specifically binds to PD1 and a second Fab fragment that specifically binds to LAG3, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E). In a particular aspect, the bispecific antibody is one, wherein in the second Fab fragment comprising the antigen binding domain that specifically binds to LAG3 the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

In a further aspect, the bispecific antibody is a bivalent antibody comprising a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other.

The antibody under a) does not contain a modification as reported under b) and the heavy chain and the light chain under a) are isolated chains.

In the antibody under b) within the light chain the variable light chain domain VL is replaced by the variable heavy chain domain VH of said antibody, and within the heavy chain the variable heavy chain domain VH is replaced by the variable light chain domain VL of said antibody.

In one aspect, (i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid, or (ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In another aspect, (i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index), or (ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one aspect, in the constant domain CL of the second heavy chain the amino acids at position 124 and 123 are substituted by K (numbering according to Kabat EU index).

In one aspect, in the constant domain CL of the second heavy chain the amino acid at position 123 is substituted by R and the amino acid as position 124 is substituted by K (numbering according to Kabat EU index).

In one aspect, in the constant domain CH1 of the second light chain the amino acids at position 147 and 213 are substituted by E (numbering according to EU index of Kabat).

In one aspect, in the constant domain CL of the first light chain the amino acids at position 124 and 123 are substituted by K, and in the constant domain CH1 of the first heavy chain the amino acids at position 147 and 213 are substituted by E (numbering according to Kabat EU index).

In one aspect, in the constant domain CL of the first light chain the amino acid at position 123 is substituted by R and the amino acid at position 124 is substituted by K, and in the constant domain CH1 of the first heavy chain the amino acids at position 147 and 213 are both substituted by E (numbering according to Kabat EU index).

In one aspect, in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

In one aspect, the bispecific antibody is a bivalent antibody comprising a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other.

The antibody under a) does not contain a modification as reported under b) and the heavy chain and the light chain und a) are isolated chains. In the antibody under b) within the light chain the variable light chain domain VL is replaced by the variable heavy chain domain VH of said antibody, and the constant light chain domain CL is replaced by the constant heavy chain domain CH1 of said antibody; and within the heavy chain the variable heavy chain domain VH is replaced by the variable light chain domain VL of said antibody, and the constant heavy chain domain CH1 is replaced by the constant light chain domain CL of said antibody.

In one aspect, the bispecific antibody is a bivalent antibody comprising a) a first light chain and a first heavy chain of an antibody specifically binding to a first antigen, and
  b) a second light chain and a second heavy chain of an antibody specifically binding to a second antigen, wherein the constant domains CL and CH1 of the second light chain and the second heavy chain are replaced by each other.

The antibody under a) does not contain a modification as reported under b) and the heavy chain and the light chain under a) are isolated chains. In the antibody under b) within the light chain the constant light chain domain CL is replaced by the constant heavy chain domain CH1of said antibody; and within the heavy chain the constant heavy chain domain CH1 is replaced by the constant light chain domain CL of said antibody.

In one aspect, the bispecific antibody is a bispecific antibody comprising a) a full length antibody specifically binding to a first antigen and consisting of two antibody heavy chains and two antibody light chains, and b) one, two, three or four single chain Fab fragments specifically binding to a second antigen, wherein said single chain Fab fragments under b) are fused to said full length antibody under a) via a peptide linker at the C- or N-terminus of the heavy or light chain of said full length antibody.

In one aspect, one or two identical single chain Fab fragments binding to a second antigen are fused to the full length antibody via a peptide linker at the C terminus of the heavy or light chains of said full length antibody.

In one aspect, one or two identical single chain Fab (scFab) fragments binding to a second antigen are fused to the full length antibody via a peptide linker at the C terminus of the heavy chains of said full length antibody.

In one aspect, one or two identical single chain Fab (scFab) fragments binding to a second antigen are fused to the full length antibody via a peptide linker at the C terminus of the light chains of said full length antibody.

In one aspect, two identical single chain Fab (scFab) fragments binding to a second antigen are fused to the full length antibody via a peptide linker at the C-terminus of each heavy or light chain of said full length antibody.

In one aspect, two identical single chain Fab (scFab) fragments binding to a second antigen are fused to the full length antibody via a peptide linker at the C-terminus of each heavy chain of said full length antibody.

In one aspect, two identical single chain Fab (scFab) fragments binding to a second antigen are fused to the full length antibody via a peptide linker at the C-terminus of each light chain of said full length antibody.

In one aspect, the bispecific antibody is a trivalent antibody comprising a) a full length antibody specifically binding to a first antigen and consisting of two antibody heavy chains and two antibody light chains, b) a first polypeptide consisting of ba) an antibody heavy chain variable domain (VH), or bb) an antibody heavy chain variable domain (VH) and an antibody constant domain 1 (CH1), wherein said first polypeptide is fused with the N-terminus of its VH domain via a peptidic linker to the C-terminus of one of the two heavy chains of said full length antibody, c) a second polypeptide consisting of ca) an antibody light chain variable domain (VL), or cb) an antibody light chain variable domain (VL) and an antibody light chain constant domain (CL), wherein said second polypeptide is fused with the N-terminus of the VL domain via a peptide linker to the C-terminus of the other of the two heavy chains of said full length antibody, and wherein the antibody heavy chain variable domain (VH) of the first polypeptide and the antibody light chain variable domain (VL) of the second polypeptide together form an antigen binding domain specifically binding to a second antigen.

In one aspect, the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:

(i) heavy chain variable domain position 44 to light chain variable domain position 100, or (ii) heavy chain variable domain position 105 to light chain variable domain position 43, or (iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-1459; Kobayashi, H., et al., Nucl. Med. Biol. 25 (1998) 387-393; and Schmidt, M., et al., Oncogene 18 (1999) 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43 (numbering always according to Kabat). In one embodiment a trivalent, bispecific antibody without said optional disulfide stabilization between the variable domains VH and VL of the single chain Fab fragments is preferred.

In one aspect, the bispecific antibody is a trispecific or tetraspecific antibody, comprising a) a first light chain and a first heavy chain of a full length antibody which specifically binds to a first antigen, and b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and c) wherein one to four antigen binding domains which specifically bind to one or two further antigens (i.e. to a third and/or fourth antigen) are fused via a peptide linker to the C- or N-terminus of the light chains or heavy chains of a) and/or b).

The antibody under a) does not contain a modification as reported under b) and the heavy chain and the light chain und a) are isolated chains.

In one aspect, the trispecific or tetraspecific antibody comprises under c) one or two antigen binding domains which specifically bind to one or two further antigens.

In one aspect, the antigen binding domains are selected from the group of a scFv fragment and a scFab fragment.

In one aspect, the antigen binding domains are scFv fragments.

In one aspect, the antigen binding domains are scFab fragments.

In one aspect, the antigen binding domains are fused to the C-terminus of the heavy chains of a) and/or b).

In one aspect, the trispecific or tetraspecific antibody comprises under c) one or two antigen binding domains which specifically bind to one further antigen.

In one aspect, the trispecific or tetraspecific antibody comprises under c) two identical antigen binding domains which specifically bind to a third antigen. In one preferred embodiment such two identical antigen binding domains are fused both via the same peptidic linker to the C-terminus of the heavy chains of a) and b). In one preferred embodiment the two identical antigen binding domains are either a scFv fragment or a scFab fragment.

In one aspect, the trispecific or tetraspecific antibody comprises under c) two antigen binding domains which specifically bind to a third and a fourth antigen. In one embodiment said two antigen binding domains are fused both via the same peptide connector to the C-terminus of the heavy chains of a) and b). In one preferred embodiment said two antigen binding domains are either a scFv fragment or a scFab fragment.

In one aspect, the bispecific antibody is a bispecific, tetravalent antibody comprising
- a) two light chains and two heavy chains of an antibody, which specifically bind to a first antigen (and comprise two Fab fragments),
- b) two additional Fab fragments of an antibody, which specifically bind to a second antigen, wherein said additional Fab fragments are fused both via a peptidic linker either to the C- or N-termini of the heavy chains of a), and
wherein in the Fab fragments the following modifications were performed
- (i) in both Fab fragments of a), or in both Fab fragments of b), the variable domains VL and VH are replaced by each other, and/or the constant domains CL and CH1 are replaced by each other, or
- (ii) in both Fab fragments of a) the variable domains VL and VH are replaced by each other, and the constant domains CL and CH1 are replaced by each other, and in both Fab fragments of b) the variable domains VL and VH are replaced by each other, or the constant domains CL and CH1 are replaced by each other, or
- (iii) in both Fab fragments of a) the variable domains VL and VH are replaced by each other, or the constant domains CL and CH1 are replaced by each other, and in both Fab fragments of b) the variable domains VL and VH are replaced by each other, and the constant domains CL and CH1 are replaced by each other, or
- (iv) in both Fab fragments of a) the variable domains VL and VH are replaced by each other, and in both Fab fragments of b) the constant domains CL and CH1 are replaced by each other, or
- (v) in both Fab fragments of a) the constant domains CL and CH1 are replaced by each other, and in both Fab fragments of b) the variable domains VL and VH are replaced by each other.

In one aspect, said additional Fab fragments are fused both via a peptidic linker either to the C-termini of the heavy chains of a), or to the N-termini of the heavy chains of a).

In one aspect, said additional Fab fragments are fused both via a peptidic linker either to the C-termini of the heavy chains of a).

In one aspect, said additional Fab fragments are fused both via a peptide linker to the N-termini of the heavy chains of a).

In one aspect, in the Fab fragments the following modifications are performed: in both Fab fragments of a), or in both Fab fragments of b), the variable domains VL and VH are replaced by each other, and/or the constant domains CL and CH1 are replaced by each other.

In one aspect, the bispecific antibody is a tetravalent antibody comprising:
- a) a (modified) heavy chain of a first antibody, which specifically binds to a first antigen and comprises a first VH-CH1 domain pair, wherein to the C terminus of said heavy chain the N-terminus of a second VH-CH1 domain pair of said first antibody is fused via a peptide linker,
- b) two light chains of said first antibody of a),
- c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptide linker, and
- d) two (modified) light chains of said second antibody of c), each comprising a CL-CH1 domain pair.

In one aspect, the bispecific antibody comprises
- a) the heavy chain and the light chain of a first full length antibody that specifically binds to a first antigen, and
- b) the heavy chain and the light chain of a second full length antibody that specifically binds to a second antigen, wherein the N-terminus of the heavy chain is connected to the C-terminus of the light chain via a peptide linker.

The antibody under a) does not contain a modification as reported under b) and the heavy chain and the light chain are isolated chains.

In one aspect, the bispecific antibody comprises
- a) a full length antibody specifically binding to a first antigen and consisting of two antibody heavy chains and two antibody light chains, and
- b) an Fv fragment specifically binding to a second antigen comprising a VH2 domain and a VL2 domain, wherein both domains are connected to each other via a disulfide bridge, wherein only either the VH2 domain or the VL2 domain is fused via a peptide linker to the heavy or light chain of the full length antibody specifically binding to a first antigen.

In the bispecific antibody the heavy chains and the light chains under a) are isolated chains.

In one aspect, the other of the VH2 domain or the VL2 domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

In one aspect, the bispecific antibody is a trivalent antibody comprising
- a) two Fab fragments that specifically binds to a first antigen,
- b) one CrossFab fragment that specifically binds to a second antigen in which the CH1 and the CL domain are exchanged for each other,
- c) one Fc-region comprising a first Fc-region heavy chain and a second Fc region heavy chain,
wherein the C-terminus of CH1 domains of the two Fab fragments are connected to the N-terminus of the heavy chain Fc-region polypeptides, and wherein the C-terminus of the CL domain of the CrossFab fragment is connected to the N-terminus of the VH domain of one of the Fab fragments.

In one aspect, the bispecific antibody is a trivalent antibody comprising
- a) two Fab fragments that specifically binds to a first antigen,
- b) one CrossFab fragment that specifically binds to a second antigen in which the CH1 and the CL domain are exchanged for each other, c) one Fc-region comprising a first Fc-region heavy chain and a second Fc region heavy chain, wherein the C-terminus of CH1 domain of the first Fab fragment is connected to the N-terminus of one of the heavy chain Fc-region polypeptides and the C-terminus of the CL-domain of the CrossFab fragment is connected to the N-terminus of the other heavy chain Fc-region polypeptide, and wherein the C-terminus of the CH1 domain of the second Fab fragment is connected to the N-terminus of the VH domain of the first Fab fragment or to the N-terminus of the VH domain of the CrossFab fragment.

In one aspect, the bispecific antibody comprises a) a full length antibody specifically binding to a first antigen and consisting of two antibody heavy chains and two antibody light chains, and b) a Fab fragment specifically binding to a second antigen comprising a VH2 domain and a VL2 domain comprising a heavy chain fragment and a light chain fragment, wherein within the light chain fragment the variable light chain domain VL2 is replaced by the variable heavy chain domain VH2 of said antibody, and within the heavy chain fragment the variable heavy chain domain VH2 is replaced by the variable light chain domain VL2 of said antibody wherein the heavy chain Fab fragment is inserted between the CH1 domain of one of the heavy chains of the full length antibody and the respective Fc-region of the full length antibody, and the N-terminus of the light chain Fab fragment is conjugated to the C-terminus of the light chain of the full length antibody that is paired with the heavy chain of the full length antibody into which the heavy chain Fab fragment has been inserted.

In one aspect, the bispecific antibody comprises a) a full length antibody specifically binding to a first antigen and consisting of two antibody heavy chains and two antibody light chains, and b) a Fab fragment specifically binding to a second antigen comprising a VH2 domain and a VL2 domain comprising a heavy chain fragment and a light chain fragment, wherein within the light chain fragment the variable light chain domain VL2 is replaced by the variable heavy chain domain VH2 of said antibody, and within the heavy chain fragment the variable heavy chain domain VH2 is replaced by the variable light chain domain VL2 of said antibody and wherein the C-terminus of the heavy chain fragment of the Fab fragment is conjugated to the N-terminus of one of the heavy chains of the full length antibody and the C-terminus of the light chain fragment of the Fab fragment is conjugated to the N-terminus of the light chain of the full length antibody that pairs with the heavy chain of the full length antibody to which the heavy chain fragment of the Fab fragment is conjugated.

Polynucleotides

The invention further provides isolated polynucleotides encoding a bispecific antibody as described herein or a fragment thereof.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/nm.4356 or EP 2 101 823 B1).

An "isolated" polynucleotide refers to a nucleic acid molecule that has been separated from a component of its natural environment. An isolated polynucleotide includes a nucleic acid molecule contained in cells that ordinarily contain the nucleic acid molecule, but the nucleic acid molecule is present extrachromosomally or at a chromosomal location that is different from its natural chromosomal location.

The isolated polynucleotides encoding bispecific antibodies of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes a polypeptide comprised in the bispecific antibody according to the invention as described herein.

In one aspect, the present invention is directed to isolated polynucleotides encoding a bispecific antibody comprising a first antigen binding domain that specifically binds to programmed cell death protein 1 (PD1) and a second antigen binding domain that specifically binds to Lymphocyte activation gene-3 (LAG3), wherein said first antigen binding domain specifically binding to PD1 comprises a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence of SEQ ID NO:3; and a VL domain comprising (i) HVR-L1 comprising the amino acid sequence of SEQ ID NO:4; (ii) HVR-L2 comprising the amino acid sequence of SEQ ID NO:5, and (iii) HVR-L3 comprising the amino acid sequence of SEQ ID NO:6.

B. Recombinant Methods

Antibodies may be produced using recombinant methods and compositions, e.g., as described in U.S. Pat. No. 4,816, 567. For these methods one or more isolated nucleic acid(s) encoding an antibody are provided.

In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors. In case of certain bispecific antibodies with heterodimeric heavy chains four nucleic acids are required, one for the first light chain, one for the first heavy chain comprising the first hetreomonomeric Fc-region polypeptide, one for the second light chain, and one for the second heavy chain comprising the second heteromonomeric Fc-region polypeptide. The four nucleic acids can be comprised in one or more nucleic acid molecules or expression vectors. For example, such nucleic acid(s) encode an amino acid sequence comprising the first VL and/or an amino acid sequence comprising the first VH including the first heteromonomeric Fc-region and/or an amino acid sequence comprising the second VL and/or an amino acid sequence comprising the second VH including the second heteromonomeric Fc-region of the antibody (e.g., the first and/or second light and/or the first and/or second heavy chains of the antibody). These nucleic acids can be on the same expression vector or on different expression vectors, normally these nucleic acids are located on two or three expression vectors, i.e. one vector can comprise more than one of these nucleic acids. Examples of these bispecific antibodies are CrossMabs and T-cell bispe-cifics (see, e.g. Schaefer, W. et al, PNAS, 108 (2011) 11187-1191). For example, one of the heteromonomeric heavy chain comprises the so-called "knob mutations" (T366W and optionally one of S354C or Y349C) and the other comprises the so-called "hole mutations" (T366S, L368A and Y407V and optionally Y349C or S354C) (see, e.g., Carter, P. et al., Immunotechnol. 2 (1996) 73).

In one aspect, isolated nucleic acid encoding a bispecific antibody described herein is provided. Such nucleic acid may encode an amino acid sequence comprising the VL and/or an amino acid sequence comprising the VH of the antigen binding domains that specifically bind to PD1 and LAG3, respectively (e.g., in the light and/or heavy chains of the antibody). In a further aspect, one or more vectors (e.g., expression vectors) comprising such nucleic acid are pro-vided. In a further aspect, a host cell comprising such nucleic acid is provided. In one such aspect, a host cell comprises (e.g., has been transformed with): (1) a first vector compris-ing a first pair of nucleic acids that encode amino acid sequences one of them comprising the first VL and the other comprising the first VH of the antibody and a second vector comprising a second pair of nucleic acids that encode amino acid sequences one of them comprising the second VL and the other comprising the second VH of the antibody, or (2) a first vector comprising a first nucleic acid that encode an amino acid sequence comprising one of the variable domains (preferably a light chain variable domain), a second vector comprising a pair of nucleic acids that encode amino acid sequences one of them comprising a light chain variable domain and the other comprising the first heavy chain variable domain, and a third vector comprising a pair of nucleic acids that encode amino acid sequences one of them comprising the respective other light chain variable domain as in the second vector and the other comprising the second heavy chain variable domain, or (3) a first vector comprising a nucleic acid that encodes an amino acid sequence com-prising the first VL of the antibody, a second vector com-prising a nucleic acid that encodes an amino acid sequence comprising the first VH of the antibody, a third vector comprising a nucleic acid that encodes an amino acid sequence comprising the second VL of the antibody, and a fourth vector comprising a nucleic acid that encodes an amino acid sequence comprising the second VH of the antibody. In one aspect, the host cell is eukaryotic, e.g. a Chinese Hamster Ovary (CHO) cell or lymphoid cell (e.g., Y0, NS0, Sp20 cell). In one aspect, a method of making a bispecific antibody is provided, wherein the method com-prises culturing a host cell comprising a nucleic acid encod-ing the antibody, as provided above, under conditions suit-able for expression of the antibody, and optionally recovering the antibody from the host cell (or host cell culture medium).

For recombinant production of the bispecific antibodies comprising a first antigen binding domain that specifically binds to PD1 and a second antigen binding domain that specifically binds to LAG3 as described herein, nucleic acid encoding the bispecific antibodies, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody frag-ments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunc-tion with insect cells, particularly for transfection of *Spo-doptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR– CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

C. Assays

The bispecific antibodies comprising a first antigen binding domain that specifically binds to PD1 and a second antigen binding domain that specifically binds to LAG3 provided herein may be identified, screened for, or characterized for their physical/chemical properties and/or biological activities by various assays known in the art.

1. Affinity Assays

The affinity of the bispecific antigen binding molecules, antibodies and antibody fragments provided herein for the corresponding antigens can be determined in accordance with the methods set forth in the Examples by surface plasmon resonance (SPR), using standard instrumentation such as a Biacore® instrument (GE Healthcare), and receptors or target proteins such as may be obtained by recombinant expression. A specific illustrative and exemplary embodiment for measuring binding affinity is described in Examples 2, 8 or 11. According to one aspect, $K_D$ is measured by surface plasmon resonance using a BIACORE® T100 machine (GE Healthcare) at 25° C.

2. Binding Assays and Other Assays

In one aspect, the bispecific antibodies of the invention are tested for its antigen binding activity, e.g., by known methods such as ELISA, Western blot, etc. Binding of the bispecific antibodies provided herein to the corresponding recombinant antigen or to antigen-expressing cells may be evaluated by ELISA as described in Examples 8 or 11.

In a further aspect, fresh peripheral blood mononuclear cells (PBMCs) are used in binding assays to show binding to different peripheral blood mononuclear cells (PBMC) such as monocytes, NK cells and T cells.

In another aspect, a cellular dimerization assay was used to demonstrate the dimerization or at last binding/interaction of two different receptors PD1 and LAG3, which are cytosolically fused with two fragments of an enzyme, upon ligation or cross-linking with a bispecific antibody against both targets. Hereby only one receptor alone shows no enzymatic activity. For this specific interaction, the cytosolic C-terminal ends of both receptors were individually fused to heterologous subunits of a reporter enzyme. A single enzyme subunit alone showed no reporter activity. However, simultaneous binding to both receptors was expected to lead to local cytosolic accumulation of both receptors, complementation of the two heterologous enzyme subunits, and finally to result in the formation of a specific and functional enzyme that hydrolyzes a substrate thereby generating a chemiluminescent signal (Example 11).

3. Activity Assays

In one aspect, assays are provided for identifying a bispecific antibody comprising a first antigen binding domain that specifically binds to PD1 and a second antigen binding domain that specifically binds to LAG3 having biological activity. Biological activity may include, e.g., the ability to enhance the activation and/or proliferation of different immune cells, especially T-cells, secretion of immune-modulating cytokines such IFNγ or TNF-alpha, blocking the PD1 pathway, blocking the LAG3 pathway, killing of tumor cells. Antibodies having such biological activity in vivo and/or in vitro are also provided.

In certain aspects, an antibody of the invention is tested for such biological activity. In one aspect, provided is an immune cell assay which measures the activation of lymphocytes from one individual (donor X) to lymphocytes from another individual (donor Y). The mixed lymphocyte reaction (MLR) can demonstrate the effect of blocking the PD1 pathway to lymphocyte effector cells. T cells in the assay were tested for activation and their IFN-gamma secretion in the presence or absence of bispecific antibodies of the invention. The assay is described in more detail in Example 9.

D. Immunoconjugates

The invention also provides immunoconjugates comprising a bispecific antibody of the invention conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

E. Methods and Compositions for Diagnostics and Detection

In certain aspects, any of the bispecific antibodies comprising a first antigen binding domain that specifically binds to PD1 and a second antigen binding domain that specifically binds to LAG3 provided herein may be useful for detecting the presence of both PD1 and LAG3 in a biological sample. The term "detecting" as used herein encompasses quantitative or qualitative detection. In certain embodiments, a biological sample comprises a cell or tissue, such as AML stem cancer cells.

In one aspect, a bispecific antibody for use in a method of diagnosis or detection is provided. In a further aspect, a method of detecting the presence of both PD1 and LAG3 in a biological sample is provided. In certain embodiments, the method comprises contacting the biological sample with a bispecific antibody as described herein under conditions permissive for binding of the bispecific antibody to both PD1 and LAG3, and detecting whether a complex is formed between the bispecific antibody and both antigens. Such method may be an in vitro or in vivo method. In one embodiment, the bispecific antibody is used to select subjects eligible for therapy with a bispecific antibody comprising a first antigen binding domain that specifically binds to PD1 and a second antigen binding domain that specifically binds to LAG3 antibody, e.g. where PD1 and LAG3 are biomarkers for selection of patients.

In certain aspects, labeled bispecific antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes 32P, 14C, 125I, 3H, and 131I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, 0-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels or stable free radicals.

F. Pharmaceutical Compositions, Formulations and Routes of Administration

In a further aspect, the invention provides pharmaceutical compositions comprising any of the bispecific antibodies comprising a first antigen binding domain that specifically binds to PD1 and a second antigen binding domain that specifically binds to LAG3 provided herein, e.g., for use in any of the below therapeutic methods. In one embodiment, a pharmaceutical composition comprises any of the bispecific antibodies provided herein and at least one pharmaceutically acceptable excipient. In another embodiment, a pharmaceutical composition comprises any of the bispecific antibodies provided herein and at least one additional therapeutic agent, e.g., as described below.

Pharmaceutical compositions of the present invention comprise a therapeutically effective amount of one or more bispecific antibodies dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific antibody and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the bispecific antibodies of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the bispecific antibodies may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX@, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

In addition to the compositions described previously, the bispecific antibodies may also be formulated as a depot preparation. Such long acting formulations may be administered by implantation (for example subcutaneously or intramuscularly) or by intramuscular injection. Thus, for example, the bispecific antibodies may be formulated with suitable polymeric or hydrophobic materials (for example as emulsion in an acceptable oil) or ion exchange resins, or as sparingly soluble derivatives, for example, as a sparingly soluble salt.

Pharmaceutical compositions comprising the bispecific antibodies of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The bispecific antibodies may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

G. Therapeutic Methods and Compositions

Any of the bispecific antibodies comprising a first antigen binding domain that specifically binds to PD1 and a second antigen binding domain that specifically binds to LAG3 provided herein may be used in therapeutic methods.

For use in therapeutic methods, bispecific antibodies comprising a first antigen binding domain that specifically binds to PD1 and a second antigen binding domain that specifically binds to LAG3 as defined herein before can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, bispecific antibodies comprising a first antigen binding domain that specifically binds to PD1 and a second antigen binding domain that specifically binds to LAG3 as defined herein for use as a medicament are provided. In further aspects, bispecific antibodies comprising a first antigen binding domain that specifically binds to PD1 and a second antigen binding domain that specifically binds to LAG3 as defined herein for use in treating a disease, in particular for use in the treatment of cancer, are provided. In certain embodiments, bispecific antibodies comprising a first antigen binding domain that specifically binds to PD1 and a second antigen binding domain that specifically binds to LAG3 for use in a method of treatment are provided. In one embodiment, the invention provides bispecific antibodies comprising a first antigen binding domain that specifically binds to PD1 and a second antigen binding domain that specifically binds to LAG3 as described herein for use in the treatment of a disease in an individual in need thereof. In certain embodiments, the invention provides bispecific antibodies comprising a first antigen binding domain that specifically binds to PD1 and a second antigen binding domain that specifically binds to LAG3 for use in a method of treating an individual having a disease comprising administering to the individual a therapeutically effective amount of the bispecific antibody. In certain embodiments the disease to be treated is cancer. In another aspect, the disease to be treated is an infectious disease, in particular a chronic viral infection like HIV (human immunodeficiency virus), HBV (hepatitis B virus), HCV (hepatitis C), HSV1 (herpes simplex virus type 1), CMV (cytomegalovirus), LCMV (lymphocytic chroriomeningitis virus) or EBV (Epstein-Barr virus). The subject, patient, or "individual" in need of treatment is typically a mammal, more specifically a human.

In a further aspect, the invention provides for the use of bispecific antibodies comprising a first antigen binding domain that specifically binds to PD1 and a second antigen binding domain that specifically binds to LAG3 as defined herein before in the manufacture or preparation of a medicament for the treatment of a disease in an individual in need thereof. In one embodiment, the medicament is for use in a method of treating a disease comprising administering to an individual having the disease a therapeutically effective amount of the medicament.

In certain aspects, the disease to be treated is a proliferative disorder, particularly cancer. Examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using bispecific antibodies comprising a first antigen binding domain that specifically binds to PD1 and a second antigen binding domain that specifically binds to LAG3 according to the invention include, but are not limited to neoplasms located in the abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain aspects, the cancer is chosen from the group consisting of renal cell cancer, skin cancer, lung cancer, colorectal cancer, breast cancer, brain cancer, head and neck cancer. In further aspects, the cancer is chosen from carcinoma, lymphoma (e.g., Hodgkin's and non-Hodgkin's lymphoma), blastoma, sarcoma, and leukemia. In another aspect, the cancer is to be treated is selected from squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

In a further aspect, the disease to be treated is an infectious disease, in particular a chronic viral infection. The term "chronic viral infection" refers to a subject afflicted or infected with a chronic virus. Examples for chronic viral infections are human immunodeficiency virus (HIV), hepatitis B viral infection (HBV), hepatitis C viral infection (HCV), herpes simplex virus 1 (HSV1), cytomegalovirus (CMV), lymphocytic choriomeningitis virus (LCMV) or Epstein-Barr virus (EBV).

A skilled artisan readily recognizes that in many cases the bispecific molecule may not provide a cure but may only provide partial benefit. In some embodiments, a physiological change having some benefit is also considered therapeutically beneficial. Thus, in some embodiments, an amount of the bispecific antibody that provides a physiological change is considered an "effective amount" or a "therapeutically effective amount".

In a further aspect, the invention provides a method for treating a disease in an individual, comprising administering to said individual a therapeutically effective amount of bispecific antibodies comprising a first antigen binding domain that specifically binds to PD1 and a second antigen binding domain that specifically binds to LAG3 of the invention. In one embodiment a composition is administered to said individual, comprising a bispecific antibody of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g. an anti-cancer agent if the disease to be treated is cancer. In another aspect, the disease is a chronic viral infection. An "individual" according to any of the above embodiments may be a mammal, preferably a human.

For the prevention or treatment of disease, the appropriate dosage of a bispecific antibodies comprising a first antigen binding domain that specifically binds to PD1 and a second antigen binding domain that specifically binds to LAG3 of the invention (when used alone or in combination with one or more other additional therapeutic agents) will depend on the type of disease to be treated, the route of administration, the body weight of the patient, the type of fusion protein, the severity and course of the disease, whether the bispecific antibody is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The bispecific antibody comprising a first antigen binding domain that specifically binds to PD1 and a second antigen binding domain that specifically binds to LAG3 as defined herein is suitably administered to the patient at one time or over a series of treatments. Depending on the type and severity of the disease, about 1 µg/kg to 15 mg/kg (e.g. 0.1 mg/kg-10 mg/kg) of the bispecific antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific antibody would be in the range from about 0.005 mg/kg to about 10 mg/kg. In other examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The bispecific antibodies comprising a first antigen binding domain that specifically binds to PD1 and a second antigen binding domain that specifically binds to LAG3 as defined herein will generally be used in an amount effective to achieve the intended purpose. For use to treat or prevent a disease condition, the bispecific antibodies of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the bispecific antibody which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the bispecific antibody may not be related to plasma concentration. One skilled in the art will be able to optimize therapeutically effective local dosages without undue experimentation.

A therapeutically effective dose of the bispecific antibodies described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Bispecific antibodies that exhibit large therapeutic indices are preferred. In one embodiment, the bispecific antibody according to the present invention exhibits a high therapeutic index. The data obtained from cell culture assays and animal studies can be used in formulating a range of dosages suitable for use in humans. The dosage lies preferably within a range of circulating concentrations that include the ED50 with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with bispecific antibodies of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The bispecific antibodies comprising a first antigen binding domain that specifically binds to PD1 and a second antigen binding domain that specifically binds to LAG3 as described herein before may be administered in combination with one or more other agents in therapy. For instance, a bispecific antibody of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

In one aspect of the invention, the bispecific antibody comprising a first antigen binding domain that specifically binds to PD1 and a second antigen binding domain that specifically binds to LAG3 as described herein or a pharmaceutical composition comprising said bispecific antibody is for use in the prevention or treatment of cancer, wherein the bispecific antibody is administered in combination with a chemotherapeutic agent, radiation and/or other agents for use in cancer immunotherapy.

In a particular aspect of the invention, the bispecific antibody comprising a first antigen binding domain that specifically binds to PD1 and a second antigen binding domain that specifically binds to LAG3 as described herein or a pharmaceutical composition comprising said bispecific antibody is for use in the prevention or treatment of cancer, wherein the bispecific antibody is administered in combination with an T-cell activating anti-CD3 bispecific antibody, in particular an anti-CEA/anti-CD3 bispecific antibody. In one aspect, the anti-CEA/anti-CD3 bispecific antibody is a T-cell activating anti-CD3 bispecific antibody comprising a second antigen binding domain comprising (a) a heavy chain variable region ($V_H$CEA) comprising CDR-H1 sequence of SEQ ID NO:154, CDR-H2 sequence of SEQ ID NO:155, and CDR-H3 sequence of SEQ ID NO:156, and/or a light chain variable region ($V_L$CEA) comprising CDR-L1 sequence of SEQ ID NO:157, CDR-L2 sequence of SEQ ID NO:158, and CDR-L3 sequence of SEQ ID NO:159, or (b) a heavy chain variable region ($V_H$CEA) comprising CDR-H1 sequence of SEQ ID NO:162, CDR-H2 sequence of SEQ ID NO:163, and CDR-H3 sequence of SEQ ID NO:164, and/or a light chain variable region ($V_L$CEA) comprising CDR-L1 sequence of SEQ ID NO:165, CDR-L2 sequence of SEQ ID NO:166, and CDR-L3 sequence of SEQ ID NO:167. In one aspect, the anti-CEA/anti-CD3 bispecific antibody is a T-cell activating anti-CD3 bispecific antibody comprising a heavy chain variable region ($V_H$CEA) comprising the amino acid sequence of SEQ ID NO:160 and/or a light chain variable region ($V_L$CEA) comprising the amino acid sequence of SEQ ID NO:161 or a second antigen binding domain comprising a heavy chain variable region ($V_H$CEA) comprising the amino acid sequence of SEQ ID NO:168 and/or a light chain variable region ($V_L$CEA) comprising the amino acid sequence of SEQ ID NO:169.

In a further aspect, the anti-CEA/anti-CD3 bispecific antibody comprises an Fc domain comprising one or more amino acid substitutions that reduce binding to an Fc receptor and/or effector function. In particular, the anti-CEA/anti-CD3 bispecific antibody comprises an IgG1 Fc domain comprising the amino acid substitutions L234A, L235A and P329G.

In a particular aspect, the anti-CEA/anti-CD3 bispecific antibody comprises a polypeptide that is at least 95%, 96%, 97%, 98%, or 99% identical to the sequence of SEQ ID NO: 146, a polypeptide that is at least 95%, 96%, 97%, 98%, or 99% identical to the sequence of SEQ ID NO: 147, a polypeptide that is at least 95%, 96%, 97%, 98%, or 99% identical to the sequence of SEQ ID NO: 148, and a polypeptide that is at least 95%, 96%, 97%, 98%, or 99% identical to the sequence of SEQ ID NO: 149. In a further particular embodiment, the bispecific antibody comprises a polypeptide sequence of SEQ ID NO: 146, a polypeptide sequence of SEQ ID NO: 147, a polypeptide sequence of SEQ ID NO: 148 and a polypeptide sequence of SEQ ID NO: 149 (CEA CD3 TCB).

In a further particular aspect, the anti-CEA/anti-CD3 bispecific antibody comprises a polypeptide that is at least 95%, 96%, 97%, 98%, or 99% identical to the sequence of SEQ ID NO:150, a polypeptide that is at least 95%, 96%, 97%, 98%, or 99% identical to the sequence of SEQ ID NO:151, a polypeptide that is at least 95%, 96%, 97%, 98%, or 99% identical to the sequence of SEQ ID NO:152, and a polypeptide that is at least 95%, 96%, 97%, 98%, or 99% identical to the sequence of SEQ ID NO:153. In a further particular embodiment, the bispecific antibody comprises a polypeptide sequence of SEQ ID NO:150, a polypeptide sequence of SEQ ID NO:151, a polypeptide sequence of SEQ ID NO:152 and a polypeptide sequence of SEQ ID NO:153 (CEACAM5 CD3 TCB).

In another aspect, a pharmaceutical composition comprising a bispecific antibody comprising a first antigen binding domain that specifically binds to PD1 and a second antigen binding domain that specifically binds to LAG3 as described herein, and a T-cell activating anti-CD3 bispecific antibody, in particular an anti-CEA/anti-CD3 bispecific antibody is provided. In a particular aspect, the pharmaceutical composition is for use in the combined, sequential or simultaneous treatment of a disease, in particular for the treatment of cancer. More particularly, the composition is for use in the treatment of solid tumors.

In another aspect, the invention provides a method for treating or delaying progression of cancer in an individual comprising administering to the subject an effective amount of bispecific antibody comprising a first antigen binding domain that specifically binds to PD1 and a second antigen binding domain that specifically binds to LAG3 as described herein, in combination with a T-cell activating anti-CD3 bispecific antibody, in particular an anti-CEA/anti-CD3 bispecific antibody or anti-FolR1/anti-CD3 bispecific antibody.

Such other agents are suitably present in combination in amounts that are effective for the purpose intended. The effective amount of such other agents depends on the amount of fusion protein used, the type of disorder or treatment, and other factors discussed above. The bispecific antibodies are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the bispecific antibody can occur prior to, simultaneously, and/or following, administration of the additional therapeutic agent and/or adjuvant.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antibody comprising a first antigen binding domain that specifically binds to PD1 and a second antigen binding domain that specifically binds to LAG3 as defined herein before.

The label or package insert indicates that the composition is used for treating the condition of choice. Moreover, the article of manufacture may comprise (a) a first container with a composition contained therein, wherein the composition comprises the bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C

| | (Sequences): | |
|---|---|---|
| SEQ ID NO: Name | | Sequence |
| 1 heavy chain HVR-H1, PD1-0103 | | GFSFSSY |
| 2 heavy chain HVR-H2, PD1-0103 | | GGR |
| 3 heavy chain HVR-H3, PD1-0103 | | TGRVYFALD |
| 4 light chain HVR-L1, PD1-0103 | | SESVDTSDNSF |
| 5 light chain HVR-L2, PD1-0103 | | RSS |
| 6 light chain HVR-L3, PD1-0103 | | NYDVPW |
| 7 heavy chain variable domain VH, PD1-0103 | | EVILVESGGGLVKPGGSLKLSCAASGFSFSSYTM SWVRQTPEKRLDWVATISGGGRDIYYPDSVKGRF TISRDNAKNTLYLEMSSLMSEDTALYYCVLLTGR VYFALDSWGQGTSVTVSS |

TABLE C-continued

| | | (Sequences): |
|---|---|---|

| SEQ ID NO: | Name | Sequence |
|---|---|---|
| 8 | light chain variable domain VL, PD1-0103 | KIVLTQSPASLPVSLGQRATISCRASESVDTSDN SFIHWYQQRPGQSPKLLIYRSSTLESGVPARFSG SGSRTDFTLTIDPVEADDVATYYCQQNYDVPWTF GGGTKLEIK |
| 9 | humanized variant -heavy chain variable domain VH of PD1-0103_01 (PD1 0376) | EVQLLESGGGLVQPGGSLRLSCAASGFSFSSYTM SWVRQAPGKGLEWVATISGGGRDIYYPDSVKGRF TISRDNSKNTLYLQMNSLRAEDTAVYYCVLLTGR VYFALDSWGQGTLVTVSS |
| 10 | humanized variant -light chain variable domain VL of PD1-0103_01 (PD1 0376) | DIVMTQSPDSLAVSLGERATINCKASESVDTSDN SFIHWYQQKPGQSPKLLIYRSSTLESGVPDRFSG SGSGTDFTLTISSLQAEDVAVYYCQQNYDVPWTF GQGTKVEIK |
| 11 | humanized variant -light chain variable domain VL of PD1-0103_02 | DVVMTQSPLSLPVTLGQPASISCRASESVDTSDN SFIHWYQQRPGQSPRLLIYRSSTLESGVPDRFSG SGSGTDFTLKISRVEAEDVGVYYCQQNYDVPWTF GQGTKVEIK |
| 12 | humanized variant -light chain variable domain VL of PD1-0103_03 | EIVLTQSPATLSLSPGERATLSCRASESVDTSDN SFIHWYQQKPGQSPRLLIYRSSTLESGIPARFSG SGSGTDFTLTISSLEPEDFAVYYCQQNYDVPWTF GQGTKVEIK |
| 13 | humanized variant -light chain variable domain VL of PD1-0103_04 | EIVLTQSPATLSLSPGERATLSCRASESVDTSDN SFIHWYQQKPGQSPRLLIYRSSTLESGIPARFSG SGSGTDFTLTISSLEPEDFAVYYCQQNYDVPWTF GQGTKVEIK |
| 14 | heavy chain HVR-H1, aLAG3(0414) | DYTMN |
| 15 | heavy chain HVR-H2, aLAG3(0414) | VISWDGGGTY YTDSVKG |
| 16 | heavy chain HVR-H3, aLAG3(0414) | GLTDTTLYGS DY |
| 17 | light chain HVR-L1, aLAG3(0414) | RASQSISSYL N |
| 18 | light chain HVR-L2, aLAG3(0414) | AASTLQS |
| 19 | light chain HVR-L3, aLAG3(0414) | QQTYSSPLT |
| 20 | heavy chain variable domain VH, aLAG3(0414) | EVQLLESGGG LVQPGGSLRL SCAASGFIFD DYTMNWVRQA PGKGLEWVAV ISWDGGGTYY TDSVKGRFTI SRDDFKNTLY LQMNSLRAED TAVYYCAKGL TDTTLYGSDY WGQGTLVTVS S |
| 21 | light chain variable domain VL, aLAG3(0414) | DIQMTQSPSS LSASVGDRVT ITCRASQSIS SYLNWYQQKP GKAPKLLIYA ASTLQSGVPS RFSGSGSGTD FTLTISSLQP EDFATYYCQQ TYSSPLTFGG GTKVEIK |
| 22 | heavy chain HVR-H1, aLAG3(0403) | DYTMH |
| 23 | heavy chain HVR-H2, aLAG3(0403) | LVSWDGGGTY YTNSVKG |
| 24 | heavy chain HVR-H3, aLAG3(0403) | AITDTSLYGY DY |
| 25 | light chain HVR-L1, aLAG3(0403) | RASQSISSYL N |
| 26 | light chain HVR-L2, aLAG3(0403) | AASSLQS |
| 27 | light chain HVR-L3, aLAG3(0403) | QQTYSTPLT |

TABLE C-continued

| | (Sequences): |
|---|---|

| SEQ ID NO: Name | Sequence |
|---|---|
| 28 heavy chain variable domain VH, aLAG3(0403) | EVQLLESGGG LVQPGGSLRL SCAASGFTFD DYTMHWVRQA PGKGLEWVSL VSWDGGGTYY TNSVKGRFTI SRDNSKNTLY LQMNSLRAED TAVYFCAKAI TDTSLYGYDY WGQGILVTVS S |
| 29 light chain variable domain VL, aLAG3(0403) | DIQMTQSPSS LSASVGDRVT ITCRASQSIS SYLNWYQQKP GNAPKLLIYA ASSLQSGVPS RFSGSGSGTD FTLTISSLQP EDFATYYCQQ TYSTPLTFGG GTKVEIK |
| 30 heavy chain HVR-H1, aLAG3(0411) | DYTMN |
| 31 heavy chain HVR-H2, aLAG3(0411) | VISWDGGATY YADSVKG |
| 32 heavy chain HVR-H3, aLAG3(0411) | GLTDDTLYGS DY |
| 33 light chain HVR-L1, aLAG3(0411) | RASQSIVSYL N |
| 34 light chain HVR-L2, aLAG3(0411) | ASSSLQS |
| 35 light chain HVR-L3, aLAG3(0411) | QQTYSTPLT |
| 36 heavy chain variable domain VH, aLAG3(0411) | EVHLLESGGG LVQPGGSLRL SCAASGFIVD DYTMNWVRQA PGKGLEWVSV ISWDGGATYY ADSVKGRFTI SRDDFKNTLY LQMNSLRAED TAVYYCAKGL TDDTLYGSDY WGQGTLVTVS S |
| 37 light chain variable domain VL, aLAG3(0411) | DIQMTQSPSS LSASVGDRVT ITCRASQSIV SYLNWYQQKP GKAPKLLIYA SSSLQSGVPS RFSGSGSGTD FTLTISSLQP EDFATYYCQQ TYSTPLTFGG GTKVEIK |
| 38 heavy chain HVR-H1, aLAG3(0417) | DYAMS |
| 39 heavy chain HVR-H2, aLAG3(0417) | GIDNSGYYTY YTDSVKG |
| 40 heavy chain HVR-H3, aLAG3(0417) | THSGLIVNDA FDI |
| 41 light chain HVR-L1, aLAG3(0417) | RASQSISSYL N |
| 42 light chain HVR-L2, aLAG3(0417) | AASSLQS |
| 43 light chain HVR-L3, aLAG3(0417) | QQTYSTPLT |
| 44 heavy chain variable domain VH, aLAG3(0417) | EVQLVESGGG LVQPGGSLRL ACAASGFTFS DYAMSWVRQA PGKGLEWVSG IDNSGYYTYY TDSVKGRFTI SRDDVKNTLY LQMNSLRAED TAVYLCTKTH SGLIVNDAFD IWGQGTMVTV SS |
| 45 light chain variable domain VL, aLAG3(0417) | DIQMTQSPSS LSASVGDRVT ITCRASQSIS SYLNWYQQKP GKAPKLLIYA ASSLQSGVPS RFSGSGSGTD FTLTISSLQP EDFATYYCQQ TYSTPLTFGG GTKVEIK |
| 46 heavy chain HVR-H1, aLAG3(0416) | DYAMS |
| 47 heavy chain HVR-H2, aLAG3(0416) | GIDNSGYYTY YTDSVKG |
| 48 heavy chain HVR-H3, aLAG3(0416) | THSGLIVNDA FDI |
| 49 light chain HVR-L1, aLAG3(0416) | RASQSISSYL N |
| 50 light chain HVR-L2, aLAG3(0416) | DASSLES |

TABLE C-continued

| | (Sequences): |
|---|---|

| SEQ ID NO: Name | Sequence |
|---|---|
| 51 light chain HVR-L3, aLAG3 (0416) | QQSYSTPLT |
| 52 heavy chain variable domain VH, aLAG3 (0416) | EVQLVESGGG LVQPGGSLRL ACAASGFTFS DYAMSWVRQA PGKGLEWVSG IDNSGYYTYY TDSVKGRFTI SRDDVKNTLY LQMNSLRAED TAVYLCTKTH SGLIVNDAFD IWGQGTMVTV SS |
| 53 light chain variable domain VL, aLAG3 (0416) | DIQLTQSPSS LSASVGDRVT ITCRASQSIS SYLNWYQQKP GKAPKLLIYD ASSLESGVPS RFSGSGSGTD ATLTISSLQP EDFATYYCQQ SYSTPLTFGG GTKVEIK |
| 54 heavy chain variable domain VH, BMS-986016 (WO2014/008218 and US2016/0326248) | QVQLQQWGAG LLKPSETLSL TCAVYGGSFS DYYWNWIRQP PGKGLEWIGE INHRGSTNSN PSLKSRVTLS LDTSKNQFSL KLRSVTAADT AVYYCAFGYS DYEYNWFDPW GQGTLVTVSS |
| 55 light chain variable domain VL BMS-986016 (WO2014/008218 and US2016/0326248) | EIVLTQSPAT LSLSPGERAT LSCRASQSIS SYLAWYQQKP GQAPRLLIYD ASNRATGIPA RFSGSGSGTD FTLTISSLEP EDFAVYYCQQ RSNWPLTFGQ GTNLEIK |
| 56 heavy chain HVR-H1, MDX25F7 (25F7) | DYYWN |
| 57 heavy chain HVR-H2, MDX25F7 (25F7) | EINHNGNTNSNPSLKS |
| 58 heavy chain HVR-H3, MDX25F7 (25F7) | GYSDYEYNWF |
| 59 light chain HVR-L1, MDX25F7 (25F7) | RASQSISSYLA |
| 60 light chain HVR-L2, MDX25F7 (25F7) | DASNRAT |
| 61 light chain HVR-L3, MDX25F7 (25F7) | QQRSNWPLT |
| 62 heavy chain variable domain VH, MDX25F7 (25F7) (US2011/0150892 and WO2014/008218) | QVQLQQWGAG LLKPSETLSL TCAVYGGSFS DYYWNWIRQP PGKGLEWIGE INHNGNTNSN PSLKSRVTLS LDTSKNQFSL KLRSVTAADT AVYYCAFGYS DYEYNWFDPW GQGTLVTVSS |
| 63 light chain variable domain VL, MDX25F7 (25F7) (US2011/0150892 and WO2014/008218) | EIVLTQSPAT LSLSPGERAT LSCRASQSIS SYLAWYQQKP GQAPRLLIYD ASNRATGIPA RFSGSGSGTD FTLTISSLEP EDFAVYYCQQ RSNWPLTFGQ GTNLEIK |
| 64 heavy chain variable domain VH, humanized BAP050 (LAG525) (US2015/0259420) | QIQLVQSGPE LKKPGETVKI SCKASGFTLT NYGMNWVRQT PGKGLKWMGW INTDTGEPTY ADDFKGRFAF SLETSASTAS LQINNLKNAD TATYFCARNP PYYYGTNNAE AMDYWGQGTT VTVSS |
| 65 light chain variable domain VL, humanized BAP050 (LAG525) (US2015/0259420) | DIQMTQTTSS LSASLGDRVT ISCSSSQDIS NYLNWYQQKP DGTVKVLIYY TSTLHLGVPS RFSGSGSGTD YSLTISNLEL EDIATYYCQQ YYNLPWTFGQ GTKVEIK |
| 66 heavy chain variable domain VH, MDX26H10 (26H10) (US 2011/0150892) | QVQLVESGGG VVQPGRSLRL SCAASGFTFS SYGMHWVRQA PGKGLEWVAV IWYDGSNKYY ADSVKGRFTI SRDNSKNTLY LQMNSLRAED TAVYYCAREW AVASWDYGMD VWGQGTTVTV SS |
| 67 light chain variable domain VL, MDX26H10 (26H10) (US 2011/0150892) | EIVLTQSPGT LSLSPGERAT LSCRASQSVS SSYLAWYQQK PGQAPRLLIY GASSRATGIP DRFSGSGSGT DFTLTISRLE PEDFAVYYCQ QYGSSPFTFG PGTKVDIK |

TABLE C-continued

| (Sequences): | | |
|---|---|---|
| SEQ ID NO: Name | Sequence | |

| SEQ ID NO: Name | Sequence | | |
|---|---|---|---|
| 68 human kappa light chain constant region | RTVAAPSVFI | FPPSDEQLKS | GTASVVCLLN |
| | NFYPREAKVQ | WKVDNALQSG | NSQESVTEQD |
| | SKDSTYSLSS | TLTLSKADYE | KHKVYACEVT |
| | HQGLSSPVTK | SFNRGEC | |
| 69 human lambda light chain constant region | QPKAAPSVTL | FPPSSEELQA | NKATLVCLIS |
| | DFYPGAVTVA | WKADSSPVKA | GVETTTPSKQ |
| | SNNKYAASSY | LSLTPEQWKS | HRSYSCQVTH |
| | EGSTVEKTVA | PTECS | |
| 70 human heavy chain constant region derived from IgG1 | ASTKGPSVFP | LAPSSKSTSG | GTAALGCLVK |
| | DYFPEPVTVS | WNSGALTSGV | HTFPAVLQSS |
| | GLYSLSSVVT | VPSSSLGTQT | YICNVNHKPS |
| | NTKVDKKVEP | KSCDKTHTCP | PCPAPELLGG |
| | PSVFLFPPKP | KDTLMISRTP | EVTCVVVDVS |
| | HEDPEVKFNW | YVDGVEVHNA | KTKPREEQYN |
| | STYRVVSVLT | VLHQDWLNGK | EYKCKVSNKA |
| | LPAPIEKTIS | KAKGQPREPQ | VYTLPPSRDE |
| | LTKNQVSLTC | LVKGFYPSDI | AVEWESNGQP |
| | ENNYKTTPPV | LDSDGSFFLY | SKLTVDKSRW |
| | QQGNVFSCSV | MHEALHNHYT | QKSLSLSPG |
| 71 human heavy chain constant region derived from IgG1 with mutations L234A, L235A and P329G | ASTKGPSVFP | LAPSSKSTSG | GTAALGCLVK |
| | DYFPEPVTVS | WNSGALTSGV | HTFPAVLQSS |
| | GLYSLSSVVT | VPSSSLGTQT | YICNVNHKPS |
| | NTKVDKKVEP | KSCDKTHTCP | PCPAPEAAGG |
| | PSVFLFPPKP | KDTLMISRTP | EVTCVVVDVS |
| | HEDPEVKFNW | YVDGVEVHNA | KTKPREEQYN |
| | STYRVVSVLT | VLHQDWLNGK | EYKCKVSNKA |
| | LGAPIEKTIS | KAKGQPREPQ | VYTLPPSRDE |
| | LTKNQVSLTC | LVKGFYPSDI | AVEWESNGQP |
| | ENNYKTTPPV | LDSDGSFFLY | SKLTVDKSRW |
| | QQGNVFSCSV | MHEALHNHYT | QKSLSLSPG |
| 72 human heavy chain constant region derived from IgG4 | ASTKGPSVFP | LAPCSRSTSE | STAALGCLVK |
| | DYFPEPVTVS | WNSGALTSGV | HTFPAVLQSS |
| | GLYSLSSVVT | VPSSSLGTKT | YTCNVDHKPS |
| | NTKVDKRVES | KYGPPCPSCP | APEFLGGPSV |
| | FLFPPKPKDT | LMISRTPEVT | CVVVDVSQED |
| | PEVQFNWYVD | GVEVHNAKTK | PREEQFNSTY |
| | RVVSVLTVLH | QDWLNGKEYK | CKVSNKGLPS |
| | SIEKTISKAK | GQPREPQVYT | LPPSQEEMTK |
| | NQVSLTCLVK | GFYPSDIAVE | WESNGQPENN |
| | YKTTPPVLDS | DGSFFLYSRL | TVDKSRWQEG |
| | NVFSCSVMHE | ALHNHYTQKS | LSLSLG |
| 73 exemplary human LAG3 sequence (without signal sequence) | VPVVWAQEGA | PAQLPCSPTI | PLQDLSLLRR |
| | AGVTWQHQPD | SGPPAAAPGH | PLAPGPHPAA |
| | PSSWGPRPRR | YTVLSVGPGG | LRSGRLPLQP |
| | RVQLDERGRQ | RGDFSLWLRP | ARRADAGEYR |
| | AAVHLRDRAL | SCRLRLRLGQ | ASMTASPPGS |
| | LRASDWVILN | CSFSRPDRPA | SVHWFRNRGQ |
| | GRVPVRESPH | HHLAESFLFL | PQVSPMDSGP |
| | WGCILTYRDG | FNVSIMYNLT | VLGLEPPTPL |
| | TVYAGAGSRV | GLPCRLPAGV | GTRSFLTAKW |
| | TPPGGGPDLL | VTGDNGDFTL | RLEDVSQAQA |
| | GTYTCHIHLQ | EQQLNATVTL | AIITVTPKSF |
| | GSPGSLGKLL | CEVTPVSGQE | RFVWSSLDTP |
| | SQRSFSGPWL | EAQEAQLLSQ | PWQCQLYQGE |
| | RLLGAAVYFT | ELSSPGAQRS | GRAPGALPAG |
| | HLLLFLILGV | LSLLLLVTGA | FGFHLWRRQW |
| | RPRRFSALEQ | GIHPPQAQSK | IEELEQEPEP |
| | EPEPEPEPEP | EPEPEQL | |
| 74 human LAG3 Extracellular Domain (ECD) | VPVVWAQEGA | PAQLPCSPTI | PLQDLSLLRR |
| | AGVTWQHQPD | SGPPAAAPGH | PLAPGPHPAA |
| | PSSWGPRPRR | YTVLSVGPGG | LRSGRLPLQP |
| | RVQLDERGRQ | RGDFSLWLRP | ARRADAGEYR |
| | AAVHLRDRAL | SCRLRLRLGQ | ASMTASPPGS |
| | LRASDWVILN | CSFSRPDRPA | SVHWFRNRGQ |
| | GRVPVRESPH | HHLAESFLFL | PQVSPMDSGP |
| | WGCILTYRDG | FNVSIMYNLT | VLGLEPPTPL |
| | TVYAGAGSRV | GLPCRLPAGV | GTRSFLTAKW |
| | TPPGGGPDLL | VTGDNGDFTL | RLEDVSQAQA |

TABLE C-continued (Sequences):

| SEQ ID NO: | Name | Sequence |
|---|---|---|
| | | GTYTCHIHLQ EQQLNATVTL AIITVTPKSF GSPGSLGKLL CEVTPVSGQE RFVWSSLDTP SQRSFSGPWL EAQEAQLLSQ PWQCQLYQGE RLLGAAVYFT ELSSPGAQRS GRAPGALPAG HL |
| 75 | KIEELE (part of LAG3 intracellular domain) | KIEELE |
| 76 | primer rbHC.up | aagcttgcca ccatggagac tgggctgcgc tggcttc |
| 77 | primer rbHCf.do | ccattggtga gggtgcccga g |
| 78 | primer BcPCR_FHLC_leader.fw | atggacatga gggtccccgc |
| 79 | primer BcPCR_huCkappa.rev | gatttcaact gctcatcaga tggc |
| 80 | heavy chain HVR-H1, PD1-0098 | GYSITSDY |
| 81 | heavy chain HVR-H2, PD1-0098 | YSG |
| 82 | heavy chain HVR-H3, PD1-0098 | HGSAPWYFD |
| 83 | light chain HVR-L1, PD1-0098 | SQNIVHSDGNTY |
| 84 | light chain HVR-L2, PD1-0098 | KVS |
| 85 | light chain HVR-L3, PD1-0098 | GSHFPL |
| 86 | heavy chain variable domain VH, PD1-0098 | DVQLQESGPGLVKPSQSLSLTCTVTGYSITSDYA WNWIRQFPGDKLEWLGYITYSGFTNYNPSLKSRI SISRDTSKNQFFLQLNSVATEDTATYYCARWHGS APWYFDYWGRGTTLTVSS |
| 87 | light chain variable domain VL, PD1-0098 | DVLMTQTPLSLPVSLGDQASISCRSSQNIVHSDG NTYLEWYLQKPGQSPNLLIYKVSRRFSGVPDRFS GSGSGTDFTLKISRVEAEDLGVYYCFQGSHFPLT FGAGTKLELK |
| 88 | heavy chain HVR-H1, PD1-0069 | GYTFTDY |
| 89 | heavy chain HVR-H2, PD1-0069 | YSG |
| 90 | heavy chain HVR-H3, PD1-0069 | GITTGFA |
| 91 | light chain HVR-L1, PD1-0069 | SKGVSTSSYSF |
| 92 | light chain HVR-L2, PD1-0069 | YAS |
| 93 | light chain HVR-L3, PD1-0069 | SREFPW |
| 94 | heavy chain variable domain VH, PD1-0069 | QVQLQQSGPELVRPGVSVKISCKGSGYTFTDYAM HWVKQSHARTLEWIGVISTYSGDTNYNQKFKDKA TMTVDKSSSTAYLELARMTSEDSAIYYCARLGIT TGFAYWGQGTLVTVSA |
| 95 | light chain variable domain VL, PD1-0069 | DIVLTQSPASLAVSLGQRATISCRASKGVSTSSY SFMHWYQQKPRQPPKLLIKYASYLESGVPARFSG SGSGTDFTLNIHPVEEEDAATYYCHHSREFPWTF GGGTKLEIK |
| 96 | heavy chain 1 of 1 + 1 PD1/LAG3 0799 based on PD1(0376)/aLAG3(0416) | DIVMTQSPDSLAVSLGERATINCKASESVDTSDN SFIHWYQQKPGQSPKLLIYRSSTLESGVPDRFSG SGSGTDFTLTISSLQAEDVAVYYCQQNYDVPWTF GQGTKVEIKSSASTKGPSVFPLAPSSKSTSGGTA ALGCLVKDYFPEPVTVSWNSGALTSGVHTFPAVL QSSGLYSLSSVVTVPSSSLGTQTYICNVNHKPSN TKVDKKVEPKSCDKTHTCPPCPAPEAAGGPSVFL FPPKPKDTLMISRTPEVTCVVVDVSHEDPEVKFN WYVDGVEVHNAKTKPREEQYNSTYRVVSVLTVLH QDWLNGKEYKCKVSNKALGAPIEKTISKAKGQPR EPQVYTLPPCRDELTKNQVSLWCLVKGFYPSDIA VEWESNGQPENNYKTTPPVLDSDGSFFLYSKLTV |

TABLE C-continued

| | (Sequences): |
|---|---|

| SEQ ID NO: Name | Sequence |
|---|---|
| | DKSRWQQGNVFSCSVMHEALHNHYTQKSLSLSPG K |
| 97 heavy chain 2 of 1 + 1 PD1/LAG3 0799 | EVQLVESGGGLVQPGGSLRLACAASGFTFSDYAM SWVRQAPGKGLEWVSGIDNSGYYTYYTDSVKGRF TISRDDVKNTLYLQMNSLRAEDTAVYLCTKTHSG LIVNDAFDIWGQGTMVTVSSASTKGPSVFPLAPS SKSTSGGTAALGCLVEDYFPEPVTVSWNSGALTS GVHTFPAVLQSSGLYSLSSVVTVPSSSLGTQTYI CNVNHKPSNTKVDEKVEPKSCDKTHTCPPCPAPE AAGGPSVFLFPPKPKDTLMISRTPEVTCVVVDVS HEDPEVKFNWYVDGVEVHNAKTKPREEQYNSTYR VVSVLTVLHQDWLNGKEYKCKVSNKALGAPIEKT ISKAKGQPREPQVCTLPPSRDELTKNQVSLSCAV KGFYPSDIAVEWESNGQPENNYKTTPPVLDSDGS FFLVSKLTVDKSRWQQGNVFSCSVMHEALHNHYT QKSLSLSPGK |
| 98 light chain 1 of 1 + 1 PD1/LAG3 0799 | EVQLLESGGGLVQPGGSLRLSCAASGFSFSSYTM SWVRQAPGKGLEWVATISGGGRDIYYPDSVKGRF TISRDNSKNTLYLQMNSLRAEDTAVYYCVLLTGR VYFALDSWGQGTLVTVSSASVAAPSVFIFPPSDE QLKSGTASVVCLLNNFYPREAKVQWKVDNALQSG NSQESVTEQDSKDSTYSLSSTLTLSKADYEKHKV YACEVTHQGLSSPVTKSFNRGEC |
| 99 light chain 2 of 1 + 1 PD1/LAG3 0799 | DIQLTQSPSSLSASVGDRVTITCRASQSISSYLN WYQQKPGKAPKLLIYDASSLESGVPSRFSGSGSG TDATLTISSLQPEDFATYYCQQSYSTPLTFGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 100 heavy chain 2 of 1 + 1 PD1/LAG3 0927 based on PD1(0376)/aLAG3(0414) | EVQLLESGGGLVQPGGSLRLSCAASGFIFDDYTM NWVRQAPGKGLEWVAVISWDGGGTYYTDSVKGRF TISRDDFKNTLYLQMNSLRAEDTAVYYCAKGLTD TTLYGSDYWGQGTLVTVSSASTKGPSVFPLAPSS KSTSGGTAALGCLVEDYFPEPVTVSWNSGALTSG VHTFPAVLQSSGLYSLSSVVTVPSSSLGTQTYIC NVNHKPSNTKVDEKVEPKSCDKTHTCPPCPAPEA AGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALGAPIEKTI SKAKGQPREPQVCTLPPSRDELTKNQVSLSCAVK GFYPSDIAVEWESNGQPENNYKTTPPVLDSDGSF FLVSKLTVDKSRWQQGNVFSCSVMHEALHNHYTQ KSLSLSPGK |
| 101 light chain 2 of 1 + 1 PD1/LAG3 0927 | DIQMTQSPSSLSASVGDRVTITCRASQSISSYLN WYQQKPGKAPKLLIYAASTLQSGVPSRFSGSGSG TDFTLTISSLQPEDFATYYCQQTYSSPLTFGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 102 heavy chain 1 of 1 + 1 PD1/LAG3 0222 based on PD1(0069)/ aLAG3(MDX25F7) | DIVLTQSPASLAVSLGQRATISCRASKGVSTSSY SFMHWYQQKPRQPPKLLIKYASYLESGVPARFSG SGSGTDFTLNIHPVEEEDAATYYCHHSREFPWTF GGGTKLEIKSSASTKGPSVFPLAPSSKSTSGGTA ALGCLVKDYFPEPVTVSWNSGALTSGVHTFPAVL QSSGLYSLSSVVTVPSSSLGTQTYICNVNHKPSN TKVDKKVEPKSCDKTHTCPPCPAPEAAGGPSVFL FPPKPKDTLMISRTPEVTCVVVDVSHEDPEVKFN WYVDGVEVHNAKTKPREEQYNSTYRVVSVLTVLH QDWLNGKEYKCKVSNKALGAPIEKTISKAKGQPR EPQVYTLPPCRDELTKNQVSLWCLVKGFYPSDIA VEWESNGQPENNYKTTPPVLDSDGSFFLYSKLTV DKSRWQQGNVFSCSVMHEALHNHYTQKSLSLSPG K |

TABLE C-continued (Sequences):

| SEQ ID NO: | Name | Sequence |
|---|---|---|
| 103 | heavy chain 2 of 1 + 1 PD1/LAG3 0222 | QVQLQQWGAGLLKPSETLSLTCAVYGGSFSDYYW NWIRQPPGKGLEWIGEINHNGNTNSNPSLKSRVT LSLDTSKNQFSLKLRSVTAADTAVYYCAFGYSDY EYNWFDPWGQGTLVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVCTLPPSRDELTKNQVSLSCAVKG FYPSDIAVEWESNGQPENNYKTTPPVLDSDGSFF LVSKLTVDKSRWQQGNVFSCSVMHEALHNHYTQK SLSLSPGK |
| 104 | light chain 1 of 1 + 1 PD1/LAG3 0222 | QVQLQQSGPELVRPGVSVKISCKGSGYTFTDYAM HWVKQSHARTLEWIGVISTYSGDTNYNQKFKDKA TMTVDKSSSTAYLELARMTSEDSAIYYCARLGIT TGFAYWGQGTLVTVSAASVAAPSVFIFPPPSDEQL KSGTASVVCLLNNFYPREAKVQWKVDNALQSGNS QESVTEQDSKDSTYSLSSTLTLSKADYEKHKVYA CEVTHQGLSSPVTKSFNRGEC |
| 105 | light chain 2 of 1 + 1 PD1/LAG3 0222 | EIVLTQSPATLSLSPGERATLSCRASQSISSYLA WYQQKPGQAPRLLIYDASNRATGIPARFSGSGSG TDFTLTISSLEPEDFAVYYCQQRSNWPLTFGQGT NLEIKRTVAAPSVFIFPPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 106 | heavy chain 1 of 1 + 1 PD1/LAG3 0224 based on PD1(0098)/ aLAG3(MDX25F7) | DVLMTQTPLSLPVSLGDQASISCRSSQNIVHSDG NTYLEWYLQKPGQSPNLLIYKVSRRFSGVPDRFS GSGSGTDFTLKISRVEAEDLGVYYCFQGSHFPLT FGAGTKLELKSSASTKGPSVFPLAPSSKSTSGGT AALGCLVKDYFPEPVTVSWNSGALTSGVHTFPAV LQSSGLYSLSSVVTVPSSSLGTQTYICNVNHKPS NTKVDKKVEPKSCDKTHTCPPCPAPEAAGGPSVF LFPPKPKDTLMISRTPEVTCVVVDVSHEDPEVKF NWYVDGVEVHNAKTKPREEQYNSTYRVVSVLTVL HQDWLNGKEYKCKVSNKALGAPIEKTISKAKGQP REPQVYTLPPCRDELTKNQVSLWCLVKGFYPSDI AVEWESNGQPENNYKTTPPVLDSDGSFFLYSKLT VDKSRWQQGNVFSCSVMHEALHNHYTQKSLSLSP GK |
| 107 | light chain 1 of 1 + 1 PD1/LAG3 0224 | DVQLQESGPGLVKPSQSLSLTCTVTGYSITSDYA WNWIRQFPGDKLEWLGYITYSGFTNYNPSLKSRI SISRDTSKNQFFLQLNSVATEDTATYYCARWHGS APWYFDYWGRGTTLTVSSASVAAPSVFIFPPPSDE QLKSGTASVVCLLNNFYPREAKVQWKVDNALQSG NSQESVTEQDSKDSTYSLSSTLTLSKADYEKHKV YACEVTHQGLSSPVTKSFNRGEC |
| 108 | aLAG3(0156) heavy chain (MDX25F7) | QVQLQQWGAGLLKPSETLSLTCAVYGGSFSDYYW NWIRQPPGKGLEWIGEINHNGNTNSNPSLKSRVT LSLDTSKNQFSLKLRSVTAADTAVYYCAFGYSDY EYNWFDPWGQGTLVTVSSGQPKAPSVFPLAPCCG DTPSSTVTLGCLVKGYLPEPVTVTWNSGTLTNGV RTFPSVRQSSGLYSLSSVVSVTSSSQPVTCNVAH PATNTKVDKTVAPSTCSKPTCPPPELLGGPSVFI FPPKPKDTLMISRTPEVTCVVVDVSQDDPEVQFT WYINNEQVRTARPPLREQQFNSTIRVVSTLPIAH QDWLRGKEFKCKVHNKALPAPIEKTISKARGQPL EPKVYTMGPPREELSSRSVSLTCMINGFYPSDIS VEWEKNGKAEDNYKTTPAVLDSDGSYFLYNKLSV PTSEWQRGDVFTCSVMHEALHNHYTQKSISRSPG K |
| 109 | aLAG3(0156) light chain (MDX25F7) | EIVLTQSPATLSLSPGERATLSCRASQSISSYLA WYQQKPGQAPRLLIYDASNRATGIPARFSGSGSG TDFTLTISSLEPEDFAVYYCQQRSNWPLTFGQGT NLEIKRTVAAPSVFIFPPPSDEQLKSGTASVVCLL |

TABLE C-continued (Sequences):

| SEQ ID NO: Name | Sequence |
|---|---|
| | NNFYPREAKVQWKVDNALQSGNSQESVTEQDSKD STYSLSSTLTLSKADYEKHKVYACEVTHQGLSSP VTKSFNRGEC |
| 110 aLAG3(0414) heavy chain | EVQLLESGGGLVQPGGSLRLSCAASGFIFDDYTM NWVRQAPGKGLEWVAVISWDGGGTYYTDSVKGRF TISRDDFKNTLYLQMNSLRAEDTAVYYCAKGLTD TTLYGSDYWGQGTLVTVSSGQPKAPSVFPLAPCC GDTPSSTVTLGCLVKGYLPEPVTVTWNSGTLTNG VRTFPSVRQSSGLYSLSSVVSVTSSSQPVTCNVA HPATNTKVDKTVAPSTCSKPTCPPPELLGGPSVF IFPPPKPKDTLMISRTPEVTCVVVDVSQDDPEVQF TWYINNEQVRTARPPLREQQFNSTIRVVSTLPIA HQDWLRGKEFKCKVHNKALPAPIEKTISKARGQP LEPKVYTMGPPREELSSRSVSLTCMINGFYPSDI SVEWEKNGKAEDNYKTTPAVLDSDGSYFLYNKLS VPTSEWQRGDVFTCSVMHEALHNHYTQKSISRSP GK |
| 111 aLAG3(0414) light chain | DIQMTQSPSSLSASVGDRVTITCRASQSISSYLN WYQQKPGKAPKLLIYAASTLQSGVPSRFSGSGSG TDFTLTISSLQPEDFATYYCQQTYSSPLTFGGGT KVEIKGTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 112 aLAG3(0416) heavy chain | EVQLVESGGGLVQPGGSLRLACAASGFTFSDYAM SWVRQAPGKGLEWVSGIDNSGYYTYYTDSVKGRF TISRDDVKNTLYLQMNSLRAEDTAVYLCTKTHSG LIVNDAFDIWGQGTMVTVSSGQPKAPSVFPLAPC CGDTPSSTVTLGCLVKGYLPEPVTVTWNSGTLTN GVRTFPSVRQSSGLYSLSSVVSVTSSSQPVTCNV AHPATNTKVDKTVAPSTCSKPTCPPPELLGGPSV FIFPPPKPKDTLMISRTPEVTCVVVDVSQDDPEVQ FTWYINNEQVRTARPPLREQQFNSTIRVVSTLPI AHQDWLRGKEFKCKVHNKALPAPIEKTISKARGQ PLEPKVYTMGPPREELSSRSVSLTCMINGFYPSD ISVEWEKNGKAEDNYKTTPAVLDSDGSYFLYNKL SVPTSEWQRGDVFTCSVMHEALHNHYTQKSISRS PGK |
| 113 aLAG3(0416) light chain | DIQLTQSPSSLSASVGDRVTITCRASQSISSYLN WYQQKPGKAPKLLIYDASSLESGVPSRFSGSGSG TDATLTISSLQPEDFATYYCQQSYSTPLTFGGGT KVEIKGTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 114 heavy chain of 2 + 2 PD1/LAG3 8970 based on PD 1(0376)/aLAG3(0414) | EVQLLESGGGLVQPGGSLRLSCAASGFIFDDYTM NWVRQAPGKGLEWVAVISWDGGGTYYTDSVKGRF TISRDDFKNTLYLQMNSLRAEDTAVYYCAKGLTD TTLYGSDYWGQGTLVTVSSASTKGPSVFPLAPSS KSTSGGTAALGCLVEDYFPEPVTVSWNSGALTSG VHTFPAVLQSSGLYSLSSVVTVPSSSLGTQTYIC NVNHKPSNTKVDEKVEPKSCDKTHTCPPCPAPEA AGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALGAPIEKTI SKAKGQPREPQVYTLPPSRDELTKNQVSLTCLVK GFYPSDIAVEWESNGQPENNYKTTPPVLDSDGSF FLYSKLTVDKSRWQQGNVFSCSVMHEALHNHYTQ KSLSLSPGGGSGGGGSGGGGSGGGGSEVQLLESG GGLVQPGGSLRLSCAASGFSFSSYTMSWVRQAPG KGLEWVATISGGGRDIYYPDSVKGRFTISRDNSK NTLYLQMNSLRAEDTAVYYCVLLTGRVYFALDSW GQGTLVTVSSASVAAPSVFIFPPSDEQLKSGTAS VVCLLNNFYPREAKVQWKVDNALQSGNSQESVTE QDSKDSTYSLSSTLTLSKADYEKHKVYACEVTHQ GLSSPVTKSFNRGEC |

TABLE C-continued

| (Sequences): | |
|---|---|

| SEQ ID NO: Name | Sequence |
|---|---|
| 115 light chain 1 of 2 + 2 PD1/LAG3 8970 | DIVMTQSPDSLAVSLGERATINCKASESVDTSDN SFIHWYQQKPGQSPKLLIYRSSTLESGVPDRFSG SGSGTDFTLTISSLQAEDVAVYYCQQNYDVPWTF GQGTKVEIKSSASTKGPSVFPLAPSSKSTSGGTA ALGCLVKDYFPEPVTVSWNSGALTSGVHTFPAVL QSSGLYSLSSVVTVPSSSLGTQTYICNVNHKPSN TKVDKKVEPKSC |
| 116 heavy chain of 2 + 2 PD1/LAG3 8984 based on PD1(0376)/aLAG3(0416) | EVQLVESGGGLVQPGGSLRLACAASGFTFSDYAM SWVRQAPGKGLEWVSGIDNSGYYTYYTDSVKGRF TISRDDVKNTLYLQMNSLRAEDTAVYLCTKTHSG LIVNDAFDIWGQGTMVTVSSASTKGPSVFPLAPS SKSTSGGTAALGCLVEDYFPEPVTVSWNSGALTS GVHTFPAVLQSSGLYSLSSVVTVPSSSLGTQTYI CNVNHKPSNTKVDEKVEPKSCDKTHTCPPCPAPE AAGGPSVFLFPPKPKDTLMISRTPEVTCVVVDVS HEDPEVKFNWYVDGVEVHNAKTKPREEQYNSTYR VVSVLTVLHQDWLNGKEYKCKVSNKALGAPIEKT ISKAKGQPREPQVYTLPPSRDELTKNQVSLTCLV KGFYPSDIAVEWESNGQPENNYKTTPPVLDSDGS FFLYSKLTVDKSRWQQGNVFSCSVMHEALHNHYT QKSLSLSPGGGSGGGGSGGGGSGGGGSEVQLLES GGGLVQPGGSLRLSCAASGFSFSSYTMSWVRQAP GKGLEWVATISGGGRDIYYPDSVKGRFTISRDNS KNTLYLQMNSLRAEDTAVYYCVLLTGRVYFALDS WGQGTLVTVSSASVAAPSVFIFPPSDEQLKSGTA SVVCLLNNFYPREAKVQWKVDNALQSGNSQESVT EQDSKDSTYSLSSTLTLSKADYEKHKVYACEVTH QGLSSPVTKSFNRGEC |
| 117 heavy chain of 2 + 2 PD1/LAG3 9010 based on PD1(0376)/ aLAG3(MDX25F7) | QVQLQQWGAGLLKPSETLSLTCAVYGGSFSDYYW NWIRQPPGKGLEWIGEINHNGNTNSNPSLKSRVT LSLDTSKNQFSLKLRSVTAADTAVYYCAFGYSDY EYNWFDPWGQGTLVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPSRDELTKNQVSLTCLVKG FYPSDIAVEWESNGQPENNYKTTPPVLDSDGSFF LYSKLTVDKSRWQQGNVFSCSVMHEALHNHYTQK SLSLSPGGGSGGGGSGGGGSGGGGSEVQLLESGG GLVQPGGSLRLSCAASGFSFSSYTMSWVRQAPGK GLEWVATISGGGRDIYYPDSVKGRFTISRDNSKN TLYLQMNSLRAEDTAVYYCVLLTGRVYFALDSWG QGTLVTVSSASVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| 118 heavy chain 1 of 2 + 1 PD1/LAG3 8310 based on aLAG3(0414)/PD1(0376) | EVQLLESGGGLVQPGGSLRLSCAASGFIFDDYTM NWVRQAPGKGLEWVAVISWDGGGTYYTDSVKGRF TISRDDFKNTLYLQMNSLRAEDTAVYYCAKGLTD TTLYGSDYWGQGTLVTVSSASTKGPSVFPLAPSS KSTSGGTAALGCLVEDYFPEPVTVSWNSGALTSG VHTFPAVLQSSGLYSLSSVVTVPSSSLGTQTYIC NVNHKPSNTKVDEKVEPKSCDKTHTCPPCPAPEA AGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALGAPIEKTI SKAKGQPREPQVYTLPPCRDELTKNQVSLWCLVK GFYPSDIAVEWESNGQPENNYKTTPPVLDSDGSF FLYSKLTVDKSRWQQGNVFSCSVMHEALHNHYTQ KSLSLSPGGGSGGGGSGGGGSGGGGSEVQLLESG GGLVQPGGSLRLSCAASGFSFSSYTMSWVRQAPG KGLEWVATISGGGRDIYYPDSVKGRFTISRDNSK NTLYLQMNSLRAEDTAVYYCVLLTGRVYFALDSW GQGTLVTVSSASVAAPSVFIFPPSDEQLKSGTAS VVCLLNNFYPREAKVQWKVDNALQSGNSQESVTE QDSKDSTYSLSSTLTLSKADYEKHKVYACEVTHQ GLSSPVTKSFNRGEC |

TABLE C-continued

| (Sequences): | |
|---|---|

| SEQ ID NO: Name | Sequence |
|---|---|
| 119 heavy chain 2 of 2 + 1 PD1/LAG3 8310 | EVQLLESGGGLVQPGGSLRLSCAASGFIFDDYTM NWVRQAPGKGLEWVAVISWDGGGTYYTDSVKGRF TISRDDFKNTLYLQMNSLRAEDTAVYYCAKGLTD TTLYGSDYWGQGTLVTVSSASTKGPSVFPLAPSS KSTSGGTAALGCLVEDYFPEPVTVSWNSGALTSG VHTFPAVLQSSGLYSLSSVVTVPSSSLGTQTYIC NVNHKPSNTKVDEKVEPKSCDKTHTCPPCPAPEA AGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALGAPIEKTI SKAKGQPREPQVCTLPPSRDELTKNQVSLSCAVK GFYPSDIAVEWESNGQPENNYKTTPPVLDSDGSF FLVSKLTVDKSRWQQGNVFSCSVMHEALHNHYTQ KSLSLSPGK |
| 120 heavy chain 1 of 2 + 1 PD1/LAG3 8311 based on aLAG3(0416)/PD1(0376) | EVQLVESGGGLVQPGGSLRLACAASGFTFSDYAM SWVRQAPGKGLEWVSGIDNSGYYTYYTDSVKGRF TISRDDVKNTLYLQMNSLRAEDTAVYLCTKTHSG LIVNDAFDIWGQGTMVTVSSASTKGPSVFPLAPS SKSTSGGTAALGCLVEDYFPEPVTVSWNSGALTS GVHTFPAVLQSSGLYSLSSVVTVPSSSLGTQTYI CNVNHKPSNTKVDEKVEPKSCDKTHTCPPCPAPE AAGGPSVFLFPPKPKDTLMISRTPEVTCVVVDVS HEDPEVKFNWYVDGVEVHNAKTKPREEQYNSTYR VVSVLTVLHQDWLNGKEYKCKVSNKALGAPIEKT ISKAKGQPREPQVYTLPPCRDELTKNQVSLWCLV KGFYPSDIAVEWESNGQPENNYKTTPPVLDSDGS FFLYSKLTVDKSRWQQGNVFSCSVMHEALHNHYT QKSLSLSPGGGSGGGGSGGGGSGGGGSEVQLLES GGGLVQPGGSLRLSCAASGFSFSSYTMSWVRQAP GKGLEWVATISGGGRDIYYPDSVKGRFTISRDNS KNTLYLQMNSLRAEDTAVYYCVLLTGRVYFALDS WGQGTLVTVSSASVAAPSVFIFPPSDEQLKSGTA SVVCLLNNFYPREAKVQWKVDNALQSGNSQESVT EQDSKDSTYSLSSTLTLSKADYEKHKVYACEVTH QGLSSPVTKSFNRGEC |
| 121 heavy chain 2 of 2 + 1 PD1/LAG3 8311 | EVQLVESGGGLVQPGGSLRLACAASGFTFSDYAM SWVRQAPGKGLEWVSGIDNSGYYTYYTDSVKGRF TISRDDVKNTLYLQMNSLRAEDTAVYLCTKTHSG LIVNDAFDIWGQGTMVTVSSASTKGPSVFPLAPS SKSTSGGTAALGCLVEDYFPEPVTVSWNSGALTS GVHTFPAVLQSSGLYSLSSVVTVPSSSLGTQTYI CNVNHKPSNTKVDEKVEPKSCDKTHTCPPCPAPE AAGGPSVFLFPPKPKDTLMISRTPEVTCVVVDVS HEDPEVKFNWYVDGVEVHNAKTKPREEQYNSTYR vvSVLTVLHQDWLNGKEYKCKVSNKALGAPIEKT ISKAKGQPREPQVCTLPPSRDELTKNQVSLSCAV KGFYPSDIAVEWESNGQPENNYKTTPPVLDSDGS FFLVSKLTVDKSRWQQGNVFSCSVMHEALHNHYT QKSLSLSPGK |
| 122 heavy chain 1 of 2 + 1 PD1/LAG3 1252 based on aLAG3(25F7)/PD1(0376) | QVQLQQWGAGLLKPSETLSLTCAVYGGSFSDYYW NWIRQPPGKGLEWIGEINHNGNTNSNPSLKSRVT LSLDTSKNQFSLKLRSVTAADTAVYYCAFGYSDY EYNWFDPWGQGTLVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKT1S KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSPGGGSGGGGSGGGGSGGGGSEVQLLESGG GLVQPGGSLRLSCAASGFSFSSYTMSWVRQAPGK GLEWVATISGGGRDIYYPDSVKGRFTISRDNSKN TLYLQMNSLRAEDTAVYYCVLLTGRVYFALDSWG QGTLVTVSSASVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |

TABLE C-continued

| (Sequences): | |
|---|---|

| SEQ ID NO: Name | Sequence |
|---|---|
| 123 heavy chain 1 of 2 + 1 PD1/LAG3 8312 based on aLAG3(0414)/PD1(0376) | EVQLLESGGGLVQPGGSLRLSCAASGFIFDDYTM NWVRQAPGKGLEWVAVISWDGGGTYYTDSVKGRF TISRDDFKNTLYLQMNSLRAEDTAVYYCAKGLTD TTLYGSDYWGQGTLVTVSSASTKGPSVFPLAPSS KSTSGGTAALGCLVEDYFPEPVTVSWNSGALTSG VHTFPAVLQSSGLYSLSSVVTVPSSSLGTQTYIC NVNHKPSNTKVDEKVEPKSCDKTHTCPPCPAPEA AGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALGAPIEKTI SKAKGQPREPQVYTLPPCRDELTKNQVSLWCLVK GFYPSDIAVEWESNGQPENNYKTTPPVLDSDGSF FLYSKLTVDKSRWQQGNVFSCSVMHEALHNHYTQ KSLSLSPGGGGSGGGGSGGGGSGGGGSDIVMTQ SPDSLAVSLGERATINCKASESVDTSDNSFIHWY QQKPGQSPKLLIYRSSTLESGVPDRFSGSGSGTD FTLTISSLQAEDVAVYYCQQNYDVPWTFGQGTKV EIKRTVAAPSVFIFPPSDEQLKSGTASVVCLLNN FYPREAKVQWKVDNALQSGNSQESVTEQDSKDST YSLSSTLTLSKADYEKHKVYACEVTHQGLSSPVT KSFNRGECGGGGSGGGGSGGGGSGGGGSGGGGSG GGGGSEVQLLESGGGLVQPGGSLRLSCAASGFSFS SYTMSWVRQAPGKGLEWVATISGGGRDIYYPDSV KGRFTISRDNSKNTLYLQMNSLRAEDTAVYYCVL LTGRVYFALDSWGQGTLVTVSSASTKGPSVFPLA PSSKSTSGGTAALGCLVKDYFPEPVTVSWNSGAL TSGVHTFPAVLQSSGLYSLSSVVTVPSSSLGTQT YICNVNHKPSNTKVDKKVEPKSC |
| 124 heavy chain 1 of 2 + 1 PD1/LAG3 8313 based on aLAG3(0416)/PD1(0376) | EVQLVESGGGLVQPGGSLRLACAASGFTFSDYAM SWVRQAPGKGLEWVSGIDNSGYYTYYTDSVKGRF TISRDDVKNTLYLQMNSLRAEDTAVYLCTKTHSG LIVNDAFDIWGQGTMVTVSSASTKGPSVFPLAPS SKSTSGGTAALGCLVEDYFPEPVTVSWNSGALTS GVHTFPAVLQSSGLYSLSSVVTVPSSSLGTQTYI CNVNHKPSNTKVDEKVEPKSCDKTHTCPPCPAPE AAGGPSVFLFPPKPKDTLMISRTPEVTCVVVDVS HEDPEVKFNWYVDGVEVHNAKTKPREEQYNSTYR VVSVLTVLHQDWLNGKEYKCKVSNKALGAPIEKT ISKAKGQPREPQVYTLPPCRDELTKNQVSLWCLV KGFYPSDIAVEWESNGQPENNYKTTPPVLDSDGS FFLYSKLTVDKSRWQQGNVFSCSVMHEALHNHYT QKSLSLSPGGGGSGGGGSGGGGSGGGGSDIVMT QSPDSLAVSLGERATINCKASESVDTSDNSFIHW YQQKPGQSPKLLIYRSSTLESGVPDRFSGSGSGT DFTLTISSLQAEDVAVYYCQQNYDVPWTFGQGTK VEIKRTVAAPSVFIFPPSDEQLKSGTASVVCLLN NFYPREAKVQWKVDNALQSGNSQESVTEQDSKDS TYSLSSTLTLSKADYEKHKVYACEVTHQGLSSPV TKSFNRGECGGGGSGGGGSGGGGSGGGGSGGGGS GGGGSEVQLLESGGGLVQPGGSLRLSCAASGFSF SSYTMSWVRQAPGKGLEWVATISGGGRDIYYPDS VKGRFTISRDNSKNTLYLQMNSLRAEDTAVYYCV LLTGRVYFALDSWGQGTLVTVSSASTKGPSVFPL APSSKSTSGGTAALGCLVKDYFPEPVTVSWNSGA LTSGVHTFPAVLQSSGLYSLSSVVTVPSSSLGTQ TYICNVNHKPSNTKVDKKVEPKSC |
| 125 heavy chain 1 of 2 + 1 PD1/LAG3 1088 based on aLAG3(25F7)/PD1(0376) | QVQLQQWGAGLLKPSETLSLTCAVYGGSFSDYYW NWIRQPPGKGLEWIGEINHNGNTNSNPSLKSRVT LSLDTSKNQFSLKLRSVTAADTAVYYCAFGYSDY EYNWFDPWGQGTLVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSPGGGGSGGGGSGGGGSGGGGSDIVMTQS PDSLAVSLGERATINCKASESVDTSDNSFIHWYQ |

TABLE C-continued (Sequences):

| SEQ ID NO: Name | Sequence |
|---|---|
| | QKPGQSPKLLIYRSSTLESGVPDRFSGSGSGTDF TLTISSLQAEDVAVYYCQQNYDVPWTFGQGTKVE IKRTVAAPSVFIFPPSDEQLKSGTASVVCLLNNF YPREAKVQWKVDNALQSGNSQESVTEQDSKDSTY SLSSTLTLSKADYEKHKVYACEVTHQGLSSPVTK SFNRGECGGGGSGGGGSGGGGSGGGGSGGGGSGG GGSEVQLLESGGGLVQPGGSLRLSCAASGFSFSS YTMSWVRQAPGKGLEWVATISGGGRDIYYPDSVK GRFTISRDNSKNTLYLQMNSLRAEDTAVYYCVLL TGRVYFALDSWGQGTLVTVSSASTKGPSVFPLAP SSKSTSGGTAALGCLVKDYFPEPVTVSWNSGALT SGVHTFPAVLQSSGLYSLSSVVTVPSSSLGTQTY ICNVNHKPSNTKVDKKVEPKSC |
| 126 heavy chain 1 of 2 + 1 PD1/LAG3 0918 based on aLAG3(25F7)/PD1(0376) | QVQLQQWGAGLLKPSETLSLTCAVYGGSFSDYYW NWIRQPPGKGLEWIGEINHNGNTNSNPSLKSRVT LSLDTSKNQFSLKLRSVTAADTAVYYCAFGYSDY EYNWFDPWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKT1S KAKGQPREPQVCTLPPSRDELTKNQVSLSCAVKG FYPSDIAVEWESNGQPENNYKTTPPVLDSDGSFF LVSKLTVDKSRWQQGNVFSCSVMHEALHNHYTQK SLSLSPGGGGGSGGGGSGGGGSGGGGSEVQLLES GGGLVQPGGSLRLSCAASGFSFSSYTMSWVRQAP GKGLEWVATISGGGRDIYYPDSVKGRFTISRDNS KNTLYLQMNSLRAEDTAVYYCVLLTGRVYFALDS WGQGTLVTVSS |
| 127 heavy chain 2 of 2 + 1 PD1/LAG3 0918 | QVQLQQWGAGLLKPSETLSLTCAVYGGSFSDYYW NWIRQPPGKGLEWIGEINHNGNTNSNPSLKSRVT LSLDTSKNQFSLKLRSVTAADTAVYYCAFGYSDY EYNWFDPWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSPGGGGGSGGGGSGGGGSGGGGSDIVMTQS PDSLAVSLGERATINCKASESVDTSDNSFIHWYQ QKPGQSPKLLIYRSSTLESGVPDRFSGSGSGTDF TLTISSLQAEDVAVYYCQQNYDVPWTFGQGTKVE IK |
| 128 human PD1 | UniProt accession no. Q15116 MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 129 Peptide linker G4S | GGGGS |
| 130 Peptide linker (G4S)2 | GGGGSGGGGS |
| 131 Peptide linker (SG4)2 | SGGGGSGGGG |
| 132 Peptide linker (G4S)2G4 | GGGGSGGGGSGGGG |
| 133 Peptide linker | GSPGSSSSGS |

TABLE C-continued (Sequences):

| SEQ ID NO: | Name | Sequence |
|---|---|---|
| 134 | Peptide linker (G4S)3 | GGGGSGGGGSGGGGS |
| 135 | Peptide linker (G4S)4 | GGGGSGGGGSGGGGSGGGGS |
| 136 | Peptide linker | GSGSGSGS |
| 137 | Peptide linker | GSGSGNGS |
| 138 | Peptide linker | GGSGSGSG |
| 139 | Peptide linker | GGSGSG |
| 140 | Peptide linker | GGSG |
| 141 | Peptide linker | GGSGNGSG |
| 142 | Peptide linker | GGNGSGSG |
| 143 | Peptide linker | GGNGSG |
| 144 | heavy chain 2 of 1 + 1 PD1/LAG3 0725 (1 + 1 trans) based on aLAG3(0414) | DKTHTCPPCPAPEAAGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALGAPIEKTISKAKGQPREPQVCTLPPSRD ELTKNQVSLSCAVKGFYPSDIAVEWESNGQPENN YKTTPPVLDSDGSFFLVSKLTVDKSRWQQGNVFS CSVMHEALHNHYTQKSLSLSPGKGGGGSGGGGSE VQLLESGGGLVQPGGSLRLSCAASGFIFDDYTMN WVRQAPGKGLEWVAVISWDGGGTYYTDSVKGRFT ISRDDFKNTLYLQMNSLRAEDTAVYYCAKGLTDT TLYGSDYWGQGTLVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSC |
| 145 | heavy chain 2 of 2 + 1 PD1/LAG3 0750 (2 + 1 trans) based on aLAG3(0414) | EVQLLESGGGLVQPGGSLRLSCAASGFIFDDYTM NWVRQAPGKGLEWVAVISWDGGGTYYTDSVKGRF TISRDDFKNTLYLQMNSLRAEDTAVYYCAKGLTD TTLYGSDYWGQGTLVTVSSASTKGPSVFPLAPSS KSTSGGTAALGCLVEDYFPEPVTVSWNSGALTSG VHTFPAVLQSSGLYSLSSVVTVPSSSLGTQTYIC NVNHKPSNTKVDEKVEPKSCDKTHTCPPCPAPEA AGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALGAPIEKTI SKAKGQPREPQVCTLPPSRDELTKNQVSLSCAVK GFYPSDIAVEWESNGQPENNYKTTPPVLDSDGSF FLVSKLTVDKSRWQQGNVFSCSVMHEALHNHYTQ KSLSLSPGKGGGGSGGGGSEVQLLESGGGLVQPG GSLRLSCAASGFIFDDYTMNWVRQAPGKGLEWVA VISWDGGGTYYTDSVKGRFTISRDDFKNTLYLQM NSLRAEDTAVYYCAKGLTDTTLYGSDYWGQGTLV TVSSASTKGPSVFPLAPSSKSTSGGTAALGCLVE DYFPEPVTVSWNSGALTSGVHTFPAVLQSSGLYS LSSVVTVPSSSLGTQTYICNVNHKPSNTKVDEKV EPKSC |
| 146 | Light chain "CEA2F1" (CEA TCB) | DIQMTQSPSSLSASVGDRVTITCKASAAVGTYVA WYQQKPGKAPKLLIYSASYRKRGVPSRFSGSGSG TDFTLTISSLQPEDFATYYCHQYYTYPLFTFGQG TKLEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC |
| 147 | Light Chain humanized CD3CH2527 (Crosstab, VL-CH1) (CEA TCB) | QAVVTQEPSLTVSPGGTVTLTCGSSTGAVTTSNY ANWVQEKPGQAFRGLIGGTNKRAPGTPARFSGSL LGGKAALTLSGAQPEDEAEYYCALWYSNLWVFGG GTKLTVLSSASTKGPSVFPLAPSSKSTSGGTAAL GCLVKDYFPEPVTVSWNSGALTSGVHTFPAVLQS SGLYSLSSVVTVPSSSLGTQTYICNVNHKPSNTK VDKKVEPKSC |

TABLE C-continued

| (Sequences): | |
| --- | --- |

| SEQ ID NO: Name | Sequence |
| --- | --- |
| 148 CEA<sub>CH1A1A 98/99</sub>-humanized CD3<sub>CH2527</sub> (Crosstab VH-Ck)- Fc(knob) P329GLALA (CEA TCB) | QVQLVQSGAEVKKPGASVKVSCKASGYTFTEFGM NWVRQAPGQGLEWMGWINTKTGEATYVEEFKGRV TFTTDTSTSTAYMELRSLRSDDTAVYYCARWDFA YYVEAMDYWGQGTTVTVSSASTKGPSVFPLAPSS KSTSGGTAALGCLVKDYFPEPVTVSWNSGALTSG VHTFPAVLQSSGLYSLSSVVTVPSSSLGTQTYIC NVNHKPSNTKVDKKVEPKSCDGGGGSGGGGSEVQ LLESGGGLVQPGGSLRLSCAASGFTFSTYAMNWV RQAPGKGLEWVSRIRSKYNNYATYYADSVKGRFT ISRDDSKNTLYLQMNSLRAEDTAVYYCVRHGNFG NSYVSWFAYWGQGTLVTVSSASVAAPSVFIFPPS DEQLKSGTASVVCLLNNFYPREAKVQWKVDNALQ SGNSQESVTEQDSKDSTYSLSSTLTLSKADYEKH KVYACEVTHQGLSSPVTKSFNRGECDKTHTCPPC PAPEAAGGPSVFLFPPKPKDTLMISRTPEVTCVV VDVSHEDPEVKFNWYVDGVEVHNAKTKPREEQYN STYRVVSVLTVLHQDWLNGKEYKCKVSNKALGAP IEKTISKAKGQPREPQVYTLPPCRDELTKNQVSL WCLVKGFYPSDIAVEWESNGQPENNYKTTPPVLD SDGSFFLYSKLTVDKSRWQQGNVFSCSVMHEALH NHYTQKSLSLSPGK |
| 149 CEA<sub>CH1A1A 98/99</sub> (VH-CH1) Fc(hole) P329GLALA (CEA TCB) | QVQLVQSGAEVKKPGASVKVSCKASGYTFTEFGM NWVRQAPGQGLEWMGWINTKTGEATYVEEFKGRV TFTTDTSTSTAYMELRSLRSDDTAVYYCARWDFA YYVEAMDYWGQGTTVTVSSASTKGPSVFPLAPSS KSTSGGTAALGCLVKDYFPEPVTVSWNSGALTSG VHTFPAVLQSSGLYSLSSVVTVPSSSLGTQTYIC NVNHKPSNTKVDKKVEPKSCDKTHTCPPCPAPEA AGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALGAPIEKTI SKAKGQPREPQVCTLPPSRDELTKNQVSLSCAVK GFYPSDIAVEWESNGQPENNYKTTPPVLDSDGSF FLVSKLTVDKSRWQQGNVFSCSVMHEALHNHYTQ KSLSLSPGK |
| 150 CD3 VH-CL (CEACAM5 TCB) | EVQLLESGGGLVQPGGSLRLSCAASGFTFSTYAM NWVRQAPGKGLEWVSRIRSKYNNYATYYADSVKG RFTISRDDSKNTLYLQMNSLRAEDTAVYYCVRHG NFGNSYVSWFAYWGQGTLVTVSSASVAAPSVFIF PPSDEQLKSGTASVVCLLNNFYPREAKVQWKVDN ALQSGNSQESVTEQDSKDSTYSLSSTLTLSKADY EKHKVYACEVTHQGLSSPVTKSFNRGEC |
| 151 humanized CEA VH-CH1(EE)-Fc (hole, P329G LALA) (CEACAM5 TCB) | QVQLVQSGAEVKKPGSSVKVSCKASGFNIKDTYM HWVRQAPGQGLEWMGRIDPANGNSKYVPKFQGRV TITADTSTSTAYMELSSLRSEDTAVYYCAPFGYY VSDYAMAYWGQGTLVTVSSASTKGPSVFPLAPSS KSTSGGTAALGCLVEDYFPEPVTVSWNSGALTSG VHTFPAVLQSSGLYSLSSVVTVPSSSLGTQTYIC NVNHKPSNTKVDEKVEPKSCDKTHTCPPCPAPEA AGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALGAPIEKTI SKAKGQPREPQVCTLPPSRDELTKNQVSLSCAVK GFYPSDIAVEWESNGQPENNYKTTPPVLDSDGSF FLVSKLTVDKSRWQQGNVFSCSVMHEALHNHYTQ KSLSLSP |
| 152 humanized CEA VH-CH1(EE)-CD3 VL-CH1-Fc (knob, P329G LALA) (CEACAM5 TCB) | QVQLVQSGAEVKKPGSSVKVSCKASGFNIKDTYM HWVRQAPGQGLEWMGRIDPANGNSKYVPKFQGRV TITADTSTSTAYMELSSLRSEDTAVYYCAPFGYY VSDYAMAYWGQGTLVTVSSASTKGPSVFPLAPSS KSTSGGTAALGCLVEDYFPEPVTVSWNSGALTSG VHTFPAVLQSSGLYSLSSVVTVPSSSLGTQTYIC NVNHKPSNTKVDEKVEPKSCDGGGGSGGGGSQAV VTQEPSLTVSPGGTVTLTCGSSTGAVTTSNYANW VQEKPGQAFRGLIGGTNKRAPGTPARFSGSLLGG KAALTLSGAQPEDEAEYYCALWYSNLWVFGGGTK LTVLSSASTKGPSVFPLAPSSKSTSGGTAALGCL VKDYFPEPVTVSWNSGALTSGVHTFPAVLQSSGL YSLSSVVTVPSSSLGTQTYICNVNHKPSNTKVDK |

TABLE C-continued

| (Sequences): |
| --- |

SEQ
ID
NO: Name                          Sequence

KVEPKSCDKTHTCPPCPAPEAAGGPSVFLFPPKP
KDTLMISRTPEVTCVVVDVSHEDPEVKFNWYVDG
VEVHNAKTKPREEQYNSTYRVVSVLTVLHQDWLN
GKEYKCKVSNKALGAPIEKTISKAKGQPREPQVY
TLPPCRDELTKNQVSLWCLVKGFYPSDIAVEWES
NGQPENNYKTTPPVLDSDGSFFLYSKLTVDKSRW
QQGNVFSCSVMHEALHNHYTQKSLSLSP 153 humanized CEA VL-CL(RK)        EIVLTQSPATLSLSPGERATLSCRAGESVDIFGV
    (CEACAM5 TCB)                   GFLHWYQQKPGQAPRLLIYRASNRATGIPARFSG
                                    SGSGTDFTLTISSLEPEDFAVYYCQQTNEDPYTF
                                    GQGTKLEIKRTVAAPSVFIFPPSDRKLKSGTASV
                                    VCLLNNFYPREAKVQWKVDNALQSGNSQESVTEQ
                                    DSKDSTYSLSSTLTLSKADYEKHKVYACEVTHQG
                                    LSSPVTKSFNRGEC

154 CEA-HCDR1                       EFGMN

155 CEA-HCDR2                       WINTKTGEATYVEEFKG

156 CEA-HCDR3                       WDFAYYVEAMDY

157 CEA-LCDR1                       KASAAVGTYVA

158 CEA-LCDR2                       SASYRKR

159 CEA-LCDR3                       HQYYTYPLFT

160 CEA VH                          QVQLVQSGAEVKKPGASVKVSCKASGYTFTEFGM
                                    NWVRQAPGQGLEWMGWINTKTGEATYVEEFKGRV
                                    TFTTDTSTSTAYMELRSLRSDDTAVYYCARWDFA
                                    YYVEAMDYWGQGTTVTVSS

161 CEA VL                          DIQMTQSPSSLSASVGDRVTITCKASAAVGTYVA
                                    WYQQKPGKAPKLLIYSASYRKRGVPSRFSGSGSG
                                    TDFTLTISSLQPEDFATYYCHQYYTYPLFTFGQG
                                    TKLEIK

162 CEA-HCDR1 (CEACAM5)             DTYMH

163 CEA-HCDR2 (CEACAM5)             RIDPANGNSKYVPKFQG

164 CEA-HCDR3 (CEACAM5)             FGYYVSDYAMAY

165 CEA-LCDR1 (CEACAM5)             RAGESVDIFGVGFLH

166 CEA-LCDR2 (CEACAM5)             RASNRAT

167 CEA-LCDR3 (CEACAM5)             QQTNEDPYT

168 CEA VH (CEACAM5)                QVQLVQSGAEVKKPGSSVKVSCKASGFNIKDTYM
                                    HWVRQAPGQGLEWMGRIDPANGNSKYVPKFQGRV
                                    TITADTSTSTAYMELSSLRSEDTAVYYCAPFGYY
                                    VSDYAMAYWGQGTLVTVSS

169 CEA VL (CEACAM5)                EIVLTQSPATLSLSPGERATLSCRAGESVDIFGV
                                    GFLHWYQQKPGQAPRLLIYRASNRATGIPARFSG
                                    SGSGTDFTLTISSLEPEDFAVYYCQQTNEDPYTF
                                    GQGTKLEIK

The following numbered paragraphs (paras) describe aspects of the present invention:

1. A bispecific antibody comprising a first antigen binding domain that specifically binds to programmed cell death protein 1 (PD1) and a second antigen binding domain that specifically binds to Lymphocyte activation gene-3 (LAG3), wherein said first antigen binding domain specifically binding to PD1 comprises a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence of SEQ ID NO:3; and a VL domain comprising (i) HVR-L1 comprising the amino acid sequence of SEQ ID NO:4;

(ii) HVR-L2 comprising the amino acid sequence of SEQ ID NO:5, and (iii) HVR-L3 comprising the amino acid sequence of SEQ ID NO:6.

2. The bispecific antibody of para 1, wherein the bispecific antibody comprises a Fc domain that is an IgG, particularly an IgG1 Fc domain or an IgG4 Fc domain and wherein the Fc domain comprises one or more amino acid substitution that reduces binding to an Fc receptor, in particular towards Fcγ receptor.

3. The bispecific antibody of paras 1 or 2, wherein the second antigen binding domain that specifically binds to LAG3 comprises (a) a VH domain comprising (i) HVR-H1 comprising the amino acid sequence of SEQ ID NO:14, (ii) HVR-H2 comprising the amino acid sequence of SEQ ID NO:15, and (iii) HVR-H3 comprising an amino acid sequence of SEQ ID NO:16; and a VL domain comprising (i) HVR-L1 comprising the amino acid sequence of SEQ ID NO:17, (ii) HVR-L2 comprising the amino acid sequence of SEQ ID NO:18, and (iii) HVR-L3 comprising the amino acid sequence of SEQ ID NO:19; or (b) a VH domain comprising (i) HVR-H1 comprising the amino acid sequence of SEQ ID NO:22, (ii) HVR-H2 comprising the amino acid sequence of SEQ ID NO:23, and (iii) HVR-H3 comprising an amino acid sequence of SEQ ID NO:24; and a VL domain comprising (i) HVR-L1 comprising the amino acid sequence of SEQ ID NO:25, (ii) HVR-L2 comprising the amino acid sequence of SEQ ID NO:26, and (iii) HVR-L3 comprising the amino acid sequence of SEQ ID NO:27; or (c) a VH domain comprising (i) HVR-H1 comprising the amino acid sequence of SEQ ID NO:30, (ii) HVR-H2 comprising the amino acid sequence of SEQ ID NO:31, and (iii) HVR-H3 comprising an amino acid sequence of SEQ ID NO:32; and a VL domain comprising (i) HVR-L1 comprising the amino acid sequence of SEQ ID NO:33, (ii) HVR-L2 comprising the amino acid sequence of SEQ ID NO:34, and (iii) HVR-L3 comprising the amino acid sequence of SEQ ID NO:35; or (d) a VH domain comprising (i) HVR-H1 comprising the amino acid sequence of SEQ ID NO:38, (ii) HVR-H2 comprising the amino acid sequence of SEQ ID NO:39, and (iii) HVR-H3 comprising an amino acid sequence of SEQ ID NO:40; and a VL domain comprising (i) HVR-L1 comprising the amino acid sequence of SEQ ID NO:41, (ii) HVR-L2 comprising the amino acid sequence of SEQ ID NO:42, and (iii) HVR-L3 comprising the amino acid sequence of SEQ ID NO:43; or (e) a VH domain comprising (i) HVR-H1 comprising the amino acid sequence of SEQ ID NO:46, (ii) HVR-H2 comprising the amino acid sequence of SEQ ID NO:47, and (iii) HVR-H3 comprising an amino acid sequence of SEQ ID NO:48; and a VL domain comprising (i) HVR-L1 comprising the amino acid sequence of SEQ ID NO:49, (ii) HVR-L2 comprising the amino acid sequence of SEQ ID NO:50, and (iii) HVR-L3 comprising the amino acid sequence of SEQ ID NO:51.

4. The bispecific antibody according to any one of paras 1 to 3, wherein the first antigen-binding domain specifically binding to PD1 comprises (a) a VH domain comprising the amino acid sequence of SEQ ID NO: 7 and a VL domain comprising the amino acid sequence of SEQ ID NO: 8, or (b) a VH domain comprising the amino acid sequence of SEQ ID NO: 9 and a VL domain comprising the amino acid sequence of SEQ ID NO: 10, or (c) a VH domain comprising the amino acid sequence of SEQ ID NO: 9 and a VL domain comprising the amino acid sequence of SEQ ID NO: 11, or (d) a VH domain comprising the amino acid sequence of SEQ ID NO: 9 and a VL domain comprising the amino acid sequence of SEQ ID NO: 12, or (e) a VH domain comprising the amino acid sequence of SEQ ID NO: 9 and a VL domain comprising the amino acid sequence of SEQ ID NO: 13.

5. The bispecific antibody according to any one of paras 1 to 4, wherein the second antigen-binding domain specifically binding to LAG3 comprises (a) a VH domain comprising the amino acid sequence of SEQ ID NO: 20 and a VL domain comprising the amino acid sequence of SEQ ID NO: 21, or (b) a VH domain comprising the amino acid sequence of SEQ ID NO: 28 and a VL domain comprising the amino acid sequence of SEQ ID NO: 29, or (c) a VH domain comprising the amino acid sequence of SEQ ID NO: 36 and a VL domain comprising the amino acid sequence of SEQ ID NO: 37, or (d) a VH domain comprising the amino acid sequence of SEQ ID NO: 44 and a VL domain comprising the amino acid sequence of SEQ ID NO: 45, or (e) a VH domain comprising the amino acid sequence of SEQ ID NO: 52 and a VL domain comprising the amino acid sequence of SEQ ID NO: 53.

6. The bispecific antibody according to any one of paras 1 to 4, wherein the second antigen-binding domain specifically binding to LAG3 comprises (a) a VH domain comprising the amino acid sequence of SEQ ID NO: 54 and a VL domain comprising the amino acid sequence of SEQ ID NO: 55, or (b) a VH domain comprising the amino acid sequence of SEQ ID NO: 62 and a VL domain comprising the amino acid sequence of SEQ ID NO: 63, or (c) a VH domain comprising the amino acid sequence of SEQ ID NO: 64 and a VL domain comprising the amino acid sequence of SEQ ID NO: 65, or (d) a VH domain comprising the amino acid sequence of SEQ ID NO: 66 and a VL domain comprising the amino acid sequence of SEQ ID NO: 67.

7. The bispecific antibody according any one of paras 1 to 5, wherein the first antigen binding domain specifically binding to PD1 comprises a VH domain comprising the amino acid sequence of SEQ ID NO: 9 and a VL domain comprising the amino acid sequence of SEQ ID NO: 10, and the second antigen binding domain specifically binding to LAG3 comprises a VH domain comprising the amino acid sequence of SEQ ID NO: 20 and a VL domain comprising the amino acid sequence of SEQ ID NO: 21 or a VH domain comprising the amino acid sequence of SEQ ID NO: 52 and a VL domain comprising the amino acid sequence of SEQ ID NO: 53.

8. The bispecific antibody according any one of paras 1 to 5, wherein the first antigen binding domain specifically binding to PD1 comprises a VH domain comprising the amino acid sequence of SEQ ID NO: 9 and a VL domain comprising the amino acid sequence of SEQ ID NO: 10, and the second antigen binding domain specifically binding to LAG3 comprises a VH domain comprising the amino acid sequence of SEQ ID NO: 20 and a VL domain comprising the amino acid sequence of SEQ ID NO: 21.

9. The bispecific antibody according any one of paras 1 to 4 or 6, wherein the first antigen binding domain specifically binding to PD1 comprises a VH domain comprising the amino acid sequence of SEQ ID NO: 9 and a VL domain comprising the amino acid sequence of SEQ ID NO: 10, and the second antigen binding domain specifically binding to LAG3 comprises a VH domain comprising the amino acid sequence of SEQ ID NO: 56 and a VL domain comprising the amino acid sequence of SEQ ID NO: 57.

10. The bispecific antibody according to any one of paras 1 to 5, wherein the bispecific antibody is a humanized or chimeric antibody.

11. The bispecific antibody of any one of paras 1 to 10, wherein the bispecific antibody comprises an Fc domain of human IgG1 subclass with the amino acid mutations L234A, L235A and P329G (numbering according to Kabat EU index).

12. The bispecific antibody of any one of paras 1 to 11, wherein the bispecific antibody comprises an Fc domain comprising a modification promoting the association of the first and second subunit of the Fc domain.

13. The bispecific antibody of any one of paras 1 to 12, wherein the first subunit of the Fc domain comprises knobs and the second subunit of the Fc domain comprises holes according to the knobs into holes method.

14. The bispecific antibody of any one of paras 1 to 13, wherein the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

15. The bispecific antibody of any one of paras 1 to 14, wherein the bispecific antibody comprises an Fc domain, a first Fab fragment comprising the antigen binding domain that specifically binds to PD1 and a second Fab fragment comprising the antigen binding domain that specifically binds to LAG3.

16. The bispecific antibody of any one of paras 1 to 15, wherein in one of the Fab fragments the the variable domains VL and VH are replaced by each other so that the VH domain is part of the light chain and the VL domain is part of the heavy chain.

17. The bispecific antibody of paras 15 or 16, wherein in the first Fab fragment comprising the antigen binding domain that specifically binds to PD1 the variable domains VL and VH are replaced by each other.

18. The bispecific antibody of any one of paras 1 to 17, wherein the bispecific antibody comprises a Fab fragment wherein in the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

19. The bispecific antibody of any one of paras 15 to 18, wherein in the second Fab fragment comprising the antigen binding domain that specifically binds to LAG3 the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

20. The bispecific antibody of any one of paras 1 to 19, comprising (a) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 97, and a second light chain comprising an amino acid sequence with at least 95% sequence identity to the sequence of SEQ ID NO:99, or (b) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 100, and a second light chain comprising an amino acid sequence with at least 95% sequence identity to the sequence of SEQ ID NO:101, or (c) a first heavy chain comprising an amino acid sequence with at least 95% sequence identity to the sequence of SEQ ID NO: 102, a first light chain comprising an amino acid sequence with at least 95% sequence identity to the sequence of SEQ ID NO: 104, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105, or (d) a first heavy chain comprising an amino acid sequence with at least 95% sequence identity to the sequence of SEQ ID NO: 106, a first light chain comprising an amino acid sequence with at least 95% sequence identity to the sequence of SEQ ID NO: 107, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105.

21. The bispecific antibody of any one of paras 1 to 19, wherein the bispecific antibody comprises a third Fab fragment comprising an antigen binding domain that specifically binds to LAG3.

22. The bispecific antibody of any one of paras 1 to 19 or 21, wherein the two Fab fragments comprising each an antigen binding domain that specifically binds to LAG3 are identical.

23. The bispecific antibody of any one of paras 1 to 19 or 21 or 22, wherein the Fab fragment comprising the antigen binding domain that specifically binds to PD1 is fused via a peptide linker to the C-terminus of one of the heavy chains.

24. The bispecific antibody of any one of paras 1 to 19 or 21 to 23, comprising (a) a first heavy chain comprising an amino acid sequence with at least 95% sequence identity to the sequence of SEQ ID NO: 118, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 119, and a second light chain comprising an amino acid sequence with at least 95% sequence identity to the sequence of SEQ ID NO:101, or (b) a first heavy chain comprising an amino acid sequence with at least 95% sequence identity to the sequence of SEQ ID NO: 120, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 121, and a second light chain comprising an amino acid sequence with at least 95% sequence identity to the sequence of SEQ ID NO:99, or (c) a first heavy chain comprising an amino acid sequence with at least 95% sequence identity to the sequence of SEQ ID NO: 122, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105.

25. The bispecific antibody of any one of paras 1 to 19 or 21 to 23, wherein the bispecific antibody comprises a fourth Fab fragment comprising an antigen binding domain that specifically binds to PD1.

26. The bispecific antibody of any one of paras 1 to 19 or 21 to 23 or 25, wherein the two Fab fragments comprising each an antigen binding domain that specifically binds to PD1 are identical.

27. The bispecific antibody of any one of paras 1 to 19 or 21 to 23 or 25 or 26, wherein the two Fab fragments comprising each an antigen binding domain that specifically binds to PD1 are each fused via a peptide linker to the C-terminus to one of the heavy chains, respectively.

28. The bispecific antibody of any one of paras 1 to 19 or 21 to 23 or 25 to 27, comprising (a) two heavy chains comprising each an amino acid sequence with at least 95% sequence identity to the sequence of SEQ ID NO: 114, two first light chains comprising each an amino acid sequence with at least 95% sequence identity to the sequence of SEQ ID NO: 115, and two second light chains comprising each an amino acid sequence with at least 95% sequence identity to the sequence of SEQ ID NO: 101, or (b) two heavy chains comprising each an amino acid sequence with at least 95% sequence identity to the sequence of SEQ ID NO: 116, two first light chains comprising each an amino acid sequence with at least 95% sequence identity to the sequence of SEQ ID NO: 115, and two second light chains comprising each an amino acid sequence with at least 95% sequence identity to the sequence of SEQ ID NO:99, or (c) two heavy chains comprising each an amino acid sequence with at least 95% sequence identity to the sequence of SEQ ID NO: 117, two first light chains comprising each an amino acid sequence with at least 95% sequence identity to the sequence of SEQ ID NO: 115, and two second light chains comprising an amino acid sequence with at least 95% sequence identity to the sequence of SEQ ID NO:105.

29. The bispecific antibody of any one of paras 1 to 14, wherein the bispecific antibody comprises an Fc domain, two Fab fragments comprising each an antigen binding domain that specifically binds to LAG3 and a single chain Fab (scFab) comprising the antigen binding domain that specifically binds to PD1.

30. The bispecific antibody of any one of paras 1 to 14 or 29, wherein the scFab comprising an antigen binding domain that specifically binds to PD1 is fused via a peptide linker to the C-terminus to one of the heavy chains.

31. The bispecific antibody of any one of paras 1 to 14 or 29 or 30, comprising (a) a first heavy chain comprising an amino acid sequence with at least 95% sequence identity to the sequence of SEQ ID NO: 123, a second heavy chain comprising an amino acid sequence with at least 95% sequence identity to the sequence of SEQ ID NO: 119, and two light chains comprising each an amino acid sequence with at least 95% sequence identity to the sequence of SEQ ID NO: 101, or (b) a first heavy chain comprising an amino acid sequence with at least 95% sequence identity to the sequence of SEQ ID NO: 124, a second heavy chain comprising an amino acid sequence with at least 95% sequence identity to the sequence of SEQ ID NO: 121, and two light chains comprising each an amino acid sequence with at least 95% sequence identity to the sequence of SEQ ID NO:99, or (c) a first heavy chain comprising an amino acid sequence with at least 95% sequence identity to the sequence of SEQ ID NO: 125, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105.

32. The bispecific antibody of any one of paras 1 to 14, wherein the bispecific antibody comprises an Fc domain, two Fab fragments comprising each an antigen binding domain that specifically binds to LAG3 and a VH and VL domain comprising the antigen binding domain that specifically binds to PD1.

33. The bispecific antibody of any one of paras 1 to 14 or 32, wherein the VH domain of the antigen binding domain that specifically binds to PD1 is fused via a peptide linker to the C-terminus of one of the heavy chains and the VL domain of the antigen binding domain that specifically binds to PD1 is fused via a peptide linker to the C-terminus of the other one of the heavy chains.

34. The bispecific antibody of any one of paras 1 to 14 or 32 or 33, comprising a first heavy chain comprising an amino acid sequence with at least 95% sequence identity to the sequence of SEQ ID NO: 126, a second heavy chain comprising an amino acid sequence with at least 95% sequence identity to the sequence of SEQ ID NO: 127, and two light chains comprising each an amino acid sequence with at least 95% sequence identity to the sequence of SEQ ID NO: 109.

35. A polynucleotide encoding the bispecific antibody of any one of paras 1 to 34.

36. A vector, particularly an expression vector, comprising the polynucleotide according to para 35.

37. A prokaryotic or eukaryotic host cell comprising the polynucleotide according to para 35 or the vector according to para 36.

38. A method of producing the bispecific antibody according to paras 1 to 34, comprising culturing the host cell of para 37 under conditions suitable for the expression of the bispecific antibody and recovering the bispecific antibody from the culture.

39. A pharmaceutical composition comprising the bispecific antibody according to any one of paras 1 to 34 and at least one pharmaceutically acceptable excipient.

40. The bispecific antibody according to any one of paras 1 to 34 or the pharmaceutical composition according to para 39 for use as a medicament.

41. The bispecific antibody according to any one of paras 1 to 34 or the pharmaceutical composition according to para 39 for use i) in the modulation of immune responses, such as restoring T cell activity, ii) in stimulating a T cell response, iii) in the treatment of infections, iv) in the treatment of cancer, v) in delaying progression of cancer, vi) in prolonging the survival of a patient suffering from cancer.

42. The bispecific antibody according to any one of paras 1 to 34 or the pharmaceutical composition according to para 39 for use in the prevention or treatment of cancer.

43. The bispecific antibody according to any one of paras 1 to 34 or the pharmaceutical composition according to para 39 for use in the treatment of a chronic viral infection.

44. The bispecific antibody according to any one of paras 1 to 34 or the pharmaceutical composition according to para 39 for use in the prevention or treatment of cancer, wherein the bispecific antibody is administered in combination with a chemotherapeutic agent, radiation and/or other agents for use in cancer immunotherapy.

45. A method of inhibiting the growth of tumor cells in an individual comprising administering to the individual an effective amount of the bispecific antibody according to any one of paras 1 to 34 to inhibit the growth of the tumor cells.

EXAMPLES

The following are examples of methods and compositions of the invention. It is understood that various other embodiments may be practiced, given the general description provided above.

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to the numbering systems according to Kabat (Kabat, E. A., et al., Sequences of Proteins of Immunological Interest, 5th ed., Public Health Service, National Institutes of Health, Bethesda, MD (1991)) as defined above.

Recombinant DNA Techniques

Standard methods were used to manipulate DNA as described in Sambrook, J. et al., Molecular Cloning: A laboratory manual; Cold Spring Harbor Laboratory Press, Cold Spring Harbor, New York, 1989. The molecular biological reagents were used according to the manufacturer's instructions.

Gene Synthesis

Desired gene segments were prepared from oligonucleotides made by chemical synthesis. The 600-1800 bp long gene segments, which were flanked by singular restriction endonuclease cleavage sites, were assembled by annealing and ligating oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wisconsin) software package version 10.2 and Infomax's Vector NT1 Advance suite version 8.0 was used for sequence creation, mapping, analysis, annotation and illustration.

Expression Vectors

For the expression of the described antibodies, variants of expression plasmids for transient expression (e.g. in HEK293) cells based either on a cDNA organization with or without a CMV-Intron A promoter or on a genomic organization with a CMV promoter were applied.

Beside the antibody expression cassette the vectors contained:

an origin of replication which allows replication of this plasmid in *E. coli*, and a β-lactamase gene which confers ampicillin resistance in *E. coli.*

The transcription unit of the antibody gene was composed of the following elements:

unique restriction site(s) at the 5' end the immediate early enhancer and promoter from the human cytomegalovirus, followed by the Intron A sequence in the case of the cDNA organization, a 5'-untranslated region of a human antibody gene, an immunoglobulin heavy chain signal sequence, the human antibody chain (wildtype or with domain exchange) either as cDNA or as genomic organization with the immunoglobulin exon-intron organization a 3' untranslated region with a polyadenylation signal sequence, and unique restriction site(s) at the 3' end.

The fusion genes comprising the antibody chains as described below were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Multispecific antibodies were expressed by transient co-transfection of the respective expression plasmids in adherently growing HEK293-EBNA or in HEK29-F cells growing in suspension as described below.

Transient Transfections in HEK293 System

All antibodies and bispecific antibodies were generated by transient transfection of 293F cells using the Freestyle system (ThermoFisher). Here the 293F cells were cultivated in F17 Medium, transfected with 293Free (Novagene) and feeded after 4 hours with VPA 4 mM and Feed 7 and 0.6% Glucose after 16h. Further the Expi293F™ Expression System Kit (ThermoFisher) was used. Here the Expi293F™ cells were cultivated in Expi293™ Expression Medium and transfected using ExpiFectamine™ 293 Transfection Kit according manufactuer's instructions. Due to the improved stability and purity and reduced aggregation tendency of the CrossMAb$^{Vh-VL}$ bispecific antibodies with additionally introduced charged pairs of amino acids in the CH1/CL interface (see positions in the respective sequences for further detail) no adjustments of plasmid ratio have been employed. Therefore the relative plasmid ratio of 1:1:1:1 for 1+1 CrossMab or 1:1:1 for 2+2 CrossMab was used for the co-transfection of LC, HC, crossed LC and crossed HC plasmids. Cell supernatants were harvested after 7 days and purified by standard methods.

Protein Determination

The protein concentration of purified antibodies and derivatives was determined by determining the optical density (OD) at 280 nm, using the molar extinction coefficient calculated on the basis of the amino acid sequence according to Pace, et al., Protein Science, 1995, 4, 2411-1423.

Antibody Concentration Determination in Supernatants

The concentration of antibodies and derivatives in cell culture supernatants was estimated by immunoprecipitation with Protein A Agarose-beads (Roche). 60 µL Protein A Agarose beads were washed three times in TBS-NP40 (50 mM Tris, pH 7.5, 150 mM NaCl, 1% Nonidet-P40). Subsequently, 1-15 mL cell culture supernatant was applied to the Protein A Agarose beads pre-equilibrated in TBS-NP40. After incubation for at 1 hour at room temperature the beads were washed on an Ultrafree-MC-filter column (Amicon) once with 0.5 mL TBS-NP40, twice with 0.5 mL 2× phosphate buffered saline (2×PBS, Roche) and briefly four times with 0.5 mL 100 mM Na-citrate pH 5.0. Bound antibody was eluted by addition of 35 µl NuPAGE® LDS Sample Buffer (Invitrogen). Half of the sample was combined with NuPAGE® Sample Reducing Agent or left unreduced, respectively, and heated for 10 min at 70° C. Consequently, 5-30 µl were applied to a 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was quantitatively measured by affinity HPLC chromatography. Briefly, cell culture supernatants containing antibodies and derivatives that bind to Protein A were applied to an Applied Biosystems Poros A/20 column in 200 mM KH2PO4, 100 mM sodium citrate, pH 7.4 and eluted from the matrix with 200 mM NaCl, 100 mM citric acid, pH 2.5 on an Agilent HPLC 1100 system. The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) are coated with 100 µL/well biotinylated anti-human IgG capture molecule F(ab')2<h-Fcγ>BI (Dianova) at 0.1 µg/mL for 1 hour at room temperature or alternatively overnight at 4° C. and subsequently washed three times with 200 µL/well PBS, 0.05% Tween (PBST, Sigma). 100 µL/well of a dilution series in PBS (Sigma) of the respective antibody containing cell culture supernatants was added to the wells and incubated for 1-2 hour on a microtiterplate shaker at room temperature. The wells were washed three times with 200 µL/well PBST and bound antibody was detected with 100 µl F(ab') 2<hFcγ>POD (Dianova) at 0.1 µg/mL as the detection antibody for 1-2 hours on a microtiterplate shaker at room temperature. Unbound detection antibody was washed away three times with 200 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multispecific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 µg deglycosylated VH/VL CrossMabs in a Tris buffer pH 8 at room temperature for 120 hours and at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Determination of Binding and Binding Affinity of Multispecific Antibodies to the Respective Antigens Using Surface Plasmon Resonance (SPR) (BIACORE)

Binding of the generated antibodies to the respective antigens is investigated by surface plasmon resonance using a BIACORE instrument (GE Healthcare Biosciences AB, Uppsala, Sweden). The respective Biacore Evaluation Software is used for analysis of sensorgrams and for calculation of affinity data.

Example 1

Generation of Anti-PD-1 Antibodies

Immunization of Mice

NMRI mice were immunized genetically, using a plasmid expression vector coding for full-length human PD-1 by intradermal application of 100 ug vector DNA (plasmid15300_hPD1-fl), followed by Electroporation (2 square pulses of 1000 V/cm, duration 0.1 ms, interval 0.125 s; followed by 4 square pulses of 287.5 V/cm, duration 10 ms, interval 0.125 s. Mice received either 6 consecutive immunizations at days 0, 14, 28, 42, 56, 70, and 84. Blood was taken at days 36, 78 and 92 and serum prepared, which was used for titer determination by ELISA (see below). Animals with highest titers were selected for boosting at day 96, by intravenous injection of 50 ug of recombinant human PD1 human Fc chimera, and monoclonal antibodies were isolated by hybridoma technology, by fusion of splenocytes to myeloma cell line 3 days after boost.

Determination of Serum Titers (ELISA)

Human recombinant PD1 human Fc chimera was immobilized on a 96-well NUNC Maxisorp plate at 0.3 ug/ml, 100 ul/well, in PBS, followed by: blocking of the plate with 2% Crotein C in PBS, 200 ul/well; application of serial dilutions of antisera, in duplicates, in 0.5% Crotein C in PBS, 100 ul/well; detection with HRP-conjugated goat anti-mouse antibody (Jackson Immunoresearch/Dianova 115-036-071; 1/16 000). For all steps, plates were incubated for 1 h at 37° C. Between all steps, plates were washed 3 times with 0.05% Tween 20 in PBS. Signal was developed by addition of BM Blue POD Substrate soluble (Roche), 100 ul/well; and stopped by addition of 1 M HCl, 100 ul/well. Absorbance was read out at 450 nm, against 690 nm as reference. Titer was defined as dilution of antisera resulting in half-maximal signal.

Example 2

Characterization Anti-PD1 Antibodies/Binding of Anti-PD1 Antibodies to Human PD1

ELISA for hu PD1

Nunc maxisorp streptavidin coated plates (MicroCoat #11974998001) were coated with 25 µl/well biotinylated PD1-ECD-AviHis and incubated at 4° C. over night. After washing (3×90 µl/well with PBST-buffer) 25 µl anti PD1 samples or reference antibodies (human anti PD1; Roche/mouse anti PD1; Biolegend; cat.:329912) were added and incubated 1 h at RT. After washing (3×90 µl/well with PBST-buffer) 25 µl/well goat-anti-human H+L-POD (JIR, JIR109-036-088)/Sheep-anti-mouse-POD (GE Healthcare; NA9310) was added in 1:2000/1:1000 dilution and incubated at RT for 1 h on shaker. After washing (3×90 µl/well with PBST-buffer) 25 µl/well TMB substrate (Roche Catalogue No. 11835033001) was added and incubated until OD 2-3. Measurement took place at 370/492 nm.

ELISA results are listed as $EC_{50}$-values [ng/ml] in Summary Tables 1 and 2 below.

Cell ELISA for PD1

Adherent CHO-K1 cell line stably transfected with plasmid 15311_hPD1-fl_pUC_Neo coding for full-length human PD1 and selection with G418 (Neomycin restistance marker on plasmid) were seeded at a concentration of 0.01×10E6 cells/well in 384-well flat bottom plates and grown over night.

The next day 25 µl/well PD1 sample or human anti PD1 (Roche)/mouse anti PD1(Biolegend; cat.:329912) reference antibody were added and incubated for 2h at 4° C. (to avoid internalization). After washing carefully (1×90 µl/well PBST) cells were fixed by adding 30 µl/well 0.05% Glutaraldehyde (Sigma, Cat.No: G5882, 25%) diluted in 1×PBS-buffer and incubated for 10 min at RT. After washing (3×90 µl/well PBST) 25 µl/well secondary antibody was added for detection: goat-anti-human H+L-POD (JIR, JIR109-036-088)/Sheep-anti-mouse-POD (GE NA9310) followed by 1h incubation at RT on shaker. After washing (3×90 µl/well PBST) 25 µl/well TMB substrate solution (Roche 11835033001) was added and incubated until OD 1.0-2.0. Plates were measured at 370/492 nm.

Cell ELISA results are listed as "$EC_{50}$ CHO-PD1"-values [ng/ml] in Table 2 below.

ELISA for Cyno PD1

Nunc maxisorp streptavidin coated plates (MicroCoat #11974998001) were coated with 25 µl/well biotinylated cynoPD1-ECD-Biotin and incubated at 4° C. over night. After washing (3×90 μl/well with PBST-buffer) 25 μl anti PD1 samples or reference antibodies (human anti PD1; Roche) were added and incubated 1 h at RT on shaker. After washing (3×90 μl/well with PBST-buffer) 25 μl/well goat-anti-human H+L-POD (JIR, JIR109-036-088) was added in 1:1000 dilution and incubated at RT for 1 h on shaker. After washing (3×90 μl/well with PBST-buffer) 25 μl/well TMB substrate (Roche, 11835033001) was added and incubated until OD 2-3. Measurement took place at 370/492 nm. ELISA results are listed as $EC_{50}$-values [ng/ml] in Summary Table 1 and 2 below.

PD Ligand 1 Replacing Assay

Nunc maxisorp streptavidin coated plates (MicroCoat #11974998001) were coated with 25 μl/well biotinylated PD1-ECD-AviHis and incubated at 4° C. over night. After washing (3×90 μl/well with PBST-buffer) 25 μl anti PD1 samples or reference antibodies (mouse anti PD1; Bioleg-end; cat.:329912) were added and incubated 1 h at RT on shaker. After washing (3×90 μl/well with PBST-buffer) 25 μl/well PD-L1 (Recombinant human B7-H1/PD-L1 Fc Chi-mera; 156-B7, R&D) was added and incubated 1 h at RT on shaker. After washing (3×90 μl/well with PBST-buffer) 25 μl/well goat-anti-human H+L-POD (JIR, 109-036-088) was added in 1:1000 dilution and incubated at RT for 1 h on shaker. After washing (3×90 μl/well with PBST-buffer) 25 μl/well TMB substrate (Roche, 11835033001) was added and incubated until OD 2-3. Measurement took place at 370/492 nm.

ELISA results are listed as $IC_{50}$-values [ng/ml] in summary Table 1 below.

PD Ligand 2 Replacing Assay

Nunc maxisorp streptavidin coated plates (MicroCoat #11974998001) were coated with 25 μl/well biotinylated PD1-ECD-AviHis and incubated at 4° C. over night. After washing (3×90 μl/well with PBST-buffer) 25 μl anti PD1 samples or reference antibodies (mouse anti huPD1; Roche) were added and incubated 1 h at RT on shaker. After washing (3×90 μl/well with PBST-buffer) 25 μl/well PD-L2 (Recom-binant human B7-DC/PD-L2 Fc Chimera; 1224-PL-100, R&D) was added and incubated 1 h at RT on shaker. After washing (3×90 μl/well with PBST-buffer) 25 μl/well goat-anti-human H+L-POD (JIR, 109-036-088) was added in 1:2000 dilution and incubated at RT for 1 h on shaker. After washing (3×90 μl/well with PBST-buffer) 25 μl/well TMB (tetramethylbenzidine) substrate (Roche, #11835033001) was added and incubated until OD 2-3. Measurement took place at 370/492 nm.

ELISA results are listed as $IC_{50}$-values [ng/ml] in summary Table 1 below.

Epitope Mapping ELISA/Binding Competition Assay

Nunc maxisorp plates (Nunc #464718) were coated with 25 μl/well capture antibody (goat anti mouse IgG; JIR; 115-006-071) and incubated for 1 h at RT on shaker. After washing (3×90 μl/well with PBST-buffer) plates were blocked for 1 h with 2% BSA containing PBS buffer at RT on shaker. After washing (3×90 μl/well with PBST-buffer) 25 μl mouse anti PD1 samples were added and incubated 1 h at RT on shaker. After washing (3×90 μl/well with PBST-buffer) capture antibody was blocked by 30 μl/well mouse IgG (JIR; 015-000-003) for 1 h at RT on shaker. At the same time biotinylated PD1-ECD-AviHis was preincubated with second sample antibody for 1 h at RT on shaker. After washing assay plate (3×90 μl/well with PBST-buffer) the PD1 antibody mix was transferred to assay plate and incu-bated at RT for 1 h on shaker. After washing (3×90 μl/well with PBST-buffer) 25 μl/well streptavidin POD (Roche,

11089153001) was added in 1:4000 dilution and incubated at RT for 1 h on shaker. After washing (3×90 μl/well with PBST-buffer) 25 μl/well TMB substrate (Roche, #11089153001) was added and incubated until GD 1.5-2.5. Measurement took place at 370/492 nm. Epitope groups were defined by hierarchical clustering against reference antibodies.

TABLE 1

Binding, PD-L1 inhibition and epitope region groups of exemplary antibodies (ELISA)

| Antibody | ELISA huPD1 $EC_{50}$ [ng/ml] | ELISA cyPD1 $EC_{50}$ [ng/ml] | ELISA PD-L1 inhibition $IC_{50}$ [ng/ml] | ELISA PD-L2 inhibition $IC_{50}$ [ng/ml] | Epitope region group (By competion assay) |
|---|---|---|---|---|---|
| PD1-0050 | 17.9 | 9.8 | 128 | 34 | 1 |
| PD1-0069 | 45.7 | 22.7 | 225 | 89 | 6 |
| PD1-0073 | 15.1 | 8.3 | 124 | 65 | 5 |
| PD1-0078 | 26.3 | 22.4 | x | 86 | 2 |
| PD1-0098 | 50.8 | 54.6 | 174 | 45 | 5 |
| PD1-0102 | 34.2 | 52.7 | >35.5 μg/ml | 140 | 4 |
| PD1-0103 | 33.7 | 36.9 | 182 | 51 | 5 |

TABLE 2

Biochemial- and Cell-binding of humanized PDI antibodies derived from parental mouse antibody PD1-0103 ( ELISA)

| Humanized antibody | ELISA huPD1 $EC_{50}$ [ng/ml] | ELISA cyPD1 $EC_{50}$ [ng/ml] | ELISA CHO-PD1 $EC_{50}$ [ng/ml] |
|---|---|---|---|
| PD1-103-0312 | 11 | 8.3 | 10.1 |
| PD1-103-0313 | 15 | 11 | 10.8 |
| PD1-103-0314 | 11 | 8.3 | 7.7 |
| PD1-103-0315 | 10 | 7.9 | 7.3 |

Biacore Characterization of the Humanized Anti-PD-1 Anti-bodies

A surface plasmon resonance (SPR) based assay has been used to determine the kinetic parameters of the binding between several murine PD1 binders as well as commercial human PD1 binding references. Therefore, an anti-human IgG was immobilized by amine coupling to the surface of a (Biacore) CM5 sensor chip. The samples were then captured and hu PD1-ECD was bound to them. The sensor chip surface was regenerated after each analysis cycle. The equilibrium constant and kinetic rate constants were finally gained by fitting the data to a 1:1 langmuir interaction model.

About 2000 response units (RU) of 20 μg/ml anti-human IgG (GE Healthcare #BR-1008-39) were coupled onto the flow cells 1 and 2 (alternatively: 3 and 4) of a CM5 sensor chip in a Biacore T200 at pH 5.0 by using an amine coupling kit supplied by GE Healthcare.

The sample and running buffer was HBS-EP+(0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer.

The samples were injected for 20 seconds with a concen-tration of 10 nM and bound to the second flow cell. Then a complete set of human PD1-ECD concentrations (144 nM, 48 nM, 16 nM, 5.33 nM, 1.78 nM, 0.59 nM, 0.20 nM and 0 nM) was injected over each sample for 120s followed by a dissociation time of 30/300s and two 20s regeneration steps with 3 M MgCl2, of which the last one contained an "extra wash after injection" with running buffer.

Finally the double referenced data was fitted to a 1:1 Langmuir interaction model with the Biacore T200 Evaluation Software. Resulting $K_D$, $k_a$ and kd values are shown in Table 3.

TABLE 3

Kinetic rate constants and equilibrium constants for
chimeric PD1-0103 and
humanized PDI-Abs determined by Biacore

| Ligand | $k_a$ $[M^{-1}s^{-1}]$ | $k_d$ $[s^{-1}]$ | $K_D$ [nM] |
|---|---|---|---|
| chimeric PD1-0103 | 3.86E+05 | 3.07E-04 | 0.8 |
| PD1-0103-0312 | 1.95E+05 | 3.45E-04 | 1.8 |
| PD1-0103-0313 | 1.60E+05 | 3.67E-04 | 2.3 |
| PD1-0103-0314 | 1.87E+05 | 2.79E-04 | 1.5 |
| PD1-0103-0315 | 1.89E+05 | 2.91E-04 | 1.5 |

As shown in Table 3, all the humanized versions of chimeric PD1-0103 (generation see Example 6) display kinetic properties similar to the parental antibody (chimeric PD1-0103).

Kinetics

A CM5 sensor series S was mounted into the Biacore 4000 System and the detection spots were hydrodynamically addressed according to the manufacturer's instructions.

The polyclonal rabbit IgG antibody <IgGFCγM>R (Jackson ImmunoResearch Laboratories Inc.) was immobilized at 10 000 Ru on the detection spots 1 and 5 in the flow cells 1, 2, 3 and 4. Coupling was done via EDC/NHS chemistry according to the manufacturer's instructions. The remaining spots in the flow cells served as a reference. The sample buffer was the system buffer supplemented with 1 mg/ml carboxymethyldextrane.

In one embodiment the assay was driven at 25° C. In another embodiment the assay was driven at 37° C. 50 nM of each murine monoclonal antibody was captured on the sensor surface by a 1 min injection at 10 µl/min. Subsequently the respective antigens were injected in a concentration series of 100 nM, 2×33 nM, 11 nM, 4 nM, 1 nM and system buffer 0 nM at 30 µl/min for 4 min association phase time. The dissociation was monitored for another 4 min. The capture system was regenerated using a 3 min injection of 10 mM glycine pH 1.5 at 30 µl/min. The relevant kinetic data was calculated using the Biacore evaluation software according to the manufacturer's instructions.

Epitope Mapping

A Biacore 4000 instrument was mounted with a Biacore CAP sensor and was prepared like recommended by the manufacturer. The instrument buffer was HBS-ET (10 mM HEPES pH 7.4, 150 mM NaCl, 3 mM EDTA, 0.005% w/v Tween 20). The instrument was running at 25° C.

All samples were diluted in system buffer. A 35 kDa biotinylated antigen PD1-ECD-AviHis was captured at 200 RU on the CAP sensor surface by a 1 min injection at 30 µl/min in the flow cells 1, 2, 3 and 4 in the spots 1 and 5. Spots 2, 3 and 4 served as a reference. In another embodiment, a 35 kDa biotinylated antigen PD1-ECD-AviHis was captured at 200 RU on the CAP sensor in the same manner.

Subsequently a primary antibody was injected at 100 nM for 3 min at 30 µl/min followed by the injection of a secondary antibody at 100 nM for 3 min at 30 µl/min. The primary antibody was injected until full saturation of the surface presented antigen. At the end of the primary and secondary antibody injection phases report points "Binding Late" (BL) were set to monitor the binding response of the respective antibodies. The Molar Ratio, a quotient between the secondary antibody binding response "BL2" and the primary antibody response "BL1" was calculated. The Molar Ratio was used as an indicator of the antigen accessibility of the secondary antibody, when the antigen was already complexed by the primary antibody.

The complexes were completely removed from the sensor surface by an injection for 2 min at $30p_1$/min 2M guanidine-HCL 250 mM NaOH regeneration buffer as recommended by the manufacturer, followed by a 1 min injection at 30 µl/min of system buffer.

Example 3

Effect of Different Anti-PD-1 Antibodies on
Cytokine Production in a Mixed Lymphocyte
Reaction (MLR)

3A) The Mixed Lymphocyte Reaction (MLR) is a immune cell assay which measures the activation of lymphocytes from one individual (donor X) to lymphocytes from another individual (donor Y). A mixed lymphocyte reaction was used to demonstrate the effect of blocking the PD1 pathway to lymphocyte effector cells. T cells in the assay were tested for activation and their IFNγ secretion in the presence or absence of an anti-PD1 mAbs.

To perform an allogeneic MLR, peripheral blood mononuclear cells (PBMCs) from at least four healthy donors of unknown HLA type were isolated by density gradient centrifugation using Leukosep (Greiner Bio One, 227 288). Briefly, heparinized blood samples were diluted with the three fold volume of PBS and 25 ml aliquots of the diluted blood were layered in 50 ml Leukosep tubes. After centrifugation at 800×g for 15 min at room temperature (w/o break) the lymphocyte containing fractions were harvested, washed in PBS and used directly in functional assay or resuspended in freezing medium (10% DMSO, 90% FCS) at 1.0E+07 cells/ml and stored in liquid nitrogen. Individual 2-way MLR reactions were set up by mixing PBMCs from two different donors at a 1:1 stimulator/responder cell ratio and co-cultures were done at least in duplicate in flat-bottomed 96-well plates for 6 days at 37° C., 5% $CO_2$, in the presence or w/o of a different concentration range of purified anti-PD1 monoclonal antibodies PD1-0050, PD1-0069, PD1-0073, PD1-0078, PD1-0098, PD1-0102, PD1-0103. As reference anti-PD1 antibodies, antibodies comprising the VH and VL domains of either nivolumab (also known as MDX-5C4 or MDX-1106) or pembrolizumab (also known as MK-3475 or Org 1.09A) were synthesized and cloned with backbones of human IgG1 (with mutations L234A, L235A and P329G (EU index of Kabat)). Either no antibody or an isotype control antibody was used as a negative control and rec hu IL-2 (20 EU/ml) was used as positive control. After day 6 100 µl of medium was taken from each culture for cytokine measurement. The levels of IFN-gamma were measured using OptEIA ELISA kit (BD Biosciences).

The results are shown in Table 4 (IFNγ secretion/release). The anti-PD1 monoclonal antibodies promoted T cell activation and IFNγ secretion in concentration dependent manner. The value of % increase of IFNγ secretion was calculated in relation to IFNγ production of MLR w/o adding of any blocking mAbs (basal allogeneic stimulation induced IFNγ value as E-c) and MLR with adding of 20 EU/ml rec hu IL-2 (positive control=100% IFNg value as E+c) and was calculated according to formula: Rel.Stimulation [%]=((Example–E–c)/(E+c–E–c)*100

TABLE 4

Percentage of of IFN gamma secretion after allogenic stimulation and treatment with anti-PD-1 antibody in comparison to effect of recombinant human IL-2 treatment (20 EU/ml) (= 100% increase) as positive control

|  | Concentration (µg/ml) | 1:12 | 1:120 | 1:1200 | Effect in MLR |
|---|---|---|---|---|---|
| PD1-0050 | 44 | 136 | 96 | 33 | +++ |
| PD1-0069 | 60 | 76 | 71 | 55 | +++ |
| PD1-0073 | 43 | 103 | 63 | 38 | ++ |
| PD1-0078 | 64 | 99 | 72 | 21 | ++ |

Several PD1 blocking antibodies PD1-0050, PD1-0069, PD1-0073, PD1-0078, PD1-0098, PD1-0102, PD1-0103 demonstrated strong immune modulating activity by enhancing secretion of interferon gamma (IFNγ) (data not shown for all antibodies).

3B) In a further experiment chimeric PD1-0103 (human IgG1 isotype with mutations L234A, L235A and P329G (EU index of Kabat)) was evaluated. Blockade of PD1 with chimeric PD1-0103 strongly enhances IFN-gamma secretion by allogenic stimulated primary human T cells. Chimeric PD1-0103 was more potent than reference anti-PD1 antibodies. For comparison the reference anti-PD1 antibodies comprising the VH and VL domains of either nivolumab (also known as MDX5C4 or MDX-1106) and pembrolizumab (also known as MK-3475 or Org 1.09A) were synthesized and cloned with backbones of human IgG1 (with mutations L234A, L235A and P329G (EU index of Kabat)) were used.

3C) In additional experiments the immune modulating activity of the humanized variants of anti-PD-1 antibody PD1-0103 (humanized antibodies PD1-0103-0312, PD1-0103-0314, in FIG. 2 and FIG. 3, see also Example 9 below) the a) IFNγ release (secretion) b) TNF-alpha release (secretion) was evaluated in MLR as described above. The effect of the chimeric PD1-0103 antibody and its humanized versions were compared to the reference anti-PD1 antibodies comprising the VH and VL domains of either nivolumab (also known as MDX5C4 or MDX-1106) and pembrolizumab (also known as MK-3475 or Org 1.09A) with backbones of human IgG1 (with mutations L234A, L235A and P329G (EU index of Kabat)). After 6 days of MLR culture 50 µl of supernatant was taken and multiple cytokines were measured in a single culture using Bio-Plex Pro™ Human Cytokine Th1/Th2 Assay (Bio-Rad Laboratories Inc.). (data not shown for all cytokines). The chimeric PD1-0103 antibody and its humanized versions (PD1-0103_0312 and PD1-0103_0314) were more potent compared to the reference anti-PD1 antibodies in enhancing the T cell activation and IFN-gamma secretion. Furthermore, the chimeric PD1-

0103 antibody and its humanization variants increased tumor necrosis factor alpha (TNF alpha) and IL-12 secretion by antigen presenting cells and enhance capacity of monocytes/macrophages or antigen presenting cells to stimulate a T cell.

Example 4

Effect of Anti-PD-1 Blockade on Cytotoxic Granzyme B Release and IFN-γ Secretion by Human CD4 T Cells Cocultured with Allogeneic Mature Dendritic Cells To further investigate the effect of anti-PD-1 treatment in an allogeneic setting we developed an assay in which freshly purified CD4 T cells are cocultured for 5 days in presence of monocyte-derived allogeneic mature dendritic cells (mDCs). Monocytes were isolated from fresh PBMCs one week before through plastic adherence followed by the removal of the non-adherent cells. We then generated immature DCs from the monocytes by culturing them for 5 days in media containing GM-CSF (50 ng/ml) and IL-4 (100 ng/ml). To induce iDCs maturation, we added TNF-α, IL-1β and IL-6 (50 ng/ml each) to the culturing media for 2 additional days. We then assessed DCs maturation by measuring their surface expression of Major Histocompatibility Complex Class II (MHCII), CD80, CD83 and CD86 thorugh flow cytometry (LSRFortessa, BD Biosciences).

On the day of the minimal mixed lymphocyte reaction (mMLR), CD4 T cells were enriched via a microbead kit (Miltenyi Biotec) from 108 PBMCs obtained from an unrelated donor. Prior culture, CD4 T cells were labeled with 5 M of Carboxy-Fluorescein-Succinimidyl Esther (CFSE). 105 CD4 T cells were then plated in a 96 well plate together with mature allo-DCs (5:1) in presence or absence of blocking anti-PD1 antibody (either PD1-0103, chimeric PD1-0103, or humanized antibodies PD1-0103-0312, PD1-0103-0313, PD1-0103-0314, PD1-0103-0315, abbreviated as 0312, 0313, 0314, 0315), at the concentration of 10 µg/ml if not differently indicated in the figures.

Five days later the cell-culture supernatants were collected and used to measure the IFN-γ levels by ELISA (R&D systems. The cells were left at 37° C. for additional 5 hours in presence of Golgi Plug (Brefeldin A) and Golgi Stop (Monensin). The cells were then washed, stained on the surface with anti-human CD4 antibody and the Live/Dead fixable dye Aqua (Invitrogen) before being fixed/permeabilized with Fix/Perm Buffer (BD Bioscience). Intracellular staining was performed for Granzyme B (BD Bioscience), IFN-γ and IL-2 (both from eBioscience).

All humanized variants PD1-0103 (humanized antibodies PD1-0103-0312, PD1-0103-0313, PD1-0103-0314, PD1-0103-0315, abbreviated as 0312, 0313, 0314, 0315) were found to be equally good in enhancing granzyme B and interferon gamma (data not shown).

Example 5

Chimeric PD1 Antibody Derivatives

Chimeric PD1 antibodies were generated by amplifying the variable heavy and light chain regions of the anti-PD1 mouse antibodies PD1-0098, PD1-0103 via PCR and cloning them into heavy chain expression vectors as fusion proteins with human IgG1 backbones/human CH1-Hinge-CH2-CH3 with mutations L234A, L235A and P329G (EU index of Kabat)) (Leucine 234 to Alanine, Leucine 235 to Alanine, Proline 329 to Glycine) abrogating effector functions and light chain expression vectors as fusion proteins to human C-kappa. LC and HC Plasmids were then cotransfected into HEK293 and purified after 7 days from supernatants by standard methods for antibody purification. The chimeric PD1-antibodies were renamed chimeric chiPD1-0098 (chiPD1-0098) and chimeric PD1-0103 (chiPD1-0103). For comparison the reference anti-PD1 antibodies comprising the VH and VL domains of either nivolumab (also known as MDX-5C4 or MDX-1106) and pembrolizumab (also known as MK-3475 or Org 1.09A) were synthesized and cloned with backbones of human IgG1 (with mutations L234A, L235A and P329G (EU index of Kabat)) were used.

Example 6

Generation, Expression and Purification of Humanized Variants of Anti-PD1 Antibody PD-0103 (huMab PD-0103) and Characterization Humanization of the VH and VL Domains of Murine Anti-PD1 Antibody 0103

Based upon the amino acid sequence of the murine VH and VL domains of murine anti-PD1 antibody PD1-0103 (SEQ ID NO: 7 and 8), humanized anti-anti-PD1 antibody variants were generated.

The humanized VH-variant is based on the human germline IMGT_hVH_3_23 in combination with the human J-element germline IGHJ5-01 with several mutations. (resulting in SEQ ID NO: 9).

The humanized variants of VL are based on the human germlines IMGT_hVK_4_1, IMGT_hVK_2_30, IMGT_hVK_3_11 and IMGT_hVK_1_39 in combination with the human J-element germline IGKJ1-01. Different mutations resulted in humanized variants of SEQ ID NO: to SEQ ID NO: 13.

The humanized amino acid sequences for heavy and light chain variable regions of PD1-0103 were backtranslated in to DNA and the resulting cNDA were synthesized (GenArt) and then cloned into heavy chain expression vectors as fusion proteins with human IgG1 backbones/human CH1-Hinge-CH2-CH3 with LALA and PG mutations (Leucine 234 to Alanine, Leucine 235 to Alanine, Proline 329 to Glycine) abrogating effector functions or into light chain expression vectors as fusion proteins to human C-kappa. LC and HC Plasmids were then cotransfected into HEK293 and purified after 7 days from supernatants by standard methods for antibody purification. The resulting humanized PD1-antibodies named as follows:

TABLE 5

VH and VL sequences of humanized variant antibodies of PD1-0103

| Humanized antibodies of PD1-0103 | humanized variant of VH/SEQ ID NO: | humanized variant of VL/SEQ ID NO: |
|---|---|---|
| PD1-0103-0312 | SEQ ID NO: 9 | SEQ ID NO: 10 |
| PD1-0103-0313 | SEQ ID NO: 9 | SEQ ID NO: 11 |
| PD1-0103-0314 | SEQ ID NO: 9 | SEQ ID NO: 12 |
| PD1-0103-0315 | SEQ ID NO: 9 | SEQ ID NO: 13 |

Humanized PD1-0103 antibody variants and parental chimeric PD1-0103 were characterized as described above. Results are shown in Table 6.

TABLE 6

Summary of results for humanized PD1-0103 antibody variants and parental chimeric PD1-0103

| Assay | chimeric PD1-0103 | PD-0103-0312 | PD-0103-0313 | PD-0103-0314 | PD-0103-0315 |
|---|---|---|---|---|---|
| Affinity $K_{D\ 37°\ C}$ [nM] | 2.0/0.8 | 1.5/1.8 | 1.9/2.3 | 1.6/1.5 | 1.7/1.5 |
| ELISA $EC_{50}$ [nM] | 0,2 | 0,1 | 0,07 | 0,07 | 0,06 |
| CHO-PD1 $EC_{50}$ | + | + | + | + | + |
| $IC_{50}$ PD-L1, 2 [nM] | 1.35 | tbd | tbd | tbd | tbd |
| Mixed Lymphocyte Reaction assay | +++ | +++ | +++ | ++++ | ++ |
| cynomolgus crossreactivity ($EC_{50}$ [nm]) | + | 0,08 | 0,06 | 0,05 | 0,04 |

The humanized variant PD-0103-0312 is termed aPD1 antibody clone PD1-0376 in the following.

Example 7

Generation of Anti-LAG3 Antibodies

Immunization of Rabbits

Roche proprietary transgenic rabbits expressing a humanized antibody repertoire were immunized with LAG3 expressing plasmid DNA.

A set of 3 rabbits was immunized genetically, using a plasmid expression vector coding for full-length human LAG3 (15352_pIntronA_fl-hLag3_DNA-IMS), by intradermal application of 400 ug vector DNA, followed by Electroporation (5 square pulses of 750 V/cm, duration 10 ms, interval 1 s). Rabbits received 7 consecutive immunizations at days 0, 14, 28, 49, 70, 98 and 126. Blood (10% of estimated total blood volume) was taken at days 35, 77, 105 and 133. Serum was prepared, which was used for titer determination by ELISA (see below), and peripheral mononuclear cells were isolated, which were used as a source of antigen-specific B cells in the B cell cloning process below.

Determination of Serum Titers (ELISA)

Human recombinant LAG3 protein was immobilized on a 96-well NUNC Maxisorp plate at 2 ug/ml, 100 ul/well, in PBS, followed by: blocking of the plate with 2% Crotein C in PBS, 200 ul/well; application of serial dilutions of antisera, in duplicates, in 0.5% Crotein C in PBS, 100 ul/well; detection with either (1) HRP-conjugated donkey anti-rabbit IgG antibody (Jackson Immunoresearch/Dianova 711-036-152; 1/16 000), or (2) HRP-conjugated rabbit anti-human IgG antibody (Pierce/Thermo Scientific 31423; 1/5000), or (3) biotinylated goat anti-human kappa antibody (Southern Biotech/Biozol 2063-08, 1/5 000) and streptavidin-HRP; each diluted in 0.5% Crotein C in PBS, 100 ul/well. For all steps, plates were incubated for 1 h at 37° C. Between all steps plates were washed 3 times with 0.05% Tween 20 in PBS. Signal was developed by addition of BM Blue POD Substrate soluble (Roche), 100 ul/well; and stopped by addition of 1 M HCl, 100 ul/well. Absorbance was read out at 450 nm, against 690 nm as reference. Titer was defined as dilution of antisera resulting in half-maximal signal.

Isolation of Rabbit Peripheral Blood Mononuclear Cells (PBMC)

Blood samples were taken of immunized transgenic rabbits. EDTA containing whole blood was diluted twofold with 1×PBS (PAA, Pasching, Austria) before density centrifugation using lympholyte mammal (Cedarlane Laboratories, Burlington, Ontario, Canada) according to the specifications of the manufacturer. The PBMCs were washed twice with 1×PBS.

EL-4 B5 Medium

RPMI 1640 (Pan Biotech, Aidenbach, Germany) supplemented with 10% FCS (Hyclone, Logan, UT, USA), 2 mM Glutamin, 1% penicillin/streptomycin solution (PAA, Pasching, Austria), 2 mM sodium pyruvate, 10 mM HEPES (PAN Biotech, Aidenbach, Germany) and 0.05 mM b-mercaptoethanole (Gibco, Paisley, Scotland) was used.

Coating of Plates with Protein Antigen

Sterile cell culture 6-well plates were coated with human LAG3 ECD conjugated to a human Fc part (2 µg/ml) in carbonate buffer (0.1 M sodium bicarbonate, 34 mM Disodiumhydrogencarbonate, pH 9.55) over night at 4° C. Plates were washed in sterile PBS three times before use.

Depletion of Cells (a) Sterile 6-well plates (cell culture grade) covered with a confluent monolayer of CHO cells were used to deplete macrophages/monocytes through unspecific adhesion as well as unspecifically binding lymphocytes.

(b) Blank sterile 6-well plates (cell culture grade) were used to deplete macrophages and monocytes and other cells through unspecific adhesion.

Half of the PBMC sample was used for (a) and half for (b).

Each well was filled at maximum with 4 ml medium and up to 6×106 PBMCs from the immunized rabbit and allowed to bind for 1 h at 37° C. in the incubator. The cells in the supernatant (peripheral blood lymphocytes (PBLs)) were used for the antigen panning step.

Enrichment of B Cells on LAG3 Antigen

Protein Antigen: 6-well tissue culture plates coated with LAG3-ECD-huFc protein were seeded with up to $6×10^6$ PBLs per 4 ml medium from the depletion steps using the blank 6-well plate and allowed to bind for 1 h at 37° C. in the incubator. Non-adherent cells were removed by carefully washing the wells 1-2 times with 1×PBS. The remaining sticky cells were detached by trypsin for 10 min at 37° C. in the incubator. Trypsination was stopped with EL-4 B5 medium. The cells were kept on ice until the immune fluorescence staining.

Cell surface antigen: 6-well tissue culture plates covered with a monolayer of human LAG3-positive CHO cells were seeded with up to $6×10^6$ PBLs per 4 ml medium from the depletion steps using the CHO-covered 6-well plate and allowed to bind for 1 h at 37° C. in the incubator. Non-adherent cells were removed by carefully washing the wells 1-2 times with 1×PBS. The remaining sticky cells were detached by trypsin for 10 min at 37° C. in the incubator. Trypsination was stopped with EL-4 B5 medium. The cells were kept on ice until the immune fluorescence staining.

Immune Fluorescence Staining and Flow Cytometry

The anti-IgG FITC (AbD Serotec, Dusseldorf, Germany) and the anti-huCk PE (Dianova, Hamburg, Germany) antibody was used for single cell sorting. For surface staining, cells from the depletion and enrichment step were incubated with the anti-IgG FITC and the anti-huCk PE antibody in PBS and incubated for 45 min in the dark at 4° C. After staining the PBMCs were washed two fold with ice cold PBS. Finally the PBMCs were resuspended in ice cold PBS and immediately subjected to the FACS analyses. Propidium iodide in a concentration of 5 µg/ml (BD Pharmingen, San Diego, CA, USA) was added prior to the FACS analyses to discriminate between dead and live cells. A Becton Dickinson FACSAria equipped with a computer and the FACSDiva software (BD Biosciences, USA) were used for single cell sort.

B-Cell Cultivation

The cultivation of the rabbit B cells was performed by a method described by Seeber et al. (S Seeber et al. PLoS One 9 (2), e86184. 2014 Feb. 4). Briefly, single sorted rabbit B cells were incubated in 96-well plates with 200 µl/well EL-4 B5 medium containing Pansorbin Cells (1:100000) (Calbiochem (Merck), Darmstadt, Deutschland), 5% rabbit thymocyte supernatant (MicroCoat, Bernried, Germany) and gamma-irradiated murine EL-4 B5 thymoma cells (5×10e5 cells/well) for 7 days at 37° C. in the incubator. The supernatants of the B-cell cultivation were removed for screening and the remaining cells were harvested immediately and were frozen at −80° C. in 100 µl RLT buffer (Qiagen, Hilden, Germany).

Isolation of V-Domains of LAG3 Antibodies

PCR Amplification of V-Domains

Total RNA was prepared from B cells lysate (resuspended in RLT buffer—Qiagen—Cat. No 79216) using the NucleoSpin 8/96 RNA kit (Macherey & Nagel; 740709.4, 740698) according to manufacturer's protocol. RNA was eluted with 60 µl RNase free water. 6 µl of RNA was used to generate cDNA by reverse transcriptase reaction using the Superscript III First-Strand Synthesis SuperMix (Invitrogen 18080-400) and an oligo dT-primer according to the manufatures's instructions. All steps were performed on a Hamilton ML Star System. 4 µl of cDNA were used to amplify the immunoglobulin heavy and light chain variable regions (VH and VL) with the AccuPrime Supermix (Invitrogen 12344-040) in a final volume of 50 µl using the primers rbHC.up and rbHC.do for the heavy chain and BcPCR_FHLC_leader.fw and BcPCR_huCkappa.rev for the light chain (Table 7). All forward primers were specific for the signal peptide (of respectively VH and VL) whereas the reverse primers were specific for the constant regions (of respectively VH and VL). The PCR conditions for the RbVH were as follows: Hot start at 94° C. for 5 min; 35 cycles of 20s at 94° C., 20s at 70° C., 45s at 68° C., and a final extension at 68° C. for 7 min. The PCR conditions for the HuVL were as follows: Hot start at 94° C. for 5 min; 40 cycles of 20s at 94° C., 20s at 52° C., 45s at 68° C., and a final extension at 68° C. for 7 min.

TABLE 7

| SEQ ID NO: 76 rbHC.up | AAGCTTGCCACCATGGAGACTGGG CTGCGCTGGCTTC |
|---|---|
| SEQ ID NO: 77 rbHCf.do | CCATTGGTGAGGGTGCCCGAG |
| SEQ ID NO: 78 BcPCR_FHLC_leader.fw | ATGGACATGAGGGTCCCCGC |
| SEQ ID NO: 79 BcPCR_huCkappa.rev | GATTTCAACTGCTCATCAGATGGC |

8 µl of 50 µl PCR solution were loaded on a 48 E-Gel 2% (Invitrogen G8008-02). Positive PCR reactions were cleaned using the NucleoSpin Extract II kit (Macherey & Nagel; 740609250) according to manufacturer's protocol and eluted in 50 µl elution buffer. All cleaning steps were performed on a Hamilton ML Starlet System.

Recombinant Expression of Rabbit Monoclonal Bivalent Antibodies

For recombinant expression of rabbit monoclonal bivalent antibodies, PCR-products coding for VH or VL were cloned as cDNA into expression vectors by the overhang cloning method (R S Haun et al., Biotechniques (1992) 13, 515-518; M Z Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Three variants of the basic plasmid were used: one plasmid containing the rabbit IgG constant region designed to accept the VH regions while containing human kappa LC constant region to accept the VL regions. Linearized expression plasmids coding for the kappa or gamma constant region and VL/VH inserts were amplified by PCR using overlapping primers. Purified PCR products were incubated with T4 DNA-polymerase which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

For antibody expression, the isolated HC and LC plasmids were transiently co-transfected into HEK293 cells and the supernatants were harvested after 1 week.

Example 8

Characterization of Anti-LAG3 Antibodies

AP502P) was added in a 1:2000 dilution and incubated at RT for 1 h. After washing (3×90 μl/well with PBST-buffer) 25 μl/well TMB substrate (Roche, 11835033001) was added and incubated for 2-10 min. Measurement took place on a Tecan Safire 2 instrument at 370/492 nm.

Cell-Surface Lag3 Binding ELISA

25 μl/well of Lag3 cells (recombinant CHO cells expressing Lag3, 10000 cells/well) were seeded into tissue culture treated 384-well plates (Corning, 3701) and incubated at 37° C. for one or two days. The next day after removal of medium, 25 μl anti-Lag3 samples (1:3 dilutions in OSEP buffer, starting at a concentration of 6-40 nM) were added and incubated for 2h at 4° C. After washing (1×90 μl in PBST) cells were fixed by addition of 30 μl/well glutaraldehyde to a final concentration of 0.05% (Sigma Cat.No: G5882), 10 min at room temperature. After washing (3×90 μl/well with PBST-buffer) 25 μl/well goat anti-Human Ig κ chain antibody-HRP conjugate (Milipore, AP502P) was added in a 1:1000 dilution and incubated at RT for 1 h. After washing (3×90 μl/well with PBST-buffer) 25 μl/well TMB substrate (Roche, 11835033001) was added and incubated for 6-10 min. Measurement took place on a Tecan Safire 2 instrument at 370/492 nm.

SPR (Biacore) Characterization of Anti-LAG3 Antibodies

A surface plasmon resonance (SPR) based assay has been used to determine the kinetic parameters of the binding between anti-Lag3 antibodies in bivalent format or as monovalent Fab fragments and human Fc tagged human Lag3 extra cellular domains (ECDs) at 25° C.

Therefore two flow cells of a C1 biosensor chip were prepared in a Biacore T200 by immobilizing neutravidin,

TABLE 8

| | | | | | | | | | Humanized BAP 050 |
| Summary of Characterization of different anti-LAG3 Antibodies | | | | | | | | | |
| anti-Lag3 antibodies | aLAG3 (0403) | aLAG3 (411) | aLAG3 (414) | aLAG3 (416) | aLAG3 (417) | MDX-25F7 (25F7) | BMS-986016 | MDX-26H10 (26H10) | (LAG525) |
|---|---|---|---|---|---|---|---|---|---|
| $K_D$ [M] monovalent | tbd | tbd | 4.63E−10 | 2.82E−11 | tbd | tbd | tbd | tbd | tbd |
| bivalent | tbd | tbd | tbd | tbd | tbd | tbd | tbd | tbd | tbd |
| kd [1/s] | 5.00 E−06 | 3.87 E−05 | 1.95 E−04 | 2.21 E−04 | 9.48 E−05 | 3.86 E−04 | | 3.99 E−04 | |
| Epitope Bin | E3 | E3 | E3 | E2b | E3 | E5 (D1-loop) | E5 | E4 | E2c |
| MHCII/ ELISA IC$_{50}$ [nM] | 0.9 | 0.8 | 0.9 | 0.9 | 0.9 | 0.8/0.6 | /0.4 | 0.9/0.6 | /1.0 |
| CHO-cell ELISA inflexion point [ng/ml] | 30.9 | 41.3 | 48.1 | 37.2 | 27.8 | 75 | | | |

ELISA for Human Lag3

Nunc maxisorp plates (Nunc 464718) were coated with 25 μl/well recombinant Human LAG-3 Fc Chimera Protein (R&D Systems, 2319-L3) at a protein concentration of 800 ng/ml and incubated at 4° C. overnight or for 1 h at room temperature. After washing (3×90 μl/well with PBST-buffer) each well was incubated with 90 μl blocking buffer (PBS+ 2% BSA+0.05% Tween 20) for 1 h at room temperature. After washing (3×90 μl/well with PBST-buffer) 25 μl anti-Lag3 samples at a concentration of 1-9 μg/mil (1:3 dilutions in OSEP buffer) were added and incubated 1 h at RT. After washing (3×90 μl/well with PBST-buffer) 25 μl/well goat anti-Human Ig κ chain antibody-HRP conjugate (Milipore, diluted to 25 μg/ml in acetate buffer pH 4.5, onto it using the 'immobilization wizard'. This yielded in immobilization levels of around 1900 RU. Then, CaptureSelect™ Biotin Anti-IgG-Fc (Human) Conjugate was bound to the neutravidin, using a 20 μg/ml dilution in running buffer (HBS-EP+, GE Healthcare).

The method itself consisted of four commands per cycle. First command: capturing of ~46 RU of huLag3-Fc (20s, 10 μl/min). Second command: sample injection for 120s followed by a 1200s long dissociation at a flow speed of 30 μl/min. Third and fourth command: regeneration by injecting Glycine-HCl pH 1.5 for 30 seconds. A dilution series (3.13 nM-200 nM, two-fold dilutions in running buffer) of each antibody Fab fragment and additional blank cycles were then measured using the previously described method. The Biacore T200 Evaluation Software was then utilized to gain kinetic values by applying a 1:1 Langmuir fit with the Rmax fit parameter set to 'local' since the capture levels were not perfectly reproducible. Results ($K_D$ values and kd values) are shown in Table 8.

Epitope Mapping

Epitope binning was performed using a surface plasmon resonance (SPR) based assay. Therefore aLag3 binders were bound to huLag3 on a Biacore T200 instrument. Then the accessibility of other binders to the previously formed aLag3 binder—huLag3 complex was assessed.

A SA CAP Kit (GE Healthcare) was used to carry out this assay. If not described otherwise, the assay was done according to the SA CAP Kit manual. The run included only one cycle type. After hybridization, a 10 nM dilution of biotinylated, huFc-tagged huLag3 was allowed to bind to the streptavidin on the sensor chip for 20s at a flow rate of 10 µl/min. Then a first 200 nM sample diluted in running buffer was injected for 180s at a flow rate of 30 µl/min and immediately followed by a second sample under the same conditions. The surface was then regenerated.

The samples were then assigned to different epitope groups with similar competition patterns. A first rough categorization was done, based on the relative response of the second injection using a threshold of 6.1 RU, which was just above the highest value observed when a binder was injected as first and second sample. All values and decisions were finally validated by visual inspection of the sensor-grams.

Results are shown in Table 8. Three major epitope patterns (E1, E2 and E3) were identified. Since aLag3-0416 and humanized BAP 050 share the same group but do not completely inhibit each other, they were assigned to sub-groups E2b and E2c.

Binding of Anti-Lag3 Antibodies from Tg Rabbits to Recombinant Cyno Lag3 Positive HEK Cells In addition to the binding analysis using HEK cells recombinantly expressing human Lag3 on the surface, binding to cynomolgus Lag3-positive HEK cells was also evaluated. For this experiment, frozen HEK293F cells, previously transiently transfected with cyno-LAG-3, were thawed, centrifuged and resupplemented in PBS/2% FBS. $1.5 \times 10^5$ cells/well were seeded into 96-well plates. Anti-Lag3 antibodies were added to a final normalized concentration of 10 µg/ml. For referencing and as controls, autofluorescence and positive control (Medarex 25F7) as well as isotype control (huIgG1 from Sigma, cat.no. #15154, data not shown) antibodies were prepared and measured in the experiment. HEK cells were incubated with indicated antibodies for 45 min on ice, washed twice with 200 µl ice-cold PBS buffer containing 2% FBS, before secondary antibody (APC-labelled goat anti-human IgG-kappa, Invitrogen, cat.no. #MH10515) was added (1:50 diluted in FACS-Puffer/well) and further incubated for 30 min on ice. Cells were again washed twice with 200 µl ice-cold PBS/2% FBS buffer before samples were finally resuspended in 150 µl FACS buffer and binding was measured on FACS CANTO-II HTS Module.

Results: Shown in the below table is the binding and cross-reactivity of different anti-Lag3 antibodies to HEK293 cells expressing cynoLAG3, binding either given in % positive cells or the GeoMean of the signal intensity.

TABLE 9

| Binding of different anti-LAG3 Antibodies to recombinant cyno Lag3 positive HEK cells | | |
|---|---|---|
| LAG3 antibody | % pos. | GeoMean |
| Reference LAG3 antibody MDX25F7 | 41.2 | 3062 |
| aLAG3(0411) | 88.6 | 11007 |
| aLAG3(0414) | 81.6 | 9169 |
| aLAG3(0416) | 67.9 | 4221 |
| aLAG3(0417) | 75.9 | 7115 |
| aLAG3(0403) | 82.0 | 7457 |

Binding of Anti-Lag3 Antibodies from Tg Rabbits to (Activated) Cynomolgus PBMC/T Cells Expressing Lag3

After binding to recombinant Lag3 protein and Lag3 expressed recombinantly on mammalian cells, binding to Lag3 expressed on activated cynomolgus T cells was also assessed.

The binding characteristics of the newly generated anti-Lag3 antibodies (derived from Roche's transgenic rabbits) to Lag3 expressed on the cell surface of cynomolgus T cells or PBMC was confirmed by FACS analysis. While Lag3 is not expressed on naïve T cells it is upregulated upon activation and/or on exhausted T cells. Thus, cynomolgus peripheral blood mononuclear cells (PBMC) were prepared from fresh cynomolgus blood and were then activated by CD3/CD28 pre-treatment (1 µg/ml) for 2-3 days. Activated cells were subsequently analyzed for Lag3 expression: Briefly, $1-3 \times 10^5$ activated cells were stained for 30-60 min on ice with indicated anti-Lag3 antibodies and respective control antibodies at 10 µg/ml final concentration. The bound anti-Lag3 antibodies were detected via fluorochrome-conjugated anti-human IgG or an anti-rabbit IgG secondary antibodies. After staining, cells were washed two times with PBS/2% FCS and analyzed on a FACS Fortessa (BD).

Results: The following table summarizes the percentage of Lag3 positive cells within activated cynomolgus PBMC.

TABLE 10

| Binding of different anti-LAG3 Antibodies to (activated) cynomolgus PBMCs/T cells expressing Lag3 | |
|---|---|
| Anti-Lag3/ctrl Antibodies | % positive cyno cells (PBLs) after CD3/CD28 activation |
| only 2nd Ab (hu) | 7.62 |
| DP47 (human isotype) | 9.19 |
| Reference LAG3 antibody (MDX25F7) | 22.1 |
| Reference LAG3 antibody BMS-986016 | 18.6 |
| Reference LAG3 antibody (humanized BAP050(LAG525)) | 50.7 |
| only 2nd Ab (rb) | 5.26 |
| aLAG3(0403) | 44.2 |
| aLAG3(0411) | 46.6 |
| aLAG3(0414) | 43.0 |
| aLAG3(0416) | 38.9 |
| aLAG3(0417) | 35.3 |

On activated cynomolgus T cells all of the rabbit anti-Lag3 antibodies demonstrated a significant binding to Lag3⁺ cells. Hereby, all newly generated antibodies showed an increased percentage of positive cells compared to human anti-Lag3 reference antibodies (e.g. such as MDX25F7, BMS-986016).

Inhibition of LAG-3 Binding to MHC-II Expressed on Human A375 Tumor Cells (by ELISA)

25 µl/well of A375 cells (10000 cells/well) were seeded into tissue culture treated 384-well plates (Corning, 3701) and incubated at 37° C. overnight. Anti-Lag3 antibodies were pre-incubated for 1 h with biotinylated-Lag3 (250 ng/ml) in cell culture medium in 1:3 dilutions starting at 3 µg/ml antibody-concentration. After removal of medium from the wells with the seeded cells, 25 µl of the antibody-Lag3 pre-incubated mixtures were transferred to the wells and incubated for 2 h at 4° C. After washing (1×90 µl in PBST) cells were fixed by addition of 30 µl/well glutaraldehyde to a final concentration of 0.05% (Sigma Cat. No: G5882), 10 min at room temperature. After washing (3×90 µl/well with PBST-buffer) 25 µl/well Poly-HRP40-Streptavidin (Fitzgerald, 65R-S104PHRPx) was added in a 1:2000 or 1:8000 dilution and incubated at RT for 1 h. After washing (3×90 µl/well with PBST-buffer) 25 µl/well TMB substrate (Roche, #11835033001) was added and incubated for 2 to 10 min. Measurement took place on a Tecan Safire 2 instrument at 370/492 nm.

Inhibition of LAG-3 Binding to MHC-II Expressed on Human A375 Tumor Cells (by FACS Analysis)

Assay principle: To study the antagonistic function of the anti-Lag3 antibodies, an MHCII:Lag3 competition assay was conducted. MHCII$^+$ human A375 cells were stained with inhouse generated biotinylated Lag3:Fc fusion protein with or without pre-incubation with anti-Lag3 antibodies. This analysis was studied in a FACS competition experiment: A375 cells (ATCC, #CRL-1619) were cultured for 2-3 passages in EM Eagle's medium supplemented with EBSS (PAN, cat.no. #P04-00509), 10% FBS, 2 mM L-Glutamin, 1×NEAA and 1× Sodium Pyruvate. All antibodies were diluted in FACS buffer to a final concentration of 20 µg/ml in 25 µl (in 96 well U-bottom plates). 25 µl of inhouse generated, biotinylated recombinant LAG-3:Fc fusion protein was added to a final concentration of 10 µg/ml either to medium or to anti-Lag3 antibodies or controls and were pre-incubated for 30 min at room temperature. A375 cells were washed with PBS and adjusted to 3×10$^6$ cells/ml in PBS. 100 µl were seeded per well in a 96 well V-bottom plate. Plates were centrifuged and supernatant was removed. Then the pre-incubated LAG-3:Fc fusion protein/antibody mix (50 µl/well) was added to the cells and incubated for 1h at room temperature. After this, cells were washed with 200 µl FACS buffer. For detection of biotinylated Lag3:Fc protein bound to cellular MHCII, an APC-conjugated goat anti-Biotin antibody was used at 3 µl/sample (Miltenyi Biotec, cat.no. #130-090-856) and incubated for additional 10-15 mins. After staining, cells were again washed and then transferred in 150 µl FACS buffer (PBS/2% FBS) to a U-bottom plate and analyzed on a FACS Canto-II using an HTS module.

Two anti-Lag3 antibodies (clones 25F7 and 26H10; Medarex) served as positive controls and a human IgG1 (Sigma, cat.no. #I5154) as appropriate isotype control. All antibodies were used at 10 µg/ml final concentration.

Results: Shown in the below table is the result of the FACS analysis demonstrating the percent inhibition of the Lag3 protein binding to MHC-II on cells (calculated as the reduced binding signal in reference to the maximal value in the absence of a blocking antibody).

TABLE 11

Binding of different anti-LAG3 Antibodies to (activated) cynomolgus PBMC/T cells expressing Lag3

| aLAG3 antibody | % Inhibition |
| --- | --- |
| aLAG3(0403) | 34.9 |
| aLAG3(0414) | 67.3 |
| aLAG3(0411) | 45.6 |
| aLAG3(0416) | 68.6 |
| aLAG3(0417) | 59.1 |
| Reference MDX25F7 | 70.0 |
| Reference MDX26H10 | 71.7 |
| Isotype control | -2.9 |
| No mAb | 0.0 |

These data support a functional interplay with Lag3 and blockade of the cellular interaction of all tested antibodies. Neutralizing Potency of the Novel Anti-Lag3 Antibodies in a Standard LAG3 Blockade Bio/Reporter Assay To test the neutralizing potency of the novel anti-Lag3 antibodies in restoring a suppressed T cell response in vitro, a commercially available reporter system was used. This system consists of Lag3$^+$ NFAT Jurkat effector cells (Promega, cat. no. #CS194801), MHC-II$^+$ Raji cells (ATCC, #CLL-86), and a super-antigen. In brief, the reporter system is based on three steps: (1) superantigen-induced NFAT cell activation, (2) inhibition of the activating signal mediated by the inhibiting interaction between MHCII (Raji cells) and Lag3$^+$ NFAT Jurkat effector cells, and (3) recovery of the NFAT activation signal by Lag3-antagonistic/neutralizing aVH-Fc fusion constructs.

For this experiment, Raji and Lag-3$^+$ Jurkat/NFAT-luc2 effector T cells were cultured as described by the provider. Serial dilutions (40 µg/ml-50 µg/ml) of several anti-Lag3 and reference antibodies were prepared in assay medium (RPMI 1640 (PAN Biotech, cat.no. #P04-18047), 1% FCS) in flat, white bottom 96-well culture plates (Costar, cat.no. #3917). 1×10$^5$ Lag3$^+$ NFAT-Jurkat cells/well) were added to the antibody solution. After this step, 2.5×10$^4$ Raji cells/well were added to the Jurkat cell/antibody mix as well as 50 ng/ml final concentration of the SED super-antigen (Toxin technology, cat.no. DT303). After an incubation of six hrs at 37° C. and 5% CO$_2$, Bio-Glo substrate (Promega, #G7940) was warmed up to room temperature and 75 µl were added per well, incubated for 5-10 min before the overall luminescence was measured at a Tecan Infinite reader according to the kit's manufacturer's recommendation.

Shown in the table is the restoration of a MHCII/Lag3-mediated suppression of the NFAT luciferase signal by different anti-Lag3 antibodies upon SED stimulation (given as EC$_{50}$ values):

TABLE 12

Results with different anti-LAG3 Antibodies in the standard LAG3 Blockade Bio/Reporterassay

| Anti-LAG3 | EC$_{50}$ [nM] in Jurkat LAG3 + SED + Raji | | |
| --- | --- | --- | --- |
| | 1st assay | 2nd assay | 3rd assay |
| Reference MDX25F7 | 7.8/5.9 | 8.6 | n.t. |
| Reference BMS-986016 | n.t. | 9.6 | n.t. |
| Reference humanized BAP050(LAG525) | n.t. | 22.6 | n.t. |
| Lag3 IgG-Fc | n.t. | no effect | n.t. |

TABLE 12-continued

Results with different anti-LAG3 Antibodies
in the standard LAG3 Blockade
Bio/Reporterassay

| | EC$_{50}$ [nM] in Jurkat LAG3 + SED + Raji | | |
|---|---|---|---|
| Anti-LAG3 | 1st assay | 2nd assay | 3rd assay |
| aLAG3(0411) | 1.1 | 1.0 | n.t. |
| aLAG3(0414) | 1.1 | 1.0 | 1.8 |
| aLAG3(0416) | 3.1 | 2.5 | 3.5 |
| aLAG3(0417) | 1.0 | n.t. | n.t. | n.t. molecules not tested in this experiment

Example 9

Functional Characterization of Anti-LAG3 Antibodies

Table 13 summarizes the biological activity and effects of different anti-LAG3 antibodies (alone or in combination with anti-PD1 antibodies) in different assays as described herein.

TABLE 13

Summary of biologival activity of different anti-LAG3 Antibodies (alone or in
combination with anti-PDl antibodies)

| Assay type | Anti-Lag3 aLAG3 (0403) | Anti-Lag3 aLAG3 (0411) | Anti-Lag3 aLAG3 (0414) | Anti-Lag3 aLAG3 (0416) | Anti-Lag3 aLAG3 (0417) | Ref. 1 BMS 986016 | Ref. 2 humanized BAP050 (LAG52) |
|---|---|---|---|---|---|---|---|
| mMLR (GrzB) | + | − | +++ | ++ | + | − | ++ |
| mMLR (IL-2) | − | − | + | + | ++ | + | ++ |
| CD4 + ARH77 | | | +++ | +++ | | + | + |
| Treg-suppression (GrzB) | | | +++ | + | | − | + |
| Treg-suppression (IFN-γ) | | | +++ | ++ | | + | + |
| Melanoma patient PBMCs | | | +++ | | | | |

Effect of PD-1 and LAG-3 Blockade on Cytotoxic Granzyme B Release and IL-2 Secretion by Human CD4 T Cells Cocultured with Allogeneic Mature Dendritic Cells To screen anti-LAG-3 blocking antibodies in combination with anti-PD-1 in an allogeneic setting an assay was developed in which freshly purified CD4 T cells are cocultured for 5 days in presence of monocyte-derived allogeneic mature dendritic cells (mDCs). Monocytes were isolated from fresh PBMCs one week before through plastic adherence followed by the removal of the non-adherent cells. Immature DCs were then generated from the monocytes by culturing them for 5 days in media containing GM-CSF (50 ng/ml) and IL-4 (100 ng/ml). To induce iDCs maturation, TNF-alpha, IL-1beta and IL-6 (50 ng/ml each) were added to the culturing media for 2 additional days. DCs maturation was then assessed by measuring their surface expression of Major Histocompatibility Complex Class II (MHCII), CD80, CD83 and CD86 through flow cytometry (LSR-Fortessa, BD Biosciences).

On the day of the minimal mixed lymphocyte reaction (mMLR), CD4 T cells were enriched via a microbead kit (Miltenyi Biotec) from 108 PBMCs obtained from an unrelated donor. Prior culture, CD4 T cells were labeled with 5 M of Carboxy-Fluorescein-Succinimidyl Esther (CFSE). 10$^5$ CD4 T cells were then plated in a 96 well plate together with mature allo-DCs (5:1) in presence or absence of blocking anti-PD-1 antibody aPD1(0376) (=PD1-0103-0312, as described herein before or in PCT Application PCT/EP2016/073248) alone or in combination with chimeric anti-LAG-3 antibodies (aLAG3(0403) to aLAG(0418)) or reference antibodies (humanized BAP050 (LAG525) and BMS 986016) at the concentration of 10 µg/ml. DP47 is a non-binding human IgG with a LALA mutation in the Fc portion to avoid recognition by FcγR and was used as negative control.

Figure 2A:
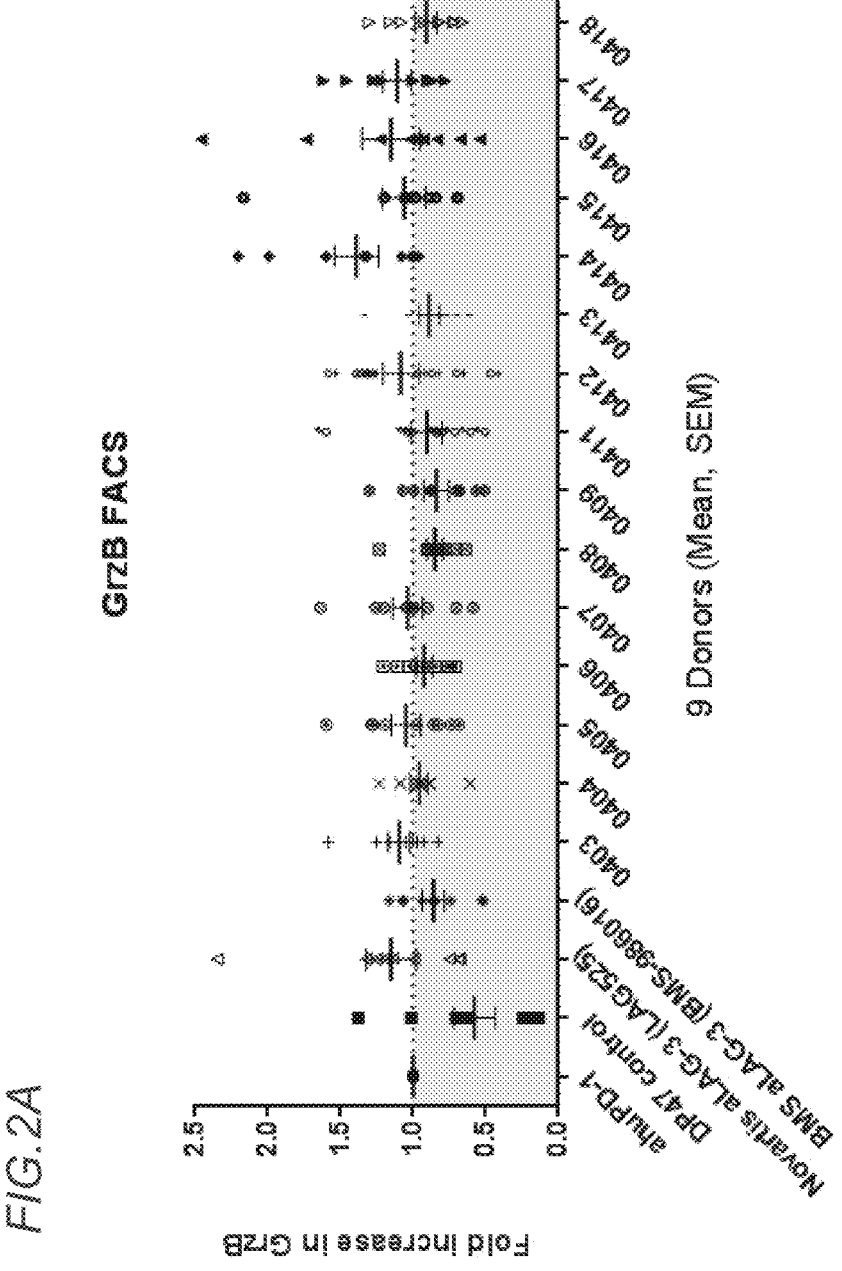
FIGS. 2A and 2B: Effect of aLAG-3 antibodies on cytotoxic Granzyme B release and IL-2 secretion by human CD4 T cells cocultured with allogeneic mature dendritic cells.
Figure 2B:
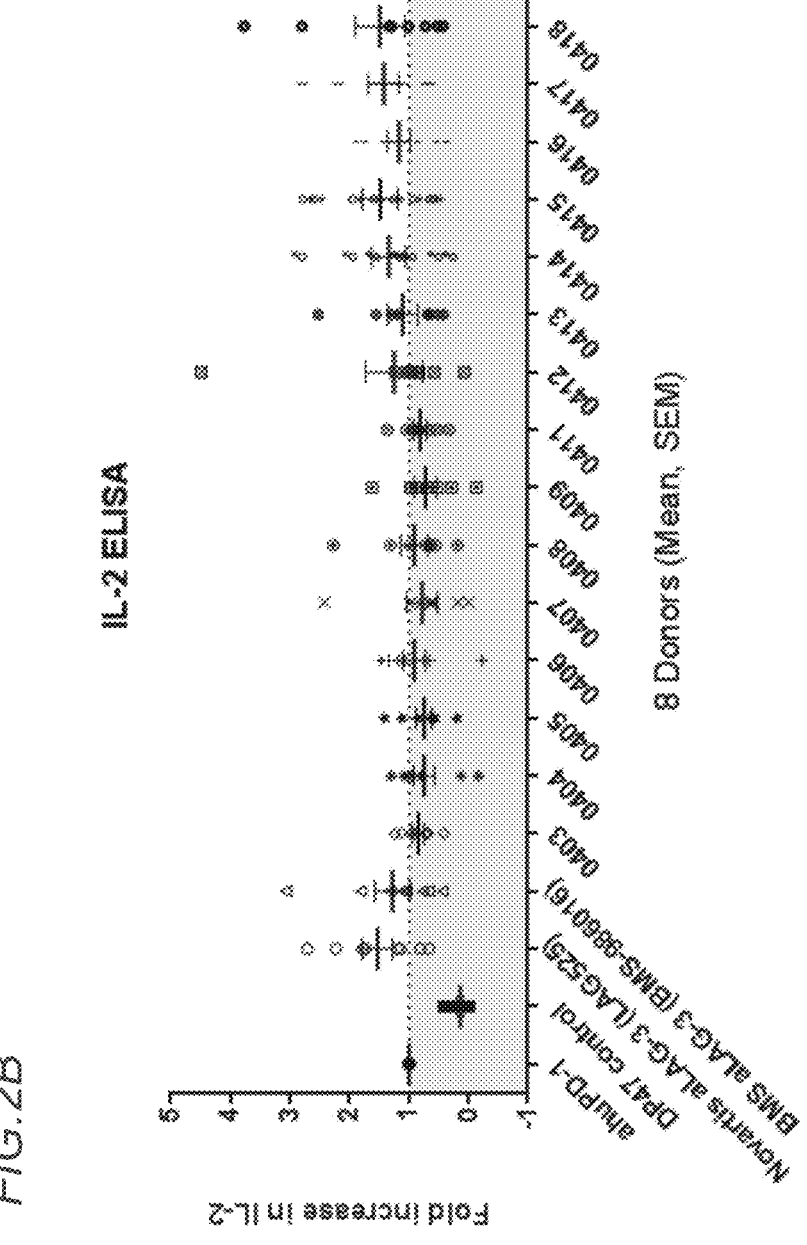

Five days later the cell-culture supernatants were collected and used to measure the IL-2 levels by ELISA (R&D systems), and the cells were left at 37° C. for additional 5 hours in presence of Golgi Plug (Brefeldin A) and Golgi Stop (Monensin). The cells were then washed, stained on the surface with anti-human CD4 antibody and the Live/Dead fixable dye Aqua (Invitrogen) before being fixed/permeabilized with Fix/Perm Buffer (BD Bioscience). We performed intracellular staining for Granzyme B (BD Bioscience) and IFN-γ (eBioscience). Results are shown in FIGS. 2A and 2B.

Effect of PD-1 and LAG-3 Blockade on Cytotoxic Granzyme B Release by Human CD4 T Cells Cocultured with a B Cell-Lymphoblatoid Cell Line (ARH77).

Figure 3:
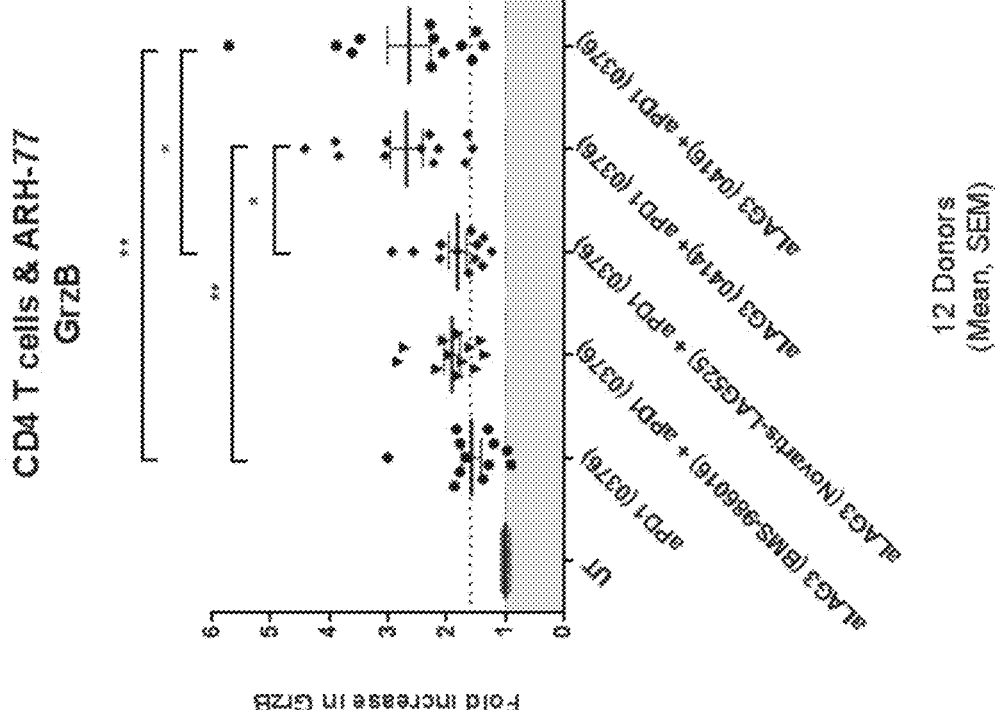
FIG. 3: Effect of aLAG3 antibodies in combination with aPD1 antibody (0376) on cytotoxic Granzyme B release by human CD4 T cells cocultured with a B cell-lymphoblatoid cell line (ARH77). Shown is a comparison of different aLAG3 antibodies in combination with aPD1 antibody (0376) and with aPD1 antibody (0376) alone.

In functional studies, CD4 T cells were co-cultured with the tumor cell line ARH77, a B cell lymphoblastoid cell line which expresses lower levels of PDL-1 than mDCs, to better characterize the contribution of LAG-3 antagonism to PD-1 blockade. The rest of the experimental set up and readout remained unchanged from the mMLR. The anti-LAG-3 antibodies (aLAG3(0414) and aLAG3(0416), chosen based on their ability to co-secrete IL-2 and Granzyme B in the mMLR) in combination with anti-PD-1 antibody caused a more significant increase in Granzyme B secretion by CD4 T cells than reference anti-LAG-3 antibodies ((humanized BAP050 (LAG525) and BMS 986016)) (P<0.05) and anti-PD-1 alone (P<0.01) as shown in FIG. 3.

Effect of PD-1 and LAG-3 Blockade on Treg Suppression of Granzyme B and IFN-γ Release by Human CD4 T Cells Cocultured with Irradiated Allogeneic PBMCs.

In functional studies involving regulatory T cells (Treg)-suppression assays, PBMCs from the same donor where divided in two samples: one was enriched in CD4 T cells and the other one in Tregs defined as CD4⁺CD25$^{high}$ CD127$^{low}$ T cells via a microbead kit (Miltenyi Biotec). Once purified the two populations, CD4 T cells were labelled with 5 M of Carboxy-Fluorescein-Succinimidyl Esther (CFSE) while Tregs with 5 M Cell-Trace-Violet (CTV) to be able to distinguish them at the FACS later on.

Both CD4 T cells ($10^5$) and Tregs ($10^5$) were then co-cultured in a 96 well plate at 1:1 ratio together with irradiated, CD4-depleted PBMCs ($10^5$) from an unrelated donor in presence or absence of anti-LAG-3 antibodies (aLAG3(0414) and aLAG3(0416) or reference anti-LAG-3 antibodies (humanized BAP050 (LAG525) and BMS 986016) in combination with anti-PD-1 antibody aPD1 (0376) at the concentration of 10 μg/ml. As control to estimate the magnitude of the suppression of CD4 T cell effector functions by Tregs, CD4 T cells ($10^5$) were also co-cultured with irradiated PBMCs ($10^5$) in the absence of Tregs.

Figures 4A, 4B:
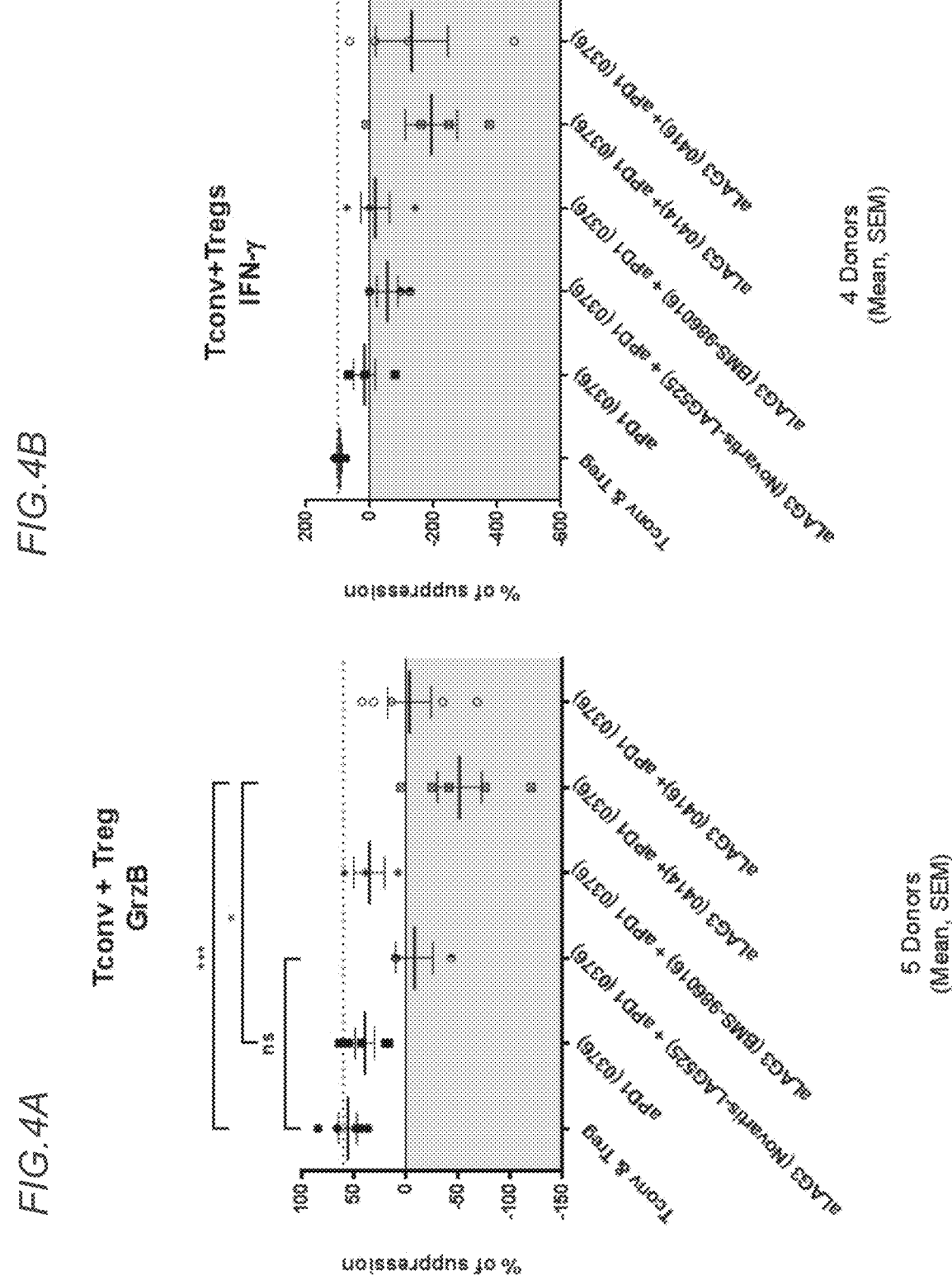
FIGS. 4A and 4B: Effect of aLAG3 antibodies in combination with aPD1 antibody (0376) on Treg suppression of Granzyme B and IFN-γ release by human CD4 T cells cocultured with irradiated allogeneic PBMCs.

Five days later the cell-culture supernatants were collected and used later to measure IFN-γ levels by ELISA (R&D systems), and the cells were left at 37° C. for additional 5 hours in presence of Golgi Plug (Brefeldin A) and Golgi Stop (Monensin). The cells were then washed, stained on the surface with anti-human CD4 antibody and the Live/Dead fixable dye Aqua (Invitrogen) before being fixed/permeabilized with Fix/Perm Buffer (BD Bioscience). Intracellular staining was performed for Granzyme B (BD Bioscience) and IFN-γ (eBioscience). Results are shown in FIGS. 4A and 4B.

The anti-LAG-3 antibodies (aLAG3(0414) and aLAG3 (0416), in combination with anti-PD-1 antibody aPD1(0376) (=PD1-0103-0312, from PCT Application PCT/EP2016/073248) elicited Tconv escape from regulatory T cell tight control as demonstrated by the secretion of significantly higher amount of Granzyme B than Tconv in presence of anti-PD-1 alone (P<0.05) or in absence of checkpoint inhibitors (P<0.001). Reference anti-LAG-3 antibodies (humanized BAP050 (LAG525) and BMS 986016) in combination with anti-PD-1 did not significantly rescue Tconv effector functions from Treg suppression. Similar results were obtained for IFN-γ even if the difference did not reach statistical significance with only 4 donors.

Effect of PD-1 and LAG-3 Blockade on Granzyme B and IFN-γ Secretion by CD4 T Cells from Melanoma Patient PBMCs after Recall with Immunogenic Melanoma-Antigen Peptide Pools.

It has been previously described that melanoma patient PBMCs contain detectable frequencies of tumor-antigen specific T cells. Therefore, for POC purposes, we tested anti-LAG-3 antibody (0414) plus anti-PD-1 versus or anti-PD-1 alone on melanoma patient PBMCs re-stimulated overnight with immunogenic melanoma associated antigens peptide pools.

$10^5$ to $10^6$ PBMCs from melanoma patients where incubated at room temperature in presence or absence of saturating concentrations (10 μg/ml) of anti-PD-1 alone (0376), in combination with anti-LAG-3 (aLAG3(0414)=(0414), 10 μg/ml) antibody. T cells were then re-stimulated over-night with a pool of immunogenic tumor related antigens like MAGEA1, MAGEA3, MAGEA4, Melan-A/MART-1, NYESO-1, Melanocyte protein Pmel 17 gp100, Tyrosinase, Tyrosinase-related protein 2 in presence of protein transport inhibitors Golgi Plug (Brefeldin A) and Golgi Stop (Monensin).

The cells were then washed, stained on the surface with anti-human CD4 antibody and the Live/Dead fixable dye Aqua (Invitrogen) before being fixed/permeabilized with Fix/Perm Buffer (BD Bioscience). Intracellular staining was performed for Granzyme B (BD Bioscience) and IFN-γ (eBioscience).

The combination of anti-LAG-3 and anti-PD-1 antibodies (P<0.01 and P<0.001) significantly (P<0.01 and P<0.0001) enhanced tumor-antigen specific T cell effector functions (i.e. Granzyme B and IFN-γ secretion) while PD-1 blockade alone did not show any effect (data not shown).

Example 10

Generation and Production of Bispecific Anti-PD1/Anti-LAG3 Antibodies

10.1 Production and Expression of Bispecific Antibodies which Bind to PD1 and LAG3 with VH/VL Domain Exchange/Replacement (CrossMAb$^{Vh-VL}$) in One Binding Arm and with Single Charged Amino Acid Substitutions in the CH1/CL Interface

Multispecific antibodies which bind to human PD1 and human LAG3 were generated is described in the general methods section by classical molecular biology techniques and were expressed transiently in 293F of Expi293F cells as described above. The multispecific 1+1 CrossMAb$^{Vh-Vl}$ antibodies are described also in WO 2009/080252. The multispecific antibodies were expressed using expression plasmids containing the nucleic acids encoding the amino acid sequences depicted in Table 14. A schematic structure of the 1+1 CrossMAb$^{Vh-Vl}$ bispecific antibodies is shown in FIG. 1A.

TABLE 14

Amino acid sequences of light chains (LC) and heavy chains (HC), with VH/VL domain exchange/replacement (1 + 1 CrossMAb$^{Vh-Vl}$)

| 1 + 1 Antibody | HC1 | HC2 | LC1 | LC2 |
|---|---|---|---|---|
| PD1/LAG3 0799 PD1(0376)/ aLAG3(0416) | SEQ ID NO:96 | SEQ ID NO:97 | SEQ ID NO:98 | SEQ ID NO:99 |
| PD1/LAG3 0927 PD1(0376)/ aLAG3(0414) | SEQ ID NO:96 | SEQ ID NO:100 | SEQ ID NO:98 | SEQ ID NO:101 |
| PD1/LAG3 0222 PD1(0069)/ aLAG3(25F7) | SEQ ID NO:102 | SEQ ID NO:103 | SEQ ID NO:104 | SEQ ID NO:105 |
| PD1/LAG3 0224 PD1(0098)/ aLAG3(25F7) | SEQ ID NO:106 | SEQ ID NO:103 | SEQ ID NO:107 | SEQ ID NO:105 |

For all constructs knobs into holes heterodimerization technology was used with a typical knob (T366W) substitution in the first CH3 domain and the corresponding hole substitutions (T366S, L368A and Y410V) in the second CH3 domain (as well as two additional introduced cysteine 026831. The multispecific antibodies were expressed using expression plasmids containing the nucleic acids encoding the amino acid sequences depicted in Table 16. A schematic structure of the 2+1 CrossMAb$^{CH1/Ck}$ bispecific antibodies is shown in FIG. 1B.

TABLE 16

| Amino acid sequences of light chains (LC) and heavy chains (HC), with CH1/Ck domain exchange/replacement (2 + 1 CrossMab$^{CH1/Ck}$) | | | | |
|---|---|---|---|---|
| 2 + 1 Antibody | HC1 | HC2 | LC1 | 2x LC2 |
| PD1/LAG3 8310 aLAG3(0414)/ PD1(0376) | SEQ ID NO:118 | SEQ ID NO:119 | SEQ ID NO:115 | SEQ ID NO:101 |
| PD1/LAG3 8311 aLAG3(0416)/ PD1(0376) | SEQ ID NO:120 | SEQ ID NO:121 | SEQ ID NO:115 | SEQ ID NO:99 |
| PD1/LAG3 1252 aLAG3(25F7)/ PD1(0376) | SEQ ID NO:122 | SEQ ID NO:103 | SEQ IDNO:115 | SEQ ID NO: 105 | residues S354C/Y349'C) (contained in the respective corresponding heavy chain (HC) sequences depicted above).

10.2 Production and Expression of Multispecific Antibodies which Bind to PD1 and LAG3 with CH1/Ck Domain Exchange/Replacement (2+2 CrossMab$^{CH1/Ck}$) in Two Binding Arms and with Charged Amino Acid Substitutions in the CH1/CL Interfaces of the Other In this example multispecific antibodies which bind to human PD1 and human TIM3 were generated as described in the general methods section by classical molecular biology techniques and were expressed transiently in 293F of Expi293F cells as described above. The multispecific 2+2 CrossMAb$^{CH1/Ck}$ antibodies are described also in WO 2010/145792. The multispecific antibodies were expressed using expression plasmids containing the nucleic acids encoding the amino acid sequences depicted in Table 15. A schematic structure of the 2+2 CrossMAb$^{CH1/Ck}$ bispecific antibodies is shown in FIG. 1A.

TABLE 15

| Amino acid sequences of light chains (LC) and heavy chains (HC), with VH/VL domain exchange/replacement (2 + 2 CrossMAb$^{CH1/Ck}$) | | | |
|---|---|---|---|
| 2 + 2 Antibody | 2x HC | 2x LCl | 2x LC2 |
| PD1/LAG3 8970 PD1(0376)/ aLAG3(0414) | SEQ ID NO:114 | SEQ ID NO:115 | SEQ ID NO:101 |
| PD1/LAG3 8984 PD1(0376)/ aLAG3(0416) | SEQ ID NO:116 | SEQ ID NO:115 | SEQ ID NO:99 |
| PD1/LAG3 9010 PD1(0376)/ aLAG3(25F7) | SEQ ID NO:117 | SEQ ID NO:115 | SEQ ID NO:105 |

10.3 Production and Expression of Multispecific Antibodies which Bind to PD1 and LAG3 with CH1/Ck Domain Exchange/Replacement (2+1 CrossMab$^{CH1/Ck}$) in One Binding Arm (PD1 crossFab Fused to the C-Terminus of the Fc Knob Heavy Chain) and with Charged Amino Acid Substitutions in the CH1/CL Interfaces of the Other In this example multispecific antibodies which bind to human PD1 and human TIM3 were generated as described in the general methods section by classical molecular biology techniques and were expressed transiently in 293F of Expi293F cells as described above. Multispecific 2+1 CrossMAb$^{CH1/Ck}$ antibodies are described also in WO2013/

Alternatively, the PD1 crossFab fused to the C-terminus of the Fc knob heavy chain can be replaced by single chain Fab (scFab). Such multispecific 2+1 antibodies comprising a scFab are described also in WO2010/136172 and can be expressed using expression plasmids containing the nucleic acids encoding the amino acid sequences depicted in Table 17. A schematic structure of the 2+1 bispecific antibodies with a scFab fused at the C-terminus of the Fc knob heavy chain is shown in FIG. 1C.

TABLE 17

| Amino acid sequences of light chains (LC) and heavy chains (HC), with PD1 scFab | | | |
|---|---|---|---|
| 2 + 1 Antibody | HC1 | HC2 | 2x LC |
| PD1/LAG3 8312 aLAG3(0414)/ PD1(0376) | SEQ ID NO:123 | SEQ ID NO:119 | SEQ ID NO:101 |
| PD1/LAG3 8313 aLAG3(0416)/ PD1(0376) | SEQ ID NO:124 | SEQ ID NO:121 | SEQ ID NO:99 |
| PD1/LAG3 1088 aLAG3(25F7)/ PD1(0376) | SEQ ID NO:125 | SEQ ID NO:103 | SEQ ID NO:105 |

10.4 Production and Expression of Multispecific Antibodies which Bind to PD1 and LAG3 with VH/VL Fused Each at a C-Terminus of the Heavy Chains (2+1 PRIT Format)

In this example multispecific antibodies which bind to human PD1 and human TIM3 were generated as described in the general methods section by classical molecular biology techniques and were expressed transiently in 293F of Expi293F cells as described above. This type of multispecific 2+1 antibodies is also described in WO 2010/115589. The multispecific antibodies were expressed using expression plasmids containing the nucleic acids encoding the amino acid sequences depicted in Table 18. A schematic structure of the 2+1 PRIT-type bispecific antibodies is shown in FIG. 1D.

TABLE 18

| Amino acid sequences of light chains (LC) and heavy chains (HC), with VH and VL domain fused C-terminally to heavy chains | | | |
|---|---|---|---|
| 2 + 1 Antibody | HC1 | HC2 | 2x LC |
| PD1/LAG3 0918 aLAG3(25F7)/ aPDl(0376) | SEQ ID NO:126 | SEQ ID NO:127 | SEQ ID NO:109 |

10.5 Production and Expression of Multispecific Antibodies which Bind to PD1 and LAG3 with VH/VL Domain Exchange/Replacement (1+1 CrossMab$^{VH/VL}$ Trans Format) in One Binding Arm and with Charged Amino Acid Substitutions in the CH1/CL Interfaces of the LAG3 Fab Fused to the C-Terminus of the Fc Hole Heavy Chain Multispecific antibodies which monovalently bind to both human PD1 and to human LAG3 were produced wherein a LAG3 Fab is fused via its variable heavy domain to the C-terminus of one of the heavy chains, preferably the Fc hole heavy chain. The molecules were generated as described in the general methods section by classical molecular biology techniques and were expressed transiently in 293F of Expi293F cells as described above. The multispecific antibodies were expressed using expression plasmids containing the nucleic acids encoding the amino acid sequences depicted in Table 19. A schematic structure of the 1+1 CrossMab$^{VH/VL}$ trans-type bispecific antibodies is shown in FIG. 1H.

TABLE 19

| Amino acid sequences of light chains (LC) and heavy chains (HC), with aLAG3 Fab fused C-terminally to heavy chains | | | |
|---|---|---|---|
| 1 + 1 Antibody | HC1 | HC2 | LC1 | LC2 |
| PD1/LAG3 0725 aLAG3(0414)/ aPD1(0376) | SEQ ID NO:96 | SEQ ID NO:144 | SEQ ID NO:98 | SEQ ID NO:101 |

10.6 Production and Expression of Multispecific Antibodies which Bind to PD1 and LAG3 with VH/VL Domain Exchange/Replacement (2+1 CrossMab$^{VH/VL}$ Trans Format) in One Binding Arm and with Charged Amino Acid Substitutions in the CH1/CL Interfaces of the Two LAG3 Fabs, One of them Fused to the C-Terminus of the Fc Hole Heavy Chain Multispecific antibodies which monovalently bind to human PD1 and bivalently bind to human LAG3 were produced wherein a LAG3 Fab is fused via its variable heavy domain to the C-terminus of one of the heavy chains, preferably the Fc hole heavy chain. The molecules were generated as described in the general methods section by classical molecular biology techniques and were expressed transiently in 293F of Expi293F cells as described above. The multispecific antibodies were expressed using expression plasmids containing the nucleic acids encoding the amino acid sequences depicted in Table 20. A schematic structure of the 2+1 CrossMab$^{VH/VL}$ trans-type bispecific antibodies is shown in FIG. 1I.

TABLE 20

| Amino acid sequences of light chains (LC) and heavy chains (HC), wherein one of the aLAG3 Fabs is fused C-terminally to heavy chains | | | |
|---|---|---|---|
| 1 + 1 Antibody | HC1 | HC2 | LC1 | 2x LC2 |
| PD1/LAG3 0750 aLAG3(0414)/ aPD1(0376) | SEQ ID NO:96 | SEQ ID NO:145 | SEQ ID NO:98 | SEQ ID NO:101 |

10.7 Purification and Characterization of Multispecific Antibodies which Bind to PD1 and TIM3

The multispecific antibodies expressed above were purified from the supernatant by a combination of Protein A affinity chromatography and size exclusion chromatography. All multispecific antibodies can be produced in good yields and are stable. The obtained products were characterized for identity by mass spectrometry and analytical properties such as purity by SDS-PAGE, monomer content and stability Mass Spectrometry The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The CH1/Ck CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 μg deglycosylated CH1/Ck CrossMabs in a Tris buffer pH 8 at room temperature for 120 hours and at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Stability of Multispecific Antibodies

In order to assess stability of the antibody constructs, thermal stability as well as aggregation onset temperatures are assessed according to the following procedure. Samples of the indicated antibodies are prepared at a concentration of 1 mg/mL in 20 mM Histidine/Histidine chloride, 140 mM NaCl, pH 6.0, transferred into a 10 μL micro-cuvette array and static light scattering data as well as fluorescence data upon excitation with a 266 nm laser are recorded with an Optim1000 instrument (Avacta Inc.), while the samples are heated at a rate of 0.1° C./min from 25° C. to 90° C.

The aggregation onset temperature ($T_{agg}$) is defined as the temperature at which the scattered light intensity starts to increase. The melting temperature ($T_m$) is defined as the inflection point in a fluorescence intensity vs. wavelength graph.

Example 11

Characterization of Bispecific Anti-PD1/Anti-LAG3 Antibodies 11.1 Binding Elisa

ELISA for hu PD1

Nunc maxisorp streptavidin coated plates (MicroCoat #11974998001) were coated with 25 μl/well biotinylated PD1-ECD-AviHis at a concentration of 500 ng/ml and incubated at 4° C. over night. After washing (3×90 μl/well with PBST-buffer) 25 μl anti PD1 antibody samples were added in increasing concentrations and incubated 1 h at RT.

After washing (3×90 µl/well with PBST-buffer) 25 µl/well goat-anti-human H+L-POD (JIR, JIR109-036-098) was added in 1:5000 dilution and incubated at RT for 1 h on a shaker. After washing (3×90 µl/well with PBST-buffer) 25 µl/well of TMB substrate (Roche, 11835033001) was added and incubated until OD 2-3. Measurement took place at 370/492 nm.

Cell ELISA for Human PD1

Adherent CHO-K1 cell line stably transfected with plasmid 15311_hPD1-fl_pUC_Neo coding for full-length human PD1 and selection with G418 (Neomycin resistance marker on plasmid) were seeded at a concentration of 0.01×10E6 cells/well in 384-well flat bottom plates and grown over night.

The next day 25 µl/well PD1 sample or human anti PD1 (Roche)/mouse anti PD1(Biolegend; cat.:329912) reference antibody were added and incubated for 2h at 4° C. (to avoid internalization). After washing carefully (1×90 µl/well PBST) cells were fixed by adding 30 µl/well 0.05% Glutaraldehyde (Sigma, Cat.No: G5882, 25%) diluted in 1×PBS-buffer and incubated for 10 min at RT. After washing (3×90 µl/well PBST) 25 µl/well secondary antibody was added for detection: goat-anti-human H+L-POD (JIR, JIR109-036-088)/Sheep-anti-mouse-POD (GE NA9310) followed by 1 h incubation at RT on shaker. After washing (3×90 µl/well PBST) 25 µl/well TMB substrate solution (Roche 11835033001) was added and incubated until OD 1.0-2.0. Plates were measured at 370/492 nm.

Cell ELISA results are listed as "EC$_{50}$ CHO-PD1"-values [nM] in Table 21 below.

ELISA for Human Lag3

Nunc maxisorp plates (Nunc 464718) were coated with 25 µl/well recombinant Human LAG-3 Fc Chimera Protein (R&D Systems, 2319-L3) at a protein concentration of 800 ng/ml and incubated at 4° C. overnight or for 1 h at room temperature. After washing (3×90 µl/well with PBST-buffer) each well was incubated with 90 µl blocking buffer (PBS+ 2% BSA+0.05% Tween 20) for 1 h at room temperature. After washing (3×90 µl/well with PBST-buffer) 25 µl anti-Lag3 samples at a concentration of 1-9 µg/ml (1:3 dilutions in OSEP buffer) were added and incubated 1 h at RT. After washing (3×90 µl/well with PBST-buffer) 25 µl/well goat anti-Human Ig κ chain antibody-HRP conjugate (Milipore, AP502P) was added in a 1:2000 dilution and incubated at RT for 1 h. After washing (3×90 µl/well with PBST-buffer) 25 µl/well TMB substrate (Roche, 11835033001) was added and incubated for 2-10 min. Measurement took place on a Tecan Safire 2 instrument at 370/492 nm.

Cell-Surface Lag3 Binding ELISA

25 µl/well of Lag3 cells (recombinant CHO cells expressing Lag3, 10000 cells/well) were seeded into tissue culture treated 384-well plates (Corning, 3701) and incubated at 37° C. for one or two days. The next day after removal of medium, 25 µl anti-Lag3 samples (1:3 dilutions in OSEP buffer, starting at a concentration of 6-40 nM) were added and incubated for 2h at 4° C. After washing (1×90 µl in PBST) cells were fixed by addition of 30 µl/well glutaraldehyde to a final concentration of 0.05% (Sigma Cat.No: G5882), 10 min at room temperature. After washing (3×90 µl/well with PBST-buffer) 25 µl/well goat anti-Human Ig κ chain antibody-HRP conjugate (Milipore, AP502P) was added in a 1:1000 dilution and incubated at RT for 1 h. After washing (3×90 µl/well with PBST-buffer) 25 µl/well TMB substrate (Roche, 11835033001) was added and incubated for 6-10 min. Measurement took place on a Tecan Safire 2 instrument at 370/492 nm. Cell ELISA results are listed as "EC$_{50}$ CHO-LAG3"-values [nM] in Table 21 below.

Inhibition of LAG-3 Binding to MHC-II Expressed on Human A375 Tumor Cells (by ELISA)

25 µl/well of A375 cells (10000 cells/well) were seeded into tissue culture treated 384-well plates (Corning, 3701) and incubated at 37° C. overnight. Anti-Lag3 antibodies were pre-incubated for 1 h with biotinylated-Lag3 (250 ng/ml) in cell culture medium in 1:3 dilutions starting at 3 µg/ml antibody-concentration. After removal of medium from the wells with the seeded cells, 25 µl of the antibody-Lag3 pre-incubated mixtures were transferred to the wells and incubated for 2 h at 4° C. After washing (1×90 µl in PBST) cells were fixed by addition of 30 µl/well glutaraldehyde to a final concentration of 0.05% (Sigma Cat.No: G5882), 10 min at room temperature. After washing (3×90 µl/well with PBST-buffer) 25 µl/well Poly-HRP40-Streptavidin (Fitzgerald, 65R-S104PHRPx) was added in a 1:2000 or 1:8000 dilution and incubated at RT for 1 h. After washing (3×90 µl/well with PBST-buffer) 25 µl/well TMB substrate (Roche, 11835033001) was added and incubated for 2 to 10 min. Measurement took place on a Tecan Safire 2 instrument at 370/492 nm. Inhibition ELISA results are listed as "IC$_{50}$ MHCII/ELISA"-values [nM] in Table 21 below.

TABLE 21

Summary of Binding of different bispecific anti-PDl/anti-LAG3 antibodies

| Bispecific antibody | ELISA huPD1 rel. EC$_{50}$ [nM] | ELISA huLAG3 rel. EC$_{50}$ [nM] | EC50 CHO-PD1 rel. EC$_{50}$ [nM] | EC50 CHO-LAGS rel. EC$_{50}$ [nM] | MHCII/ ELISA IC$_{50}$ [nM] |
|---|---|---|---|---|---|
| PD1/LAG3 0927 (PD1-0376/LAG3-0414) (1 + 1) | 0.07 | 0.18 | 0.1 | 0.23 | 1.11 |
| PD1/LAG3 0799 (PD1-0376/LAG3-0416) (1 + 1) | 0.06 | 0.07 | 0.07 | 0.20 | 0.72 |
| PD1/LAG3 0222 (PD1-0069/ LAG3 25F7) (1 + 1) | 0.16 | 1.14 | 0.28 | 0.72 | 0.77 |
| PD1/LAG3 0224 (PD1-0098/LAG3 25F7) (1 + 1) | 0.04 | 0.86 | 0.06 | 0.86 | 0.79 |
| PD1/LAG3 8310 (PD1-0376/LAG3-0414) (1 + 2) | 0.06 | 0.06 | 0.34 | 0.20 | 0.47 |
| PD1/LAG3 8311 (PD1-0376/LAG3-0416) (1 + 2) | 0.05 | 0.06 | 0.32 | 0.17 | 0.39 |
| PD1/LAG3 1252 (PD1-0376/LAG3 25F7) (1 + 2) | 0.03 | 0.02 | 0.31 | 0.64 | 0.47 |
| PD1/LAG3 8970 (PD1-0376/LAG3-0414) (2 + 2) | 0.05 | 0.04 | 0.46 | 0.20 | 0.45 |
| PD1/LAG3 8984 (PD1-0376/LAG3-0416) (2 + 2) | 0.05 | 0.05 | 0.54 | 0.17 | 0.44 |
| PD1/LAG3 9010 (PD1-0376/LAG3-25F7) (2 + 2) | 0.04 | 0.05 | 0.36 | 0.48 | 0.52 |

11.2 Binding Biacore

Antigen Binding Properties of Multispecific Antibodies which Bind to PD1 and LAG3

Binding of the multispecific antibodies to their respective target antigens, i.e. PD1 and TIM3, was assessed by Biacore®.

PD1 Binding can be Assessed According to the Following Procedure:

Anti-human Fc IgG was immobilized by amine coupling to the surface of a (Biacore) CM5 sensor chip. The samples were then captured and hu PD1-ECD was bound to them.

The sensor chip surface was regenerated after each analysis cycle. The equilibrium constant and kinetic rate constants were finally gained by fitting the data to a 1:1 Langmuir interaction model.

About 10,000 response units (RU) of 20 µg/ml anti-human IgG (GE Healthcare #BR-1008-39) were coupled onto all flow cells of a CM5 sensor chip in a Biacore T200 using an amine coupling kit supplied by GE Healthcare. The sample and running buffer was HBS-EP+(0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer.

Different samples were injected for 15 seconds with a concentration of 10 nM and consecutively bound to the flow cells 2, 3 and 4. Then a complete set of human PD1-ECD concentrations (300 nM, 100 nM, 2×33.3 nM, 11.1 nM, 3.7 nM, 1.2 nM and 2×0 nM) was injected over each sample for 300s followed by a dissociation time of 10/600s and two 30s regeneration steps with 3 M MgCl$_2$, of which the last one contained an "extra wash after injection" with running buffer. Finally the double referenced data was fitted to a 1:1 Langmuir interaction model with the Biacore T200 Evaluation Software.

LAG3 Binding was Assessed According to the Following Procedure:

A Biacore SA CAP Kit provided by GE Healthcare was used to perform this assy. The kinetic values were obtained at 25° C. in HBS-EP+(Ge Healthcare) buffer.

The SA CAP Chip was docked to a Biacore T200 as prescribed in the manual of the CAP Kit. The run method contains four commands. Firstly CAP reagent was injected for 300s at a flow rate of 10 µl/min to hybridize the immobilized single stranded DNAs using a 'General' command. The command is followed by a 15 seconds long injection of a 1 µg/ml dilution of biotinylated Fc-tagged, human Lag3 extra cellular domain in running buffer. This results in a capture level of about 50 RU. A single-cycle command was used to inject five different sample concentrations (100 nM-6.25 nM, 2-fold dilutions) followed by a 1200 seconds long dissociation phase. The chip was then regenerated as prescribed in the SA CAP Kit manual.

Finally, the obtained curves were evaluated using the Biacore T200 Evaluation software version 3.0.

Results: The interactions did not fit to a 1:1 Langmuir binding model, because all samples aside from 0799 and 0927 have two Lag3 binding moieties and therefore show avidity. Since 0799 and 0927 contained a small miss-paired, bivalent sample population, they also showed some avidity.

Therefore the sensorgrams were only ranked according to their off rates. This was done by visual comparison of the single-cycle kinetic curves. By doing this, it was shown that the 0416-Lag3 ECD complex is more stable than any other in this sample set. The monovalent <Lag3> Crossmab format (0799) still displays a slower offrate than any other sample in this experiment.

Furthermore, it was seen that the affine Lag3-0414/Lag3-0927—Lag3 ECD complex is the weakest of those, observed in this experiment. The affine binding portions of 0414 and 0416 are roughly comparable to the affine portions of their monovalent Crossmab counter parts 0927 and 0799. Results are indicated in Table 22.

TABLE 22

| Binding Quality of PD1-LAG3 Bispecific Antibodies determined by SPR measurement | |
| --- | --- |
| Sample | Binding quality |
| aLAG3(0414) | ++ |
| aLAG3(0416) | +++ |
| PD1/LAG3 0927 (1 + 1) | + |
| PD1/LAG3 0799 (1 + 1) | +++ |
| aLAG3(25F7) | ++ |
| aLAG3(MDX26H10) | ++ |
| aLAG3(BMS986016) | ++ |
| aLAG3(BAP050) | + |

Avidity Assessment of the Trans Formats Compared to the 1+1 Bispecific Antibodies 0927 and 0799:

The dissociation constants of the bispecific molecules (sample) and their individual targets as well as a combination of PD1 and LAG3 (analyte) were determined to assess the avidity gain provided by binding with all valences at the same time.

Previous to the measurement on a Biacore 8K, a CM5 sensor chip was prepared using the standard amine coupling kit provided by GE Healthcare. An in-house produced antibody directed against a specific mutation in the Fc part of the sample (i.e. an Fc part carrying the PGLALA mutations), herein called anti-PGLALA antibody (such antibodies are described in WO 2017/072210), was therefore diluted to a concentration of 50 µg/ml in acetate buffer pH 5.0. It was coupled to all flow cells and channels at a 8 µl/min flow speed over 1200s, yielding in a bound response of about 19000 RU.

HBS-EP$^+$ buffer (GE HC) was used as running buffer for the sensor chip preparation as well as the main run itself. The analysis started after a startup consisting of three 17s long sample injections followed by a regeneration step utilizing a 10 mM NaOH solution. In a first step, the different samples were captured by the anti-PGLALA antibody onto the individual channels' flow-cell two on the sensor chip surface by injecting it for 17s at a flow rate of 10 µl/min. Secondly, one of the three analytes (PD1, LAG3-Fc, 2+2 PD1/LAG3-Fc Fusion) was injected into both flow-cells for 200s at a flow rate of 50 µl/min followed by a 1000s long (600s in case of the LAG3-Fc) dissociation phase. Finally, the anti-PGLALA antibody/sample complex was dissolved by two consecutive injections (30s long) of 10 mM NaOH. Each individual kinetic determination consisted of four cycles with different analyte concentrations (0 nM, 5 nM, 25 nM and 100 nM).

The resulting data was evaluated using the Biacore 8K Evaluation Software. A 1:1 dissociation fit was applied and resulting kd values were converted into complex half-life in minutes. The difference between the avidity binding of the PD1/Lag3-Fc fusion antigen binding molecule and its main individual contributor (either PD1 or Lag3) was calculated and sorted into one of three categories describing the stability gain by multivalent and bispecific binding (Table 23).

TABLE 23

| Increase of Complex Stability provided by the avidity of PD1-LAG3 Bispecific Antibodies determined by SPR measurement | |
| --- | --- |
| Sample | Binding quality |
| PD1/LAG3 0927 (1 + 1) | ++ |
| PD1/LAG3 0799 (1 + 1) | +++ |

TABLE 23-continued

Increase of Complex Stability provided by the avidity of PD1-LAG3
Bispecific Antibodies determined by SPR measurement

| Sample | Binding quality |
|---|---|
| PD1/LAG3 0725 (1 + 1 trans) | + |
| PD1/LAG3 0750 (1 + 2 trans) | ++ |

11.3 Dimerization of Cellular PD1 and LAG3 after Simultaneous Engagement Via Bispecific Anti-PD1/Anti-LAG3 Bispecific Antibodies Bispecific anti-PD1/anti-LAG3 antibodies were generated in various formats as described in Example 10. This cellular assay was used to demonstrate the dimerization or at last binding/interaction of two different receptors, which are cytosolically fused with two fragments of an enzyme, upon ligation or cross-linking with a bispecific antibody against both targets. Hereby only one receptor alone shows no enzymatic activity. For this specific interaction, the cytosolic C-terminal ends of both receptors were individually fused to heterologous subunits of a reporter enzyme. A single enzyme subunit alone showed no reporter activity. However, simultaneous binding of an anti-PD1/anti-LAG3 bispecific antibody construct to both receptors was expected to lead to local cytosolic accumulation of both receptors, complementation of the two heterologous enzyme subunits, and finally to result in the formation of a specific and functional enzyme that hydrolyzes a substrate thereby generating a chemiluminescent signal.

In order to analyze the cross-linking effect of the bispecific anti-PD1/anti-LAG3 antibodies, 10,000 PD1$^+$LAG3$^+$ human U2OS cells/well were seeded into white flat bottom 96-well plates (costar, cat.no. #3917) and cultured overnight in assay medium. On the next day cell medium was discarded and replaced by fresh medium. Antibody or ligand dilutions were prepared and titrated amounts of indicated (bispecific) antibodies were added and incubated at 37° C. for 2 hours. Next, a substrate/buffer mix (e.g. PathHunter-Flash detection reagent) was added and again incubated for 1h. For measuring chemoluminescence induced upon simultaneous binding and dimerization a Tecan infinite reader was used.

Figure 5A:
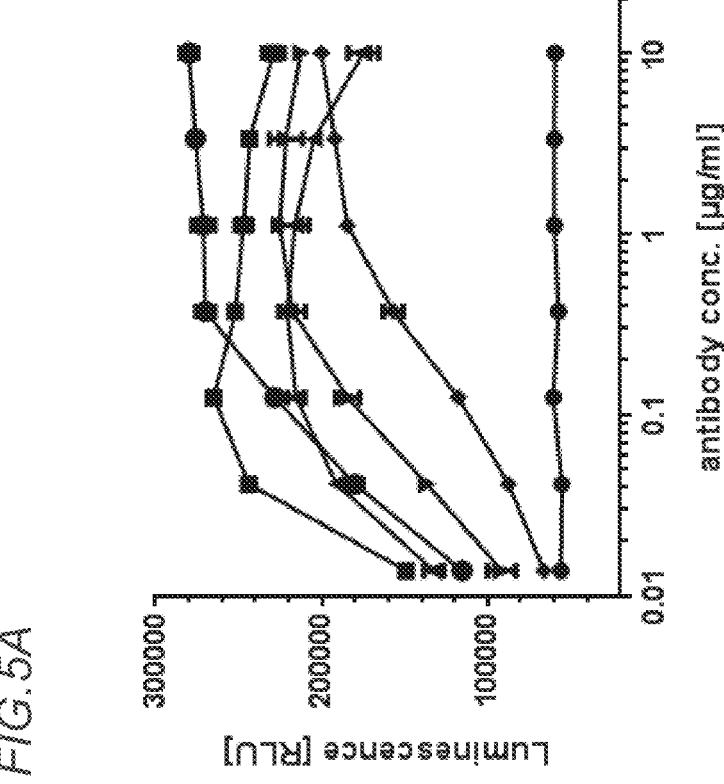
FIGS. 5A-5D: Simultaneous binding and receptor dimerization caused by binding of bispecific anti-PD1/anti-LAG3 antibodies to recombinant PD1+Lag3+ cells. Plotted is the chemoluminescence (measured in RU) against the antibody concentration.
Figure 5B:
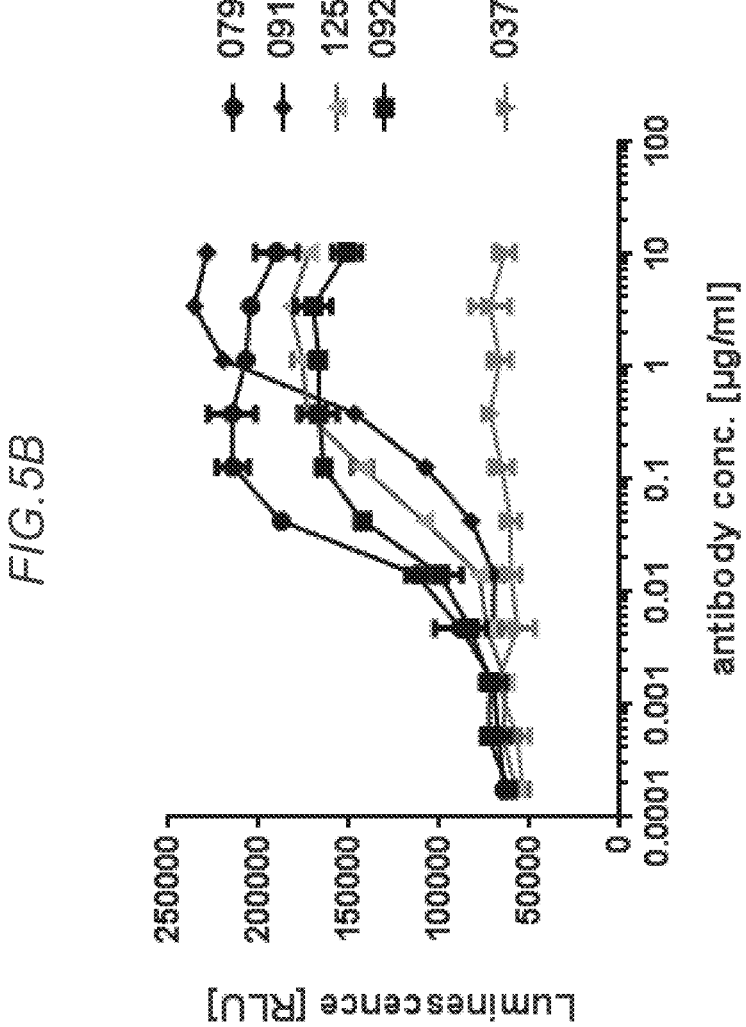

The results are shown in FIGS. 5A and 5B. Plotted is the chemoluminescence (measured in RU) against the antibody concentration. Monospecific (bivalent) anti-LAG3 antibodies were not able to provoke a chemoluminescence signal whereas all bispecific anti-PD1/anti-LAG3 antibodies induced a chemoluminescence signal in a concentration dependent manner.

Figure 5C:
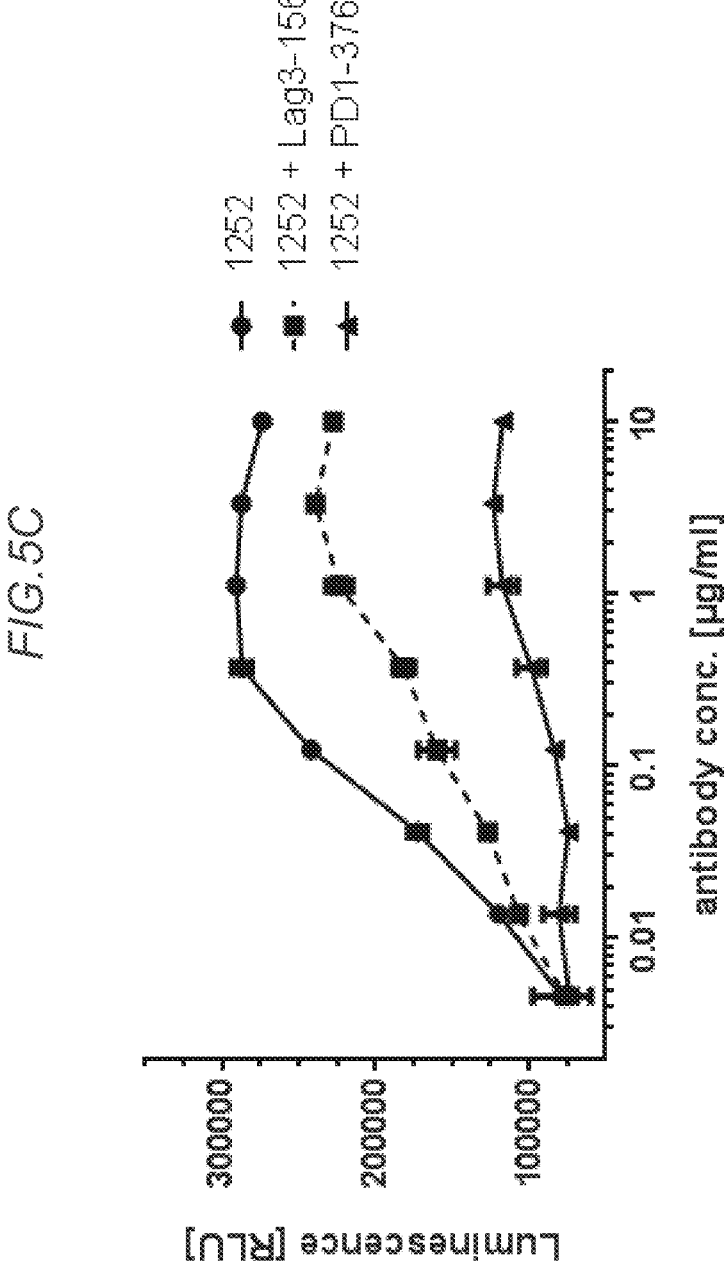

To show the specificity of the simultaneous binding (and induction of a luminiscence signal) a competition experiment was performed: As shown before treatment with a bispecific antibody (1252) induced a luminiscence signal in a dose-dependent fashion (FIG. 5C). If the same bispecific antibody was provided in the presence of either an aLAG3 antibody (0156, MDX25F7) or anti-PD1 antibody (0376), the signal was either almost inhibited (for PD1 competition) or at least significantly reduced (LAG3). Both parental antibodies are the same binders as comprised in the bispecific antibody (1252, 2+1 LAG3/PD1-format). The competing antibodies were given each at a constant concentration of 20 µg/ml.

Figure 5D:
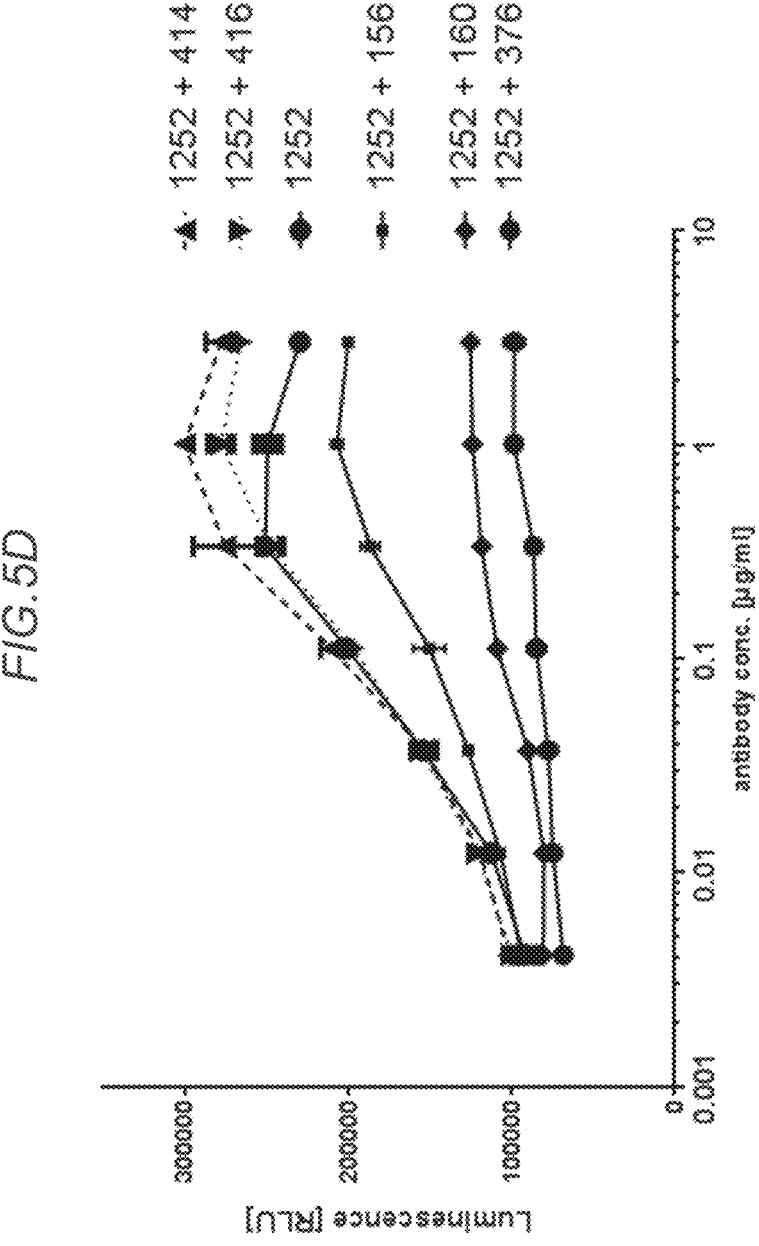

The results of a further experiment are shown in FIG. 5D. Similar to the previous competition experiment the incubation with parental aLAG3 (0156) or PD1 antibodies (0376; each constantly at 10 µg/ml) had an effect on the binding properties of the bispecific antibody (1252, 2+1 format of the bispecific aLAG3-0156 and PD1-0376) to PD1 Lag3 double-expressing cells, as measured by the luminiscence signal. Competition with anti-PD1 antibody (0376) and also recombinant LAG3:Fc protein (0160) almost abolished the signal, whereas presence of the single aLAG3 binder (0156) only led to partial inhibition. The two further anti-LAG3 antibodies 0414 and 0416, which are binding to a different epitope than 0156, did not compete for binding with the bispecific antibody comprising aLAG3 binder (0156), because they did not modulate the signal significantly.

Figures 6A, 6B, 6C, 6D:
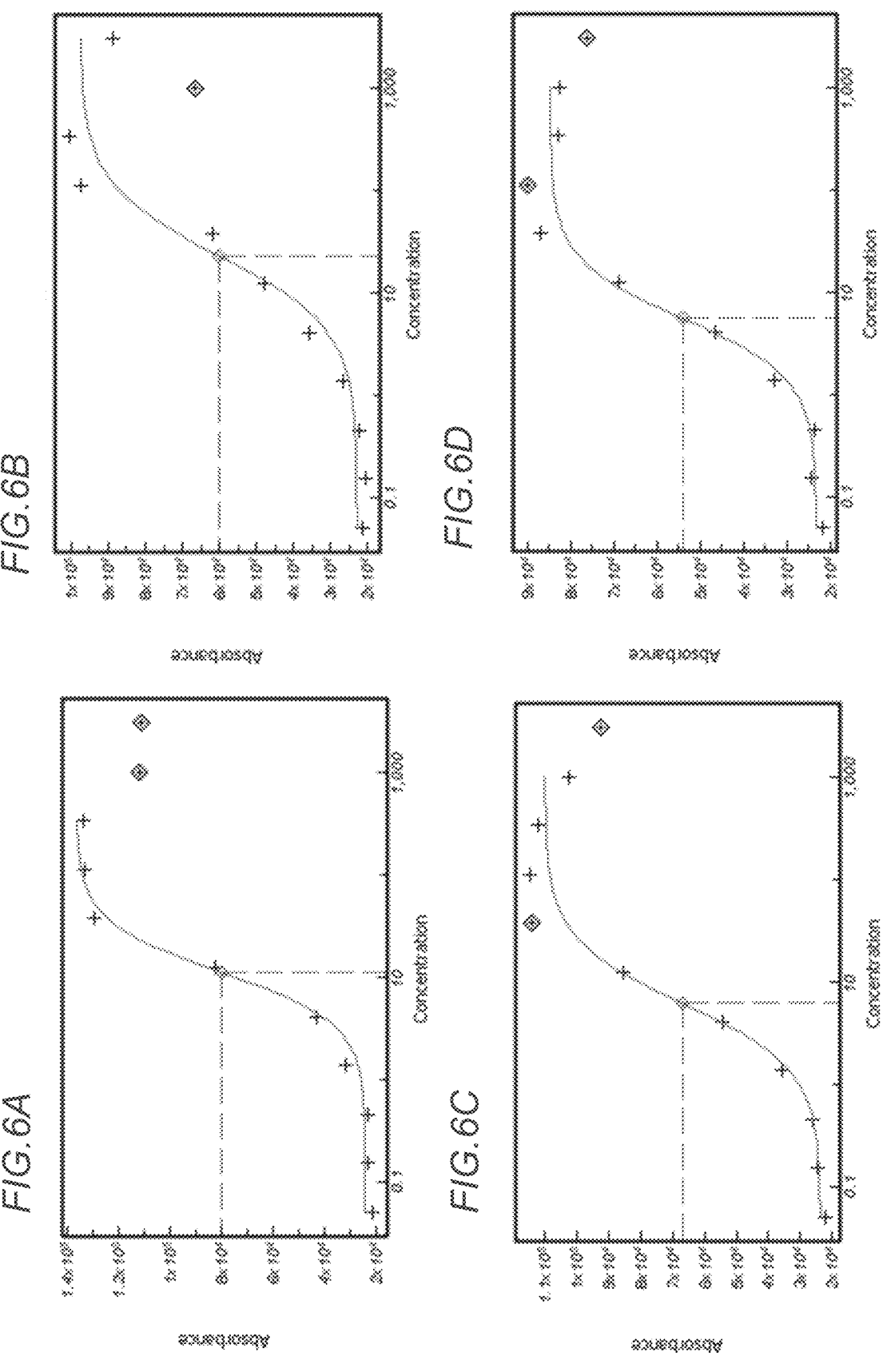
FIGS. 6A-6D: Comparison of the simultaneous binding of bispecific anti-PD1/anti-LAG3 antibodies in different formats (1+1 vs. 2+1) and with different aLAG3 binders. FIG.

In a further experiment, the simultaneous binding of bispecific anti-LAG3/anti-PD1 antibodies comprising different aLAG3 binder (0414 vs. 0416) and different formats (1+1 vs. 2+1) was compared (FIGS. 6A to 6D). As described before, several anti-LAG3/anti-PD1 bispecific antibodies were tested, either in an 1+1 CrossMab format (0799 and 0927) or 2+1 format (two Lag3 binding arms and one PD1 crossFab fragment fused C-terminal: 8311 and 8310). In FIGS. 6A and 6B the curves (absorbance vs. concentration) for the constructs with binder aLAG3-0416 and in FIGS. 6C and 6D those for the corresponding constructs with aLAG4-0414 are shown. All constructs tested were able to bind to the cells and to induce chemoluminescence. The calculated EC$_{50}$ values for the binding curves are shown in Table 24 below.

TABLE 24

EC$_{50}$ values as measured in the dimerization binding assay

| Bispecific Antibody | Format | MW [kD] | EC$_{50}$ [pM] |
|---|---|---|---|
| 0927 (PD1-0376/LAG3-0414) | 1 + 1 | 145 | 41 |
| 0799 (PD1-0376/LAG3-0416) | 1 + 1 | 145 | 76 |
| 8310 (PD1-0376/LAG3-0414) | 1 + 2 | 193 | 28 |
| 8311 (PD1-0376/LAG3-0416) | 1 + 2 | 193 | 119 |

In another experiment, the simultaneous binding of bispecific anti-LAG3/anti-PD1 antibodies comprising different aLAG3 binder (0414 vs. 0416) and different formats (2+1 vs. 2+2) was compared (FIGS. 7A to 7D). Anti-LAG3/anti-PD1 bispecific antibodies were tested, either in or 2+1 format (two LAG3 binding arms and one PD1 crossFab fragment fused C-terminal: 8311 and 8310) or in 2+2 crossmab format (two LAG3 binding arms and two PD1 crossFab fragments fused C-terminal: 8970 and 8984). In FIGS. 7A and 7B the curves (absorbance vs. concentration) for the constructs with binder aLAG3-0414 and in FIGS. 7C and 7D those for the corresponding constructs with aLAG4-0416 are shown. All constructs tested were able to bind to the cells and to induce chemoluminescence. The calculated EC$_{50}$ values for the binding curves are shown in Table 25 below.

TABLE 25

EC$_{50}$ values as measured in the dimerization binding assay

| Bispecific Antibody | Format | MW [kD] | EC$_{50}$ [pM] |
|---|---|---|---|
| 8310 (PD1-0376/LAG3-0414) | 2 + 1 | 193 | 114 |
| 8311 (PD1-0376/LAG3-0416) | 2 + 1 | 193 | 124 |
| 8970 (PD1-376/LAG3-0414) | 2 + 2 | 242 | 83 |
| 8984 (PD1-0376/LAG3-0416) | 2 + 2 | 242 | 91 |

In a further experiment, the simultaneous binding of bispecific anti-LAG3/anti-PD1 antibody PD1/LAG3 0927 in the classical 1+1 CrossMAb$^{Vh-VL}$ format was compared with the bispecific anti-LAG3/anti-PD1 antibodies in the 1+1 trans format (PD1/LAG3 0725) and 2+1 trans format (PD1/LAG3 0750) For this experiment, the following changes to the method were applied. In order to analyze the cross-linking effect of the different anti-LAG3/anti-PD1 antibody formats, 7500 PD1$^+$LAG3$^+$ human U2OS cells/well were seeded into white flat bottom 96-well plates together with non-serial dilutions of antibodies (final concentration of 0.29 pM to 5484 μM) and were incubated for 20h at 37° C. in a $CO_2$ incubator. Next, assay plates were equilibrated to room temperature and a substrate/buffer mix (PathHunterFlash detection reagent, Discoverx) was added and again incubated for 4h. For measuring chemoluminescence induced upon simultaneous binding and dimerization a SpectraMax L plate reader (Molecular Devices) was used.

Figure 7E:
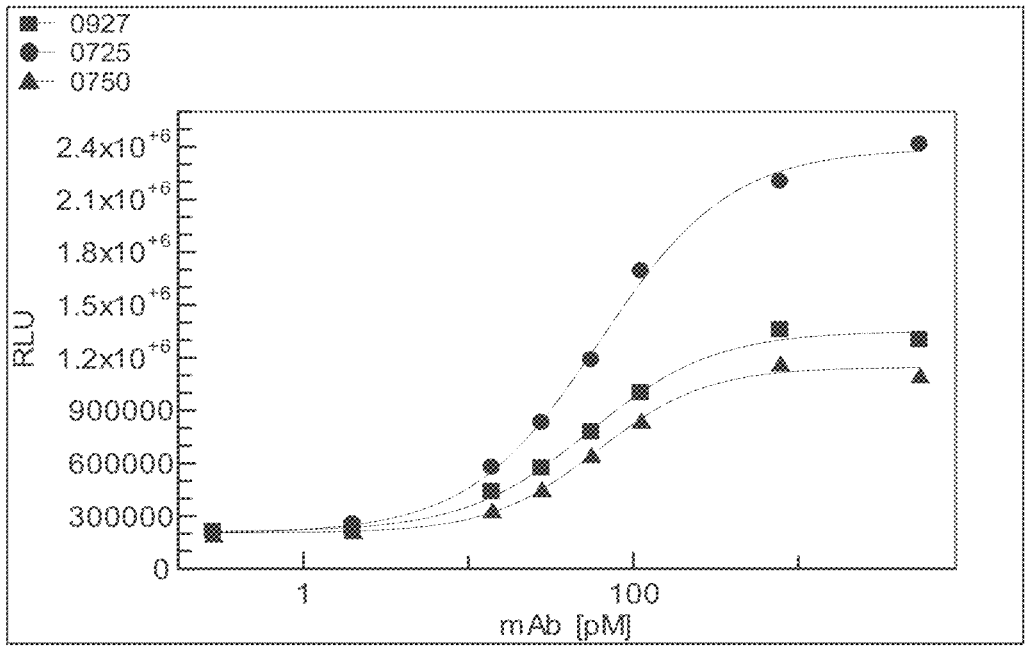

In FIG. 7E the dose-response curves (luminescence vs. concentration) of the PD1-LAG3 bispecific antibodies 1+1 CrossMab (0927), 1+1 trans CrossMab with N-terminal aPD1 and C-terminal aLAG3 (0725) as well as 2+1 trans CrossMab with N-terminal aPD1 and N-plus C-terminal aLAG3 (0750) are depicted. Compared to PD1/LAG3 0927 the PD1 LAG3 receptor crosslinking effect of PD1/LAG3 0725 is clearly higher whereas it is slightly lower for PD1/LAG3 0750.

11.4 Measurement of Bispecific Anti-LAG3/Anti-PD1 Trans CrossMab Variants in a PD-1 & LAG-3 Combo Reporter Assay To test the neutralizing potency of the different anti-PD1-LAG3 antibody formats in restoring a suppressed T cell response in vitro, a commercially available reporter system was used. The PD1 & LAG3 combo bioassay consists of PD1–, LAG3– and T cell receptor (TCR)-expressing reporter cells, MHC-II- and PDL1-expressing tumor cells and a TCR-activating-antigen.

The effector cells are Jurkat T cells expressing human PD1, human LAG3, a human TCR and a luciferase reporter driven by an NFAT response element (NFAT-RE). The target cells are A375 cells expressing human PD-L1. In brief, the reporter system is based on three steps: (1) TCR activating-antigen-induced NFAT cell activation, (2) inhibition of the activating signal mediated by the interaction between MHCII (A375 cells) and LAG3$^+$ (Jurkat cells) as well as PD-L1 (A375 cells) and PD1 (Jurkat cells), and (3) recovery of the NFAT activation signal by PD1 and LAG3-antagonistic/neutralizing antibodies.

Figure 7F:
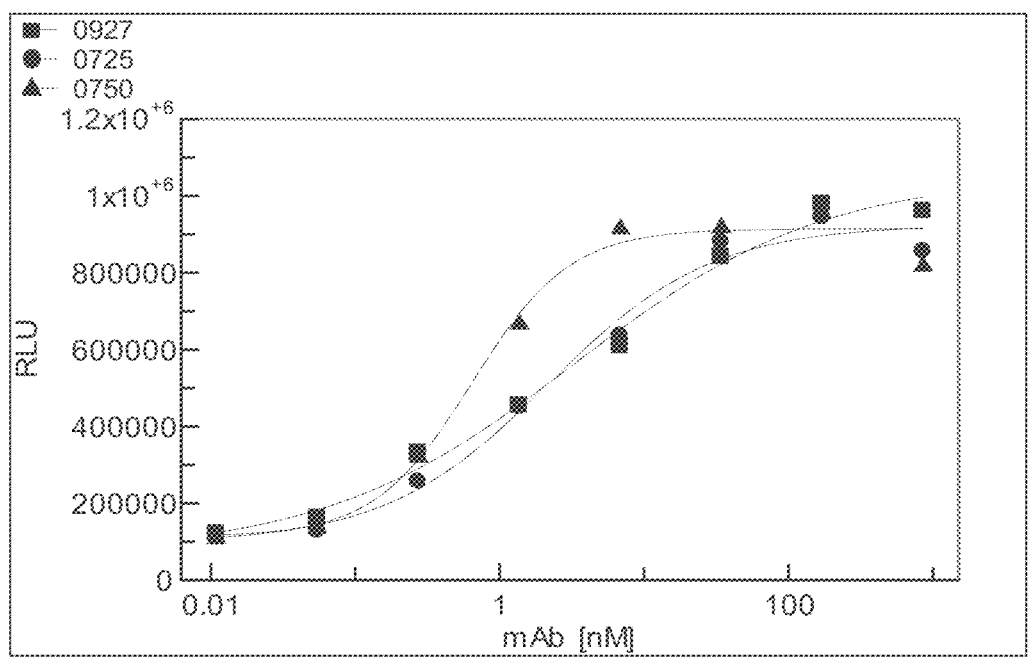

For this experiment, 1×10$^4$ A375 target cells per well were incubated overnight with TCR activating antigen (Promega) in 96-well flat bottom assay plates in a $CO_2$ incubator at 37° C. Next, media from plates was removed and serial dilutions (final assay concentration of 0.01 nM to 857 nM) of anti-LAG3/anti-PD1 antibodies as well as 5×10$^4$ Jurkat effector cells per well were added. After 6 hours of incubation at 37° C. in a $CO_2$ incubator, assay plates were equilibrated to room temperature and 80 μl ONE-Glo Ex substrate (Promega) was added to each well. After 10 min of incubation luminescence was measured in a SpectraMax L plate reader (Molecular Devices). Simultaneous binding of an anti-PD1/anti-LAG3 bispecific antibody construct to both receptors was expected to lead to local cytosolic accumulation of both receptors, complementation of the two heter-ologous enzyme subunits, and finally to result in the forma-tion of a specific and functional enzyme that hydrolyzes a substrate thereby generating a chemiluminescent signal. In FIG. 7F the dose-response curves (luminescence vs. concentration) of the anti-PD1/anti-LAG3 bispecific antibodies 1+1 CrossMab (0927), 1+1 trans CrossMab with N-terminal aPD1 and C-terminal aLAG3 (0725) as well as 2+1 trans CrossMab with N-terminal aPD1 and N-plus C-terminal aLAG3 (0750) are depicted. The ability of 0927 and 0725 to recover reporter cell activation by blocking PD1 and LAG3 interaction with their respective ligands is comparable whereas it is higher for 0750. This is furthermore indicated by the $EC_{50}$ values listed in Table 26.

TABLE 26

| $EC_{50}$ values as measured in the PD-1 & LAG-3 combo reporter assay | | | |
|---|---|---|---|
| Bispecific Antibody | Format | MW [kD] | $EC_{50}$ [nM] |
| PD1/LAG3 0927 | 1 + 1 cis | 145259 | 3.1 |
| PD1/LAG3 0725 | 1 + 1 trans | 145890 | 2.2 |
| PD1/LAG3 0750 | 2 + 1 trans | 192888 | 0.6 |

Example 12

Functional Characterization of Bispecific Anti-PD1/Anti-LAG3 Antibodies 12.1 Reduced Internalization Upon Binding to T-Cell Surface Measurement of Receptor Internalization by Flow Cytometry Receptor internalization represents an important sink for the molecule which can be degraded within few hours while the targeted receptors are rapidly re-expressed on the cell-surface ready to inhibit TCR-signalling. We therefore assessed receptor internalization upon the binding of our constructs by flow cytometry where samples stained with different bispecific formats at 4° C. were used as reference for comparison with samples incubated at 37° C. for 3 hours after the staining at 4° C.

Three days polyclonally activated CD4 T cells, previously cultured with 1 mg/ml of plate bound anti-CD3 and 1 mg/ml of soluble anti-CD28 antibodies, were incubated in presence of either anti-LAG3 or anti-PD1/anti-LAG3 bispecific anti-bodies (in duplicates) for 30 minutes at 4° C. The cells were then washed, divided in two groups, one of which incubated for 3 additional hours at 37° C. and the other one was immediately stained with a labelled secondary antibody (eBioscience) before being fixed with BD Cell Fix. After the 3 hours incubations also the second group of the cells were stained with the labelled secondary antibody before fixation. After staining, cells were washed two times with PBS/2% FCS and analyzed.

Figures 8A, 8B:
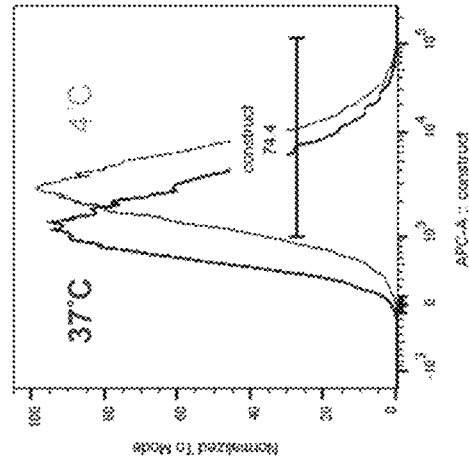
FIGS. 8A and 8B: Internalization of bispecific anti-PD1/anti-LAG3 antibodies in different formats and parental anti-LAG3 antibody after 3 hours from the addition to administration to activated T cells as measured with flow cytometry.

Therefore, the cells were acquired at LSRFortessa (BD Biosciences) and the expression levels of detectable anti-body on the cell surface were compared among the two groups. The results are shown in FIG. 8B. We observed that after 3 hours all the bispecific formats as well as the monospecific bivalent aLAG-3 antibody have been internal-ized, however the bispecific anti-PD1/anti-LAG3 antibodies in the 1+1 format (PD1/LAG3 0799 and PD1/LAG3 0927) were the least internalized.

Figure 9A:
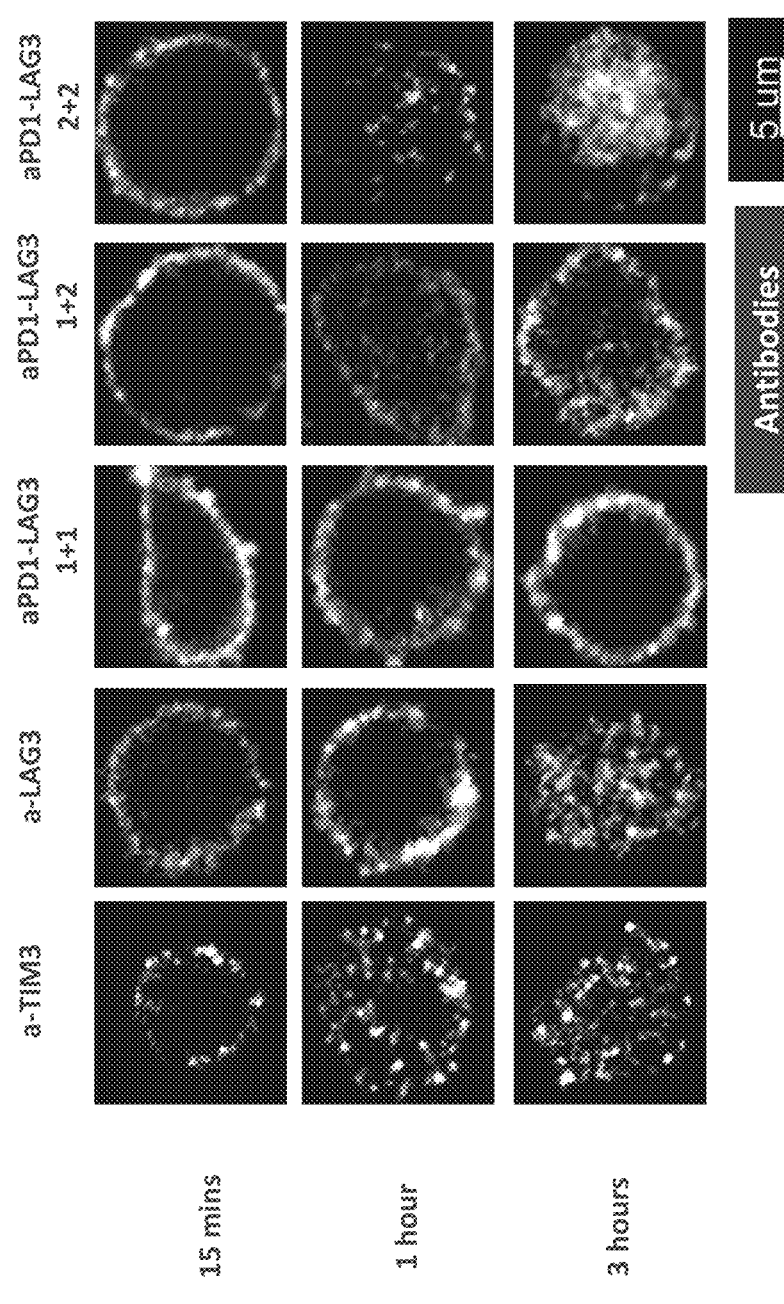
FIGS. 9A and 9B: Analysis over time shows higher membrane localization of the 1+1 format of the bispecific anti-PD1/anti-LAG3 antibody (0927) when compared to the other formats which show a higher degree of internalization.
Figure 9B:
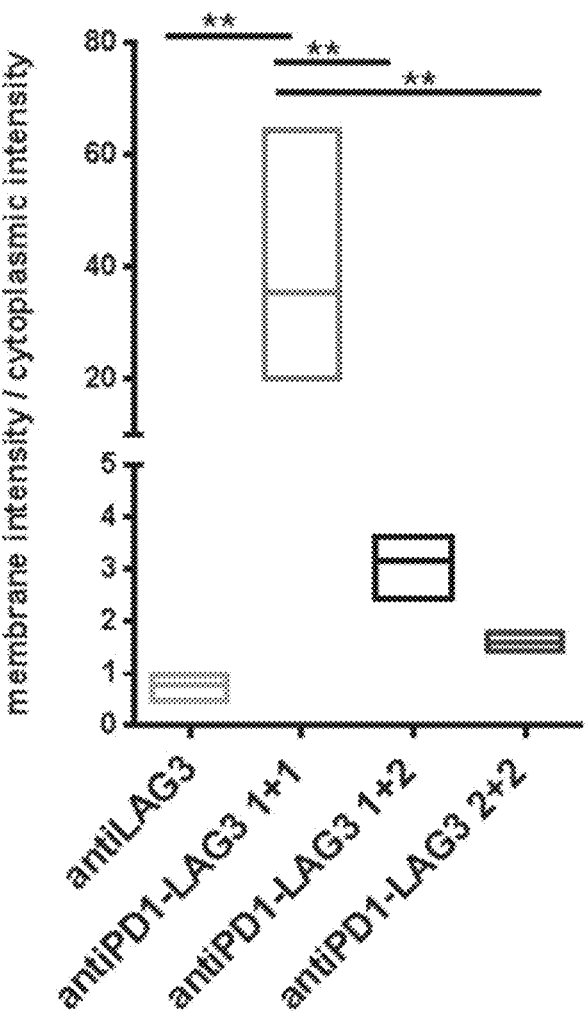

Visualization of Antibody Localization and Internalization by Fluorescence Confocal Microscopy Activated CD4-positive cells were stained with CMFDA (Invitrogen) and plated on round coverslips treated with Retronectin (Takara Bio). Cells were allowed 4 hours to adhere at 37° C. before fluorescently-tagged antibodies (1 μg/mL: a-LAG3 (1256), 1+1 PD1/LAG3 Bispec (0927), PD1-LAG3 1+2 Bispec (8310) and PD1-LAG3 2+2 Bispec (8970) labeled with Alexa 647) were added directly into growth media for different durations (15 min, 1 hour and 3 hours). Cold PBS (Lonza) was used to quench the reaction and to wash off unbounded antibodies. Cells were then fixed with Cytofix (BD) for 20 minutes at 4° C. and washed twice with PBS (Lonza). Coverslips were then transferred and mounted on glass slides with Fluoromount G (eBioscience) and kept in the dark at 4° C. overnight before imaging. A) The fluorescent images are shown in FIG. 9A. The white signal represents the localization of the labeled antibody. B) The intensity of the fluorescent signal from the membrane ROI, of highly targeted cells, was divided by the intensity of the fluorescent signal from the cytoplasm ROI of the same cells, resulting in a ratio displayed in the Box Charts. In order to compare samples, One Way ANOVA analysis Uncorrected Fisher's LSD was used (*=p<0.05; **=p<0.01). The results are shown in FIG. 9B. The analysis over time shows higher membrane localization in the bispecific antibodies and LAG3 antibodies when compared to intracellular clustering of TIM3 antibodies (used as control). We observed that after 3 hours all the bispecific formats as well as the monospecific bivalent aLAG-3 antibody have been internalized with the only exception of the 1+1 PD1/LAG3 Bispec (0927) (FIG. 9A).

Fluorescence confocal microscopy was performed with an inverted LSM 700 from Zeiss with a 60× oil objective. Images were collected using Zen software (Zeiss) coupled to the microscope. The analysis of the images was performed with Imaris Software (Bitplane; Oxford Instrument) and the statistical analysis was performed by GraphPad Prism (Graphpad Software).

12.2 Binding to Conventional T Cells Versus Tregs

A desired property of the lead PD1-LAG3 BsAb is the ability to preferentially bind to conventional T cells rather than to Tregs, because LAG3 on Tregs appears to negatively regulate their suppressive function. Therefore targeting LAG3 on Tregs with blocking antibodies could be detrimental by increasing their suppressive function and eventually mask the positive blocking effect on other T cells. We therefore assessed the competitive binding of the different anti-PD1/anti-LAG3 bispecific antibody formats to activated conventional and regulatory T cells cultured together.

Regulatory T cells (Tregs) and conventional T cells (Tconv) were sorted from heathy donor PBMCs (Miltenyi), labelled with 5 mM CellTraceViolet or CFSE membrane dyes respectively and cultured together at 1:1 ratio for 3 days with 1 mg/ml of plate bound anti-CD3 and 1 mg/ml of soluble anti-CD28 antibodies. On day 3 the cells were incubated for 30 min at 4° C. with either directly labelled anti-PD1, anti-LAG3 or bispecific antibodies, fixed with BD Cell Fix, and acquired at LSRFortessa (BD Biosciences).

Figures 10A, 10B, 10C:
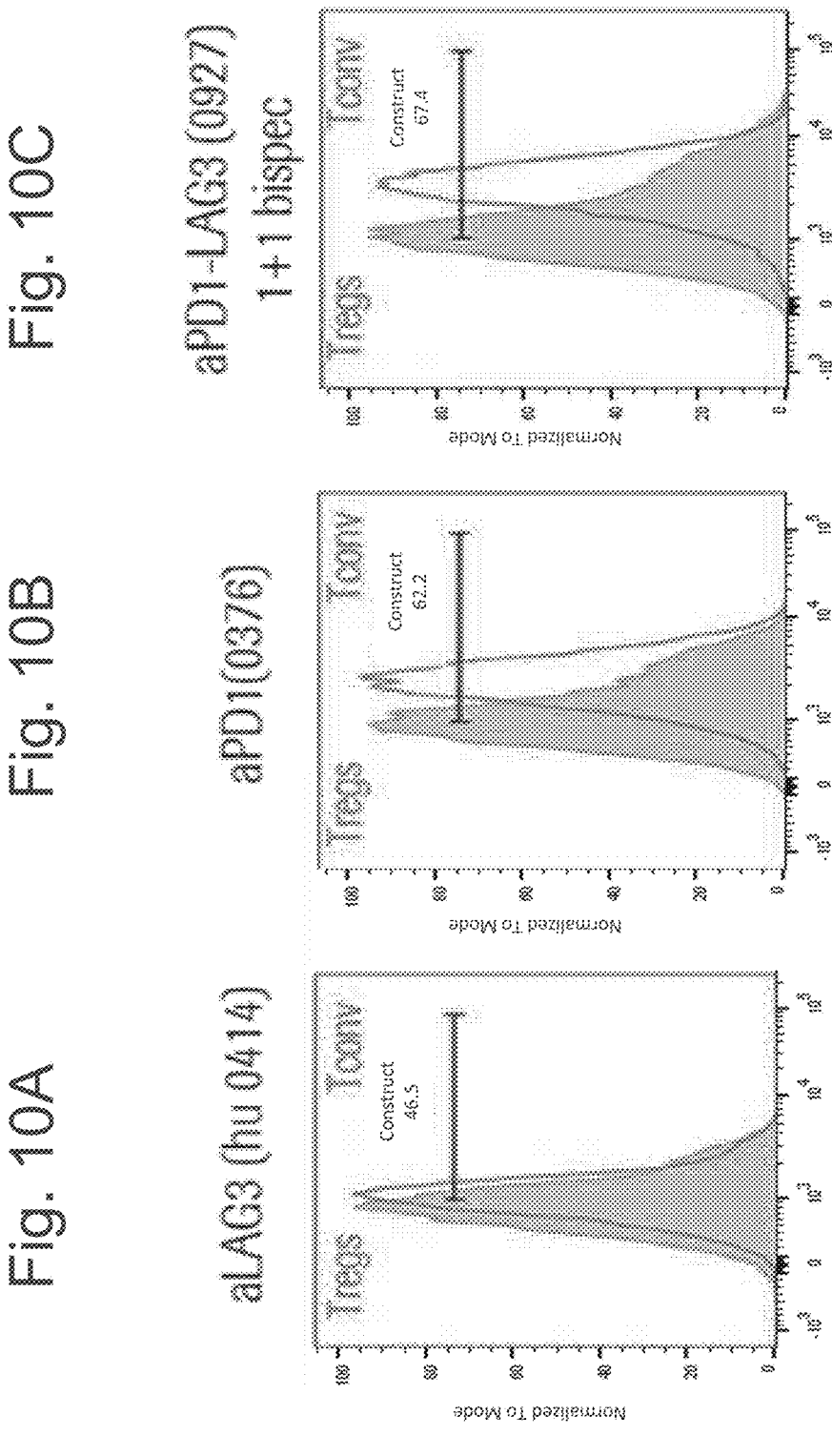
FIGS. 10A-10D: Binding to conventional T cells versus Tregs.
Figure 10D:
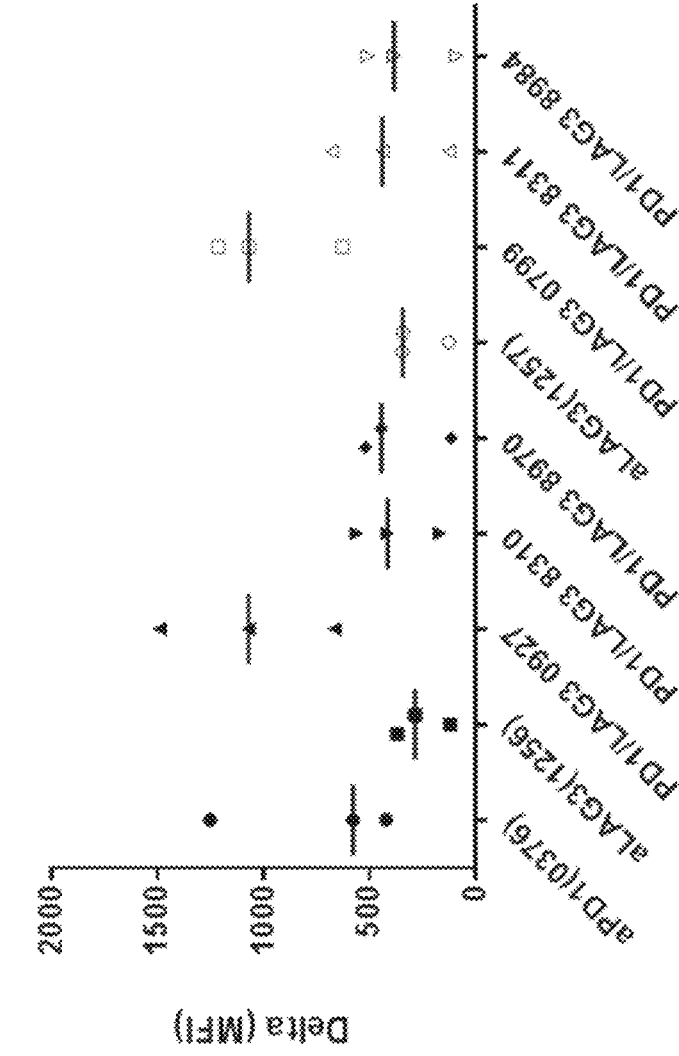

While the monospecific anti-LAG3 parental antibody binds equally well to Tregs and conventional T cells (FIG. 10A), the anti-PD1 counterpart binds preferentially to conventional T cells due to higher expression levels of PD1 on effector T cells than on Tregs (FIG. 10B). Interestingly, also the 1+1 format of the PD1/LAG3 bispecific antibody (0927) retained the ability to preferentially bind to conventional T cells than Tregs (FIG. 10C). This preferential binding to conventional T cells can also be visualized by depicting the difference (delta) of the signal on conventional T cells versus the one on Tregs (FIG. 10D). The 2+1 and the 2+2 formats did not show an avidity driven selectivity for effector T cells and are comparable in their binding to monospecific anti-LAG3 antibody.

12.3 Effect of PD-1 and LAG-3 Blockade on Treg Suppression of Granzyme B and IFN-g Release by Human CD4 T Cells Cocultured with Irradiated Allogeneic PBMCs It was further tested whether the differences in binding property of the bispecific antibody formats would provide any functional advantage to Tconv over Tregs. In functional studies involving regulatory T cells (Treg)-suppression assays, PBMCs from the same donor where divided in two samples: one was enriched in CD4 T cells and the other one in Tregs defined as CD4+CD25$^{high}$ CD127$^{low}$ T cells via a microbead kit (Miltenyi Biotec). Once the two populations were purified, CD4 T cells were labelled with 5 mM of Carboxy-Fluorescein-Succinimidyl Esther (CFSE) while Tregs were labelled with 5 mM Cell-Trace-Violet (CTV) to be able to distinguish them at the FACS later on.

Both CD4 T cells ($10^5$) and Tregs ($10^5$) were then co-cultured in a 96 well plate at 1:1 ratio together with irradiated PBMCs ($10^5$) from an unrelated donor in presence or absence of our anti-LAG3 antibodies (lead 0414 and backup 0416) or competitor anti-LAG3 antibodies (BMS-986016 and humanized BAP050) in combination with our anti-PD1 antibody at the concentration of 10 mg/ml. As control to estimate the magnitude of the suppression of CD4 T cell effector functions by Tregs, CD4 T cells ($10^5$) were also co-cultured with irradiated PBMCs ($10^5$) in the absence of Tregs.

Figure 11:
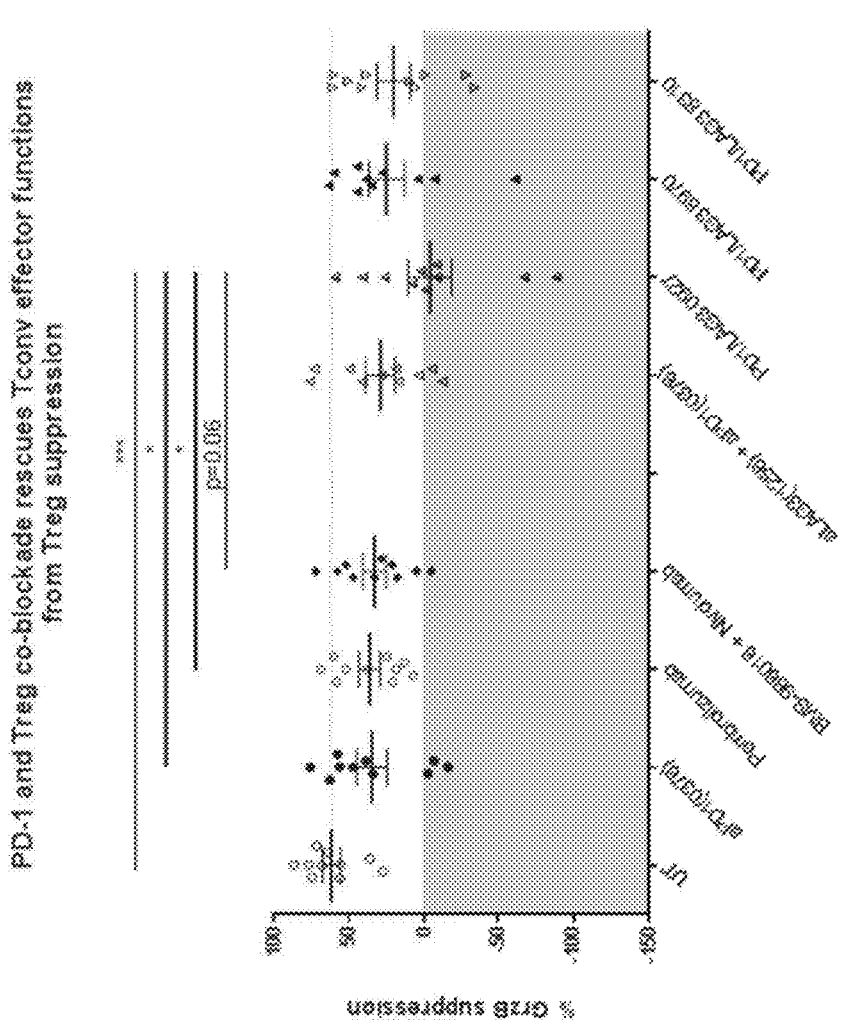
FIG. 11: PD1 and Treg co-blockade rescues tconv effector functions from Treg suppression. Shown is the percentage of suppression by Tregs of granzyme B secreted by Tconv after 5 days of coculture. Results (Median) are from 10 independent experiments with 10 different donors. P was calculated using two-way ANOVA.

Five days later we collected the cell-culture supernatants, used later to measure IFNγ levels by ELISA (R&D systems), and left the cells at 37° C. for additional 5 hours in presence of Golgi Plug (Brefeldin A) and Golgi Stop (Monensin). The cells were then washed, stained on the surface with anti-human CD4 antibody and the Live/Dead fixable dye Aqua (Invitrogen) before being fixed/permeabilized with Fix/Perm Buffer (BD Bioscience). We performed intracellular staining for Granzyme B (BD Bioscience) and IFNγ (eBioscience). Results are shown in FIG. 11.

Our PD1/LAG-3 bispecific antibody (0927) elicited Tconv escape from regulatory T cell tight control as demonstrated by the secretion of significantly higher amount of Granzyme B than Tconv in presence of parental anti-PD1 antibody or Pembrolizumab alone (P<0.05) or in absence of checkpoint inhibitors (P<0.001). Competitor anti-LAG3 antibody BMS-986016 in combination with Nivolumab did not significantly rescue Tconv effector functions from Treg suppression.

12.4 Effect of PD-1 and LAG-3 Blockade on Granzyme B and IFN-γ Secretion by CD4 T Cells from Melanoma Patient PBMCs after Recall with Immunogenic Melanoma-Antigen Peptide Pools It has been previously described that melanoma patient PBMCs contain detectable frequencies of tumor-antigen specific T cells. Therefore, for proof of concept purposes, the combination of anti-LAG-3 antibody (0414) plus anti-PD-1(0376) versus the derived bispecific antibody in 1+1 (0927) format or anti-PD-1 alone were tested on melanoma patient PBMCs re-stimulated overnight with immunogenic melanoma associated antigens peptide pools.

$10^5$ to $10^6$ PBMCs from melanoma patients where incubated at room temperature in presence or absence of saturating concentrations (10 µg/ml) of anti-PD-1 alone (0376), in combination with anti-LAG-3 (0414, 10 µg/ml) antibody or as bispecific 1+1 format (0927, 20 g/ml) antibody. T cells were then re-stimulated over-night with a pool of immunogenic tumor related antigens like MAGEA1, MAGEA3, MAGEA4, Melan-A/MART-1, NYESO-1, Melanocyte protein Pmel 17 gp100, Tyrosinase, Tyrosinase-related protein 2 in presence of protein transport inhibitors Golgi Plug (Brefeldin A) and Golgi Stop (Monensin).

The cells were then washed, stained on the surface with anti-human CD4 antibody and the Live/Dead fixable dye Aqua (Invitrogen) before being fixed/permeabilized with Fix/Perm Buffer (BD Bioscience). Intracellular staining was performed for Granzyme B (BD Bioscience) and IFN-γ (eBioscience).

Figure 12:
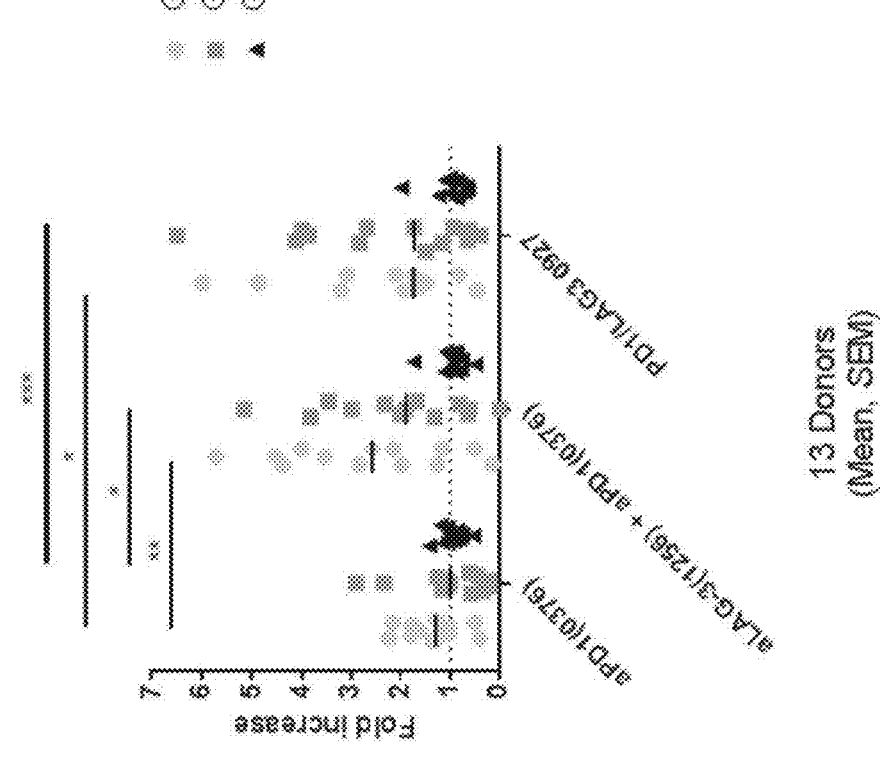
FIG. 12: Effect of PD-1 and LAG-3 blockade on Granzyme B and IFN-$\gamma$ secretion by CD4 T cells from melanoma patient PBMCs after recall with immunogenic melanoma-antigen peptide pools.

Both the combination of anti-LAG-3 and anti-PD-1 antibodies (P<0.01 and P<0.001) and the bispecific antibody significantly (P<0.01 and P<0.0001) enhanced tumor-antigen specific T cell effector functions (i.e. Granzyme B and IFN-γ secretion) while PD-1 blockade alone did not show any effect (FIG. 12).

12.5 Effect of PD-1/LAG-3 Bispecific Antibodies on Cytotoxic Granzyme B Release by Human CD4 T Cells Cocultured with a B Cell-Lymphoblatoid Cell Line (ARH77)

We assessed the ability of our different bispecific antibody formats to induce Granzyme B secretion by CD4 T cells, when co-cultured with the tumor cell line ARH77, in comparison to the combination of anti-PD-1 and anti-LAG-3 parental antibodies and to anti-PD1 antibodies used in standard of care.

In total 6 formats were tested, 3 generated from the combination of anti-PD1(0376) and anti-LAG3 (hu 1256, chi 0414) antibodies and 3 additional formats from anti-PD1 (0376) and anti-LAG-3 (hu1257, chi 0416) antibodies.

Figure 13:
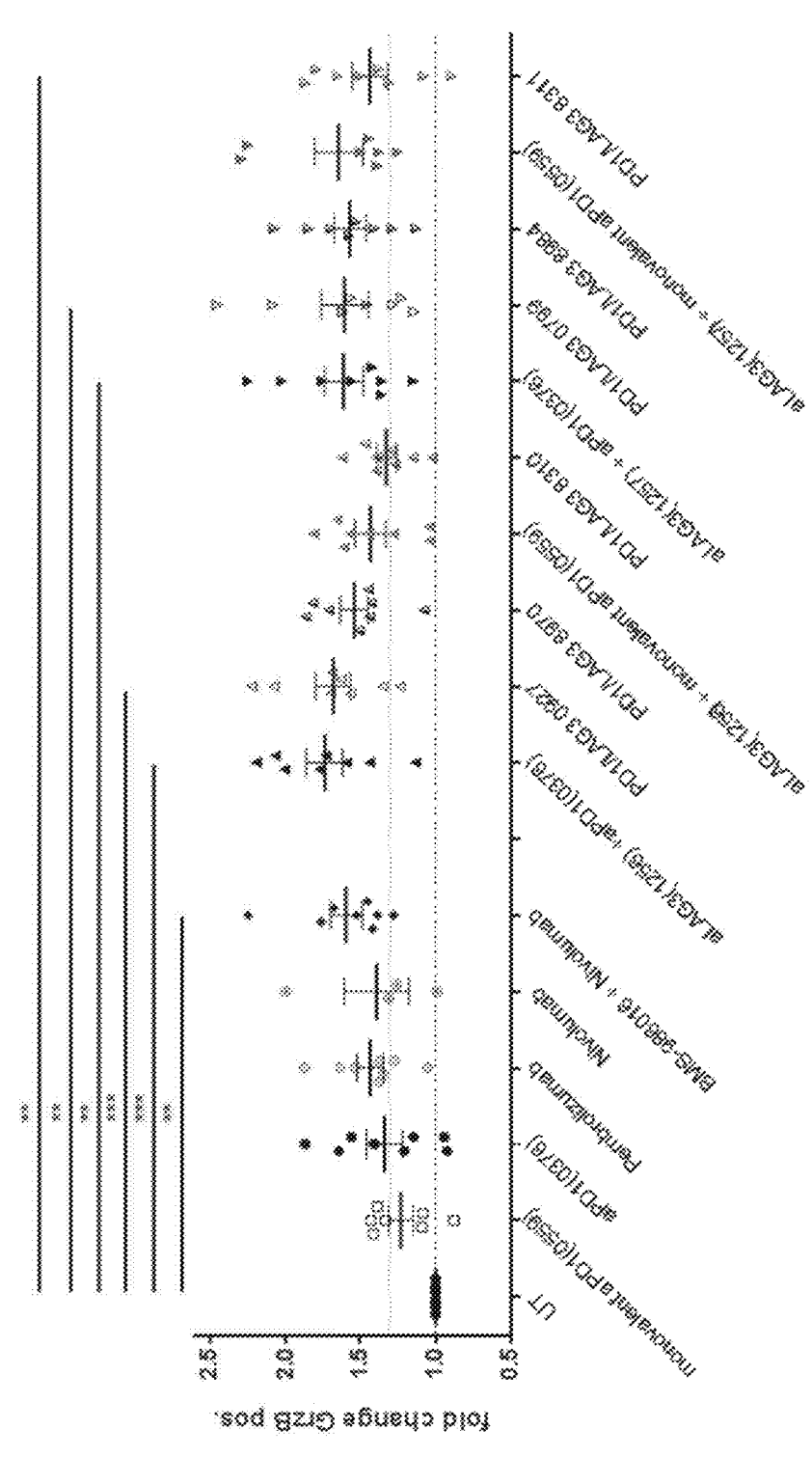
FIG. 13: Effect of aPD1/aLAG3 bispecific antibodies on cytotoxic Granzyme B release by human CD4 T cells cocultured with a B cell-lymphoblatoid cell line (ARH77). Different bispecific anti-PD1/anti-LAG3 antibodies as described herein are compared with antibodies used in standard of care or clinical trials.

As can be seen in FIG. 13, two bispecific formats, 1+1 (0927) and 2+2 (8970) generated from anti-LAG3 (hu 1256, anti-LAG3 0414 as IgG1 PGLALA) and anti-PD1(0376) and as well as the combination of the parental antibodies significantly enhanced Granzyme B secretion by CD4 T cells when compared to untreated CD4 T cells (P=0.0005, P=0.01 and P=0.0001 respectively). The corresponding 2+1 format (8310) showed a similar trend, however it did not reach statistical significance (P=0.07).

Regarding the bispecific antibodies generated by combining anti-LAG-3 (hu 1257, anti-LAG3 0416 as IgG1 PGLALA) with anti-PD1(0376), the 1+1 format (0799) and 2+2 (8984) significantly increased the frequencies of Granzyme B positive CD4 T cells when compared to untreated CD4 cells (P=0.0032 and P=0.0064 respectively).

Neither Nivolumab nor Pembrolizumab did significantly promote a higher Granzyme B secretion by CD4 T cells when compared to cells cultured in the absence of checkpoint inhibitors. (FIG. 13).

TABLE 27

Effect of tested PD1-LAG3 bispecific antibodies on cytotoxic Granzyme B release

| Sample | Effect |
|---|---|
| PD1/LAG3 0927 (1 + 1) | +++ |
| PD1/LAG3 8970 (2 + 2) | + |
| PD1/LAG3 8310 (1 + 2) | +/− |
| PD1/LAG3 0799 (1 + 1) | ++ |
| PD1/LAG3 8984 (2 + 2) | ++ |
| PD1/LAG3 8311 (1 + 2) | +/− |
| aLAG3(BMS986016) | ++ |

Example 13

Potent Anti-Tumor Effect by Combination Therapy of PD1/LAG3 Bispecific Antibodies and CEACAM5 CD3 TCB In Vivo TCB molecules have been prepared according to the methods described in WO 2014/131712 A1 or WO 2016/ 079076 A1. The preparation of the anti-CEA/anti-CD3 bispecific antibody (CEA CD3 TCB or CEA TCB) used in the experiments is described in Example 3 of WO 2014/131712 A1. CEA CD3 TCB is a "2+1 IgG CrossFab" antibody and is comprised of two different heavy chains and two different light chains. Point mutations in the CH3 domain ("knobs into holes") were introduced to promote the assembly of the two different heavy chains. Exchange of the VH and VL domains in the CD3 binding Fab were made in order to promote the correct assembly of the two different light chains. 2+1 means that the molecule has two antigen binding domains specific for CEA and one antigen binding domain specific for CD3. CEA CD3 TCB comprises the amino acid sequences of SEQ ID NO:146, SEQ ID NO:147, SEQ ID NO:148 and SEQ ID NO:149. CEACAM5 CD3 TCB has the same format, but comprises another CEA binder and comprises point mutations in the CH and CL domains of the CD3 binder in order to support correct pairing of the light chains. CEACAM5 CD TCB comprises the amino acid sequences of SEQ ID NO:150, SEQ ID NO:151, SEQ ID NO:152 and SEQ ID NO:153.

a) Experimental Material and Methods

The PD1/LAG3 bispecific antibody 0927 was tested in a concentration of 1.5 mg/kg or 3 mg/kg in combination with the human CEACAM5 CD3 TCB in a human pancreatic BXPC3 cancer model. BXPC3 cells were cografted subcutaneously with a mouse fibroblast cell line (3T3) in NSG humanized mice.

Preparation of BXPC3 cell line: BXPC3 cells (human pancreatic cancer cells) were originally obtained from ECACC (European Collection of Cell Culture) and after expansion deposited in the Glycart internal cell bank. BXPC3 cells were cultured in RPMI containing 10% FCS (PAA Laboratories, Austria), 1% Glutamax. The cells were cultured at 37° C. in a water-saturated atmosphere at 5% $CO_2$.

Production of fully humanized mice: Female NSG mice, age 4-5 weeks at start of the experiment (Jackson Laboratory), were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis. The NSG mice were injected i.p. with 15 mg/kg of Busulfan followed one day later by an i.v. injection of 1×105 human hematopoietic stem cells isolated from cord blood. At week 14-16 after stem cell injection mice were bled sublingual and blood was analyzed by flow cytometry for successful humanization. Efficiently engrafted mice were randomized according to their human T cell frequencies into the different treatment groups.

Efficacy Experiment: Fully humanized HSC-NSG mice were challenged subcutaneously with $1\times10^6$ BXPC3 cells (human pancreatic carcinoma cell line, expressing CEACAM5) at day 0 in the presence of matrigel at 1:1 ratio. Tumors were measured 2 to 3 times per week during the whole experiment by Caliper. At day 15 mice were randomized for tumor size with an average tumor size of 250 mm³ and a weekly scheduled therapy (vehicle (histidine buffer), anti-PD1(0376), Nivolumab, Pembrolizumab or anti PD1-LAG3 0927) started and was given by intra-peritoneal injection in 400 μl max. Tumor growth was measured 2-3 times weekly using a caliper and tumor volume was calculated as followed:

$$Tv: (W^2/2) \times L \qquad (W: Width, L: Length)$$

The study was terminated at day 47.

b) Results

Figure 14:
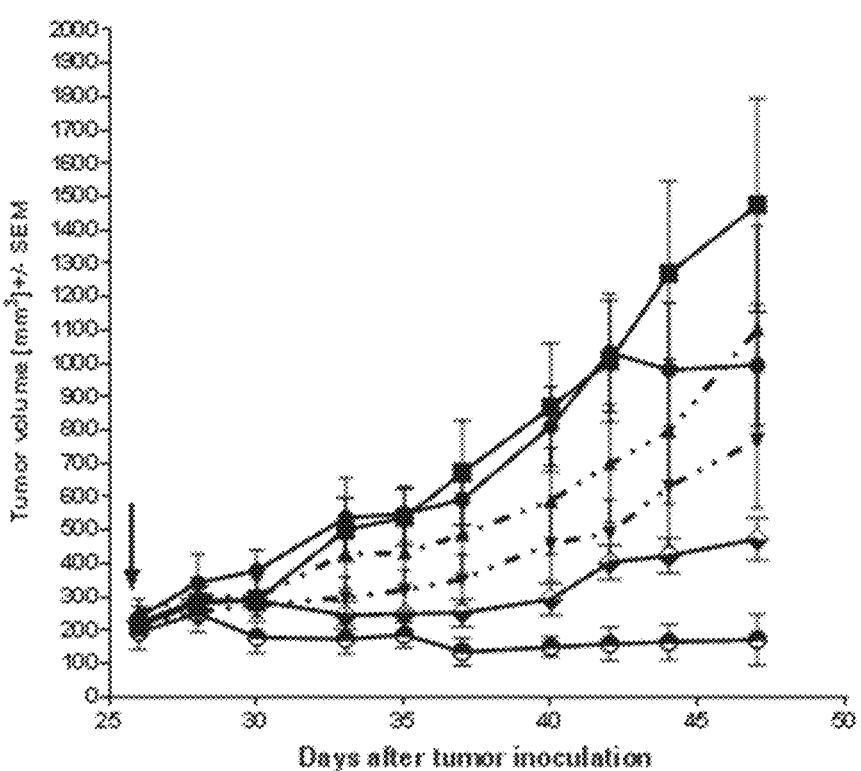
FIG. 14: Efficacy study in humanized mice challenged with pancreatic adenocarcinoma, BxPC3. In combination with CEACAM CD3 TCB, only the aPD1/aLAG3 bispecific antibody provided a statistical significant tumor protection when compared to conventional PD1 antibodies. Shown are the tumor growth curves in humanized mice challenged subcutaneously with BxPC3 cells and treated with the indicated molecules in combination with CEACAM5-TCB.
Figure 15A:
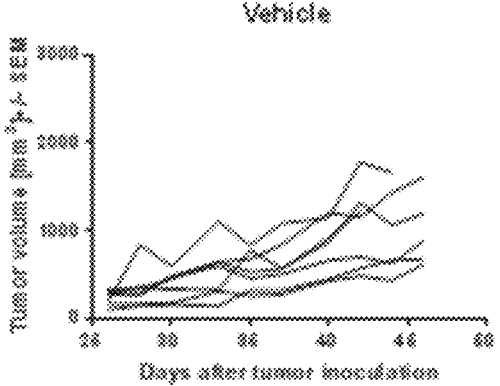
FIG. 15A-15F: The measurements of tumor volumes (mm$^3$+/−SEM), over a period of 47 days, are shown for each individual animal showing the homogeneity of group anti-tumor response. The tumor growth curves are shown for the vehicle group in FIG. 15A, for CEACAM5 CD3 TCB alone (2.5 mg/kg) in FIG. 15B, for the combination of CEACAM5 CD3 TCB with Nivolumab (1.5 mg/kg) in FIG. 15C, for the combination of CEACAM5 CD3 TCB with Pembrolizumab (1.5 mg/kg) in FIG. 15D, for the combination of CEACAM5 CD3 TCB with PD1/LAG3 0927 in FIG. 15E (1.5 mg/kg) and in FIG. 15F (3 mg/kg bispecific antibody).
Figure 15B:
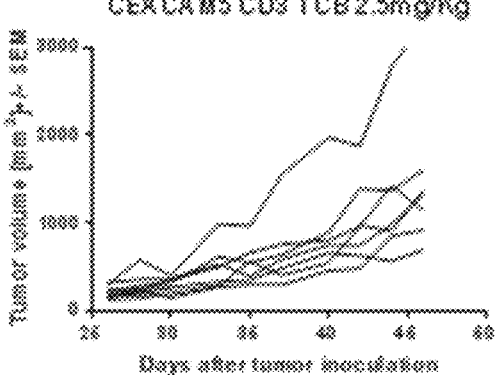
Figure 15C:
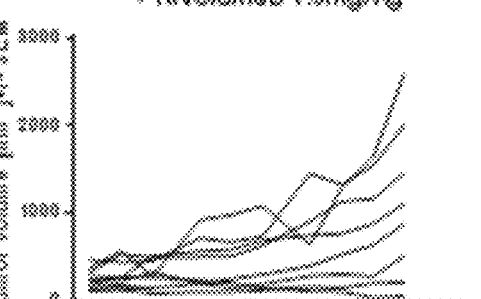
Figure 15D:
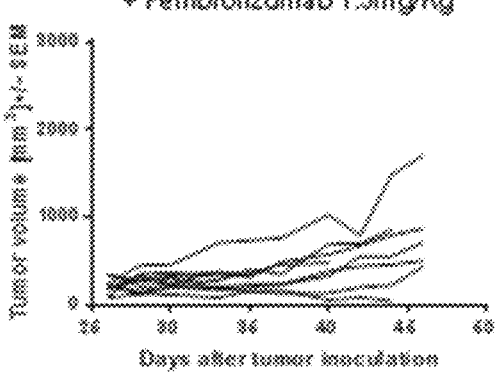
Figure 15E:
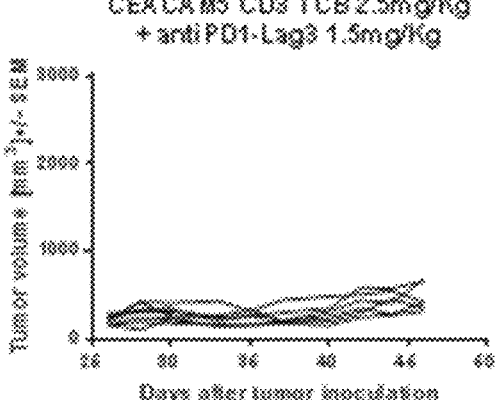
Figure 15F:
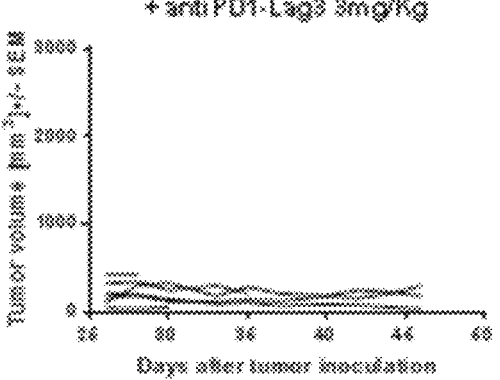

The measurements of tumor volumes ($mm^3$+/−SEM), over a period of 47 days, are shown as mean volume within the respective treatment group of mice in FIG. 14. Treatment with CEACAM5-TCB only shows a disease progression identical to the untreated vehicle group Conversely, Nivolumab and Pembrolizumab reduced the tumor growth, however, without reaching tumor-growth control. Surprisingly, PD1/LAG3 bispecific antibody 0927, at the concentration of 3 mg/Kg, fully suppressed tumor growth in all treated animals showing synergism of the LAG-3 co-blockade in addition to PD-1.

In FIGS. 15A to 15F the measurements of tumor volumes ($mm^3$+/−SEM), over a period of 47 days, are shown for each individual animal showing the homogeneity of the anti-tumor response in each group.

The statistical significance was calculated by using the Dunnett's Method against the CEACAM5 CD3 TCB single treatment. To test for significant differences in group means for multiple comparisons, the standard analysis of variance (ANOVA) is automatically produced, using the Dunnett's method. Dunnett's method tests whether means are different from the mean of a control group.

The resulting TGI and TCR values are shown in Table 28 (TGI means tumor growth inhibition, TGI>100 means tumor regression and TGI=100 is defined as tumor stasis, TCR means treatment to control ratio, TCR=1 means no effect and TCR=0 is defined as complete regression).

TABLE 28

| Tumor growth inhibition (TGI) and Treatment to control ration (TCR) on day 46 | | | |
| --- | --- | --- | --- |
| Group (Day 46 reference CEACAM5-TCB | TGI | TCR | p-value |
| CEACAM5 CD3 TCB 2.5 mg/kg + anti-PDI/LAG3 0927 1.5 mg/kg | 93.06119 | 0.207878 | 0.0056 |
| CEACAM5 CD3 TCB 2.5 mg/kg + anti-PDI/LAG3 0927 3 mg/kg | 79.22326 | 0.006863 | 0.005 |
| CEACAM5 CD3 TCB 2.5 mg/kg + Nivolumab 1.5 mg/kg | 32.9787 | 0.668563 | 0.513 |
| CEACAM5 CD3 TCB 2.5 mg/kg + Pembrolizumab 1.5 mg/kg | 55.33328 | 0.437398 | 0.07 |

The comparison with the control is further shown as p-values using Dunnett's method.

The treatment with CEACAM5 CD3 TCB cannot control tumor growth in the context of pancreatic cancer. However, its combination with the bi-specific antibody anti-PD1/LAG3 0927, lead to a strong impact on tumor control in a dose specific manner. The statistical analysis showed that the combination with anti-PD1/LAG3 0927, but not with the anti-PD1 antibodies Nivolumab and Pembrolizumab, at both concentration resulted in statistical significant difference in control of tumor growth when compared to single treatment, suggesting the superiority of the bi-specific anti-PD1/LAG3 antibody over inhibition of only PD1, bringing the tumor growth to stasis.

The invention claimed is:

1. A method of treating an individual having a cancer comprising administering to the individual an effective amount of a bispecific antibody comprising a first antigen binding domain that specifically binds to programmed cell death protein 1 (PD1) and a second antigen binding domain that specifically binds to Lymphocyte activation gene-3 (LAG3), wherein said first antigen binding domain specifically binding to PD1 comprises a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence of SEQ ID NO:3; and a VL domain comprising (i) HVR-L1 comprising the amino acid sequence of SEQ ID NO: 4;

(ii) HVR-L2 comprising the amino acid sequence of SEQ ID NO:5, and (iii) HVR-L3 comprising the amino acid sequence of SEQ ID NO:6, and the second antigen binding domain that specifically binds to LAG3 comprises (a) a VH domain comprising (i) HVR-H1 comprising the amino acid sequence of SEQ ID NO: 14, (ii) HVR-H2 comprising the amino acid sequence of SEQ ID NO:15, and (iii) HVR-H3 comprising an amino acid sequence of SEQ ID NO:16; and a VL domain comprising (i) HVR-L1 comprising the amino acid sequence of SEQ ID NO: 17, (ii) HVR-L2 comprising the amino acid sequence of SEQ ID NO:18, and (iii) HVR-L3 comprising the amino acid sequence of SEQ ID NO:19; or (b) a VH domain comprising (i) HVR-H1 comprising the amino acid sequence of SEQ ID NO: 22, (ii) HVR-H2 comprising the amino acid sequence of SEQ ID NO:23, and (iii) HVR-H3 comprising an amino acid sequence of SEQ ID NO:24; and a VL domain comprising (i) HVR-L1 comprising the amino acid sequence of SEQ ID NO: 25, (ii) HVR-L2 comprising the amino acid sequence of SEQ ID NO:26, and (iii) HVR-L3 comprising the amino acid sequence of SEQ ID NO:27; or (c) a VH domain comprising (i) HVR-H1 comprising the amino acid sequence of SEQ ID NO: 30, (ii) HVR-H2 comprising the amino acid sequence of SEQ ID NO:31, and (iii) HVR-H3 comprising an amino acid sequence of SEQ ID NO:32; and a VL domain comprising (i) HVR-L1 comprising the amino acid sequence of SEQ ID NO: 33, (ii) HVR-L2 comprising the amino acid sequence of SEQ ID NO:34, and (iii) HVR-L3 comprising the amino acid sequence of SEQ ID NO:35; or (d) a VH domain comprising (i) HVR-H1 comprising the amino acid sequence of SEQ ID NO: 38, (ii) HVR-H2 comprising the amino acid sequence of SEQ ID NO:39, and (iii) HVR-H3 comprising an amino acid sequence of SEQ ID NO:40; and a VL domain comprising (i) HVR-L1 comprising the amino acid sequence of SEQ ID NO: 41, (ii) HVR-L2 comprising the amino acid sequence of SEQ ID NO:42, and (iii) HVR-L3 comprising the amino acid sequence of SEQ ID NO:43; or (e) a VH domain comprising (i) HVR-H1 comprising the amino acid sequence of SEQ ID NO: 46, (ii) HVR-H2 comprising the amino acid sequence of SEQ ID NO:47, and (iii) HVR-H3 comprising an amino acid sequence of SEQ ID NO:48; and a VL domain comprising (i) HVR-L1 comprising the amino acid sequence of SEQ ID NO: 49, (ii) HVR-L2 comprising the amino acid sequence of SEQ ID NO:50, and (iii) HVR-L3 comprising the amino acid sequence of SEQ ID NO:51.

2. The method of claim 1, wherein the bispecific antibody comprises a Fc domain that is an IgG and wherein the Fc domain comprises one or more amino acid substitution that reduces binding to an Fc receptor.

3. The method of according to claim 1, wherein the first antigen-binding domain specifically binding to PD1 comprises (a) a VH domain comprising the amino acid sequence of SEQ ID NO: 7 and a VL domain comprising the amino acid sequence of SEQ ID NO: 8, or (b) a VH domain comprising the amino acid sequence of SEQ ID NO: 9 and a VL domain comprising the amino acid sequence of SEQ ID NO: 10, or (c) a VH domain comprising the amino acid sequence of SEQ ID NO: 9 and a VL domain comprising the amino acid sequence of SEQ ID NO: 11, or (d) a VH domain comprising the amino acid sequence of SEQ ID NO: 9 and a VL domain comprising the amino acid sequence of SEQ ID NO: 12, or (e) a VH domain comprising the amino acid sequence of SEQ ID NO: 9 and a VL domain comprising the amino acid sequence of SEQ ID NO: 13.

4. The method according to claim 1, wherein the first antigen-binding domain specifically binding to PD1 comprises a VH domain comprising the amino acid sequence of SEQ ID NO: 9 and a VL domain comprising the amino acid sequence of SEQ ID NO: 10.

5. The method according to claim 3, wherein the second antigen-binding domain specifically binding to LAG3 comprises (a) a VH domain comprising the amino acid sequence of SEQ ID NO: 20 and a VL domain comprising the amino acid sequence of SEQ ID NO: 21, or (b) a VH domain comprising the amino acid sequence of SEQ ID NO: 28 and a VL domain comprising the amino acid sequence of SEQ ID NO: 29, or (c) a VH domain comprising the amino acid sequence of SEQ ID NO: 36 and a VL domain comprising the amino acid sequence of SEQ ID NO: 37, or (d) a VH domain comprising the amino acid sequence of SEQ ID NO: 44 and a VL domain comprising the amino acid sequence of SEQ ID NO: 45, or (e) a VH domain comprising the amino acid sequence of SEQ ID NO: 52 and a VL domain comprising the amino acid sequence of SEQ ID NO: 53.

6. The method according to claim 1, wherein the first antigen binding domain specifically binding to PD1 comprises a VH domain comprising the amino acid sequence of SEQ ID NO: 9 and a VL domain comprising the amino acid sequence of SEQ ID NO: 10, and the second antigen binding domain specifically binding to LAG3 comprises a VH domain comprising the amino acid sequence of SEQ ID NO: 20 and a VL domain comprising the amino acid sequence of SEQ ID NO: 21 or a VH domain comprising the amino acid sequence of SEQ ID NO: 52 and a VL domain comprising the amino acid sequence of SEQ ID NO: 53.

7. The method according to claim 1, wherein the first antigen binding domain specifically binding to PD1 comprises a VH domain comprising the amino acid sequence of SEQ ID NO: 9 and a VL domain comprising the amino acid sequence of SEQ ID NO: 10, and the second antigen binding domain specifically binding to LAG3 comprises a VH domain comprising the amino acid sequence of SEQ ID NO: 20 and a VL domain comprising the amino acid sequence of SEQ ID NO: 21.

8. The method of claim 1, wherein the bispecific antibody comprises an Fc domain of human IgG1 subclass with the amino acid mutations L234A, L235A and P329G, wherein the numbering is according to Kabat EU index.

9. The method of claim 1, wherein the bispecific antibody comprises an Fc domain comprising a modification promoting the association of the first and second subunit of the Fc domain.

10. The method of claim 9, wherein the first subunit of the Fc domain comprises the amino acid substitutions S354C and T366W, wherein the numbering is according to Kabat EU index, and the second subunit of the Fc domain comprises the amino acid substitutions Y349C, T366S and Y407V, wherein the numbering is according to Kabat EU index.

11. The method of claim 1, wherein the bispecific antibody comprises an Fc domain, a first Fab fragment comprising the antigen binding domain that specifically binds to PD1 and a second Fab fragment comprising the antigen binding domain that specifically binds to LAG3.

12. The method of claim 11, wherein in one of the Fab fragments the variable domains VL and VH are replaced by each other so that the VH domain is part of the light chain and the VL domain is part of the heavy chain.

13. The method of claim 11, wherein in the first Fab fragment comprising the antigen binding domain that specifically binds to PD1 the variable domains VL and VH are replaced by each other.

14. The method of claim 11, wherein the first Fab fragment comprising the antigen binding domain that specifically binds to PD1 or the second Fab fragment comprising the antigen binding domain that specifically binds to LAG3 comprises a Fab fragment wherein in the constant domain CL the amino acid at position 124 is substituted independently by lysine (K), arginine (R) or histidine (H), wherein the numbering is according to Kabat EU index, and in the constant domain CH1 the amino acids at positions 147 and 213 are substituted independently by glutamic acid (E) or aspartic acid (D), wherein the numbering is according to Kabat EU index.

15. The method of claim 11, wherein in the second Fab fragment comprising the antigen binding domain that specifically binds to LAG3 the constant domain CL the amino acid at position 124 is substituted independently by lysine (K), arginine (R) or histidine (H), wherein the numbering is according to Kabat EU index, and in the constant domain CH1 the amino acids at positions 147 and 213 are substituted independently by glutamic acid (E) or aspartic acid (D), wherein the numbering is according to Kabat EU index.

16. The method of claim 1, comprising (a) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, and a second heavy chain comprising an amino acid sequence with at least 95% sequence identity to the sequence of SEQ ID NO: 97, and a second light chain comprising an amino acid sequence with at least 95% sequence identity to the sequence of SEQ ID NO:99, or (b) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, and a second heavy chain comprising an amino acid sequence with at least 95% sequence identity to the sequence of SEQ ID NO: 100, and a second light chain comprising an amino acid sequence with at least 95% sequence identity to the sequence of SEQ ID NO:101, or (c) a first heavy chain comprising an amino acid sequence with at least 95% sequence identity to the sequence of SEQ ID NO: 102, a first light chain comprising an amino acid sequence with at least 95% sequence identity to the sequence of SEQ ID NO: 104, and a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105, or (d) a first heavy chain comprising an amino acid sequence with at least 95% sequence identity to the sequence of SEQ ID NO: 106, a first light chain comprising an amino acid sequence with at least 95% sequence identity to the sequence of SEQ ID NO: 107, and a second heavy chain comprising an amino acid sequence with at least 95% sequence identity to the sequence of SEQ ID NO: 103, and a second light chain comprising an amino acid sequence with at least 95% sequence identity to the sequence of SEQ ID NO: 105.

17. The method of claim 1, comprising a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 100, and a second light chain comprising an amino acid sequence with at least 95% sequence identity to the sequence of SEQ ID NO:101.

18. The method of claim 11, wherein the bispecific antibody comprises a second Fab fragment comprising the antigen binding domain that specifically binds to LAG3 which is fused to the C-terminus of the Fc domain.

19. The method of claim 18, comprising a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 144, and a second light chain comprising an amino acid sequence with at least 95% sequence identity to the sequence of SEQ ID NO:101.

20. The method of claim 11, wherein the bispecific antibody comprises a third Fab fragment comprising an antigen binding domain that specifically binds to LAG3.

21. The method of claim 11, wherein the Fab fragment comprising the antigen binding domain that specifically binds to PD1 is fused via a peptide linker to the C-terminus of one of the heavy chains.

22. The method of claim 21, comprising (a) a first heavy chain comprising an amino acid sequence with at least 95% sequence identity to the sequence of SEQ ID NO: 118, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 119, and two second light chains comprising an amino acid sequence with at least 95% sequence identity to the sequence of SEQ ID NO: 101, or (b) a first heavy chain comprising an amino acid sequence with at least 95% sequence identity to the sequence of SEQ ID NO: 120, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 121, and two second light chains comprising an amino acid sequence with at least 95% sequence identity to the sequence of SEQ ID NO:99, or (c) a first heavy chain comprising an amino acid sequence with at least 95% sequence identity to the sequence of SEQ ID NO: 122, a first light chain comprising an amino acid sequence with at least 95% sequence identity to the sequence of SEQ ID NO: 115, a second heavy chain comprising an amino acid sequence with at least 95% sequence identity to the sequence of SEQ ID NO: 103, and two second light chains comprising an amino acid sequence with at least 95% sequence identity to the sequence of SEQ ID NO:105.

23. The method of claim 11, wherein one of the Fab fragments comprising the antigen binding domain that specifically binds to LAG3 is fused via a peptide linker to the C-terminus of one of the heavy chains.

24. The method of claim 23, comprising (a) a first heavy chain comprising an amino acid sequence with at least 95% sequence identity to the sequence of SEQ ID NO: 96, a first light chain comprising an amino acid sequence with at least 95% sequence identity to the sequence of SEQ ID NO: 98, a second heavy chain comprising an amino acid sequence with at least 95% sequence identity to the sequence of SEQ ID NO: 145, and two second light chains comprising an amino acid sequence with at least 95% sequence identity to the sequence of SEQ ID NO: 101.

25. The method of claim 20, wherein the bispecific antibody comprises a fourth Fab fragment comprising an antigen binding domain that specifically binds to PD1.

26. The method of claim 25, wherein the two Fab fragments comprising each an antigen binding domain that specifically binds to PD1 are identical.

27. The method of claim 25, wherein the two Fab fragments comprising each an antigen binding domain that specifically binds to PD1 are each fused via a peptide linker to the C-terminus to one of the heavy chains, respectively.

28. The method of claim 27, comprising
(a) two heavy chains comprising each an amino acid sequence with at least 95% sequence identity to the sequence of SEQ ID NO: 114, two first light chains comprising each an amino acid sequence with at least 95% sequence identity to the sequence of SEQ ID NO: 115, and two second light chains comprising each an amino acid sequence with at least 95% sequence identity to the sequence of SEQ ID NO: 101, or
(b) two heavy chains comprising each an amino acid sequence with at least 95% sequence identity to the sequence of SEQ ID NO: 116, two first light chains comprising each an amino acid sequence with at least 95% sequence identity to the sequence of SEQ ID NO: 115, and two second light chains comprising each an amino acid sequence with at least 95% sequence identity to the sequence of SEQ ID NO:99, or (c) two heavy chains comprising each an amino acid sequence with at least 95% sequence identity to the sequence of SEQ ID NO: 117, two first light chains comprising each an amino acid sequence with at least 95% sequence identity to the sequence of SEQ ID NO: 115, and two second light chains comprising an amino acid sequence with at least 95% sequence identity to the sequence of SEQ ID NO:105.

29. The method of claim 1, wherein the bispecific antibody comprises an Fc domain, two Fab fragments comprising each an antigen binding domain that specifically binds to LAG3 and a single chain Fab (scFab) comprising the antigen binding domain that specifically binds to PD1.

30. The method of claim 29, wherein the scFab comprising an antigen binding domain that specifically binds to PD1 is fused via a peptide linker to the C-terminus to one of the heavy chains.

31. The method of claim 30, comprising
(a) a first heavy chain comprising an amino acid sequence with at least 95% sequence identity to the sequence of SEQ ID NO: 123, a second heavy chain comprising an amino acid sequence with at least 95% sequence identity to the sequence of SEQ ID NO: 119, and two light chains comprising each an amino acid sequence with at least 95% sequence identity to the sequence of SEQ ID NO: 101, or
(b) a first heavy chain comprising an amino acid sequence with at least 95% sequence identity to the sequence of SEQ ID NO: 124, a second heavy chain comprising an amino acid sequence with at least 95% sequence identity to the sequence of SEQ ID NO: 121, and two light chains comprising each an amino acid sequence with at least 95% sequence identity to the sequence of SEQ ID NO:99, or
(c) a first heavy chain comprising an amino acid sequence with at least 95% sequence identity to the sequence of SEQ ID NO: 125, a second heavy chain comprising an amino acid sequence with at least 95% sequence identity to the sequence of SEQ ID NO: 103, and a second light chain comprising an amino acid sequence with at least 95% sequence identity to the sequence of SEQ ID NO:105.

32. The method of claim 1, comprising a first heavy chain comprising an amino acid sequence of SEQ ID NO: 96, a first light chain comprising an amino acid sequence of SEQ ID NO: 98, a second heavy chain comprising an amino acid sequence of SEQ ID NO: 100, and a second light chain comprising an amino acid sequence of SEQ ID NO: 101.

* * * * *

SEQUENCE LISTING

```
<160> NUMBER OF SEQ ID NOS: 169

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain HVR-H1, PD1-0103

<400> SEQUENCE: 1

Gly Phe Ser Phe Ser Ser Tyr
1               5

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      heavy chain HVR-H2, PD1-0103

<400> SEQUENCE: 2

Gly Gly Arg
1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued heavy chain HVR-H3, PD1-0103

<400> SEQUENCE: 3

Thr Gly Arg Val Tyr Phe Ala Leu Asp
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain HVR-L1, PD1-0103

<400> SEQUENCE: 4

Ser Glu Ser Val Asp Thr Ser Asp Asn Ser Phe
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      light chain HVR-L2, PD1-0103

<400> SEQUENCE: 5

Arg Ser Ser
1

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      light chain HVR-L3, PD1-0103

<400> SEQUENCE: 6

Asn Tyr Asp Val Pro Trp
1               5

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      heavy chain variable domain VH, PD1-0103

<400> SEQUENCE: 7

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln

-continued

```
                  100             105             110

Gly Thr Ser Val Thr Val Ser Ser
        115             120

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      light chain variable domain VL, PD1-0103

<400> SEQUENCE: 8

Lys Ile Val Leu Thr Gln Ser Pro Ala Ser Leu Pro Val Ser Leu Gly
1               5                   10                  15

Gln Arg Ala Thr Ile Ser Cys Arg Ala Ser Glu Ser Val Asp Thr Ser
            20                  25                  30

Asp Asn Ser Phe Ile His Trp Tyr Gln Gln Arg Pro Gly Gln Ser Pro
        35                  40                  45

Lys Leu Leu Ile Tyr Arg Ser Ser Thr Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Asn Tyr
                85                  90                  95

Asp Val Pro Trp Thr Phe Gly Gly Gly Thr Lys Leu Glu Ile Lys
            100             105             110

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized variant -heavy chain variable domain VH
      of PD1-0103_01 (PD1 0376)

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100             105             110

Gly Thr Leu Val Thr Val Ser Ser
        115             120

<210> SEQ ID NO 10
<211> LENGTH: 111
<212> TYPE: PRT
<213> ORGANISM: Artificial Sequence
<220> FEATURE:
```

-continued

<223> OTHER INFORMATION: Description of Artificial Sequence: Synthetic
      humanized variant -light chain variable domain VL
      of PD1-0103_01 (PD1 0376)

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Asp Val Pro Trp Thr Phe Gly Gln Gly Thr Lys Val Glu Ile Lys
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      humanized variant -light chain variable domain VL
      of PD1-0103_02

<400> SEQUENCE: 11

Asp Val Val Met Thr Gln Ser Pro Leu Ser Leu Pro Val Thr Leu Gly
1               5                   10                  15

Gln Pro Ala Ser Ile Ser Cys Arg Ala Ser Glu Ser Val Asp Thr Ser
            20                  25                  30

Asp Asn Ser Phe Ile His Trp Tyr Gln Gln Arg Pro Gly Gln Ser Pro
        35                  40                  45

Arg Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Tyr
                85                  90                  95

Asp Val Pro Trp Thr Phe Gly Gln Gly Thr Lys Val Glu Ile Lys
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: Description of Artificial Sequence: Synthetic
      humanized variant -light chain variable domain VL
      of PD1-0103_03

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Thr Ser
            20                  25                  30

Asp Asn Ser Phe Ile His Trp Tyr Gln Gln Lys Pro Gly Gln Ser Pro

```
        35              40              45
Arg Leu Leu Ile Tyr Arg Ser Ser Thr Leu Glu Ser Gly Ile Pro Ala
    50              55              60

Arg Phe Ser Gly Ser Gly Ser Gly Thr Asp Phe Thr Leu Thr Ile Ser
65              70              75              80

Ser Leu Glu Pro Glu Asp Phe Ala Val Tyr Tyr Cys Gln Gln Asn Tyr
                85              90              95

Asp Val Pro Trp Thr Phe Gly Gln Gly Thr Lys Val Glu Ile Lys
                100             105             110
```

<210> SEQ ID NO 13
<211> LENGTH: 111
<212> TYPE: PRT
<213> ORGANISM: Artificial Sequence
<220> FEATURE:
<223> OTHER INFORMATION: Description of Artificial Sequence: Synthetic
      humanized variant -light chain variable domain VL
      of PD1-0103_04

<400> SEQUENCE: 13

```
Glu Ile Val Leu Thr Gln Ser Pro Ala Thr Leu Ser Leu Ser Pro Gly
1               5               10              15

Glu Arg Ala Thr Leu Ser Cys Arg Ala Ser Glu Ser Val Asp Thr Ser
                20              25              30

Asp Asn Ser Phe Ile His Trp Tyr Gln Gln Lys Pro Gly Gln Ser Pro
        35              40              45

Arg Leu Leu Ile Tyr Arg Ser Ser Thr Leu Glu Ser Gly Ile Pro Ala
    50              55              60

Arg Phe Ser Gly Ser Gly Ser Gly Thr Asp Phe Thr Leu Thr Ile Ser
65              70              75              80

Ser Leu Glu Pro Glu Asp Phe Ala Val Tyr Tyr Cys Gln Gln Asn Tyr
                85              90              95

Asp Val Pro Trp Thr Phe Gly Gln Gly Thr Lys Val Glu Ile Lys
                100             105             110
```

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain HVR-H1, aLAG3(0414)

<400> SEQUENCE: 14

```
Asp Tyr Thr Met Asn
1               5
```

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain HVR-H2, aLAG3(0414)

<400> SEQUENCE: 15

```
Val Ile Ser Trp Asp Gly Gly Gly Thr Tyr Tyr Thr Asp Ser Val Lys
1               5               10              15

Gly
```

<210> SEQ ID NO 16

```
<211> LENGTH: 12
<212> TYPE: PRT
<213> ORGANISM: Artificial Sequence
<220> FEATURE:
<223> OTHER INFORMATION: Description of Artificial Sequence: Synthetic
      heavy chain HVR-H3, aLAG3(0414)

<400> SEQUENCE: 16

Gly Leu Thr Asp Thr Thr Leu Tyr Gly Ser Asp Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain HVR-L1, aLAG3(0414)

<400> SEQUENCE: 17

Arg Ala Ser Gln Ser Ile Ser Ser Tyr Leu Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain HVR-L2, aLAG3(0414)

<400> SEQUENCE: 18

Ala Ala Ser Thr Leu Gln Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain HVR-L3, aLAG3(0414)

<400> SEQUENCE: 19

Gln Gln Thr Tyr Ser Ser Pro Leu Thr
1               5

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: Synthetic
      heavy chain variable domain VH, aLAG3(0414)

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Asp Asp Tyr
            20                  25                  30

Thr Met Asn Trp Val Arg Gln Ala Pro Gly Lys Gly Leu Glu Trp Val
        35                  40                  45

Ala Val Ile Ser Trp Asp Gly Gly Thr Tyr Tyr Thr Asp Ser Val
    50                  55                  60

Lys Gly Arg Phe Thr Ile Ser Arg Asp Asp Phe Lys Asn Thr Leu Tyr
65                  70                  75                  80
```

```
Leu Gln Met Asn Ser Leu Arg Ala Glu Asp Thr Ala Val Tyr Tyr Cys
            85                  90                  95

Ala Lys Gly Leu Thr Asp Thr Thr Leu Tyr Gly Ser Asp Tyr Trp Gly
            100                 105                 110

Gln Gly Thr Leu Val Thr Val Ser Ser
        115                 120
```

```
<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable domain VL, aLAG3(0414)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ser Pro Leu
            85                  90                  95

Thr Phe Gly Gly Gly Thr Lys Val Glu Ile Lys
            100                 105
```

```
<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain HVR-H1, aLAG3(0403)

<400> SEQUENCE: 22

Asp Tyr Thr Met His
1               5
```

```
<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain HVR-H2, aLAG3(0403)

<400> SEQUENCE: 23

Leu Val Ser Trp Asp Gly Gly Gly Thr Tyr Tyr Thr Asn Ser Val Lys
1               5                   10                  15

Gly
```

```
<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued heavy chain HVR-H3, aLAG3(0403)

<400> SEQUENCE: 24

Ala Ile Thr Asp Thr Ser Leu Tyr Gly Tyr Asp Tyr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain HVR-L1, aLAG3(0403)

<400> SEQUENCE: 25

Arg Ala Ser Gln Ser Ile Ser Ser Tyr Leu Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain HVR-L2, aLAG3(0403)

<400> SEQUENCE: 26

Ala Ala Ser Ser Leu Gln Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain HVR-L3, aLAG3(0403)

<400> SEQUENCE: 27

Gln Gln Thr Tyr Ser Thr Pro Leu Thr
1               5

<210> SEQ ID NO 28
<211> LENGTH: 121
<212> TYPE: PRT
<213> ORGANISM: Artificial Sequence
<220> FEATURE:
<223> OTHER INFORMATION: Description of Artificial Sequence: Synthetic
      heavy chain variable domain VH, aLAG3(0403)

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Thr Met His Trp Val Arg Gln Ala Pro Gly Lys Gly Leu Glu Trp Val
            35                  40                  45

Ser Leu Val Ser Trp Asp Gly Gly Thr Tyr Tyr Thr Asn Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Ala Ile Thr Asp Thr Ser Leu Tyr Gly Tyr Asp Tyr Trp Gly

-continued

```
              100              105              110

Gln Gly Ile Leu Val Thr Val Ser Ser
      115              120

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable domain VL, aLAG3(0403)

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Asn Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gly Gly Thr Lys Val Glu Ile Lys
            100              105

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain HVR-H1, aLAG3(0411)

<400> SEQUENCE: 30

Asp Tyr Thr Met Asn
1               5

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain HVR-H2, aLAG3(0411)

<400> SEQUENCE: 31

Val Ile Ser Trp Asp Gly Gly Ala Thr Tyr Tyr Ala Asp Ser Val Lys
1               5                   10                  15

Gly

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      heavy chain HVR-H3, aLAG3(0411)

<400> SEQUENCE: 32

Gly Leu Thr Asp Asp Thr Leu Tyr Gly Ser Asp Tyr
```

1               5                    10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain HVR-L1, aLAG3(0411)

<400> SEQUENCE: 33

Arg Ala Ser Gln Ser Ile Val Ser Tyr Leu Asn
1               5                    10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain HVR-L2, aLAG3(0411)

<400> SEQUENCE: 34

Ala Ser Ser Ser Leu Gln Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain HVR-L3, aLAG3(0411)

<400> SEQUENCE: 35

Gln Gln Thr Tyr Ser Thr Pro Leu Thr
1               5

<210> SEQ ID NO 36
<211> LENGTH: 121
<212> TYPE: PRT
<213> ORGANISM: Artificial Sequence
<220> FEATURE:
<223> OTHER INFORMATION: Description of Artificial Sequence: Synthetic
      heavy chain variable domain VH, aLAG3(0411)

<400> SEQUENCE: 36

Glu Val His Leu Leu Glu Ser Gly Gly Gly Leu Val Gln Pro Gly Gly
1               5                    10                   15

Ser Leu Arg Leu Ser Cys Ala Ala Ser Gly Phe Ile Val Asp Asp Tyr
            20                   25                   30

Thr Met Asn Trp Val Arg Gln Ala Pro Gly Lys Gly Leu Glu Trp Val
        35                   40                   45

Ser Val Ile Ser Trp Asp Gly Gly Ala Thr Tyr Tyr Ala Asp Ser Val
    50                   55                   60

Lys Gly Arg Phe Thr Ile Ser Arg Asp Asp Phe Lys Asn Thr Leu Tyr
65                   70                   75                   80

Leu Gln Met Asn Ser Leu Arg Ala Glu Asp Thr Ala Val Tyr Tyr Cys
                85                   90                   95

Ala Lys Gly Leu Thr Asp Asp Thr Leu Tyr Gly Ser Asp Tyr Trp Gly
            100                  105                  110

Gln Gly Thr Leu Val Thr Val Ser Ser
        115                  120

```
<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable domain VL, aLAG3(0411)

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Val Ser Tyr
            20                  25                  30

Leu Asn Trp Tyr Gln Gln Lys Pro Gly Lys Ala Pro Lys Leu Leu Ile
        35                  40                  45

Tyr Ala Ser Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gly Gly Thr Lys Val Glu Ile Lys
            100                 105

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain HVR-H1, aLAG3(0417)

<400> SEQUENCE: 38

Asp Tyr Ala Met Ser
1               5

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain HVR-H2, aLAG3(0417)

<400> SEQUENCE: 39

Gly Ile Asp Asn Ser Gly Tyr Tyr Thr Tyr Tyr Thr Asp Ser Val Lys
1               5                   10                  15

Gly

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      heavy chain HVR-H3, aLAG3(0417)

<400> SEQUENCE: 40

Thr His Ser Gly Leu Ile Val Asn Asp Ala Phe Asp Ile
1               5                   10

<210> SEQ ID NO 41
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      light chain HVR-L1, aLAG3(0417)

<400> SEQUENCE: 41

Arg Ala Ser Gln Ser Ile Ser Ser Tyr Leu Asn
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain HVR-L2, aLAG3(0417)

<400> SEQUENCE: 42

Ala Ala Ser Ser Leu Gln Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain HVR-L3, aLAG3(0417)

<400> SEQUENCE: 43

Gln Gln Thr Tyr Ser Thr Pro Leu Thr
1               5

<210> SEQ ID NO 44
<211> LENGTH: 122
<212> TYPE: PRT
<213> ORGANISM: Artificial Sequence
<220> FEATURE:
<223> OTHER INFORMATION: Description of Artificial Sequence: Synthetic
      heavy chain variable domain VH, aLAG3(0417)

<400> SEQUENCE: 44

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Asp Asn Ser Gly Tyr Tyr Thr Tyr Tyr Thr Asp Ser Val
    50                  55                  60

Lys Gly Arg Phe Thr Ile Ser Arg Asp Asp Val Lys Asn Thr Leu Tyr
65                  70                  75                  80

Leu Gln Met Asn Ser Leu Arg Ala Glu Asp Thr Ala Val Tyr Leu Cys
                85                  90                  95

Thr Lys Thr His Ser Gly Leu Ile Val Asn Asp Ala Phe Asp Ile Trp
            100                 105                 110

Gly Gln Gly Thr Met Val Thr Val Ser Ser
        115                 120

<210> SEQ ID NO 45
<211> LENGTH: 107
<212> TYPE: PRT
<213> ORGANISM: Artificial Sequence
```

```
<220> FEATURE:
<223> OTHER INFORMATION: Description of Artificial Sequence: Synthetic
      light chain variable domain VL, aLAG3(0417)

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gly Gly Thr Lys Val Glu Ile Lys
            100                 105

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain HVR-H1, aLAG3(0416)

<400> SEQUENCE: 46

Asp Tyr Ala Met Ser
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain HVR-H2, aLAG3(0416)

<400> SEQUENCE: 47

Gly Ile Asp Asn Ser Gly Tyr Tyr Thr Tyr Tyr Thr Asp Ser Val Lys
1               5                   10                  15

Gly

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      heavy chain HVR-H3, aLAG3(0416)

<400> SEQUENCE: 48

Thr His Ser Gly Leu Ile Val Asn Asp Ala Phe Asp Ile
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain HVR-L1, aLAG3(0416)
```

-continued

<400> SEQUENCE: 49

```
Arg Ala Ser Gln Ser Ile Ser Ser Tyr Leu Asn
1               5                   10
```

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain HVR-L2, aLAG3(0416)

<400> SEQUENCE: 50

```
Asp Ala Ser Ser Leu Glu Ser
1               5
```

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain HVR-L3, aLAG3(0416)

<400> SEQUENCE: 51

```
Gln Gln Ser Tyr Ser Thr Pro Leu Thr
1               5
```

<210> SEQ ID NO 52
<211> LENGTH: 122
<212> TYPE: PRT
<213> ORGANISM: Artificial Sequence
<220> FEATURE:
<223> OTHER INFORMATION: Description of Artificial Sequence: Synthetic
      heavy chain variable domain VH, aLAG3(0416)

<400> SEQUENCE: 52

```
Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Asp Asn Ser Gly Tyr Tyr Thr Tyr Tyr Thr Asp Ser Val
    50                  55                  60

Lys Gly Arg Phe Thr Ile Ser Arg Asp Asp Val Lys Asn Thr Leu Tyr
65                  70                  75                  80

Leu Gln Met Asn Ser Leu Arg Ala Glu Asp Thr Ala Val Tyr Leu Cys
                85                  90                  95

Thr Lys Thr His Ser Gly Leu Ile Val Asn Asp Ala Phe Asp Ile Trp
            100                 105                 110

Gly Gln Gly Thr Met Val Thr Val Ser Ser
        115                 120
```

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable domain VL, aLAG3(0416)

<400> SEQUENCE: 53

-continued

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Ala Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 54
<211> LENGTH: 120
<212> TYPE: PRT
<213> ORGANISM: Artificial Sequence
<220> FEATURE:
<223> OTHER INFORMATION: Description of Artificial Sequence: Synthetic
      heavy chain variable domain VH, BMS-986016

<400> SEQUENCE: 54

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
                20                  25                  30

Tyr Trp Asn Trp Ile Arg Gln Pro Pro Gly Lys Gly Leu Glu Trp Ile
            35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120
```

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable domain VL BMS-986016

<400> SEQUENCE: 55

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60
```

-continued

```
Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys
            100                 105
```

```
<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain HVR-H1, MDX25F7 (25F7)

<400> SEQUENCE: 56

Asp Tyr Tyr Trp Asn
1               5
```

```
<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain HVR-H2, MDX25F7 (25F7)

<400> SEQUENCE: 57

Glu Ile Asn His Asn Gly Asn Thr Asn Ser Asn Pro Ser Leu Lys Ser
1               5                   10                  15
```

```
<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain HVR-H3, MDX25F7 (25F7)

<400> SEQUENCE: 58

Gly Tyr Ser Asp Tyr Glu Tyr Asn Trp Phe
1               5                   10
```

```
<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain HVR-L1, MDX25F7 (25F7)

<400> SEQUENCE: 59

Arg Ala Ser Gln Ser Ile Ser Ser Tyr Leu Ala
1               5                   10
```

```
<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain HVR-L2, MDX25F7 (25F7)

<400> SEQUENCE: 60

Asp Ala Ser Asn Arg Ala Thr
1               5
```

```
<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain HVR-L3, MDX25F7 (25F7)

<400> SEQUENCE: 61

Gln Gln Arg Ser Asn Trp Pro Leu Thr
1               5

<210> SEQ ID NO 62
<211> LENGTH: 120
<212> TYPE: PRT
<213> ORGANISM: Artificial Sequence
<220> FEATURE:
<223> OTHER INFORMATION: Description of Artificial Sequence: Synthetic
      heavy chain variable domain VH, MDX25F7 (25F7)

<400> SEQUENCE: 62

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable domain VL, MDX25F7 (25F7)

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95
```

```
Thr Phe Gly Gln Gly Thr Asn Leu Glu Ile Lys
            100                 105

<210> SEQ ID NO 64
<211> LENGTH: 125
<212> TYPE: PRT
<213> ORGANISM: Artificial Sequence
<220> FEATURE:
<223> OTHER INFORMATION: Description of Artificial Sequence: Synthetic
      heavy chain variable domain VH, humanized BAP050 (LAG525)

<400> SEQUENCE: 64

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Leu Thr Asn Tyr
            20                  25                  30

Gly Met Asn Trp Val Arg Gln Thr Pro Gly Lys Gly Leu Lys Trp Met
        35                  40                  45

Gly Trp Ile Asn Thr Asp Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Ala Asp Thr Ala Thr Tyr Phe Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable domain VL, humanized BAP050 (LAG525)

<400> SEQUENCE: 65

Asp Ile Gln Met Thr Gln Thr Thr Ser Ser Leu Ser Ala Ser Leu Gly
1               5                   10                  15

Asp Arg Val Thr Ile Ser Cys Ser Ser Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Tyr Ser Leu Thr Ile Ser Asn Leu Glu Leu
65                  70                  75                  80

Glu Asp Ile Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 66
<211> LENGTH: 122
<212> TYPE: PRT
<213> ORGANISM: Artificial Sequence
<220> FEATURE:
<223> OTHER INFORMATION: Description of Artificial Sequence: Synthetic
      heavy chain variable domain VH, MDX26H10 (26H10)
```

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Ala Val Ala Ser Trp Asp Tyr Gly Met Asp Val Trp
            100                 105                 110

Gly Gln Gly Thr Thr Val Thr Val Ser Ser
        115                 120

<210> SEQ ID NO 67
<211> LENGTH: 108
<212> TYPE: PRT
<213> ORGANISM: Artificial Sequence
<220> FEATURE:
<223> OTHER INFORMATION: Description of Artificial Sequence: Synthetic
      light chain variable domain VL, MDX26H10 (26H10)

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      human kappa light chain constant region

<400> SEQUENCE: 68

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser

```
            50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
                85              90              95

Pro Val Thr Lys Ser Phe Asn Arg Gly Glu Cys
            100             105

<210> SEQ ID NO 69
<211> LENGTH: 105
<212> TYPE: PRT
<213> ORGANISM: Artificial Sequence
<220> FEATURE:
<223> OTHER INFORMATION: Description of Artificial Sequence: Synthetic
      human lambda light chain constant region

<400> SEQUENCE: 69

Gln Pro Lys Ala Ala Pro Ser Val Thr Leu Phe Pro Pro Ser Ser Glu
1               5               10              15

Glu Leu Gln Ala Asn Lys Ala Thr Leu Val Cys Leu Ile Ser Asp Phe
                20              25              30

Tyr Pro Gly Ala Val Thr Val Ala Trp Lys Ala Asp Ser Ser Pro Val
        35              40              45

Lys Ala Gly Val Glu Thr Thr Thr Pro Ser Lys Gln Ser Asn Asn Lys
        50              55              60

Tyr Ala Ala Ser Ser Tyr Leu Ser Leu Thr Pro Glu Gln Trp Lys Ser
65              70              75              80

His Arg Ser Tyr Ser Cys Gln Val Thr His Glu Gly Ser Thr Val Glu
                85              90              95

Lys Thr Val Ala Pro Thr Glu Cys Ser
            100             105

<210> SEQ ID NO 70
<211> LENGTH: 329
<212> TYPE: PRT
<213> ORGANISM: Artificial Sequence
<220> FEATURE:
<223> OTHER INFORMATION: Description of Artificial Sequence: Synthetic
      human heavy chain constant region derived from IgG1

<400> SEQUENCE: 70

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
                20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
        50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
```

```
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 71
<211> LENGTH: 329
<212> TYPE: PRT
<213> ORGANISM: Artificial Sequence
<220> FEATURE:
<223> OTHER INFORMATION: Description of Artificial Sequence: Synthetic
      human heavy chain constant region derived from IgG1 with
      mutations L234A, L235A and P329G

<400> SEQUENCE: 71

```
Ala Ser Thr Lys Gly Pro Ser Val Phe Pro Leu Ala Pro Ser Ser Lys
1                 5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325
```

```
<210> SEQ ID NO 72
<211> LENGTH: 326
<212> TYPE: PRT
<213> ORGANISM: Artificial Sequence
<220> FEATURE:
<223> OTHER INFORMATION: Description of Artificial Sequence: Synthetic
      human heavy chain constant region derived from IgG4

<400> SEQUENCE: 72
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
```

```
                180             185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 73
<211> LENGTH: 497
<212> TYPE: PRT
<213> ORGANISM: Homo sapiens

<400> SEQUENCE: 73

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
            85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
            115                 120                 125

Ala Leu Ser Cys Arg Leu Arg Leu Arg Leu Gly Gln Ala Ser Met Thr
        130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220
```

Ile Met Tyr Asn Leu Thr Val Leu Gly Leu Glu Pro Pro Thr Pro Leu
225             230             235             240

Thr Val Tyr Ala Gly Ala Gly Ser Arg Val Gly Leu Pro Cys Arg Leu
            245             250             255

Pro Ala Gly Val Gly Thr Arg Ser Phe Leu Thr Ala Lys Trp Thr Pro
            260             265             270

Pro Gly Gly Gly Pro Asp Leu Leu Val Thr Gly Asp Asn Gly Asp Phe
            275             280             285

Thr Leu Arg Leu Glu Asp Val Ser Gln Ala Gln Ala Gly Thr Tyr Thr
            290             295             300

Cys His Ile His Leu Gln Glu Gln Leu Asn Ala Thr Val Thr Leu
305             310             315             320

Ala Ile Ile Thr Val Thr Pro Lys Ser Phe Gly Ser Pro Gly Ser Leu
            325             330             335

Gly Lys Leu Leu Cys Glu Val Thr Pro Val Ser Gly Gln Glu Arg Phe
            340             345             350

Val Trp Ser Ser Leu Asp Thr Pro Ser Gln Arg Ser Phe Ser Gly Pro
            355             360             365

Trp Leu Glu Ala Gln Glu Ala Gln Leu Leu Ser Gln Pro Trp Gln Cys
            370             375             380

Gln Leu Tyr Gln Gly Glu Arg Leu Leu Gly Ala Ala Val Tyr Phe Thr
385             390             395             400

Glu Leu Ser Ser Pro Gly Ala Gln Arg Ser Gly Arg Ala Pro Gly Ala
            405             410             415

Leu Pro Ala Gly His Leu Leu Leu Phe Leu Ile Leu Gly Val Leu Ser
            420             425             430

Leu Leu Leu Leu Val Thr Gly Ala Phe Gly Phe His Leu Trp Arg Arg
            435             440             445

Gln Trp Arg Pro Arg Arg Phe Ser Ala Leu Glu Gln Gly Ile His Pro
            450             455             460

Pro Gln Ala Gln Ser Lys Ile Glu Glu Leu Glu Gln Glu Pro Glu Pro
465             470             475             480

Glu Pro Glu Pro Glu Pro Glu Pro Glu Pro Glu Pro Glu Pro Glu Gln
            485             490             495

Leu

<210> SEQ ID NO 74
<211> LENGTH: 422
<212> TYPE: PRT
<213> ORGANISM: Homo sapiens

<400> SEQUENCE: 74

Val Pro Val Val Trp Ala Gln Glu Gly Ala Pro Ala Gln Leu Pro Cys
1               5               10              15

Ser Pro Thr Ile Pro Leu Gln Asp Leu Ser Leu Leu Arg Arg Ala Gly
            20              25              30

Val Thr Trp Gln His Gln Pro Asp Ser Gly Pro Pro Ala Ala Ala Pro
            35              40              45

Gly His Pro Leu Ala Pro Gly Pro His Pro Ala Ala Pro Ser Ser Trp
            50              55              60

Gly Pro Arg Pro Arg Arg Tyr Thr Val Leu Ser Val Gly Pro Gly Gly
65              70              75              80

Leu Arg Ser Gly Arg Leu Pro Leu Gln Pro Arg Val Gln Leu Asp Glu
            85              90              95

-continued

```
Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
            115                 120                 125

Ala Leu Ser Cys Arg Leu Arg Leu Arg Leu Gly Gln Ala Ser Met Thr
        130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
            195                 200                 205

Gly Pro Trp Gly Cys Ile Leu Thr Tyr Arg Asp Gly Phe Asn Val Ser
        210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
                260                 265                 270

Pro Gly Gly Gly Pro Asp Leu Leu Val Thr Gly Asp Asn Gly Asp Phe
            275                 280                 285

Thr Leu Arg Leu Glu Asp Val Ser Gln Ala Gln Ala Gly Thr Tyr Thr
        290                 295                 300

Cys His Ile His Leu Gln Glu Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
            355                 360                 365

Trp Leu Glu Ala Gln Glu Ala Gln Leu Leu Ser Gln Pro Trp Gln Cys
        370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu
            420
```

```
<210> SEQ ID NO 75
<211> LENGTH: 6
<212> TYPE: PRT
<213> ORGANISM: Homo sapiens

<400> SEQUENCE: 75

Lys Ile Glu Glu Leu Glu
1               5

<210> SEQ ID NO 76
<211> LENGTH: 37
<212> TYPE: DNA
<213> ORGANISM: Artificial Sequence
```

<220> FEATURE:
<223> OTHER INFORMATION: Description of Artificial Sequence: Synthetic
     primer rbHC.up

<400> SEQUENCE: 76
aagcttgcca ccatggagac tgggctgcgc tggcttc                                    37

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
     primer rbHCf.do

<400> SEQUENCE: 77
ccattggtga gggtgcccga g                                                     21

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
     primer BcPCR_FHLC_leader.fw

<400> SEQUENCE: 78
atggacatga gggtccccgc                                                       20

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
     primer BcPCR_huCkappa.rev

<400> SEQUENCE: 79
gatttcaact gctcatcaga tggc                                                  24

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
     heavy chain HVR-H1, PD1-0098

<400> SEQUENCE: 80

Gly Tyr Ser Ile Thr Ser Asp Tyr
1               5

<210> SEQ ID NO 81
<211> LENGTH: 3
<212> TYPE: PRT
<213> ORGANISM: Artificial Sequence
<220> FEATURE:
<223> OTHER INFORMATION: Description of Artificial Sequence: Synthetic
     heavy chain HVR-H2, PD1-0098

<400> SEQUENCE: 81

Tyr Ser Gly
1

<210> SEQ ID NO 82
<211> LENGTH: 9
<212> TYPE: PRT

<213> ORGANISM: Artificial Sequence
<220> FEATURE:
<223> OTHER INFORMATION: Description of Artificial Sequence: Synthetic
      heavy chain HVR-H3, PD1-0098

<400> SEQUENCE: 82

His Gly Ser Ala Pro Trp Tyr Phe Asp
1               5

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      light chain HVR-L1, PD1-0098

<400> SEQUENCE: 83

Ser Gln Asn Ile Val His Ser Asp Gly Asn Thr Tyr
1               5                   10

<210> SEQ ID NO 84
<211> LENGTH: 3
<212> TYPE: PRT
<213> ORGANISM: Artificial Sequence
<220> FEATURE:
<223> OTHER INFORMATION: Description of Artificial Sequence: Synthetic
      light chain HVR-L2, PD1-0098

<400> SEQUENCE: 84

Lys Val Ser
1

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      light chain HVR-L3, PD1-0098

<400> SEQUENCE: 85

Gly Ser His Phe Pro Leu
1               5

<210> SEQ ID NO 86
<211> LENGTH: 120
<212> TYPE: PRT
<213> ORGANISM: Artificial Sequence
<220> FEATURE:
<223> OTHER INFORMATION: Description of Artificial Sequence: Synthetic
      heavy chain variable domain VH, PD1-0098

<400> SEQUENCE: 86

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asp Lys Leu Glu Trp
        35                  40                  45

Leu Gly Tyr Ile Thr Tyr Ser Gly Phe Thr Asn Tyr Asn Pro Ser Leu
    50                  55                  60

Lys Ser Arg Ile Ser Ile Ser Arg Asp Thr Ser Lys Asn Gln Phe Phe
65                  70                  75                  80

Leu Gln Leu Asn Ser Val Ala Thr Glu Asp Thr Ala Thr Tyr Tyr Cys

-continued

```
                    85                  90                  95

Ala Arg Trp His Gly Ser Ala Pro Trp Tyr Phe Asp Tyr Trp Gly Arg
            100                 105                 110

Gly Thr Thr Leu Thr Val Ser Ser
        115                 120
```

<210> SEQ ID NO 87
<211> LENGTH: 112
<212> TYPE: PRT
<213> ORGANISM: Artificial Sequence
<220> FEATURE:
<223> OTHER INFORMATION: Description of Artificial Sequence: Synthetic
      light chain variable domain VL, PD1-0098

<400> SEQUENCE: 87

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Asn Leu Leu Ile Tyr Lys Val Ser Arg Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Leu Thr Phe Gly Ala Gly Thr Lys Leu Glu Leu Lys
            100                 105                 110
```

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain HVR-H1, PD1-0069

<400> SEQUENCE: 88

```
Gly Tyr Thr Phe Thr Asp Tyr
1               5
```

<210> SEQ ID NO 89
<211> LENGTH: 3
<212> TYPE: PRT
<213> ORGANISM: Artificial Sequence
<220> FEATURE:
<223> OTHER INFORMATION: Description of Artificial Sequence: Synthetic
      heavy chain HVR-H2, PD1-0069

<400> SEQUENCE: 89

```
Tyr Ser Gly
1
```

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain HVR-H3, PD1-0069

<400> SEQUENCE: 90

```
Gly Ile Thr Thr Gly Phe Ala
1               5

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain HVR-L1, PD1-0069

<400> SEQUENCE: 91

Ser Lys Gly Val Ser Thr Ser Ser Tyr Ser Phe
1               5                   10

<210> SEQ ID NO 92
<211> LENGTH: 3
<212> TYPE: PRT
<213> ORGANISM: Artificial Sequence
<220> FEATURE:
<223> OTHER INFORMATION: Description of Artificial Sequence: Synthetic
      light chain HVR-L2, PD1-0069

<400> SEQUENCE: 92

Tyr Ala Ser
1

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      light chain HVR-L3, PD1-0069

<400> SEQUENCE: 93

Ser Arg Glu Phe Pro Trp
1               5

<210> SEQ ID NO 94
<211> LENGTH: 118
<212> TYPE: PRT
<213> ORGANISM: Artificial Sequence
<220> FEATURE:
<223> OTHER INFORMATION: Description of Artificial Sequence: Synthetic
      heavy chain variable domain VH, PD1-0069

<400> SEQUENCE: 94

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Arg Thr Leu Glu Trp Ile
        35                  40                  45

Gly Val Ile Ser Thr Tyr Ser Gly Asp Thr Asn Tyr Asn Gln Lys Phe
    50                  55                  60

Lys Asp Lys Ala Thr Met Thr Val Asp Lys Ser Ser Ser Thr Ala Tyr
65                  70                  75                  80

Leu Glu Leu Ala Arg Met Thr Ser Glu Asp Ser Ala Ile Tyr Tyr Cys
                85                  90                  95

Ala Arg Leu Gly Ile Thr Thr Gly Phe Ala Tyr Trp Gly Gln Gly Thr
            100                 105                 110

Leu Val Thr Val Ser Ala
        115
```

```
<210> SEQ ID NO 95
<211> LENGTH: 111
<212> TYPE: PRT
<213> ORGANISM: Artificial Sequence
<220> FEATURE:
<223> OTHER INFORMATION: Description of Artificial Sequence: Synthetic
      light chain variable domain VL, PD1-0069

<400> SEQUENCE: 95

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Gly Val Ser Thr Ser
            20                  25                  30

Ser Tyr Ser Phe Met His Trp Tyr Gln Gln Lys Pro Arg Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His His Ser Arg
                85                  90                  95

Glu Phe Pro Trp Thr Phe Gly Gly Gly Thr Lys Leu Glu Ile Lys
            100                 105                 110

<210> SEQ ID NO 96
<211> LENGTH: 443
<212> TYPE: PRT
<213> ORGANISM: Artificial Sequence
<220> FEATURE:
<223> OTHER INFORMATION: Description of Artificial Sequence: Synthetic
      heavy chain 1 of 1+1 PD1/LAG3 0799

<400> SEQUENCE: 96

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Asp Val Pro Trp Thr Phe Gly Gln Gly Thr Lys Val Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190
```

```
Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
                340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
        435                 440
```

```
<210> SEQ ID NO 97
<211> LENGTH: 452
<212> TYPE: PRT
<213> ORGANISM: Artificial Sequence
<220> FEATURE:
<223> OTHER INFORMATION: Description of Artificial Sequence: Synthetic
      heavy chain 2 of 1+1 PD1/LAG3 0799

<400> SEQUENCE: 97
```

```
Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Asp Asn Ser Gly Tyr Tyr Thr Tyr Tyr Thr Asp Ser Val
    50                  55                  60

Lys Gly Arg Phe Thr Ile Ser Arg Asp Asp Lys Asn Thr Leu Tyr
65                  70                  75                  80

Leu Gln Met Asn Ser Leu Arg Ala Glu Asp Thr Ala Val Tyr Leu Cys
                85                  90                  95

Thr Lys Thr His Ser Gly Leu Ile Val Asn Asp Ala Phe Asp Ile Trp
```

-continued

```
              100                 105                 110
Gly Gln Gly Thr Met Val Thr Val Ser Ser Ala Ser Thr Lys Gly Pro
          115                 120                 125

Ser Val Phe Pro Leu Ala Pro Ser Ser Lys Ser Thr Ser Gly Gly Thr
      130                 135                 140

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
                  165                 170                 175

Ala Val Leu Gln Ser Ser Gly Leu Tyr Ser Leu Ser Ser Val Val Thr
                  180                 185                 190

Val Pro Ser Ser Ser Leu Gly Thr Gln Thr Tyr Ile Cys Asn Val Asn
                  195                 200                 205

His Lys Pro Ser Asn Thr Lys Val Asp Glu Lys Val Glu Pro Lys Ser
          210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                  245                 250                 255

Met Ile Ser Arg Thr Pro Glu Val Thr Cys Val Val Val Asp Val Ser
                  260                 265                 270

His Glu Asp Pro Glu Val Lys Phe Asn Trp Tyr Val Asp Gly Val Glu
                  275                 280                 285

Val His Asn Ala Lys Thr Lys Pro Arg Glu Glu Gln Tyr Asn Ser Thr
          290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                  325                 330                 335

Ile Glu Lys Thr Ile Ser Lys Ala Lys Gly Gln Pro Arg Glu Pro Gln
                  340                 345                 350

Val Cys Thr Leu Pro Pro Ser Arg Asp Glu Leu Thr Lys Asn Gln Val
                  355                 360                 365

Ser Leu Ser Cys Ala Val Lys Gly Phe Tyr Pro Ser Asp Ile Ala Val
      370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                  405                 410                 415

Val Asp Lys Ser Arg Trp Gln Gln Gly Asn Val Phe Ser Cys Ser Val
                  420                 425                 430

Met His Glu Ala Leu His Asn His Tyr Thr Gln Lys Ser Leu Ser Leu
          435                 440                 445

Ser Pro Gly Lys
    450

<210> SEQ ID NO 98
<211> LENGTH: 227
<212> TYPE: PRT
<213> ORGANISM: Artificial Sequence
<220> FEATURE:
<223> OTHER INFORMATION: Description of Artificial Sequence: Synthetic
      light chain 1 of 1+1 PD1/LAG3 0799

<400> SEQUENCE: 98
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
            35                  40                  45

Ala Thr Ile Ser Gly Gly Gly Arg Asp Ile Tyr Tyr Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
            165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
            195                 200                 205

Val Thr His Gln Gly Leu Ser Ser Pro Val Thr Lys Ser Phe Asn Arg
    210                 215                 220

Gly Glu Cys
225
```

```
<210> SEQ ID NO 99
<211> LENGTH: 214
<212> TYPE: PRT
<213> ORGANISM: Artificial Sequence
<220> FEATURE:
<223> OTHER INFORMATION: Description of Artificial Sequence: Synthetic
      light chain 2 of 1+1 PD1/LAG3 0799

<400> SEQUENCE: 99
```

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Ala Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
    115                 120                 125
```

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 100
<211> LENGTH: 451
<212> TYPE: PRT
<213> ORGANISM: Artificial Sequence
<220> FEATURE:
<223> OTHER INFORMATION: Description of Artificial Sequence: Synthetic
      heavy chain 2 of 1+1 PD1/LAG3 0927

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Asp Asp Tyr
            20                  25                  30

Thr Met Asn Trp Val Arg Gln Ala Pro Gly Lys Gly Leu Glu Trp Val
            35                  40                  45

Ala Val Ile Ser Trp Asp Gly Gly Thr Tyr Tyr Thr Asp Ser Val
        50                  55                  60

Lys Gly Arg Phe Thr Ile Ser Arg Asp Asp Phe Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Thr Asp Thr Thr Leu Tyr Gly Ser Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His

-continued

```
                260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
                340                 345                 350
Cys Thr Leu Pro Pro Ser Arg Asp Glu Leu Thr Lys Asn Gln Val Ser
            355                 360                 365
Leu Ser Cys Ala Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 101
<211> LENGTH: 214
<212> TYPE: PRT
<213> ORGANISM: Artificial Sequence
<220> FEATURE:
<223> OTHER INFORMATION: Description of Artificial Sequence: Synthetic
      light chain 2 of 1+1 PD1/LAG3 0927

<400> SEQUENCE: 101

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Tyr Ser Ser Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Arg Lys Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
```

-continued

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 102
<211> LENGTH: 443
<212> TYPE: PRT
<213> ORGANISM: Artificial Sequence
<220> FEATURE:
<223> OTHER INFORMATION: Description of Artificial Sequence: Synthetic
      heavy chain 1 of 1+1 PD1/LAG3 0222

<400> SEQUENCE: 102

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Gly Val Ser Thr Ser
                20                  25                  30

Ser Tyr Ser Phe Met His Trp Tyr Gln Gln Lys Pro Arg Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His His Ser Arg
                85                  90                  95

Glu Phe Pro Trp Thr Phe Gly Gly Gly Thr Lys Leu Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

```
Leu His Gln Asp Trp Leu Asn Gly Lys Glu Tyr Lys Cys Lys Val Ser
305             310             315             320

Asn Lys Ala Leu Gly Ala Pro Ile Glu Lys Thr Ile Ser Lys Ala Lys
            325             330             335

Gly Gln Pro Arg Glu Pro Gln Val Tyr Thr Leu Pro Pro Cys Arg Asp
            340             345             350

Glu Leu Thr Lys Asn Gln Val Ser Leu Trp Cys Leu Val Lys Gly Phe
            355             360             365

Tyr Pro Ser Asp Ile Ala Val Glu Trp Glu Ser Asn Gly Gln Pro Glu
            370             375             380

Asn Asn Tyr Lys Thr Thr Pro Pro Val Leu Asp Ser Asp Gly Ser Phe
385             390             395             400

Phe Leu Tyr Ser Lys Leu Thr Val Asp Lys Ser Arg Trp Gln Gln Gly
            405             410             415

Asn Val Phe Ser Cys Ser Val Met His Glu Ala Leu His Asn His Tyr
            420             425             430

Thr Gln Lys Ser Leu Ser Leu Ser Pro Gly Lys
            435             440
```

```
<210> SEQ ID NO 103
<211> LENGTH: 450
<212> TYPE: PRT
<213> ORGANISM: Artificial Sequence
<220> FEATURE:
<223> OTHER INFORMATION: Description of Artificial Sequence: Synthetic
      heavy chain 2 of 1+1 PD1/LAG3 0222

<400> SEQUENCE: 103
```

```
Gln Val Gln Leu Gln Gln Trp Gly Ala Gly Leu Leu Lys Pro Ser Glu
1               5               10              15

Thr Leu Ser Leu Thr Cys Ala Val Tyr Gly Gly Ser Phe Ser Asp Tyr
            20              25              30

Tyr Trp Asn Trp Ile Arg Gln Pro Pro Gly Lys Gly Leu Glu Trp Ile
            35              40              45

Gly Glu Ile Asn His Asn Gly Asn Thr Asn Ser Asn Pro Ser Leu Lys
            50              55              60

Ser Arg Val Thr Leu Ser Leu Asp Thr Ser Lys Asn Gln Phe Ser Leu
65              70              75              80

Lys Leu Arg Ser Val Thr Ala Ala Asp Thr Ala Val Tyr Tyr Cys Ala
            85              90              95

Phe Gly Tyr Ser Asp Tyr Glu Tyr Asn Trp Phe Asp Pro Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
            130             135             140

Leu Gly Cys Leu Val Glu Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Glu Lys Val Glu Pro Lys Ser Cys Asp
```

-continued

```
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
                340                 345                 350

Thr Leu Pro Pro Ser Arg Asp Glu Leu Thr Lys Asn Gln Val Ser Leu
                355                 360                 365

Ser Cys Ala Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450
```

```
<210> SEQ ID NO 104
<211> LENGTH: 225
<212> TYPE: PRT
<213> ORGANISM: Artificial Sequence
<220> FEATURE:
<223> OTHER INFORMATION: Description of Artificial Sequence: Synthetic
      light chain 1 of 1+1 PD1/LAG3 0222

<400> SEQUENCE: 104

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Arg Thr Leu Glu Trp Ile
        35                  40                  45

Gly Val Ile Ser Thr Tyr Ser Gly Asp Thr Asn Tyr Asn Gln Lys Phe
        50                  55                  60

Lys Asp Lys Ala Thr Met Thr Val Asp Lys Ser Ser Ser Thr Ala Tyr
65                  70                  75                  80

Leu Glu Leu Ala Arg Met Thr Ser Glu Asp Ser Ala Ile Tyr Tyr Cys
                85                  90                  95

Ala Arg Leu Gly Ile Thr Thr Gly Phe Ala Tyr Trp Gly Gln Gly Thr
        100                 105                 110
```

-continued

```
Leu Val Thr Val Ser Ala Ala Ser Val Ala Ala Pro Ser Val Phe Ile
        115                 120                 125

Phe Pro Pro Ser Asp Glu Gln Leu Lys Ser Gly Thr Ala Ser Val Val
        130                 135                 140

Cys Leu Leu Asn Asn Phe Tyr Pro Arg Glu Ala Lys Val Gln Trp Lys
145                     150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
                180                 185                 190

Ser Lys Ala Asp Tyr Glu Lys His Lys Val Tyr Ala Cys Glu Val Thr
                195                 200                 205

His Gln Gly Leu Ser Ser Pro Val Thr Lys Ser Phe Asn Arg Gly Glu
        210                 215                 220

Cys
225
```

<210> SEQ ID NO 105
<211> LENGTH: 214
<212> TYPE: PRT
<213> ORGANISM: Artificial Sequence
<220> FEATURE:
<223> OTHER INFORMATION: Description of Artificial Sequence: Synthetic
      light chain 2 of 1+1 PD1/LAG3 0222

<400> SEQUENCE: 105

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
        100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210
```

<210> SEQ ID NO 106

-continued

<211> LENGTH: 444
<212> TYPE: PRT
<213> ORGANISM: Artificial Sequence
<220> FEATURE:
<223> OTHER INFORMATION: Description of Artificial Sequence: Synthetic
      heavy chain 1 of 1+1 PD1/LAG3 0224

<400> SEQUENCE: 106

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Asn Leu Leu Ile Tyr Lys Val Ser Arg Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Leu Thr Phe Gly Ala Gly Thr Lys Leu Glu Leu Lys
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Gly Ala Pro Ile Glu Lys Thr Ile Ser Lys Ala
            325                 330                 335

Lys Gly Gln Pro Arg Glu Pro Gln Val Tyr Thr Leu Pro Pro Cys Arg
            340                 345                 350

Asp Glu Leu Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro

-continued

```
        370                 375                 380
Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
        435                 440

<210> SEQ ID NO 107
<211> LENGTH: 227
<212> TYPE: PRT
<213> ORGANISM: Artificial Sequence
<220> FEATURE:
<223> OTHER INFORMATION: Description of Artificial Sequence: Synthetic
      light chain 1 of 1+1 PD1/LAG3 0224

<400> SEQUENCE: 107

Asp Val Gln Leu Gln Glu Ser Gly Pro Gly Leu Val Lys Pro Ser Gln
1                 5                 10                 15

Ser Leu Ser Leu Thr Cys Thr Val Thr Gly Tyr Ser Ile Thr Ser Asp
                20                 25                 30

Tyr Ala Trp Asn Trp Ile Arg Gln Phe Pro Gly Asp Lys Leu Glu Trp
        35                 40                 45

Leu Gly Tyr Ile Thr Tyr Ser Gly Phe Thr Asn Tyr Asn Pro Ser Leu
    50                 55                 60

Lys Ser Arg Ile Ser Ile Ser Arg Asp Thr Ser Lys Asn Gln Phe Phe
65                 70                 75                 80

Leu Gln Leu Asn Ser Val Ala Thr Glu Asp Thr Ala Thr Tyr Tyr Cys
                85                 90                 95

Ala Arg Trp His Gly Ser Ala Pro Trp Tyr Phe Asp Tyr Trp Gly Arg
                100                 105                 110

Gly Thr Thr Leu Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
                180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 108
<211> LENGTH: 443
<212> TYPE: PRT
<213> ORGANISM: Artificial Sequence
<220> FEATURE:
<223> OTHER INFORMATION: Description of Artificial Sequence: Synthetic
      aLAG3(0156) heavy chain (MDX25F7)
```

<400> SEQUENCE: 108

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
            85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Gly Gln Pro Lys Ala Pro Ser Val
            115                 120                 125

Phe Pro Leu Ala Pro Cys Cys Gly Asp Thr Pro Ser Ser Thr Val Thr
    130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
            165                 170                 175

Arg Gln Ser Ser Gly Leu Tyr Ser Leu Ser Ser Val Val Ser Val Thr
            180                 185                 190

Ser Ser Ser Gln Pro Val Thr Cys Asn Val Ala His Pro Ala Thr Asn
            195                 200                 205

Thr Lys Val Asp Lys Thr Val Ala Pro Ser Thr Cys Ser Lys Pro Thr
    210                 215                 220

Cys Pro Pro Pro Glu Leu Leu Gly Gly Pro Ser Val Phe Ile Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Asp Asp Pro Glu Val Gln Phe Thr
            260                 265                 270

Trp Tyr Ile Asn Asn Glu Gln Val Arg Thr Ala Arg Pro Pro Leu Arg
        275                 280                 285

Glu Gln Gln Phe Asn Ser Thr Ile Arg Val Val Ser Thr Leu Pro Ile
    290                 295                 300

Ala His Gln Asp Trp Leu Arg Gly Lys Glu Phe Lys Cys Lys Val His
305                 310                 315                 320

Asn Lys Ala Leu Pro Ala Pro Ile Glu Lys Thr Ile Ser Lys Ala Arg
            325                 330                 335

Gly Gln Pro Leu Glu Pro Lys Val Tyr Thr Met Gly Pro Pro Arg Glu
            340                 345                 350

Glu Leu Ser Ser Arg Ser Val Ser Leu Thr Cys Met Ile Asn Gly Phe
            355                 360                 365

Tyr Pro Ser Asp Ile Ser Val Glu Trp Glu Lys Asn Gly Lys Ala Glu
    370                 375                 380

Asp Asn Tyr Lys Thr Thr Pro Ala Val Leu Asp Ser Asp Gly Ser Tyr
385                 390                 395                 400

Phe Leu Tyr Asn Lys Leu Ser Val Pro Thr Ser Glu Trp Gln Arg Gly
            405                 410                 415
```

```
Asp Val Phe Thr Cys Ser Val Met His Glu Ala Leu His Asn His Tyr
            420                 425                 430

Thr Gln Lys Ser Ile Ser Arg Ser Pro Gly Lys
        435                 440
```

<210> SEQ ID NO 109
<211> LENGTH: 214
<212> TYPE: PRT
<213> ORGANISM: Artificial Sequence
<220> FEATURE:
<223> OTHER INFORMATION: Description of Artificial Sequence: Synthetic
      aLAG3(0156) light chain (MDX25F7)

<400> SEQUENCE: 109

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 110
<211> LENGTH: 444
<212> TYPE: PRT
<213> ORGANISM: Artificial Sequence
<220> FEATURE:
<223> OTHER INFORMATION: Description of Artificial Sequence: Synthetic
      aLAG3(0414) heavy chain

<400> SEQUENCE: 110

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Asp Asp Tyr
            20                  25                  30

Thr Met Asn Trp Val Arg Gln Ala Pro Gly Lys Gly Leu Glu Trp Val
        35                  40                  45
```

-continued

```
Ala Val Ile Ser Trp Asp Gly Gly Thr Tyr Tyr Thr Asp Ser Val
    50              55              60

Lys Gly Arg Phe Thr Ile Ser Arg Asp Asp Phe Lys Asn Thr Leu Tyr
65              70              75              80

Leu Gln Met Asn Ser Leu Arg Ala Glu Asp Thr Ala Val Tyr Tyr Cys
            85              90              95

Ala Lys Gly Leu Thr Asp Thr Thr Leu Tyr Gly Ser Asp Tyr Trp Gly
        100             105             110

Gln Gly Thr Leu Val Thr Val Ser Ser Gly Gln Pro Lys Ala Pro Ser
        115             120             125

Val Phe Pro Leu Ala Pro Cys Cys Gly Asp Thr Pro Ser Ser Thr Val
    130             135             140

Thr Leu Gly Cys Leu Val Lys Gly Tyr Leu Pro Glu Pro Val Thr Val
145             150             155             160

Thr Trp Asn Ser Gly Thr Leu Thr Asn Gly Val Arg Thr Phe Pro Ser
            165             170             175

Val Arg Gln Ser Ser Gly Leu Tyr Ser Leu Ser Ser Val Val Ser Val
            180             185             190

Thr Ser Ser Ser Gln Pro Val Thr Cys Asn Val Ala His Pro Ala Thr
            195             200             205

Asn Thr Lys Val Asp Lys Thr Val Ala Pro Ser Thr Cys Ser Lys Pro
    210             215             220

Thr Cys Pro Pro Pro Glu Leu Leu Gly Gly Pro Ser Val Phe Ile Phe
225             230             235             240

Pro Pro Lys Pro Lys Asp Thr Leu Met Ile Ser Arg Thr Pro Glu Val
            245             250             255

Thr Cys Val Val Val Asp Val Ser Gln Asp Asp Pro Glu Val Gln Phe
            260             265             270

Thr Trp Tyr Ile Asn Asn Glu Gln Val Arg Thr Ala Arg Pro Pro Leu
            275             280             285

Arg Glu Gln Gln Phe Asn Ser Thr Ile Arg Val Val Ser Thr Leu Pro
    290             295             300

Ile Ala His Gln Asp Trp Leu Arg Gly Lys Glu Phe Lys Cys Lys Val
305             310             315             320

His Asn Lys Ala Leu Pro Ala Pro Ile Glu Lys Thr Ile Ser Lys Ala
            325             330             335

Arg Gly Gln Pro Leu Glu Pro Lys Val Tyr Thr Met Gly Pro Pro Arg
            340             345             350

Glu Glu Leu Ser Ser Arg Ser Val Ser Leu Thr Cys Met Ile Asn Gly
            355             360             365

Phe Tyr Pro Ser Asp Ile Ser Val Glu Trp Glu Lys Asn Gly Lys Ala
    370             375             380

Glu Asp Asn Tyr Lys Thr Thr Pro Ala Val Leu Asp Ser Asp Gly Ser
385             390             395             400

Tyr Phe Leu Tyr Asn Lys Leu Ser Val Pro Thr Ser Glu Trp Gln Arg
            405             410             415

Gly Asp Val Phe Thr Cys Ser Val Met His Glu Ala Leu His Asn His
            420             425             430

Tyr Thr Gln Lys Ser Ile Ser Arg Ser Pro Gly Lys
            435             440
```

<210> SEQ ID NO 111
<211> LENGTH: 214

<212> TYPE: PRT
<213> ORGANISM: Artificial Sequence
<220> FEATURE:
<223> OTHER INFORMATION: Description of Artificial Sequence: Synthetic
     aLAG3(0414) light chain

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ser Pro Leu
                85                  90                  95

Thr Phe Gly Gly Gly Thr Lys Val Glu Ile Lys Gly Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 112
<211> LENGTH: 445
<212> TYPE: PRT
<213> ORGANISM: Artificial Sequence
<220> FEATURE:
<223> OTHER INFORMATION: Description of Artificial Sequence: Synthetic
     aLAG3(0416) heavy chain

<400> SEQUENCE: 112

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Asp Asn Ser Gly Tyr Tyr Thr Tyr Tyr Thr Asp Ser Val
    50                  55                  60

Lys Gly Arg Phe Thr Ile Ser Arg Asp Asp Val Lys Asn Thr Leu Tyr
65                  70                  75                  80

Leu Gln Met Asn Ser Leu Arg Ala Glu Asp Thr Ala Val Tyr Leu Cys
                85                  90                  95

```
Thr Lys Thr His Ser Gly Leu Ile Val Asn Asp Ala Phe Asp Ile Trp
        100                 105                 110

Gly Gln Gly Thr Met Val Thr Val Ser Ser Gly Gln Pro Lys Ala Pro
        115                 120                 125

Ser Val Phe Pro Leu Ala Pro Cys Cys Gly Asp Thr Pro Ser Ser Thr
    130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                165                 170                 175

Ser Val Arg Gln Ser Ser Gly Leu Tyr Ser Leu Ser Ser Val Val Ser
            180                 185                 190

Val Thr Ser Ser Ser Gln Pro Val Thr Cys Asn Val Ala His Pro Ala
        195                 200                 205

Thr Asn Thr Lys Val Asp Lys Thr Val Ala Pro Ser Thr Cys Ser Lys
    210                 215                 220

Pro Thr Cys Pro Pro Pro Glu Leu Leu Gly Gly Pro Ser Val Phe Ile
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Asp Asp Pro Glu Val Gln
            260                 265                 270

Phe Thr Trp Tyr Ile Asn Asn Glu Gln Val Arg Thr Ala Arg Pro Pro
        275                 280                 285

Leu Arg Glu Gln Gln Phe Asn Ser Thr Ile Arg Val Val Ser Thr Leu
    290                 295                 300

Pro Ile Ala His Gln Asp Trp Leu Arg Gly Lys Glu Phe Lys Cys Lys
305                 310                 315                 320

Val His Asn Lys Ala Leu Pro Ala Pro Ile Glu Lys Thr Ile Ser Lys
                325                 330                 335

Ala Arg Gly Gln Pro Leu Glu Pro Lys Val Tyr Thr Met Gly Pro Pro
            340                 345                 350

Arg Glu Glu Leu Ser Ser Arg Ser Val Ser Leu Thr Cys Met Ile Asn
        355                 360                 365

Gly Phe Tyr Pro Ser Asp Ile Ser Val Glu Trp Glu Lys Asn Gly Lys
    370                 375                 380

Ala Glu Asp Asn Tyr Lys Thr Thr Pro Ala Val Leu Asp Ser Asp Gly
385                 390                 395                 400

Ser Tyr Phe Leu Tyr Asn Lys Leu Ser Val Pro Thr Ser Glu Trp Gln
                405                 410                 415

Arg Gly Asp Val Phe Thr Cys Ser Val Met His Glu Ala Leu His Asn
            420                 425                 430

His Tyr Thr Gln Lys Ser Ile Ser Arg Ser Pro Gly Lys
        435                 440                 445
```

<210> SEQ ID NO 113
<211> LENGTH: 214
<212> TYPE: PRT
<213> ORGANISM: Artificial Sequence
<220> FEATURE:
<223> OTHER INFORMATION: Description of Artificial Sequence: Synthetic
     aLAG3(0416) light chain

<400> SEQUENCE: 113

```
Asp Ile Gln Leu Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
        20                  25                  30

Leu Asn Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Ala Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 114
<211> LENGTH: 695
<212> TYPE: PRT
<213> ORGANISM: Artificial Sequence
<220> FEATURE:
<223> OTHER INFORMATION: Description of Artificial Sequence: Synthetic
      heavy chain of 2+2 PD1/LAG3 8970

<400> SEQUENCE: 114
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Asp Asp Tyr
        20                  25                  30

Thr Met Asn Trp Val Arg Gln Ala Pro Gly Lys Gly Leu Glu Trp Val
        35                  40                  45

Ala Val Ile Ser Trp Asp Gly Gly Thr Tyr Tyr Thr Asp Ser Val
    50                  55                  60

Lys Gly Arg Phe Thr Ile Ser Arg Asp Asp Phe Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Thr Asp Thr Thr Leu Tyr Gly Ser Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
```

```
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
            195             200             205

Lys Pro Ser Asn Thr Lys Val Asp Glu Lys Val Glu Pro Lys Ser Cys
    210             215             220

Asp Lys Thr His Thr Cys Pro Pro Cys Pro Ala Pro Glu Ala Ala Gly
225             230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
            275             280             285

His Asn Ala Lys Thr Lys Pro Arg Glu Glu Gln Tyr Asn Ser Thr Tyr
    290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Gly Ala Pro Ile
            325             330             335

Glu Lys Thr Ile Ser Lys Ala Lys Gly Gln Pro Arg Glu Pro Gln Val
            340             345             350

Tyr Thr Leu Pro Pro Ser Arg Asp Glu Leu Thr Lys Asn Gln Val Ser
            355             360             365

Leu Thr Cys Leu Val Lys Gly Phe Tyr Pro Ser Asp Ile Ala Val Glu
            370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
            435             440             445

Pro Gly Gly Gly Ser Gly Gly Gly Gly Ser Gly Gly Gly Gly Ser Gly
    450             455             460

Gly Gly Gly Ser Glu Val Gln Leu Leu Glu Ser Gly Gly Gly Leu Val
465             470             475             480

Gln Pro Gly Gly Ser Leu Arg Leu Ser Cys Ala Ala Ser Gly Phe Ser
            485             490             495

Phe Ser Ser Tyr Thr Met Ser Trp Val Arg Gln Ala Pro Gly Lys Gly
            500             505             510

Leu Glu Trp Val Ala Thr Ile Ser Gly Gly Gly Arg Asp Ile Tyr Tyr
            515             520             525

Pro Asp Ser Val Lys Gly Arg Phe Thr Ile Ser Arg Asp Asn Ser Lys
    530             535             540

Asn Thr Leu Tyr Leu Gln Met Asn Ser Leu Arg Ala Glu Asp Thr Ala
545             550             555             560

Val Tyr Tyr Cys Val Leu Leu Thr Gly Arg Val Tyr Phe Ala Leu Asp
            565             570             575
```

```
Ser Trp Gly Gln Gly Thr Leu Val Thr Val Ser Ser Ala Ser Val Ala
            580                 585                 590

Ala Pro Ser Val Phe Ile Phe Pro Pro Ser Asp Glu Gln Leu Lys Ser
            595                 600                 605

Gly Thr Ala Ser Val Val Cys Leu Leu Asn Asn Phe Tyr Pro Arg Glu
            610                 615                 620

Ala Lys Val Gln Trp Lys Val Asp Asn Ala Leu Gln Ser Gly Asn Ser
625                 630                 635                 640

Gln Glu Ser Val Thr Glu Gln Asp Ser Lys Asp Ser Thr Tyr Ser Leu
            645                 650                 655

Ser Ser Thr Leu Thr Leu Ser Lys Ala Asp Tyr Glu Lys His Lys Val
            660                 665                 670

Tyr Ala Cys Glu Val Thr His Gln Gly Leu Ser Ser Pro Val Thr Lys
            675                 680                 685

Ser Phe Asn Arg Gly Glu Cys
    690                 695
```

```
<210> SEQ ID NO 115
<211> LENGTH: 216
<212> TYPE: PRT
<213> ORGANISM: Artificial Sequence
<220> FEATURE:
<223> OTHER INFORMATION: Description of Artificial Sequence: Synthetic
      light chain 1 of 2+2 PD1/LAG3 8970

<400> SEQUENCE: 115
```

```
Asp Ile Val Met Thr Gln Ser Pro Asp Ser Leu Ala Val Ser Leu Gly
1                   5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
            35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
            85                  90                  95

Asp Val Pro Trp Thr Phe Gly Gln Gly Thr Lys Val Glu Ile Lys Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys
    210                 215
```

<210> SEQ ID NO 116
<211> LENGTH: 696
<212> TYPE: PRT
<213> ORGANISM: Artificial Sequence
<220> FEATURE:
<223> OTHER INFORMATION: Description of Artificial Sequence: Synthetic
      heavy chain of 2+2 PD1/LAG3 8984

<400> SEQUENCE: 116

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
            35                  40                  45

Ser Gly Ile Asp Asn Ser Gly Tyr Tyr Thr Tyr Tyr Thr Asp Ser Val
        50                  55                  60

Lys Gly Arg Phe Thr Ile Ser Arg Asp Asp Val Lys Asn Thr Leu Tyr
65                  70                  75                  80

Leu Gln Met Asn Ser Leu Arg Ala Glu Asp Thr Ala Val Tyr Leu Cys
                85                  90                  95

Thr Lys Thr His Ser Gly Leu Ile Val Asn Asp Ala Phe Asp Ile Trp
            100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Glu Lys Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

```
Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
            405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
            435             440             445

Ser Pro Gly Gly Gly Ser Gly Gly Gly Gly Ser Gly Gly Gly Gly Ser
    450             455             460

Gly Gly Gly Gly Ser Glu Val Gln Leu Leu Glu Ser Gly Gly Gly Leu
465             470             475             480

Val Gln Pro Gly Gly Ser Leu Arg Leu Ser Cys Ala Ala Ser Gly Phe
            485             490             495

Ser Phe Ser Ser Tyr Thr Met Ser Trp Val Arg Gln Ala Pro Gly Lys
            500             505             510

Gly Leu Glu Trp Val Ala Thr Ile Ser Gly Gly Gly Arg Asp Ile Tyr
            515             520             525

Tyr Pro Asp Ser Val Lys Gly Arg Phe Thr Ile Ser Arg Asp Asn Ser
    530             535             540

Lys Asn Thr Leu Tyr Leu Gln Met Asn Ser Leu Arg Ala Glu Asp Thr
545             550             555             560

Ala Val Tyr Tyr Cys Val Leu Leu Thr Gly Arg Val Tyr Phe Ala Leu
            565             570             575

Asp Ser Trp Gly Gln Gly Thr Leu Val Thr Val Ser Ser Ala Ser Val
            580             585             590

Ala Ala Pro Ser Val Phe Ile Phe Pro Pro Ser Asp Glu Gln Leu Lys
            595             600             605

Ser Gly Thr Ala Ser Val Val Cys Leu Leu Asn Asn Phe Tyr Pro Arg
    610             615             620

Glu Ala Lys Val Gln Trp Lys Val Asp Asn Ala Leu Gln Ser Gly Asn
625             630             635             640

Ser Gln Glu Ser Val Thr Glu Gln Asp Ser Lys Asp Ser Thr Tyr Ser
            645             650             655

Leu Ser Ser Thr Leu Thr Leu Ser Lys Ala Asp Tyr Glu Lys His Lys
            660             665             670

Val Tyr Ala Cys Glu Val Thr His Gln Gly Leu Ser Ser Pro Val Thr
            675             680             685

Lys Ser Phe Asn Arg Gly Glu Cys
    690             695
```

```
<210> SEQ ID NO 117
<211> LENGTH: 694
<212> TYPE: PRT
<213> ORGANISM: Artificial Sequence
<220> FEATURE:
<223> OTHER INFORMATION: Description of Artificial Sequence: Synthetic
      heavy chain of 2+2 PD1/LAG3 9010

<400> SEQUENCE: 117

Gln Val Gln Leu Gln Gln Trp Gly Ala Gly Leu Leu Lys Pro Ser Glu
1               5               10              15

Thr Leu Ser Leu Thr Cys Ala Val Tyr Gly Gly Ser Phe Ser Asp Tyr
            20              25              30
```

```
Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
            85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445
```

-continued

```
Gly Gly Gly Ser Gly Gly Gly Gly Ser Gly Gly Gly Gly Ser Gly Gly
    450             455             460
```

```
Gly Gly Ser Glu Val Gln Leu Leu Glu Ser Gly Gly Gly Leu Val Gln
465             470             475             480
```

```
Pro Gly Gly Ser Leu Arg Leu Ser Cys Ala Ala Ser Gly Phe Ser Phe
            485             490             495
```

```
Ser Ser Tyr Thr Met Ser Trp Val Arg Gln Ala Pro Gly Lys Gly Leu
            500             505             510
```

```
Glu Trp Val Ala Thr Ile Ser Gly Gly Gly Arg Asp Ile Tyr Tyr Pro
            515             520             525
```

```
Asp Ser Val Lys Gly Arg Phe Thr Ile Ser Arg Asp Asn Ser Lys Asn
    530             535             540
```

```
Thr Leu Tyr Leu Gln Met Asn Ser Leu Arg Ala Glu Asp Thr Ala Val
545             550             555             560
```

```
Tyr Tyr Cys Val Leu Leu Thr Gly Arg Val Tyr Phe Ala Leu Asp Ser
            565             570             575
```

```
Trp Gly Gln Gly Thr Leu Val Thr Val Ser Ser Ala Ser Val Ala Ala
            580             585             590
```

```
Pro Ser Val Phe Ile Phe Pro Pro Ser Asp Glu Gln Leu Lys Ser Gly
            595             600             605
```

```
Thr Ala Ser Val Val Cys Leu Leu Asn Asn Phe Tyr Pro Arg Glu Ala
    610             615             620
```

```
Lys Val Gln Trp Lys Val Asp Asn Ala Leu Gln Ser Gly Asn Ser Gln
625             630             635             640
```

```
Glu Ser Val Thr Glu Gln Asp Ser Lys Asp Ser Thr Tyr Ser Leu Ser
            645             650             655
```

```
Ser Thr Leu Thr Leu Ser Lys Ala Asp Tyr Glu Lys His Lys Val Tyr
            660             665             670
```

```
Ala Cys Glu Val Thr His Gln Gly Leu Ser Ser Pro Val Thr Lys Ser
            675             680             685
```

```
Phe Asn Arg Gly Glu Cys
    690
```

```
<210> SEQ ID NO 118
<211> LENGTH: 695
<212> TYPE: PRT
<213> ORGANISM: Artificial Sequence
<220> FEATURE:
<223> OTHER INFORMATION: Description of Artificial Sequence: Synthetic
      heavy chain 1of 2+1 PD1/LAG3 8310

<400> SEQUENCE: 118
```

```
Glu Val Gln Leu Leu Glu Ser Gly Gly Gly Leu Val Gln Pro Gly Gly
1               5               10              15
```

```
Ser Leu Arg Leu Ser Cys Ala Ala Ser Gly Phe Ile Phe Asp Asp Tyr
            20              25              30
```

```
Thr Met Asn Trp Val Arg Gln Ala Pro Gly Lys Gly Leu Glu Trp Val
            35              40              45
```

```
Ala Val Ile Ser Trp Asp Gly Gly Thr Tyr Tyr Thr Asp Ser Val
    50              55              60
```

```
Lys Gly Arg Phe Thr Ile Ser Arg Asp Asp Phe Lys Asn Thr Leu Tyr
65              70              75              80
```

```
Leu Gln Met Asn Ser Leu Arg Ala Glu Asp Thr Ala Val Tyr Tyr Cys
            85              90              95
```

```
Ala Lys Gly Leu Thr Asp Thr Thr Leu Tyr Gly Ser Asp Tyr Trp Gly
            100             105             110
```

```
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Glu Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Cys Arg Asp Glu Leu Thr Lys Asn Gln Val Ser
                355                 360                 365

Leu Trp Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Gly Gly Ser Gly Gly Gly Gly Ser Gly Gly Gly Gly Ser Gly
        450                 455                 460

Gly Gly Gly Ser Glu Val Gln Leu Leu Glu Ser Gly Gly Gly Leu Val
465                 470                 475                 480

Gln Pro Gly Gly Ser Leu Arg Leu Ser Cys Ala Ala Ser Gly Phe Ser
                485                 490                 495

Phe Ser Ser Tyr Thr Met Ser Trp Val Arg Gln Ala Pro Gly Lys Gly
                500                 505                 510

Leu Glu Trp Val Ala Thr Ile Ser Gly Gly Gly Arg Asp Ile Tyr Tyr
        515                 520                 525
```

```
Pro Asp Ser Val Lys Gly Arg Phe Thr Ile Ser Arg Asp Asn Ser Lys
    530             535             540

Asn Thr Leu Tyr Leu Gln Met Asn Ser Leu Arg Ala Glu Asp Thr Ala
545             550             555             560

Val Tyr Tyr Cys Val Leu Leu Thr Gly Arg Val Tyr Phe Ala Leu Asp
            565             570             575

Ser Trp Gly Gln Gly Thr Leu Val Thr Val Ser Ser Ala Ser Val Ala
            580             585             590

Ala Pro Ser Val Phe Ile Phe Pro Pro Ser Asp Glu Gln Leu Lys Ser
            595             600             605

Gly Thr Ala Ser Val Val Cys Leu Leu Asn Asn Phe Tyr Pro Arg Glu
    610             615             620

Ala Lys Val Gln Trp Lys Val Asp Asn Ala Leu Gln Ser Gly Asn Ser
625             630             635             640

Gln Glu Ser Val Thr Glu Gln Asp Ser Lys Asp Ser Thr Tyr Ser Leu
            645             650             655

Ser Ser Thr Leu Thr Leu Ser Lys Ala Asp Tyr Glu Lys His Lys Val
            660             665             670

Tyr Ala Cys Glu Val Thr His Gln Gly Leu Ser Ser Pro Val Thr Lys
            675             680             685

Ser Phe Asn Arg Gly Glu Cys
    690             695

<210> SEQ ID NO 119
<211> LENGTH: 451
<212> TYPE: PRT
<213> ORGANISM: Artificial Sequence
<220> FEATURE:
<223> OTHER INFORMATION: Description of Artificial Sequence: Synthetic
      heavy chain 2 of 2+1 PD1/LAG3 8310

<400> SEQUENCE: 119

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Ile Phe Asp Asp Tyr
            20              25              30

Thr Met Asn Trp Val Arg Gln Ala Pro Gly Lys Gly Leu Glu Trp Val
            35              40              45

Ala Val Ile Ser Trp Asp Gly Gly Thr Tyr Tyr Thr Asp Ser Val
    50              55              60

Lys Gly Arg Phe Thr Ile Ser Arg Asp Asp Phe Lys Asn Thr Leu Tyr
65              70              75              80

Leu Gln Met Asn Ser Leu Arg Ala Glu Asp Thr Ala Val Tyr Tyr Cys
            85              90              95

Ala Lys Gly Leu Thr Asp Thr Thr Leu Tyr Gly Ser Asp Tyr Trp Gly
            100             105             110

Gln Gly Thr Leu Val Thr Val Ser Ser Ala Ser Thr Lys Gly Pro Ser
            115             120             125

Val Phe Pro Leu Ala Pro Ser Ser Lys Ser Thr Ser Gly Gly Thr Ala
    130             135             140

Ala Leu Gly Cys Leu Val Glu Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
            180             185             190
```

-continued

```
Pro Ser Ser Ser Leu Gly Thr Gln Thr Tyr Ile Cys Asn Val Asn His
        195             200             205

Lys Pro Ser Asn Thr Lys Val Asp Glu Lys Val Glu Pro Lys Ser Cys
    210             215             220

Asp Lys Thr His Thr Cys Pro Pro Cys Pro Ala Pro Glu Ala Ala Gly
225             230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
            275             280             285

His Asn Ala Lys Thr Lys Pro Arg Glu Glu Gln Tyr Asn Ser Thr Tyr
    290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Gly Ala Pro Ile
            325             330             335

Glu Lys Thr Ile Ser Lys Ala Lys Gly Gln Pro Arg Glu Pro Gln Val
            340             345             350

Cys Thr Leu Pro Pro Ser Arg Asp Glu Leu Thr Lys Asn Gln Val Ser
            355             360             365

Leu Ser Cys Ala Val Lys Gly Phe Tyr Pro Ser Asp Ile Ala Val Glu
    370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Val Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
    435             440             445

Pro Gly Lys
    450
```

```
<210> SEQ ID NO 120
<211> LENGTH: 696
<212> TYPE: PRT
<213> ORGANISM: Artificial Sequence
<220> FEATURE:
<223> OTHER INFORMATION: Description of Artificial Sequence: Synthetic
      heavy chain 1of 2+1 PD1/LAG3 8311

<400> SEQUENCE: 120
```

```
Glu Val Gln Leu Val Glu Ser Gly Gly Gly Leu Val Gln Pro Gly Gly
1               5               10              15

Ser Leu Arg Leu Ala Cys Ala Ala Ser Gly Phe Thr Phe Ser Asp Tyr
        20              25              30

Ala Met Ser Trp Val Arg Gln Ala Pro Gly Lys Gly Leu Glu Trp Val
        35              40              45

Ser Gly Ile Asp Asn Ser Gly Tyr Tyr Thr Tyr Tyr Thr Asp Ser Val
    50              55              60

Lys Gly Arg Phe Thr Ile Ser Arg Asp Asp Val Lys Asn Thr Leu Tyr
65              70              75              80

Leu Gln Met Asn Ser Leu Arg Ala Glu Asp Thr Ala Val Tyr Leu Cys
```

-continued

```
                    85                  90                  95
Thr Lys Thr His Ser Gly Leu Ile Val Asn Asp Ala Phe Asp Ile Trp
            100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Glu Asp Tyr Phe Pro Glu Pro Val Thr
        145                 150                 155             160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Glu Lys Val Glu Pro Lys Ser
            210                 215                 220

Cys Asp Lys Thr His Thr Cys Pro Pro Cys Pro Ala Pro Glu Ala Ala
        225                 230                 235             240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
        305                 310                 315             320

Gly Lys Glu Tyr Lys Cys Lys Val Ser Asn Lys Ala Leu Gly Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Asp Glu Leu Thr Lys Asn Gln Val
            355                 360                 365

Ser Leu Trp Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
        385                 390                 395             400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Gly Gly Ser Gly Gly Gly Ser Gly Gly Gly Gly Ser
            450                 455                 460

Gly Gly Gly Gly Ser Glu Val Gln Leu Leu Glu Ser Gly Gly Gly Leu
        465                 470                 475             480

Val Gln Pro Gly Gly Ser Leu Arg Leu Ser Cys Ala Ala Ser Gly Phe
            485                 490                 495

Ser Phe Ser Ser Tyr Thr Met Ser Trp Val Arg Gln Ala Pro Gly Lys
            500                 505                 510
```

```
Gly Leu Glu Trp Val Ala Thr Ile Ser Gly Gly Gly Arg Asp Ile Tyr
        515                 520                 525

Tyr Pro Asp Ser Val Lys Gly Arg Phe Thr Ile Ser Arg Asp Asn Ser
        530                 535                 540

Lys Asn Thr Leu Tyr Leu Gln Met Asn Ser Leu Arg Ala Glu Asp Thr
545                 550                 555                 560

Ala Val Tyr Tyr Cys Val Leu Leu Thr Gly Arg Val Tyr Phe Ala Leu
                565                 570                 575

Asp Ser Trp Gly Gln Gly Thr Leu Val Thr Val Ser Ser Ala Ser Val
                580                 585                 590

Ala Ala Pro Ser Val Phe Ile Phe Pro Pro Ser Asp Glu Gln Leu Lys
                595                 600                 605

Ser Gly Thr Ala Ser Val Val Cys Leu Leu Asn Asn Phe Tyr Pro Arg
        610                 615                 620

Glu Ala Lys Val Gln Trp Lys Val Asp Asn Ala Leu Gln Ser Gly Asn
625                 630                 635                 640

Ser Gln Glu Ser Val Thr Glu Gln Asp Ser Lys Asp Ser Thr Tyr Ser
                645                 650                 655

Leu Ser Ser Thr Leu Thr Leu Ser Lys Ala Asp Tyr Glu Lys His Lys
                660                 665                 670

Val Tyr Ala Cys Glu Val Thr His Gln Gly Leu Ser Ser Pro Val Thr
                675                 680                 685

Lys Ser Phe Asn Arg Gly Glu Cys
        690                 695
```

<210> SEQ ID NO 121
<211> LENGTH: 452
<212> TYPE: PRT
<213> ORGANISM: Artificial Sequence
<220> FEATURE:
<223> OTHER INFORMATION: Description of Artificial Sequence: Synthetic
      heavy chain 2of 2+1 PD1/LAG3 8311

<400> SEQUENCE: 121

```
Glu Val Gln Leu Val Glu Ser Gly Gly Gly Leu Val Gln Pro Gly Gly
1                   5                   10                  15

Ser Leu Arg Leu Ala Cys Ala Ala Ser Gly Phe Thr Phe Ser Asp Tyr
                20                  25                  30

Ala Met Ser Trp Val Arg Gln Ala Pro Gly Lys Gly Leu Glu Trp Val
                35                  40                  45

Ser Gly Ile Asp Asn Ser Gly Tyr Tyr Thr Tyr Tyr Thr Asp Ser Val
        50                  55                  60

Lys Gly Arg Phe Thr Ile Ser Arg Asp Asp Val Lys Asn Thr Leu Tyr
65                  70                  75                  80

Leu Gln Met Asn Ser Leu Arg Ala Glu Asp Thr Ala Val Tyr Leu Cys
                85                  90                  95

Thr Lys Thr His Ser Gly Leu Ile Val Asn Asp Ala Phe Asp Ile Trp
                100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
        130                 135                 140

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
```

-continued

```
                165              170              175
Ala Val Leu Gln Ser Ser Gly Leu Tyr Ser Leu Ser Ser Val Val Thr
            180              185              190

Val Pro Ser Ser Ser Leu Gly Thr Gln Thr Tyr Ile Cys Asn Val Asn
            195              200              205

His Lys Pro Ser Asn Thr Lys Val Asp Glu Lys Val Glu Pro Lys Ser
    210              215              220

Cys Asp Lys Thr His Thr Cys Pro Pro Cys Pro Ala Pro Glu Ala Ala
225              230              235              240

Gly Gly Pro Ser Val Phe Leu Phe Pro Pro Lys Pro Lys Asp Thr Leu
            245              250              255

Met Ile Ser Arg Thr Pro Glu Val Thr Cys Val Val Val Asp Val Ser
            260              265              270

His Glu Asp Pro Glu Val Lys Phe Asn Trp Tyr Val Asp Gly Val Glu
            275              280              285

Val His Asn Ala Lys Thr Lys Pro Arg Glu Glu Gln Tyr Asn Ser Thr
    290              295              300

Tyr Arg Val Val Ser Val Leu Thr Val Leu His Gln Asp Trp Leu Asn
305              310              315              320

Gly Lys Glu Tyr Lys Cys Lys Val Ser Asn Lys Ala Leu Gly Ala Pro
            325              330              335

Ile Glu Lys Thr Ile Ser Lys Ala Lys Gly Gln Pro Arg Glu Pro Gln
            340              345              350

Val Cys Thr Leu Pro Pro Ser Arg Asp Glu Leu Thr Lys Asn Gln Val
            355              360              365

Ser Leu Ser Cys Ala Val Lys Gly Phe Tyr Pro Ser Asp Ile Ala Val
    370              375              380

Glu Trp Glu Ser Asn Gly Gln Pro Glu Asn Asn Tyr Lys Thr Thr Pro
385              390              395              400

Pro Val Leu Asp Ser Asp Gly Ser Phe Phe Leu Val Ser Lys Leu Thr
            405              410              415

Val Asp Lys Ser Arg Trp Gln Gln Gly Asn Val Phe Ser Cys Ser Val
            420              425              430

Met His Glu Ala Leu His Asn His Tyr Thr Gln Lys Ser Leu Ser Leu
            435              440              445

Ser Pro Gly Lys
    450
```

```
<210> SEQ ID NO 122
<211> LENGTH: 694
<212> TYPE: PRT
<213> ORGANISM: Artificial Sequence
<220> FEATURE:
<223> OTHER INFORMATION: Description of Artificial Sequence: Synthetic
      heavy chain 1of 2+1 PD1/LAG3 1252

<400> SEQUENCE: 122

Gln Val Gln Leu Gln Gln Trp Gly Ala Gly Leu Leu Lys Pro Ser Glu
1               5               10              15

Thr Leu Ser Leu Thr Cys Ala Val Tyr Gly Gly Ser Phe Ser Asp Tyr
            20              25              30

Tyr Trp Asn Trp Ile Arg Gln Pro Pro Gly Lys Gly Leu Glu Trp Ile
            35              40              45

Gly Glu Ile Asn His Asn Gly Asn Thr Asn Ser Asn Pro Ser Leu Lys
    50              55              60
```

-continued

```
Ser Arg Val Thr Leu Ser Leu Asp Thr Ser Lys Asn Gln Phe Ser Leu
65              70              75              80

Lys Leu Arg Ser Val Thr Ala Ala Asp Thr Ala Val Tyr Tyr Cys Ala
                85              90              95

Phe Gly Tyr Ser Asp Tyr Glu Tyr Asn Trp Phe Asp Pro Trp Gly Gln
            100             105             110

Gly Thr Leu Val Thr Val Ser Ser Ala Ser Thr Lys Gly Pro Ser Val
        115             120             125

Phe Pro Leu Ala Pro Ser Ser Lys Ser Thr Ser Gly Gly Thr Ala Ala
    130             135             140

Leu Gly Cys Leu Val Glu Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Glu Lys Val Glu Pro Lys Ser Cys Asp
    210             215             220

Lys Thr His Thr Cys Pro Pro Cys Pro Ala Pro Glu Ala Ala Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Gly Ala Pro Ile Glu
            325             330             335

Lys Thr Ile Ser Lys Ala Lys Gly Gln Pro Arg Glu Pro Gln Val Tyr
            340             345             350

Thr Leu Pro Pro Cys Arg Asp Glu Leu Thr Lys Asn Gln Val Ser Leu
            355             360             365

Trp Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Gly Gly Ser Gly Gly Gly Gly Ser Gly Gly Gly Ser Gly Gly
            450             455             460

Gly Gly Ser Glu Val Gln Leu Leu Glu Ser Gly Gly Gly Leu Val Gln
465             470             475             480

Pro Gly Gly Ser Leu Arg Leu Ser Cys Ala Ala Ser Gly Phe Ser Phe
```

-continued

```
              485              490              495
Ser Ser Tyr Thr Met Ser Trp Val Arg Gln Ala Pro Gly Lys Gly Leu
         500              505              510

Glu Trp Val Ala Thr Ile Ser Gly Gly Gly Arg Asp Ile Tyr Tyr Pro
         515              520              525

Asp Ser Val Lys Gly Arg Phe Thr Ile Ser Arg Asp Asn Ser Lys Asn
    530              535              540

Thr Leu Tyr Leu Gln Met Asn Ser Leu Arg Ala Glu Asp Thr Ala Val
545              550              555              560

Tyr Tyr Cys Val Leu Leu Thr Gly Arg Val Tyr Phe Ala Leu Asp Ser
             565              570              575

Trp Gly Gln Gly Thr Leu Val Thr Val Ser Ser Ala Ser Val Ala Ala
         580              585              590

Pro Ser Val Phe Ile Phe Pro Pro Ser Asp Glu Gln Leu Lys Ser Gly
         595              600              605

Thr Ala Ser Val Val Cys Leu Leu Asn Asn Phe Tyr Pro Arg Glu Ala
    610              615              620

Lys Val Gln Trp Lys Val Asp Asn Ala Leu Gln Ser Gly Asn Ser Gln
625              630              635              640

Glu Ser Val Thr Glu Gln Asp Ser Lys Asp Ser Thr Tyr Ser Leu Ser
             645              650              655

Ser Thr Leu Thr Leu Ser Lys Ala Asp Tyr Glu Lys His Lys Val Tyr
         660              665              670

Ala Cys Glu Val Thr His Gln Gly Leu Ser Ser Pro Val Thr Lys Ser
         675              680              685

Phe Asn Arg Gly Glu Cys
    690
```

<210> SEQ ID NO 123
<211> LENGTH: 941
<212> TYPE: PRT
<213> ORGANISM: Artificial Sequence
<220> FEATURE:
<223> OTHER INFORMATION: Description of Artificial Sequence: Synthetic
      heavy chain 1of 2+1 PD1/LAG3 8312

<400> SEQUENCE: 123

```
Glu Val Gln Leu Leu Glu Ser Gly Gly Gly Leu Val Gln Pro Gly Gly
1               5              10              15

Ser Leu Arg Leu Ser Cys Ala Ala Ser Gly Phe Ile Phe Asp Asp Tyr
         20              25              30

Thr Met Asn Trp Val Arg Gln Ala Pro Gly Lys Gly Leu Glu Trp Val
         35              40              45

Ala Val Ile Ser Trp Asp Gly Gly Thr Tyr Tyr Thr Asp Ser Val
    50              55              60

Lys Gly Arg Phe Thr Ile Ser Arg Asp Asp Phe Lys Asn Thr Leu Tyr
65              70              75              80

Leu Gln Met Asn Ser Leu Arg Ala Glu Asp Thr Ala Val Tyr Tyr Cys
             85              90              95

Ala Lys Gly Leu Thr Asp Thr Thr Leu Tyr Gly Ser Asp Tyr Trp Gly
         100              105              110

Gln Gly Thr Leu Val Thr Val Ser Ser Ala Ser Thr Lys Gly Pro Ser
         115              120              125

Val Phe Pro Leu Ala Pro Ser Ser Lys Ser Thr Ser Gly Gly Thr Ala
    130              135              140
```

-continued

```
Ala Leu Gly Cys Leu Val Glu Asp Tyr Phe Pro Glu Pro Val Thr Val
145             150             155             160

Ser Trp Asn Ser Gly Ala Leu Thr Ser Gly Val His Thr Phe Pro Ala
                165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
            195             200             205

Lys Pro Ser Asn Thr Lys Val Asp Glu Lys Val Glu Pro Lys Ser Cys
        210             215             220

Asp Lys Thr His Thr Cys Pro Pro Cys Pro Ala Pro Glu Ala Ala Gly
225             230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
            275             280             285

His Asn Ala Lys Thr Lys Pro Arg Glu Glu Gln Tyr Asn Ser Thr Tyr
    290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Gly Ala Pro Ile
            325             330             335

Glu Lys Thr Ile Ser Lys Ala Lys Gly Gln Pro Arg Glu Pro Gln Val
            340             345             350

Tyr Thr Leu Pro Pro Cys Arg Asp Glu Leu Thr Lys Asn Gln Val Ser
            355             360             365

Leu Trp Cys Leu Val Lys Gly Phe Tyr Pro Ser Asp Ile Ala Val Glu
    370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
            435             440             445

Pro Gly Gly Gly Gly Ser Gly Gly Gly Gly Ser Gly Gly Gly Gly
    450             455             460

Ser Gly Gly Gly Gly Ser Asp Ile Val Met Thr Gln Ser Pro Asp Ser
465             470             475             480

Leu Ala Val Ser Leu Gly Glu Arg Ala Thr Ile Asn Cys Lys Ala Ser
            485             490             495

Glu Ser Val Asp Thr Ser Asp Asn Ser Phe Ile His Trp Tyr Gln Gln
            500             505             510

Lys Pro Gly Gln Ser Pro Lys Leu Leu Ile Tyr Arg Ser Ser Thr Leu
            515             520             525

Glu Ser Gly Val Pro Asp Arg Phe Ser Gly Ser Gly Ser Gly Thr Asp
            530             535             540

Phe Thr Leu Thr Ile Ser Ser Leu Gln Ala Glu Asp Val Ala Val Tyr
545             550             555             560

Tyr Cys Gln Gln Asn Tyr Asp Val Pro Trp Thr Phe Gly Gln Gly Thr
```

-continued

```
                        565                    570                    575
Lys Val Glu Ile Lys Arg Thr Val Ala Ala Pro Ser Val Phe Ile Phe
                580                    585                    590
Pro Pro Ser Asp Glu Gln Leu Lys Ser Gly Thr Ala Ser Val Val Cys
                595                    600                    605
Leu Leu Asn Asn Phe Tyr Pro Arg Glu Ala Lys Val Gln Trp Lys Val
        610                    615                    620
Asp Asn Ala Leu Gln Ser Gly Asn Ser Gln Glu Ser Val Thr Glu Gln
625                    630                    635                    640
Asp Ser Lys Asp Ser Thr Tyr Ser Leu Ser Ser Thr Leu Thr Leu Ser
                645                    650                    655
Lys Ala Asp Tyr Glu Lys His Lys Val Tyr Ala Cys Glu Val Thr His
                660                    665                    670
Gln Gly Leu Ser Ser Pro Val Thr Lys Ser Phe Asn Arg Gly Glu Cys
                675                    680                    685
Gly Gly Gly Gly Ser Gly Gly Gly Gly Ser Gly Gly Gly Gly Ser Gly
        690                    695                    700
Gly Gly Gly Ser Gly Gly Gly Gly Ser Gly Gly Gly Gly Ser Glu Val
705                    710                    715                    720
Gln Leu Leu Glu Ser Gly Gly Gly Leu Val Gln Pro Gly Gly Ser Leu
                725                    730                    735
Arg Leu Ser Cys Ala Ala Ser Gly Phe Ser Phe Ser Ser Tyr Thr Met
                740                    745                    750
Ser Trp Val Arg Gln Ala Pro Gly Lys Gly Leu Glu Trp Val Ala Thr
                755                    760                    765
Ile Ser Gly Gly Gly Arg Asp Ile Tyr Tyr Pro Asp Ser Val Lys Gly
        770                    775                    780
Arg Phe Thr Ile Ser Arg Asp Asn Ser Lys Asn Thr Leu Tyr Leu Gln
785                    790                    795                    800
Met Asn Ser Leu Arg Ala Glu Asp Thr Ala Val Tyr Tyr Cys Val Leu
                805                    810                    815
Leu Thr Gly Arg Val Tyr Phe Ala Leu Asp Ser Trp Gly Gln Gly Thr
                820                    825                    830
Leu Val Thr Val Ser Ser Ala Ser Thr Lys Gly Pro Ser Val Phe Pro
                835                    840                    845
Leu Ala Pro Ser Ser Lys Ser Thr Ser Gly Gly Thr Ala Ala Leu Gly
        850                    855                    860
Cys Leu Val Lys Asp Tyr Phe Pro Glu Pro Val Thr Val Ser Trp Asn
865                    870                    875                    880
Ser Gly Ala Leu Thr Ser Gly Val His Thr Phe Pro Ala Val Leu Gln
                885                    890                    895
Ser Ser Gly Leu Tyr Ser Leu Ser Ser Val Val Thr Val Pro Ser Ser
                900                    905                    910
Ser Leu Gly Thr Gln Thr Tyr Ile Cys Asn Val Asn His Lys Pro Ser
                915                    920                    925
Asn Thr Lys Val Asp Lys Lys Val Glu Pro Lys Ser Cys
        930                    935                    940
```

```
<210> SEQ ID NO 124
<211> LENGTH: 942
<212> TYPE: PRT
<213> ORGANISM: Artificial Sequence
<220> FEATURE:
<223> OTHER INFORMATION: Description of Artificial Sequence: Synthetic
      heavy chain 1of 2+1 PD1/LAG3 8313
```

<400> SEQUENCE: 124

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Asp Asn Ser Gly Tyr Tyr Thr Tyr Tyr Thr Asp Ser Val
    50                  55                  60

Lys Gly Arg Phe Thr Ile Ser Arg Asp Asp Val Lys Asn Thr Leu Tyr
65                  70                  75                  80

Leu Gln Met Asn Ser Leu Arg Ala Glu Asp Thr Ala Val Tyr Leu Cys
                85                  90                  95

Thr Lys Thr His Ser Gly Leu Ile Val Asn Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Glu Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Glu Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Asp Glu Leu Thr Lys Asn Gln Val
            355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr

-continued

```
                    405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly Gly Gly Gly Ser Gly Gly Gly Ser Gly Gly Gly
        450                 455                 460

Gly Ser Gly Gly Gly Gly Ser Asp Ile Val Met Thr Gln Ser Pro Asp
465                 470                 475                 480

Ser Leu Ala Val Ser Leu Gly Glu Arg Ala Thr Ile Asn Cys Lys Ala
                485                 490                 495

Ser Glu Ser Val Asp Thr Ser Asp Asn Ser Phe Ile His Trp Tyr Gln
                500                 505                 510

Gln Lys Pro Gly Gln Ser Pro Lys Leu Leu Ile Tyr Arg Ser Ser Thr
        515                 520                 525

Leu Glu Ser Gly Val Pro Asp Arg Phe Ser Gly Ser Gly Ser Gly Thr
        530                 535                 540

Asp Phe Thr Leu Thr Ile Ser Ser Leu Gln Ala Glu Asp Val Ala Val
545                 550                 555                 560

Tyr Tyr Cys Gln Gln Asn Tyr Asp Val Pro Trp Thr Phe Gly Gln Gly
                565                 570                 575

Thr Lys Val Glu Ile Lys Arg Thr Val Ala Ala Pro Ser Val Phe Ile
                580                 585                 590

Phe Pro Pro Ser Asp Glu Gln Leu Lys Ser Gly Thr Ala Ser Val Val
        595                 600                 605

Cys Leu Leu Asn Asn Phe Tyr Pro Arg Glu Ala Lys Val Gln Trp Lys
        610                 615                 620

Val Asp Asn Ala Leu Gln Ser Gly Asn Ser Gln Glu Ser Val Thr Glu
625                 630                 635                 640

Gln Asp Ser Lys Asp Ser Thr Tyr Ser Leu Ser Ser Thr Leu Thr Leu
                645                 650                 655

Ser Lys Ala Asp Tyr Glu Lys His Lys Val Tyr Ala Cys Glu Val Thr
                660                 665                 670

His Gln Gly Leu Ser Ser Pro Val Thr Lys Ser Phe Asn Arg Gly Glu
        675                 680                 685

Cys Gly Gly Gly Gly Ser Gly Gly Gly Gly Ser Gly Gly Gly Gly Ser
        690                 695                 700

Gly Gly Gly Gly Ser Gly Gly Gly Gly Ser Gly Gly Gly Gly Ser Glu
705                 710                 715                 720

Val Gln Leu Leu Glu Ser Gly Gly Gly Leu Val Gln Pro Gly Gly Ser
                725                 730                 735

Leu Arg Leu Ser Cys Ala Ala Ser Gly Phe Ser Phe Ser Ser Tyr Thr
                740                 745                 750

Met Ser Trp Val Arg Gln Ala Pro Gly Lys Gly Leu Glu Trp Val Ala
                755                 760                 765

Thr Ile Ser Gly Gly Gly Arg Asp Ile Tyr Tyr Pro Asp Ser Val Lys
        770                 775                 780

Gly Arg Phe Thr Ile Ser Arg Asp Asn Ser Lys Asn Thr Leu Tyr Leu
785                 790                 795                 800

Gln Met Asn Ser Leu Arg Ala Glu Asp Thr Ala Val Tyr Tyr Cys Val
                805                 810                 815

Leu Leu Thr Gly Arg Val Tyr Phe Ala Leu Asp Ser Trp Gly Gln Gly
        820                 825                 830
```

```
Thr Leu Val Thr Val Ser Ser Ala Ser Thr Lys Gly Pro Ser Val Phe
        835             840             845

Pro Leu Ala Pro Ser Ser Lys Ser Thr Ser Gly Gly Thr Ala Ala Leu
    850             855             860

Gly Cys Leu Val Lys Asp Tyr Phe Pro Glu Pro Val Thr Val Ser Trp
865             870             875             880

Asn Ser Gly Ala Leu Thr Ser Gly Val His Thr Phe Pro Ala Val Leu
                885             890             895

Gln Ser Ser Gly Leu Tyr Ser Leu Ser Ser Val Val Thr Val Pro Ser
            900             905             910

Ser Ser Leu Gly Thr Gln Thr Tyr Ile Cys Asn Val Asn His Lys Pro
        915             920             925

Ser Asn Thr Lys Val Asp Lys Lys Val Glu Pro Lys Ser Cys
    930             935             940
```

```
<210> SEQ ID NO 125
<211> LENGTH: 940
<212> TYPE: PRT
<213> ORGANISM: Artificial Sequence
<220> FEATURE:
<223> OTHER INFORMATION: Description of Artificial Sequence: Synthetic
      heavy chain 1of 2+1 PD1/LAG3 1088

<400> SEQUENCE: 125
```

```
Gln Val Gln Leu Gln Gln Trp Gly Ala Gly Leu Leu Lys Pro Ser Glu
1               5               10              15

Thr Leu Ser Leu Thr Cys Ala Val Tyr Gly Gly Ser Phe Ser Asp Tyr
        20              25              30

Tyr Trp Asn Trp Ile Arg Gln Pro Pro Gly Lys Gly Leu Glu Trp Ile
        35              40              45

Gly Glu Ile Asn His Asn Gly Asn Thr Asn Ser Asn Pro Ser Leu Lys
    50              55              60

Ser Arg Val Thr Leu Ser Leu Asp Thr Ser Lys Asn Gln Phe Ser Leu
65              70              75              80

Lys Leu Arg Ser Val Thr Ala Ala Asp Thr Ala Val Tyr Tyr Cys Ala
            85              90              95

Phe Gly Tyr Ser Asp Tyr Glu Tyr Asn Trp Phe Asp Pro Trp Gly Gln
            100             105             110

Gly Thr Leu Val Thr Val Ser Ser Ala Ser Thr Lys Gly Pro Ser Val
        115             120             125

Phe Pro Leu Ala Pro Ser Ser Lys Ser Thr Ser Gly Gly Thr Ala Ala
    130             135             140

Leu Gly Cys Leu Val Glu Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
        180             185             190

Ser Ser Ser Leu Gly Thr Gln Thr Tyr Ile Cys Asn Val Asn His Lys
        195             200             205

Pro Ser Asn Thr Lys Val Asp Glu Lys Val Glu Pro Lys Ser Cys Asp
    210             215             220

Lys Thr His Thr Cys Pro Pro Cys Pro Ala Pro Glu Ala Ala Gly Gly
225             230             235             240

Pro Ser Val Phe Leu Phe Pro Pro Lys Pro Lys Asp Thr Leu Met Ile
```

```
                 245              250              255
 Ser Arg Thr Pro Glu Val Thr Cys Val Val Val Asp Val Ser His Glu
             260              265              270

Asp Pro Glu Val Lys Phe Asn Trp Tyr Val Asp Gly Val Glu Val His
             275              280              285

Asn Ala Lys Thr Lys Pro Arg Glu Glu Gln Tyr Asn Ser Thr Tyr Arg
     290              295              300

Val Val Ser Val Leu Thr Val Leu His Gln Asp Trp Leu Asn Gly Lys
 305              310              315              320

Glu Tyr Lys Cys Lys Val Ser Asn Lys Ala Leu Gly Ala Pro Ile Glu
             325              330              335

Lys Thr Ile Ser Lys Ala Lys Gly Gln Pro Arg Glu Pro Gln Val Tyr
             340              345              350

Thr Leu Pro Pro Cys Arg Asp Glu Leu Thr Lys Asn Gln Val Ser Leu
             355              360              365

Trp Cys Leu Val Lys Gly Phe Tyr Pro Ser Asp Ile Ala Val Glu Trp
     370              375              380

Glu Ser Asn Gly Gln Pro Glu Asn Asn Tyr Lys Thr Thr Pro Pro Val
 385              390              395              400

Leu Asp Ser Asp Gly Ser Phe Phe Leu Tyr Ser Lys Leu Thr Val Asp
             405              410              415

Lys Ser Arg Trp Gln Gln Gly Asn Val Phe Ser Cys Ser Val Met His
             420              425              430

Glu Ala Leu His Asn His Tyr Thr Gln Lys Ser Leu Ser Leu Ser Pro
             435              440              445

Gly Gly Gly Gly Ser Gly Gly Gly Gly Ser Gly Gly Gly Gly Ser
             450              455              460

Gly Gly Gly Gly Ser Asp Ile Val Met Thr Gln Ser Pro Asp Ser Leu
 465              470              475              480

Ala Val Ser Leu Gly Glu Arg Ala Thr Ile Asn Cys Lys Ala Ser Glu
             485              490              495

Ser Val Asp Thr Ser Asp Asn Ser Phe Ile His Trp Tyr Gln Gln Lys
             500              505              510

Pro Gly Gln Ser Pro Lys Leu Leu Ile Tyr Arg Ser Ser Thr Leu Glu
             515              520              525

Ser Gly Val Pro Asp Arg Phe Ser Gly Ser Gly Ser Gly Thr Asp Phe
             530              535              540

Thr Leu Thr Ile Ser Ser Leu Gln Ala Glu Asp Val Ala Val Tyr Tyr
 545              550              555              560

Cys Gln Gln Asn Tyr Asp Val Pro Trp Thr Phe Gly Gln Gly Thr Lys
             565              570              575

Val Glu Ile Lys Arg Thr Val Ala Ala Pro Ser Val Phe Ile Phe Pro
             580              585              590

Pro Ser Asp Glu Gln Leu Lys Ser Gly Thr Ala Ser Val Val Cys Leu
             595              600              605

Leu Asn Asn Phe Tyr Pro Arg Glu Ala Lys Val Gln Trp Lys Val Asp
     610              615              620

Asn Ala Leu Gln Ser Gly Asn Ser Gln Glu Ser Val Thr Glu Gln Asp
 625              630              635              640

Ser Lys Asp Ser Thr Tyr Ser Leu Ser Ser Thr Leu Thr Leu Ser Lys
             645              650              655

Ala Asp Tyr Glu Lys His Lys Val Tyr Ala Cys Glu Val Thr His Gln
             660              665              670
```

```
Gly Leu Ser Ser Pro Val Thr Lys Ser Phe Asn Arg Gly Glu Cys Gly
        675                 680                 685

Gly Gly Gly Ser Gly Gly Gly Gly Ser Gly Gly Gly Gly Ser Gly Gly
        690                 695                 700

Gly Gly Ser Gly Gly Gly Gly Ser Gly Gly Gly Gly Ser Glu Val Gln
705                 710                 715                 720

Leu Leu Glu Ser Gly Gly Gly Leu Val Gln Pro Gly Gly Ser Leu Arg
                725                 730                 735

Leu Ser Cys Ala Ala Ser Gly Phe Ser Phe Ser Ser Tyr Thr Met Ser
                740                 745                 750

Trp Val Arg Gln Ala Pro Gly Lys Gly Leu Glu Trp Val Ala Thr Ile
        755                 760                 765

Ser Gly Gly Gly Arg Asp Ile Tyr Tyr Pro Asp Ser Val Lys Gly Arg
        770                 775                 780

Phe Thr Ile Ser Arg Asp Asn Ser Lys Asn Thr Leu Tyr Leu Gln Met
785                 790                 795                 800

Asn Ser Leu Arg Ala Glu Asp Thr Ala Val Tyr Tyr Cys Val Leu Leu
                805                 810                 815

Thr Gly Arg Val Tyr Phe Ala Leu Asp Ser Trp Gly Gln Gly Thr Leu
                820                 825                 830

Val Thr Val Ser Ser Ala Ser Thr Lys Gly Pro Ser Val Phe Pro Leu
                835                 840                 845

Ala Pro Ser Ser Lys Ser Thr Ser Gly Gly Thr Ala Ala Leu Gly Cys
        850                 855                 860

Leu Val Lys Asp Tyr Phe Pro Glu Pro Val Thr Val Ser Trp Asn Ser
865                 870                 875                 880

Gly Ala Leu Thr Ser Gly Val His Thr Phe Pro Ala Val Leu Gln Ser
                885                 890                 895

Ser Gly Leu Tyr Ser Leu Ser Ser Val Val Thr Val Pro Ser Ser Ser
                900                 905                 910

Leu Gly Thr Gln Thr Tyr Ile Cys Asn Val Asn His Lys Pro Ser Asn
        915                 920                 925

Thr Lys Val Asp Lys Lys Val Glu Pro Lys Ser Cys
    930                 935                 940
```

```
<210> SEQ ID NO 126
<211> LENGTH: 589
<212> TYPE: PRT
<213> ORGANISM: Artificial Sequence
<220> FEATURE:
<223> OTHER INFORMATION: Description of Artificial Sequence: Synthetic
      heavy chain 1of 2+1 PD1/LAG3 0918

<400> SEQUENCE: 126
```

```
Gln Val Gln Leu Gln Gln Trp Gly Ala Gly Leu Leu Lys Pro Ser Glu
1               5               10              15

Thr Leu Ser Leu Thr Cys Ala Val Tyr Gly Gly Ser Phe Ser Asp Tyr
        20              25              30

Tyr Trp Asn Trp Ile Arg Gln Pro Pro Gly Lys Gly Leu Glu Trp Ile
        35              40              45

Gly Glu Ile Asn His Asn Gly Asn Thr Asn Ser Asn Pro Ser Leu Lys
    50              55              60

Ser Arg Val Thr Leu Ser Leu Asp Thr Ser Lys Asn Gln Phe Ser Leu
65              70              75              80

Lys Leu Arg Ser Val Thr Ala Ala Asp Thr Ala Val Tyr Tyr Cys Ala
```

```
                85              90              95

Phe Gly Tyr Ser Asp Tyr Glu Tyr Asn Trp Phe Asp Pro Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
    210             215             220

Lys Thr His Thr Cys Pro Pro Cys Pro Ala Pro Glu Ala Ala Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Gly Ala Pro Ile Glu
            325             330             335

Lys Thr Ile Ser Lys Ala Lys Gly Gln Pro Arg Glu Pro Gln Val Cys
            340             345             350

Thr Leu Pro Pro Ser Arg Asp Glu Leu Thr Lys Asn Gln Val Ser Leu
            355             360             365

Ser Cys Ala Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Val Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Gly Gly Gly Gly Ser Gly Gly Gly Ser Gly Gly Gly Gly Ser
    450             455             460

Gly Gly Gly Gly Ser Glu Val Gln Leu Leu Glu Ser Gly Gly Gly Leu
465             470             475             480

Val Gln Pro Gly Gly Ser Leu Arg Leu Ser Cys Ala Ala Ser Gly Phe
            485             490             495

Ser Phe Ser Ser Tyr Thr Met Ser Trp Val Arg Gln Ala Pro Gly Lys
            500             505             510
```

-continued

```
Gly Leu Glu Trp Val Ala Thr Ile Ser Gly Gly Gly Arg Asp Ile Tyr
        515                 520                 525

Tyr Pro Asp Ser Val Lys Gly Arg Phe Thr Ile Ser Arg Asp Asn Ser
    530                 535                 540

Lys Asn Thr Leu Tyr Leu Gln Met Asn Ser Leu Arg Ala Glu Asp Thr
545                 550                 555                 560

Ala Val Tyr Tyr Cys Val Leu Leu Thr Gly Arg Val Tyr Phe Ala Leu
            565                 570                 575

Asp Ser Trp Gly Gln Gly Thr Leu Val Thr Val Ser Ser
        580                 585
```

```
<210> SEQ ID NO 127
<211> LENGTH: 580
<212> TYPE: PRT
<213> ORGANISM: Artificial Sequence
<220> FEATURE:
<223> OTHER INFORMATION: Description of Artificial Sequence: Synthetic
      heavy chain 2 of 2+1 PD1/LAG3 0918

<400> SEQUENCE: 127
```

```
Gln Val Gln Leu Gln Gln Trp Gly Ala Gly Leu Leu Lys Pro Ser Glu
1                   5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
            85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

-continued

```
                 275                 280                 285
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Asp Glu Leu Thr Lys Asn Gln Val Ser Leu
                355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
    435                 440                 445

Gly Gly Gly Gly Gly Ser Gly Gly Gly Gly Ser Gly Gly Gly Gly Ser
    450                 455                 460

Gly Gly Gly Gly Ser Asp Ile Val Met Thr Gln Ser Pro Asp Ser Leu
465                 470                 475                 480

Ala Val Ser Leu Gly Glu Arg Ala Thr Ile Asn Cys Lys Ala Ser Glu
                485                 490                 495

Ser Val Asp Thr Ser Asp Asn Ser Phe Ile His Trp Tyr Gln Gln Lys
                500                 505                 510

Pro Gly Gln Ser Pro Lys Leu Leu Ile Tyr Arg Ser Ser Thr Leu Glu
                515                 520                 525

Ser Gly Val Pro Asp Arg Phe Ser Gly Ser Gly Ser Gly Thr Asp Phe
    530                 535                 540

Thr Leu Thr Ile Ser Ser Leu Gln Ala Glu Asp Val Ala Val Tyr Tyr
545                 550                 555                 560

Cys Gln Gln Asn Tyr Asp Val Pro Trp Thr Phe Gly Gln Gly Thr Lys
                565                 570                 575

Val Glu Ile Lys
                580
```

```
<210> SEQ ID NO 128
<211> LENGTH: 288
<212> TYPE: PRT
<213> ORGANISM: Homo sapiens

<400> SEQUENCE: 128

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
    50                  55                  60
```

-continued

```
Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
            165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide linker G4S

<400> SEQUENCE: 129

```
Gly Gly Gly Gly Ser
1               5
```

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide linker (G4S)2

<400> SEQUENCE: 130

```
Gly Gly Gly Gly Ser Gly Gly Gly Gly Ser
1               5                   10
```

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide linker (SG4)2

<400> SEQUENCE: 131

Ser Gly Gly Gly Gly Ser Gly Gly Gly Gly
1               5                   10

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide linker G4(SG4)2

<400> SEQUENCE: 132

Gly Gly Gly Gly Ser Gly Gly Gly Gly Ser Gly Gly Gly Gly
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 133

Gly Ser Pro Gly Ser Ser Ser Ser Gly Ser
1               5                   10

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide linker (G4S)3

<400> SEQUENCE: 134

Gly Gly Gly Gly Ser Gly Gly Gly Gly Ser Gly Gly Gly Gly Ser
1               5                   10                  15

<210> SEQ ID NO 135
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide linker (G4S)4

<400> SEQUENCE: 135

Gly Gly Gly Gly Ser Gly Gly Gly Gly Ser Gly Gly Gly Gly Ser Gly
1               5                   10                  15

Gly Gly Gly Ser
            20

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 136

Gly Ser Gly Ser Gly Ser Gly Ser
1               5

-continued

```
<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 137

Gly Ser Gly Ser Gly Asn Gly Ser
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 138

Gly Gly Ser Gly Ser Gly Ser Gly
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 139

Gly Gly Ser Gly Ser Gly
1               5

<210> SEQ ID NO 140
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 140

Gly Gly Ser Gly
1

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 141

Gly Gly Ser Gly Asn Gly Ser Gly
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 142
```

```
Gly Gly Asn Gly Ser Gly Ser Gly
1               5
```

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide linker

<400> SEQUENCE: 143

```
Gly Gly Asn Gly Ser Gly
1               5
```

<210> SEQ ID NO 144
<211> LENGTH: 461
<212> TYPE: PRT
<213> ORGANISM: Artificial Sequence
<220> FEATURE:
<223> OTHER INFORMATION: Description of Artificial Sequence: Synthetic
      heavy chain 2 of 1+1 PD1/LAG3 0725 (1+1 trans)

<400> SEQUENCE: 144

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
                100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys Gly Gly Gly Gly Ser Gly Gly Gly Ser Glu Val Gln
225                 230                 235                 240

Leu Leu Glu Ser Gly Gly Gly Leu Val Gln Pro Gly Gly Ser Leu Arg
                245                 250                 255

Leu Ser Cys Ala Ala Ser Gly Phe Ile Phe Asp Asp Tyr Thr Met Asn
                260                 265                 270
```

```
Trp Val Arg Gln Ala Pro Gly Lys Gly Leu Glu Trp Val Ala Val Ile
        275             280             285

Ser Trp Asp Gly Gly Gly Thr Tyr Tyr Thr Asp Ser Val Lys Gly Arg
    290             295             300

Phe Thr Ile Ser Arg Asp Asp Phe Lys Asn Thr Leu Tyr Leu Gln Met
305             310             315             320

Asn Ser Leu Arg Ala Glu Asp Thr Ala Val Tyr Tyr Cys Ala Lys Gly
            325             330             335

Leu Thr Asp Thr Thr Leu Tyr Gly Ser Asp Tyr Trp Gly Gln Gly Thr
            340             345             350

Leu Val Thr Val Ser Ser Ala Ser Thr Lys Gly Pro Ser Val Phe Pro
            355             360             365

Leu Ala Pro Ser Ser Lys Ser Thr Ser Gly Gly Thr Ala Ala Leu Gly
    370             375             380

Cys Leu Val Glu Asp Tyr Phe Pro Glu Pro Val Thr Val Ser Trp Asn
385             390             395             400

Ser Gly Ala Leu Thr Ser Gly Val His Thr Phe Pro Ala Val Leu Gln
            405             410             415

Ser Ser Gly Leu Tyr Ser Leu Ser Ser Val Val Thr Val Pro Ser Ser
            420             425             430

Ser Leu Gly Thr Gln Thr Tyr Ile Cys Asn Val Asn His Lys Pro Ser
            435             440             445

Asn Thr Lys Val Asp Glu Lys Val Glu Pro Lys Ser Cys
    450             455             460

<210> SEQ ID NO 145
<211> LENGTH: 685
<212> TYPE: PRT
<213> ORGANISM: Artificial Sequence
<220> FEATURE:
<223> OTHER INFORMATION: Description of Artificial Sequence: Synthetic
      heavy chain 2 of 2+1 PD1/LAG3 0750 (2+1 trans)

<400> SEQUENCE: 145

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Ile Phe Asp Asp Tyr
            20              25              30

Thr Met Asn Trp Val Arg Gln Ala Pro Gly Lys Gly Leu Glu Trp Val
        35              40              45

Ala Val Ile Ser Trp Asp Gly Gly Gly Thr Tyr Tyr Thr Asp Ser Val
    50              55              60

Lys Gly Arg Phe Thr Ile Ser Arg Asp Asp Phe Lys Asn Thr Leu Tyr
65              70              75              80

Leu Gln Met Asn Ser Leu Arg Ala Glu Asp Thr Ala Val Tyr Tyr Cys
            85              90              95

Ala Lys Gly Leu Thr Asp Thr Thr Leu Tyr Gly Ser Asp Tyr Trp Gly
            100             105             110

Gln Gly Thr Leu Val Thr Val Ser Ser Ala Ser Thr Lys Gly Pro Ser
            115             120             125

Val Phe Pro Leu Ala Pro Ser Ser Lys Ser Thr Ser Gly Gly Thr Ala
    130             135             140

Ala Leu Gly Cys Leu Val Glu Asp Tyr Phe Pro Glu Pro Val Thr Val
145             150             155             160

Ser Trp Asn Ser Gly Ala Leu Thr Ser Gly Val His Thr Phe Pro Ala
```

-continued

```
                165                 170                 175
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
            325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Ser Glu Val Gln
            450                 455                 460

Leu Leu Glu Ser Gly Gly Gly Leu Val Gln Pro Gly Gly Ser Leu Arg
465                 470                 475                 480

Leu Ser Cys Ala Ala Ser Gly Phe Ile Phe Asp Asp Tyr Thr Met Asn
            485                 490                 495

Trp Val Arg Gln Ala Pro Gly Lys Gly Leu Glu Trp Val Ala Val Ile
            500                 505                 510

Ser Trp Asp Gly Gly Gly Thr Tyr Tyr Thr Asp Ser Val Lys Gly Arg
            515                 520                 525

Phe Thr Ile Ser Arg Asp Asp Phe Lys Asn Thr Leu Tyr Leu Gln Met
            530                 535                 540

Asn Ser Leu Arg Ala Glu Asp Thr Ala Val Tyr Tyr Cys Ala Lys Gly
545                 550                 555                 560

Leu Thr Asp Thr Thr Leu Tyr Gly Ser Asp Tyr Trp Gly Gln Gly Thr
            565                 570                 575

Leu Val Thr Val Ser Ser Ala Ser Thr Lys Gly Pro Ser Val Phe Pro
            580                 585                 590
```

```
Leu Ala Pro Ser Ser Lys Ser Thr Ser Gly Gly Thr Ala Ala Leu Gly
        595                 600                 605

Cys Leu Val Glu Asp Tyr Phe Pro Glu Pro Val Thr Val Ser Trp Asn
        610                 615                 620

Ser Gly Ala Leu Thr Ser Gly Val His Thr Phe Pro Ala Val Leu Gln
625                 630                 635                 640

Ser Ser Gly Leu Tyr Ser Leu Ser Ser Val Val Thr Val Pro Ser Ser
                645                 650                 655

Ser Leu Gly Thr Gln Thr Tyr Ile Cys Asn Val Asn His Lys Pro Ser
                660                 665                 670

Asn Thr Lys Val Asp Glu Lys Val Glu Pro Lys Ser Cys
        675                 680                 685
```

<210> SEQ ID NO 146
<211> LENGTH: 215
<212> TYPE: PRT
<213> ORGANISM: Artificial Sequence
<220> FEATURE:
<223> OTHER INFORMATION: Description of Artificial Sequence: Synthetic
      Light chain CEA (CEA TCB)

<400> SEQUENCE: 146

```
Asp Ile Gln Met Thr Gln Ser Pro Ser Ser Leu Ser Ala Ser Val Gly
1                   5                   10                  15

Asp Arg Val Thr Ile Thr Cys Lys Ala Ser Ala Ala Val Gly Thr Tyr
                20                  25                  30

Val Ala Trp Tyr Gln Gln Lys Pro Gly Lys Ala Pro Lys Leu Leu Ile
            35                  40                  45

Tyr Ser Ala Ser Tyr Arg Lys Arg Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 147
<211> LENGTH: 214
<212> TYPE: PRT
<213> ORGANISM: Artificial Sequence
<220> FEATURE:
<223> OTHER INFORMATION: Description of Artificial Sequence: Synthetic Light chain CD3 (CEA TCB)

<400> SEQUENCE: 147

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
            165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210
```

<210> SEQ ID NO 148
<211> LENGTH: 694
<212> TYPE: PRT
<213> ORGANISM: Artificial Sequence
<220> FEATURE:
<223> OTHER INFORMATION: Description of Artificial Sequence: Synthetic
      CEA CD3 crossfab VHck fc knob P329GLALA (CEA TCB)

<400> SEQUENCE: 148

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
```

-continued

```
               115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Gly Gly Gly Gly Ser Gly Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Ala Ala Ser Gly Phe Thr Phe Ser Thr Tyr Ala Met Asn Trp Val
                260                 265                 270

Arg Gln Ala Pro Gly Lys Gly Leu Glu Trp Val Ser Arg Ile Arg Ser
            275                 280                 285

Lys Tyr Asn Asn Tyr Ala Thr Tyr Tyr Ala Asp Ser Val Lys Gly Arg
    290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
            325                 330                 335

Gly Asn Phe Gly Asn Ser Tyr Val Ser Trp Phe Ala Tyr Trp Gly Gln
            340                 345                 350

Gly Thr Leu Val Thr Val Ser Ser Ala Ser Val Ala Ala Pro Ser Val
            355                 360                 365

Phe Ile Phe Pro Pro Ser Asp Glu Gln Leu Lys Ser Gly Thr Ala Ser
    370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
            405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
            435                 440                 445

Val Thr His Gln Gly Leu Ser Ser Pro Val Thr Lys Ser Phe Asn Arg
    450                 455                 460

Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
            515                 520                 525

Val Glu Val His Asn Ala Lys Thr Lys Pro Arg Glu Glu Gln Tyr Asn
    530                 535                 540
```

```
Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
                565                 570                 575

Ala Pro Ile Glu Lys Thr Ile Ser Lys Ala Lys Gly Gln Pro Arg Glu
                580                 585                 590

Pro Gln Val Tyr Thr Leu Pro Pro Cys Arg Asp Glu Leu Thr Lys Asn
            595                 600                 605

Gln Val Ser Leu Trp Cys Leu Val Lys Gly Phe Tyr Pro Ser Asp Ile
        610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
                660                 665                 670

Ser Val Met His Glu Ala Leu His Asn His Tyr Thr Gln Lys Ser Leu
                675                 680                 685

Ser Leu Ser Pro Gly Lys
        690

<210> SEQ ID NO 149
<211> LENGTH: 451
<212> TYPE: PRT
<213> ORGANISM: Artificial Sequence
<220> FEATURE:
<223> OTHER INFORMATION: Description of Artificial Sequence: Synthetic
      CEA VHCH1 Fc hole P329GLALA (CEA TCB)

<400> SEQUENCE: 149

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
        50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

-continued

```
                195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
                340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 150
<211> LENGTH: 232
<212> TYPE: PRT
<213> ORGANISM: Artificial Sequence
<220> FEATURE:
<223> OTHER INFORMATION: Description of Artificial Sequence: Synthetic
      CD3 VH-CL (CEACAM5 TCB)

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
        180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

```
<210> SEQ ID NO 151
<211> LENGTH: 449
<212> TYPE: PRT
<213> ORGANISM: Artificial Sequence
<220> FEATURE:
<223> OTHER INFORMATION: Description of Artificial Sequence: Synthetic
      CEACAM5 VH-CH1(EE)-Fc (hole, P329G LALA)

<400> SEQUENCE: 151
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
        100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220
```

-continued

```
Asp Lys Thr His Thr Cys Pro Pro Cys Pro Ala Pro Glu Ala Ala Gly
225                 230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
        275             280             285

His Asn Ala Lys Thr Lys Pro Arg Glu Glu Gln Tyr Asn Ser Thr Tyr
    290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Gly Ala Pro Ile
            325             330             335

Glu Lys Thr Ile Ser Lys Ala Lys Gly Gln Pro Arg Glu Pro Gln Val
            340             345             350

Cys Thr Leu Pro Pro Ser Arg Asp Glu Leu Thr Lys Asn Gln Val Ser
            355             360             365

Leu Ser Cys Ala Val Lys Gly Phe Tyr Pro Ser Asp Ile Ala Val Glu
        370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Val Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
        435             440             445

Pro
```

```
<210> SEQ ID NO 152
<211> LENGTH: 674
<212> TYPE: PRT
<213> ORGANISM: Artificial Sequence
<220> FEATURE:
<223> OTHER INFORMATION: Description of Artificial Sequence: Synthetic
      CEACAM5 VH-CH1(EE)-CD3 VL-CH1-Fc (knob, P329G LALA)

<400> SEQUENCE: 152
```

```
Gln Val Gln Leu Val Gln Ser Gly Ala Glu Val Lys Lys Pro Gly Ser
1               5               10              15

Ser Val Lys Val Ser Cys Lys Ala Ser Gly Phe Asn Ile Lys Asp Thr
            20              25              30

Tyr Met His Trp Val Arg Gln Ala Pro Gly Gln Gly Leu Glu Trp Met
        35              40              45

Gly Arg Ile Asp Pro Ala Asn Gly Asn Ser Lys Tyr Val Pro Lys Phe
    50              55              60

Gln Gly Arg Val Thr Ile Thr Ala Asp Thr Ser Thr Ser Thr Ala Tyr
65              70              75              80

Met Glu Leu Ser Ser Leu Arg Ser Glu Asp Thr Ala Val Tyr Tyr Cys
            85              90              95

Ala Pro Phe Gly Tyr Tyr Val Ser Asp Tyr Ala Met Ala Tyr Trp Gly
            100             105             110

Gln Gly Thr Leu Val Thr Val Ser Ser Ala Ser Thr Lys Gly Pro Ser
        115             120             125
```

-continued

```
Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Glu Lys Val Glu Pro Lys Ser Cys
    210                 215                 220

Asp Gly Gly Gly Gly Ser Gly Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Gly Ser Ser Thr Gly Ala Val Thr Thr Ser Asn Tyr Ala Asn Trp
                260                 265                 270

Val Gln Glu Lys Pro Gly Gln Ala Phe Arg Gly Leu Ile Gly Gly Thr
                275                 280                 285

Asn Lys Arg Ala Pro Gly Thr Pro Ala Arg Phe Ser Gly Ser Leu Leu
    290                 295                 300

Gly Gly Lys Ala Ala Leu Thr Leu Ser Gly Ala Gln Pro Glu Asp Glu
305                 310                 315                 320

Ala Glu Tyr Tyr Cys Ala Leu Trp Tyr Ser Asn Leu Trp Val Phe Gly
                325                 330                 335

Gly Gly Thr Lys Leu Thr Val Leu Ser Ser Ala Ser Thr Lys Gly Pro
                340                 345                 350

Ser Val Phe Pro Leu Ala Pro Ser Ser Lys Ser Thr Ser Gly Gly Thr
                355                 360                 365

Ala Ala Leu Gly Cys Leu Val Lys Asp Tyr Phe Pro Glu Pro Val Thr
    370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
                420                 425                 430

His Lys Pro Ser Asn Thr Lys Val Asp Lys Lys Val Glu Pro Lys Ser
                435                 440                 445

Cys Asp Lys Thr His Thr Cys Pro Pro Cys Pro Ala Pro Glu Ala Ala
    450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
                500                 505                 510

Val His Asn Ala Lys Thr Lys Pro Arg Glu Glu Gln Tyr Asn Ser Thr
                515                 520                 525

Tyr Arg Val Val Ser Val Leu Thr Val Leu His Gln Asp Trp Leu Asn
    530                 535                 540
```

-continued

Gly Lys Glu Tyr Lys Cys Lys Val Ser Asn Lys Ala Leu Gly Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
                580                 585                 590

Ser Leu Trp Cys Leu Val Lys Gly Phe Tyr Pro Ser Asp Ile Ala Val
            595                 600                 605

Glu Trp Glu Ser Asn Gly Gln Pro Glu Asn Asn Tyr Lys Thr Thr Pro
    610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
                660                 665                 670

Ser Pro

<210> SEQ ID NO 153
<211> LENGTH: 218
<212> TYPE: PRT
<213> ORGANISM: Artificial Sequence
<220> FEATURE:
<223> OTHER INFORMATION: Description of Artificial Sequence: Synthetic
      CEACAM5 VL-CL(RK)

<400> SEQUENCE: 153

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
                20                  25                  30

Gly Val Gly Phe Leu His Trp Tyr Gln Gln Lys Pro Gly Gln Ala Pro
            35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Arg Lys
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
      CEA-HCDR1

<400> SEQUENCE: 154

Glu Phe Gly Met Asn
1               5

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      CEA-HCDR2

<400> SEQUENCE: 155

Trp Ile Asn Thr Lys Thr Gly Glu Ala Thr Tyr Val Glu Glu Phe Lys
1               5                   10                  15

Gly

<210> SEQ ID NO 156
<211> LENGTH: 12
<212> TYPE: PRT
<213> ORGANISM: Artificial Sequence
<220> FEATURE:
<223> OTHER INFORMATION: Description of Artificial Sequence: Synthetic
      CEA-HCDR3

<400> SEQUENCE: 156

Trp Asp Phe Ala Tyr Tyr Val Glu Ala Met Asp Tyr
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      CEA-LCDR1

<400> SEQUENCE: 157

Lys Ala Ser Ala Ala Val Gly Thr Tyr Val Ala
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      CEA-LCDR2

<400> SEQUENCE: 158

Ser Ala Ser Tyr Arg Lys Arg
1               5

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic

CEA-LCDR3

<400> SEQUENCE: 159

His Gln Tyr Tyr Thr Tyr Pro Leu Phe Thr
1               5                   10

<210> SEQ ID NO 160
<211> LENGTH: 121
<212> TYPE: PRT
<213> ORGANISM: Artificial Sequence
<220> FEATURE:
<223> OTHER INFORMATION: Description of Artificial Sequence: Synthetic
      CEA VH

<400> SEQUENCE: 160

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120

<210> SEQ ID NO 161
<211> LENGTH: 108
<212> TYPE: PRT
<213> ORGANISM: Artificial Sequence
<220> FEATURE:
<223> OTHER INFORMATION: Description of Artificial Sequence: Synthetic
      CEA VL

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 162
<211> LENGTH: 5
<212> TYPE: PRT
<213> ORGANISM: Artificial Sequence -continued

```
<220> FEATURE:
<223> OTHER INFORMATION: Description of Artificial Sequence: Synthetic
      CEA-HCDR1 (CEACAM5)

<400> SEQUENCE: 162

Asp Thr Tyr Met His
1               5

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      CEA-HCDR2 (CEACAM5)

<400> SEQUENCE: 163

Arg Ile Asp Pro Ala Asn Gly Asn Ser Lys Tyr Val Pro Lys Phe Gln
1               5                   10                  15

Gly

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      CEA-HCDR3 (CEACAM5)

<400> SEQUENCE: 164

Phe Gly Tyr Tyr Val Ser Asp Tyr Ala Met Ala Tyr
1               5                   10

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      CEA-LCDR1 (CEACAM5)

<400> SEQUENCE: 165

Arg Ala Gly Glu Ser Val Asp Ile Phe Gly Val Gly Phe Leu His
1               5                   10                  15

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      CEA-LCDR2 (CEACAM5)

<400> SEQUENCE: 166

Arg Ala Ser Asn Arg Ala Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      CEA-LCDR3 (CEACAM5)

<400> SEQUENCE: 167

Gln Gln Thr Asn Glu Asp Pro Tyr Thr
```

-continued 1                    5

<210> SEQ ID NO 168
<211> LENGTH: 121
<212> TYPE: PRT
<213> ORGANISM: Artificial Sequence
<220> FEATURE:
<223> OTHER INFORMATION: Description of Artificial Sequence: Synthetic
      CEA VH (CEACAM5)

<400> SEQUENCE: 168

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
        115                 120

<210> SEQ ID NO 169
<211> LENGTH: 111
<212> TYPE: PRT
<213> ORGANISM: Artificial Sequence
<220> FEATURE:
<223> OTHER INFORMATION: Description of Artificial Sequence: Synthetic
      CEA VL (CEACAM5)

<400> SEQUENCE: 169

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
            85                  90                  95

Glu Asp Pro Tyr Thr Phe Gly Gln Gly Thr Lys Leu Glu Ile Lys
            100                 105                 110